United States Patent
Britton et al.

(10) Patent No.: US 6,255,494 B1
(45) Date of Patent: Jul. 3, 2001

(54) BENZIMIDZOLYL NEUROPEPTIDE Y RECEPTOR ANTAGONISTS

(75) Inventors: Thomas Charles Britton; Robert Frederick Bruns, Jr., both of Carmel; Buddy Eugene Cantrell, Fountaintown; Philip Arthur Hipskind, New Palestine; Karen Lynn Lobb; James Arthur Nixon, both of Indianapolis; Paul Leslie Ornstein, Carmel; Edward C. R. Smith, Indianapolis; Hamideh Zarrinmayeh, Carmel; Dennis Michael Zimmerman, Zionsville, all of IN (US); Anne Marie Nunes, Andover, MA (US); James Jeffry Howbert, Bellevue, WA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/775,538

(22) Filed: Jan. 9, 1997

Related U.S. Application Data
(60) Provisional application No. 60/021,636, filed on Jul. 12, 1996.

(30) Foreign Application Priority Data

Jan. 9, 1996 (GB) .................................................. 9600344

(51) Int. Cl.[7] ..................... C07D 235/12; C07D 235/22; A01N 43/52; A61K 31/415
(52) U.S. Cl. ......................................... 548/310.1; 514/394
(58) Field of Search .......................... 514/394; 548/310.1

(56) References Cited

U.S. PATENT DOCUMENTS 4,772,703   9/1988 Musser et al. .................... 544/283
5,552,426 * 9/1996 Lunn et al. ....................... 514/394

OTHER PUBLICATIONS

Database CAPLUS, Abstract No. 1998:19821, Lulkarin, Y.D., et al., "Synthesis of 2–(1–substituted benzimidazol–2–yl)methylamino/methylenoxy–5–chloro/ nitrobenzo phenones as possible anticonvulsants," Biol. Mem. 1987, 12(2), 182–187. See Registry No. 114192–53–9.
Database CAPLUS, Abstract No. 1983:46775, Shukla, J.S., et al., "Synthesis of some newer 1–heterocyclic amino/ iminomethyl–2–substituted benzimidazoles as a potent CNS, anticonvulsant and monoamine oxidase inhibitory agents," Curr. Sci., 1982, 51(17), 820–822. See Registry No. 84138–39–6.
Database CAPLUS, Abstract No. 1984:591782, Chen, R, et al., "Synthesis of some 1–acylbenzimidazole and 1–acylimidazole derivates," Gaodeng Xuexiao Huaxue Xuebao 1984, 5(3), 361–365. See Registry Numbers 92756–25–7, 92756–28–0, 92756–30–4, 92756–32–6, 92756–33–7, 92756–34–8 and 92772–55–9.
Abstract to JP 61161267 A2, Jul. 21, 1986.*
Abstract to DE 3505609 A1, Aug. 21, 1986.*
Abstract of Khilya et al., "Synthesis and biological activity of furan, pyridine, and benzimidazole analogs to isoflavones.", Khim.–Farm. Zh., 14(1), pp. 24–32, 1980.*

* cited by examiner

*Primary Examiner*—Dwayne C. Jones
(74) *Attorney, Agent, or Firm*—Manisha A. Desai; Paul J. Gaylo

(57) ABSTRACT

This invention provides a series of substituted benzimidazoles which are useful in treating or preventing a condition associated with an excess of neuropeptide Y. This invention also provides methods employing these substituted benzimidazoles as well as pharmaceutical formulations with comprise as an active ingredient one or more of these compounds.

10 Claims, No Drawings

BENZIMIDZOLYL NEUROPEPTIDE Y RECEPTOR ANTAGONISTS

PRIORITY CLAIM

This application claims the benefit of U.S. Provisional Application No. 60/021,636, filed Jul. 12, 1996 and United Kingdom Patent Application 9600344.7, filed Jan. 9, 1996.

BACKGROUND OF THE INVENTION

Neuropeptide Y is a peptide present in the central and peripheral nervous systems. The peptide co-exists with noradrenaline in many neurons and acts as a neurotransmitter per se or synergistically together with noradrenaline. Neuropeptide Y-containing fibers are numerous around arteries in the heart, but are also found around the arteries in the respiratory tract, the gastrointestinal tract, and the genitourinary tract. Neuropeptide Y is also present in the cerebrum with effects on blood pressure, feeding, and the release of different hormones. Alterations in central concentrations of neuropeptide Y have been implicated in the etiology of psychiatric disorders.

Neuropeptide Y was discovered, isolated and sequenced in 1982 from porcine brain as part of a general screening protocol to discover carboxy-terminal amidated peptides and was named neuropeptide Y due to its isolation from neural tissue and the presence of tyrosine as both the amino and carboxy terminal amino acid. Neuropeptide Y is a member of the pancreatic family of peptides and shares significant sequence homology with pancreatic polypeptide and peptide YY.

Neuropeptide Y and the other members of its family of peptides all feature a tertiary structure consisting of an N-terminal polyproline helix and an amphiphilic α-helix, connected with a β-turn, creating a hairpin-like loop, which is sometimes referred to as the pancreatic polypeptide (PP) fold. The helices are kept together by hydrophobic interactions. The amidated C-terminal end projects away from the hairpin loop.

Subsequent to its discovery neuropeptide Y was identified as being the most abundant peptide in the central nervous system with widespread distribution including the cortex, brainstem, hippocampus, hypotahlamus, amygdala, and thalamus as well as being present in the peripheral nervous system in sympathetic neurons and adrenal chromaffin cells.

Neuropeptide Y seems to fulfill the main criteria for a role as a neurotransmitter, as it is stored in synaptic granules, is released upon electrical nerve stimulation, and acts at specific receptors. It is clear that neuropeptide Y is an important messenger in its own right, probably in the brain, where neuropeptide Y potently inhibits the activity of adenylate cyclase and induces an increase in the intracellular levels of calcium. Central injection of neuropeptide Y results in blood pressure changes, increased feeding, increased fat storage, elevated blood sugar and insulin, decreased locomotor activity, reduced body temperature, and catalepsy.

Neuropeptide Y (as well as its chemical relatives) acts upon membrane receptors that are dependent on guanyl-nucleotide binding proteins, known as G protein-coupled receptors. G proteins are a family of membrane proteins that become activated only after binding guanosine triphosphate. Activated G proteins in turn activate an amplifier enzyme on the inner face of a membrane; the enzyme then converts precursor molecules into second messengers.

Neuropeptide Y appears to interact with a family of closely related receptors. These receptors are generally classified into several subtypes based upon the ability of different tissues and receptors to bind different fragments of neuropeptide Y and other members of the PP family of peptides. The Y1 receptor subtype appears to be the major vascular neuropeptide Y receptor. The Y2 receptor subtypes can also occur postjunctionally on vascular smooth muscle. The as-yet-unisolated Y3 receptor subtype appears to be neuropeptide Y-specific, not binding peptide YY. This receptor is likely to be present in the adrenal tissues, medulla, heart, and brain stem, among other areas. [For a review of neuropeptide Y and neuropeptide Y receptors, see. e.g., C. Wahlestedt and D. Reis, *Annual Review of Pharmacology and Toxicology*, 33:309–352 (1993); D. Gehlert and P. Hipskind, *Current Pharmaceutical Design*, 1:295–304 (1995)].

In view of the wide number of clinical maladies associated with an excess of neuropeptide Y, the development of neuropeptide Y receptor antagonists will serve to control these clinical conditions. The earliest such receptor antagonists, such as Patent Cooperation Treaty Patent Publication WO 91/08223, published Jun. 13, 1991, and Patent Cooperation Treaty Patent Publication WO 94/00486, published Jan. 6, 1994, were peptide derivatives. These antagonists are of limited pharmaceutical utility because of their metabolic instability.

This invention provides a class of potent non-peptide neuropeptide Y receptor antagonists. By virtue of their non-peptide nature, the compounds of the present invention do not suffer from the shortcomings, in terms of metabolic instability, of known peptide-based neuropeptide Y receptor antagonists.

SUMMARY OF THE INVENTION

This invention encompasses methods for the treatment or prevention of a physiological disorder associated with an excess of neuropeptide Y, which method comprises administering to a mammal in need of said treatment an effective amount of a compound of Formula I

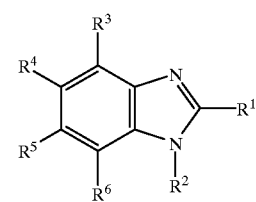

wherein:

$R^1$ is phenyl, $C_3$–$C_8$ cycloalkyl, $C_3$–$C_8$ cycloalkenyl, phenyl($C_1$–$C_6$ alkylenyl)-, phenyl($C_1$–$C_6$ alkoxy), phenoxy($C_1$–$C_6$ alkylenyl)-, phenyl($C_1$–$C_6$ alkoxy)-($C_1$–$C_6$ alkylenyl)-, naphthyl, naphthyl($C_1$–$C_6$ alkylenyl)-, naphthyl($C_1$–$C_6$ alkoxy), naphthyloxy ($C_1$–$C_6$ alkylenyl)-, or naphthyl($C_1$–$C_6$ alkoxy)-($C_1$–$C_6$ alkylenyl)-, any one of which phenyl, $C_3$–$C_8$ cycloalkyl, phenoxy, naphthyl, or naphthyloxy moieties may be substituted with one or groups selected from the group consisting of halo, trifluoromethyl, $C_1$–$C_6$ alkyl, $C_2$–$C_7$ alkenyl, $C_2$–$C_7$ alkynyl, $C_1$–$C_6$ alkoxy, $C_1$–$C_6$ alkylthio, $C_1$–$C_6$ alkylamino, heterocyclic, unsaturated heterocyclic, $C_3$–$C_8$ cycloalkyl, $C_3$–$C_8$ cycloalkenyl, phenyl, phenoxy, phenyl($C_1$–$C_6$ alkylenyl)-, phenyl($C_1$–$C_6$ alkoxy)-, benzoyl, phenyl ($C_2$–$C_7$ alkanoyl)-, and phenyl($C_2$–$C_7$ alkanoyloxy)-;

$R^2$ is $C_1$–$C_{12}$ alkyl, $C_2$–$C_7$ alkenyl, $C_2$–$C_7$ alkynyl, $C_2$–$C_7$ alkanoyl, $C_1$–$C_6$ alkoxy, heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, heterocyclic($C_1$–$C_6$ alkoxy)-, unsaturated heterocyclic ($C_1$–$C_6$ alkoxy)-, phenyl, phenyl($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, benzoyl ($C_1$–$C_6$ alkylenyl)-, $C_2$–$C_7$ alkenyl, $C_2$–$C_7$ carbamoyl, $C_2$–$C_7$ amido, $C_1$–$C_6$ alkoxycarbonyl-, or $C_1$–$C_6$ haloalkyl, any one of which $C_1$–$C_{12}$ alkyl, phenyl, naphthyl, phenoxy, naphthyloxy, benzoyl, $C_3$–$C_8$ cycloalkyl, $C_3$–$C_8$ cycloalkenyl, heterocyclic($C_1$–$C_6$ alkoxy)-, unsaturated heterocyclic($C_1$–$C_6$ alkoxy)-, heterocyclic, or unsaturated heterocyclic moieties may be substituted with one or more groups selected from the group consisting of $C_1$–$C_6$ alkyl, $C_1$–$C_6$ alkoxy, phenyl, naphthyl, phenyl($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, $C_1$–$C_6$ alkoxy, heterocyclic, unsaturated heterocyclic, heterocyclic ($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, $C_1$–$C_6$ alkylthio, $C_1$–$C_6$ haloalkyl, amino, nitro, and hydroxy, or $R^2$ may also be —$(CH_2)_n$—$NR^7R^8$, where,
n is 0 to 10, and
$R^7$ and $R^8$ are independently hydrogen, $C_1$–$C_6$ alkyl, $C_2$–$C_7$ alkanoyl, $C_1$–$C_6$ alkoxy, heterocyclic($C_1$–$C_6$ alkylenyl)-, unsaturated heterocyclic($C_1$–$C_6$ alkylenyl)-, phenyl, phenyl($C_1$–$C_6$ alkylenyl)-, naphthyl, naphthyl($C_1$–$C_6$ alkylenyl)-, phenoxy ($C_1$–$C_6$ alkylenyl)-, naphthyloxy($C_1$–$C_6$ alkylenyl)-, benzoyl($C_1$–$C_6$ alkylenyl)-, heterocyclic($C_1$–$C_6$ alkoxy)-, unsaturated heterocyclic($C_1$–$C_6$ alkoxy)-, $C_1$–$C_6$ haloalkyl, $C_2$–$C_7$ alkenyl, $C_2$–$C_7$ alkynyl, $C_3$–$C_8$ cycloalkenyl, or $C_3$–$C_8$ cycloalkyl, any one of which phenyl, naphthyl, phenoxy, naphthyloxy, $C_3$–$C_8$ cycloalkyl, benzoyl, heterocyclic, unsaturated heterocyclic, heterocyclic($C_1$–$C_6$ alkoxy)-, or unsaturated heterocyclic($C_1$–$C_6$ alkoxy)- moieties may be substituted with one or more groups selected from the group consisting of $C_1$–$C_6$ alkyl, $C_1$–$C_6$ alkoxy, halo, trifluoromethyl, alkoxy, $C_3$–$C_8$ cycloalkyl, $C_3$–$C_8$ cycloalkenyl, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_2$–$C_7$ alkanoyl, $C_2$–$C_7$ alkanoyloxy, $C_1$–$C_6$ alkylamino, $C_1$–$C_6$ alkylthio, $C_2$–$C_7$ alkenyl, $C_2$–$C_7$ alkynyl, $C_1$–$C_6$ haloalkyl, amino, nitro, and hydroxy;

and
$R^3$, $R^4$, $R^5$, and $R^6$ are independently hydrogen, halo, $C_1$–$C_6$ alkyl, $C_1$–$C_6$ alkoxy, $C_2$–$C_7$ alkenyl, $C_2$–$C_7$ alkynyl, $C_2$–$C_7$ alkanoyl, $C_2$–$C_7$ alkanoyloxy, $C_1$–$C_6$ alkylamino, $C_1$–$C_6$ alkylthio, benzoyl, phenoxy, phenyl ($C_1$–$C_6$ alkylenyl)-, $C_3$–$C_8$ cycloalkyl, $C_3$–$C_8$ cycloalkenyl, phenyl($C_1$–$C_6$ alkoxy)-, phenyl($C_1$–$C_6$ alkyleneamino)-, phenyl($C_1$–$C_6$ alkyleneamino)-, phenyl($C_2$–$C_7$ alkanoyl)-, phenyl($C_2$–$C_7$ alkanoyloxy)-, heterocyclic, unsaturated heterocyclic, heterocyclic($C_1$–$C_6$ alkylenyl)-, heterocyclic($C_1$–$C_6$ alkoxy)-, unsaturated heterocyclic($C_1$–$C_6$ alkylenyl)-, unsaturated heterocyclic($C_1$–$C_6$ alkoxy)-, amino, nitro, hydroxy, trifluoromethyl, —O—$(CH_2)_n$—$NR^7R^8$, or —$(CH_2)_n$—$NR^7R^8$;

or a pharmaceutically acceptable salt or solvate thereof.

This invention also encompasses, in additional embodiments, the novel compounds of Formula I, and the salts and solvates thereof, as well as pharmaceutical formulations comprising a compound of Formula I, or a pharmaceutically acceptable salt or solvate thereof, in combination with one or more pharmaceutically acceptable carriers, excipients, or diluents therefor.

DETAILED DESCRIPTION AND PREFERRED EMBODIMENTS

The current invention concerns the discovery that a select group of substituted benzimidazoles, those of Formula I, are useful as neuropeptide Y receptor antagonists.

The terms and abbreviations used in the instant examples have their normal meanings unless otherwise designated. For example "C" refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1$–$C_{12}$ alkyl" refers to straight or branched, monovalent, saturated aliphatic chains of 1 to 12 carbon atoms and includes, but is not limited to, methyl, ethyl, propyl, isopropyl, butyl, isobutyl, t-butyl, pentyl, isopentyl, and hexyl. The term "$C_1$–$C_{12}$ alkyl" includes within its definition the terms "$C_1$–$C_6$ alkyl" and "$C_1$–$C_4$ alkyl".

"$C_2$–$C_7$ alkanoyloxy" represents a straight or branched alkyl chain having from one to six carbon atoms attached to a carbonyl moiety joined through an oxygen atom. Typical $C_2$–$C_7$ alkanoyloxy groups include acetoxy, propanoyloxy, isopropanoyloxy, butanoyloxy, t-butanoyloxy, pentanoyloxy, hexanoyloxy, 3-methylpentanoyloxy and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

The term "carbamoyl" as employed herein refers to a group of the structure —NH—C(O)—. The term "$C_2$–$C_7$ carbamoyl" as employed herein refers to a group of the structure ($C_1$–$C_6$ alkyl)—NH—C(O)—

"Halo" represents chloro, fluoro, bromo or iodo.

The term "$C_1$–$C_6$ haloalkyl" refers to a straight or branched, monovalent, saturated aliphatic chains of 1 to 6 carbon atoms substituted with one or more halo groups.

"$C_1$–$C_{10}$ alkylthio" represents a straight or branched alkyl chain having from one to ten carbon atoms attached to a sulfur atom. Typical $C_1$–$C_{10}$ alkylthio groups include methylthio, ethylthio, propylthio, isopropylthio, butylthio and the like. The term "$C_1$–$C_{10}$ alkylthio" includes within its definition the term "$C_1$–$C_6$ alkylthio" and "$C_1$–$C_3$ alkylthio".

"$C_1$–$C_{12}$ alkylenyl" refers to a straight or branched, divalent, saturated aliphatic chains of 1 to 12 carbon atoms and includes, but is not limited to, methylenyl, ethylenyl, propylenyl, isopropylenyl, butylenyl, isobutylenyl, t-butylenyl, pentylenyl, isopentylenyl, hexylenyl, octylenyl, 3-methyloctylenyl, decylenyl. The term "$C_1$–$C_6$ alkylenyl" is encompassed within the term "$C_1$–$C_{12}$ alkylenyl".

"$C_1$–$C_{10}$ alkylamino" represents a group of the formula

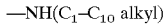

wherein a chain having from one to ten carbon atoms is attached to an amino group. Typical $C_1$–$C_4$ alkylamino groups include methylamino, ethylamino, propylamino, isopropylamino, butylamino, sec-butylamino and the like.

The term "$C_2$–$C_{10}$ alkenyl" as used herein represents a straight or branched, monovalent, unsaturated aliphatic chain having from two to ten carbon atoms. Typical $C_2$–$C_{10}$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

The term "$C_2$–$C_{10}$ alkynyl" as used herein represents a straight or branched, monovalent, unsaturated aliphatic chain having from two to ten carbon atoms with at least one triple bond. Typical $C_2$–$C_{10}$ alkynyl groups include ethynyl, 1-methylethenyl, 1-propynyl, 1-butynyl, 1-hexynyl, 2-propynyl, 2-butynyl, 2-pentynyl, and the like.

"$C_3$–$C_8$ cycloalkenyl" represents a hydrocarbon ring structure containing from three to eight carbon atoms and having at least one double bond within that ring, which is unsubstituted or substituted with 1, 2 or 3 substituents independently selected from halo, halo($C_1$–$C_4$ alkyl), $C_1$–$C_4$ alkyl, $C_1$–$C_4$ alkoxy, carboxy, $C_1$–$C_4$ alkoxycarbonyl, carbamoyl, N-($C_1$–$C_4$ alkyl)carbamoyl, amino, $C_1$–$C_4$ alkylamino, di($C_1$–$C_4$ alkyl)amino or —$(CH_2)_a$—$R^y$ where a is 1, 2, 3 or 4 and $R^y$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$ alkyl)amino.

"$C_1$–$C_6$ alkylamino" represents a straight or branched alkylamino chain having from one to six carbon atoms attached to an amino group. Typical $C_1$–$C_6$ alkyl-amino groups include methylamino, ethylamino, propylamino, isopropylamino, butylamino, sec-butylamino and the like. "$C_1$–$C_6$ alkylamino" encompasses within this term "$C_1$–$C_4$ alkylamino".

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_3$ alkoxy".

"$C_2$–$C_7$ alkanoyl" represents a straight or branched alkyl chain having from one to six carbon atoms attached to a carbonyl moiety. Typical $C_2$–$C_7$ alkanoyl groups include ethanoyl, propanoyl, isopropanoyl, butanoyl, t-butanoyl, pentanoyl, hexanoyl, 3-methylpentanoyl and the like.

"$C_1$–$C_6$ alkoxycarbonyl" represents a straight or branched alkoxy chain having from one to six carbon atoms attached to a carbonyl moiety. Typical $C_1$–$C_6$ alkoxycarbonyl groups include methoxycarbonyl, ethoxycarbonyl, propoxycarbonyl, isopropoxycarbonyl, butoxycarbonyl, t-butoxycarbonyl and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

In those substitutions employing naphthyl, naphthyloxy, naphthoyl, or the like groups, the naphthyl moiety may be attached at the one, two, or three position.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The hetero-cycle is unsubstituted or substituted with 1, 2 or 3 substituents independently selected from halo, halo($C_1$–$C_4$)-alkyl, $C_1$–$C_4$ alkyl, $C_1$–$C_4$ alkoxy, carboxy, $C_1$–$C_4$ alkoxycarbonyl, carbamoyl, N-($C_1$–$C_4$)-alkylcarbamoyl, amino, $C_1$–$C_4$ alkylamino, di($C_1$–$C_4$)alkylamino or —$(CH_2)_a$—$R^d$ where a is 1, 2, 3 or 4; and $R^d$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, $C_1$–$C_6$ haloalkyl, $C_1$–$C_4$ alkyl, $C_1$–$C_4$ alkoxy, carboxy, $C_1$–$C_4$ alkoxycarbonyl, carbamoyl, N-($C_1$–$C_4$) alkylcarbamoyl, amino, $C_1$–$C_4$ alkylamino, di($C_1$–$C_4$) alkylamino or —$(CH_2)_a$—$R^e$ where a is 1, 2, 3 or 4; and $R^e$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$) alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinyl-sulfoxide, thiamorpholinylsulfone, oxadiazolyl, triazolyl, tetrahydroquinolinyl, tetrahydrisoquinolinyl, 4,5-dihydrothiazolyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethyl-naphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

The term "amino-protecting group" as used in the specification refers to substituents of the amino group commonly employed to block or protect the amino fınctionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichoroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (BoC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, PROTECTIVE GROUPS IN ORGANIC SYNTHESIS, (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5, and T. W. Greene, et al., supra, at Chapter 5.

The term "hydroxy-protecting groups" as used herein refers to substitents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, $C_1$–$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl. Further examples of these groups may be found in T. W. Greene and P. G. M. Wuts, PROTECTIVE GROUPS IN ORGANIC SYNTHESIS, (1991) at Chapter 3.

The compounds of the present invention may have one or more asymmetric centers. As a consequence of these chiral centers, those compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in NOMENCLATURE OF ORGANIC COMPOUNDS: PRINCIPLES AND PRACTICE, (J. H. Fletcher, et al., eds., 1974) at pages 103–120.

In addition to the (R)-(S) system, the older D-L system may also be used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active salt or base. These diastereomers can then be separated using differential solubility, fractional crystallization, chromatography, or like methods. Further details regarding resolution of enantiomeric mixtures can be found in J. Jacques, et al., ENANTIOMERS, RACEMATES, AND RESOLUTIONS, (1991).

In addition to the schemes described above, the practitioner of this invention may also choose an enantiospecific protocol for the preparation of the compounds of Formula I. Such a protocol employs a synthetic reaction design which maintains the chiral center present in the starting material in a desired orientation. These reaction schemes usually produce compounds in which greater than 95 percent of the title product is the desired enantiomer.

As noted supra, this invention includes methods employing the pharmaceutically acceptable salts of the compounds defined by Formula I as well as salts of the compounds of Formula II. A compound of this invention can possess a sufficiently acidic, a sufficiently basic, or both finctional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses methods employing the pharmaceutically acceptable solvates of the compounds of Formula I. Many of the compounds of Formula I can combine with solvents such as water, methanol, ethanol and acetonitrile to form pharmaceutically acceptable solvates such as the corresponding hydrate, methanolate, ethanolate and acetonitrilate.

This invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H, Bundgaard, DESIGN OF PRODRUGS, (1985).

The compounds of the present invention are derivatives of benzimidazole which are named and numbered according to the RING INDEX, The American Chemical Society, as follows.

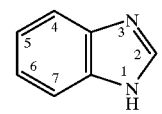

The preferred methods of this invention employ those compounds of Formula I wherein:

a) $R^1$ is phenyl, naphthyl, phenyl($C_1$–$C_6$ alkylenyl)-, naphthyl($C_1$–$C_6$ alkylenyl)-, phenyl($C_1$–$C_6$ alkoxy)-, naphthyl($C_1$–$C_6$ alkoxy)-, phenoxy($C_1$–$C_6$ alkylenyl)-, naphthyloxy($C_1$–$C_6$ alkylenyl)-, or substituted derivatives thereof;

b) $R^2$ is phenyl, heterocyclic, unsaturated heterocyclic, phenyl($C_1$–$C_6$ alkylenyl)-, naphthyl($C_1$–$C_6$ alkylenyl)-, phenyl($C_1$–$C_6$ alkoxy)-, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, —$(CH_2)_n$—$NR^7R^8$, or substituted derivatives thereof;

c) $R^3$, $R^4$, $R^5$, and $R^6$, are independently hydrogen, chloro, fluoro, bromo, $C_1$–$C_6$ alkyl, trifluoromethyl, $C_1$–$C_6$ alkoxy, benzoyl, $C_2$–$C_7$ alkanoyl, phenyl($C_1$–$C_6$ alkylenyl)-, phenyl($C_1$–$C_6$ alkoxy)-, or —$(CH_2)_n$—$NR^7R^8$, or substituted derivatives thereof; and d) at least one of $R^3$, $R^4$, $R^5$, and $R^6$ is not hydrogen.

The preferred compounds of this invention are those compounds which are employed in the preferred methods of this invention.

In the scientific literature derivatives of benzimidazole are already known to possess different biological activities, such as analgesic and antiinflammatory activity (Japan Kokai 75,126,682; U.S. Pat. No. 4,925,853), gastric antisecretory activity (European Patent Publication 246,126), antihistaminic activity (U.S. Pat. Nos. 4,200,641 and 5,182,280), dopaminergic and andrenergic activity (U.S. Pat. No. 4,925,854), bronchodilatory activity, growth promotion (U.S. Pat. No. 4,960,783), tachykinin receptor antagonist (U.S. patent application Ser. No. 08/235,401, filed Apr. 29, 1994), and inhibitor of β-amyloid peptide production (U.S. patent application Ser. No. 08/235,400, filed Apr. 29, 1994).

The compounds of Formula I can be prepared by processes known in the literature. See. e.g., G. W. H. Cheeseman and R. F. Cookson, THE CHEMISTRY OF HETEROCYCLIC COMPOUNDS, (A. Weissberger, et al., eds. 1979).

Synthesis of the Benzimidazole Nucleus

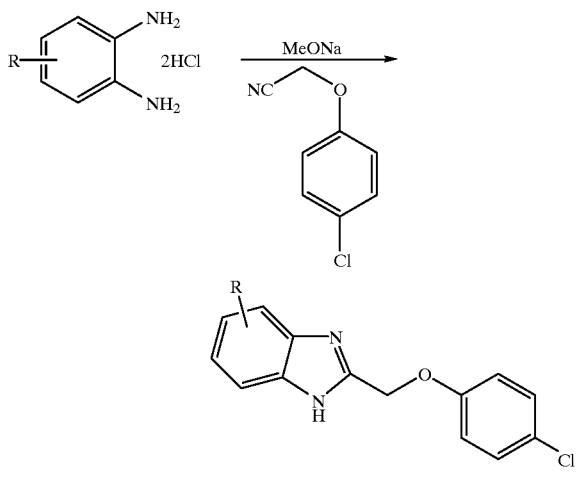

Synthesis of the N-1 Substituted Benzimidazoles (Scheme I)

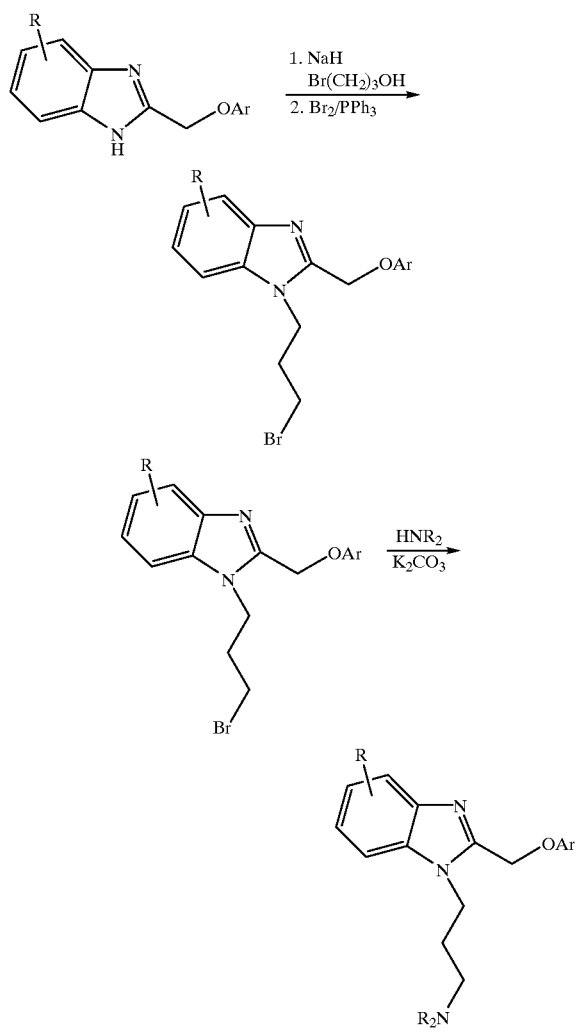

Synthesis of the N-1 Substituted Benzimidazoles (Scheme II)

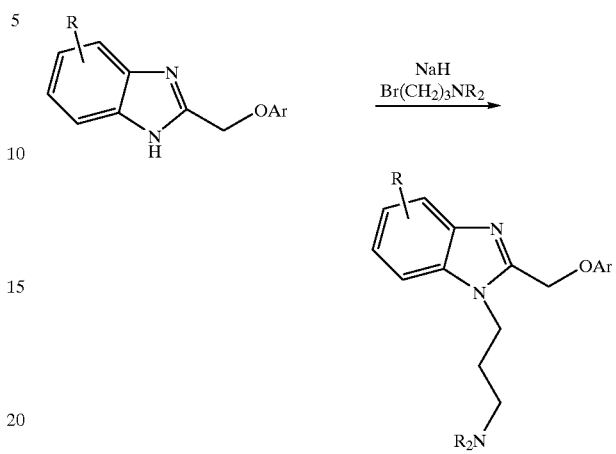

Another means of preparing the compounds of Formula I is by cyclization of an appropriately substituted o-phenylenediamine such as the one depicted in Formula II

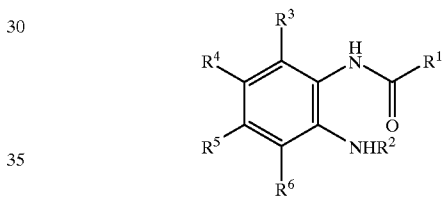

II in a solvent or solvent mixture. It is generally preferred that the solvent or solvent mixture be heated, preferably to the boiling point of the solvent. Suitable solvents include ethanol, isopropanol, glacial acetic acid, benzene, toluene, chlorobenzene, glycol, ethylene glycol, dimethyl ether, diethyl ether, dimethylformamide, chloroform, ethyl acetate, and the like. It is generally preferred to add a condensation agent such as phosphorous oxychloride, thionyl chloride, p-toluenesulfonic acid, hydrochloric acid, sulfuric acid, phosphoric acid, polyphosphoric acid, phosphorous pentoxide, methanesulfonyl hydroxide, methanesulfonyl chloride, and the like. The cyclization reaction may also optionally be performed in the presence of a base such as sodium hydroxide, sodium mesylate, or potassium tert-butylate.

In those compounds in which $R^2$ is phenyl a derivative of N-phenyl-o-phenylenediamine was used as the starting material for the cyclization reaction. The examples infra provide sufficient guidance in the preparation of those compounds of Formula I wherein all of $R^3$, $R^4$, $R^5$, and $R^6$ are hydrogen.

Those compounds of Formula I wherein at least one of $R^3$, $R^4$, $R^5$, and $R^6$ is not hydrogen, can be prepared by methods taught in the literature. For example, the compounds of this invention wherein phenyl portion of the benzimidazole is substituted with $C_2$–$C_7$ alkanoyl can be prepared from the appropriate keto o-phenylenediamine of the formula

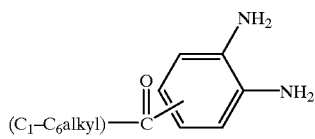

by methods known in the benzimidazole art such as the procedures described in U.S. Pat. No. 4,401,817, issued Aug. 30, 1983, the entire contents of which are herein incorporated by reference. The method of preparation involves the ammonolysis and reduction of a 4-halo-3-nitrophenyl ketone which is prepared by the Friedel-Crafts reaction of either a 4-halo-3-nitrobenzoyl chloride with an appropriate hydrocarbon or a halobenzene with an appropriate acid chloride followed by aromatic nitration.

Alternatively, the keto benzimidazole reactants can be prepared from acetanilide by a Friedel-Crafts acylation with the appropriate derivative of $C_2$–$C_7$ alkanoic acid. The resulting 4-keto acetanilide is nitrated to give a 2-nitro-4-ketoacetanilide. The acetanilide is hydrolyzed to give a 2-nitro-4-ketoaniline, which can then be catalytically hydrogenated to yield a 4-keto-o-phenylenediamine which can then be ring closed to provide the 5 or 6-substituted benzimidazole.

Those compounds of Formula III wherein phenyl portion of the benzimidazole is substituted with alkyl or alkylenyl may be prepared by means of a Friedel-Crafts alkylation with the appropriate derivative of the substituting moiety using standard procedures, usually employing an alkyl halide or an olefin in the presence of a catalyst such as aluminum chloride, aluminum bromide or another Lewis acid.

An alternative strategy for preparing those compounds of Formula I wherein $R^5$ is $C_1$–$C_6$ alkoxy, $R^7R^8N$-($C_1$–$C_6$ alkoxy)-, or heterocyclic-($C_1$–$C_6$ alkoxy)-, or a substituted derivative thereof, involves first reacting a 3-nitro-4-aminophenol with an acyl halide in the presence of a base

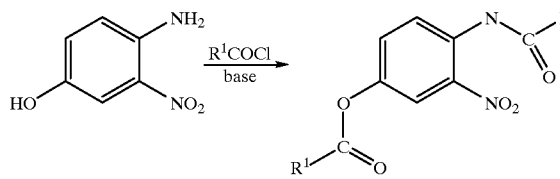

to get substitution of the primary amine as well as substitution of the hydroxy group, the ester moiety serving as a hydroxy-protecting group for subsequent reactions. In the next step of this synthesis the nitro group is then reduced to an amino group, usually by catalytic hydrogenation.

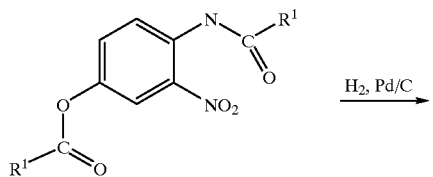

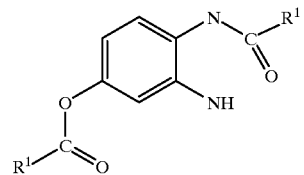

The primary amine of the above compound is then substituted, usually using an aldehyde, such as benzaldehyde or a substituted derivative thereof, followed by hydrogenation, if necessary. In an alternative embodiment, those compounds of Formula I in which $R^2$ is alkyl or substituted alkyl may be produced by alkylation of an aromatic amine with alkyl halide or tosylate, or the like, in the presence of a suitable base, such as trialkylamine, potassium carbonate, 1,8-diazabicyclo[5.4.0]undec-7-ene (DBU), and the like.

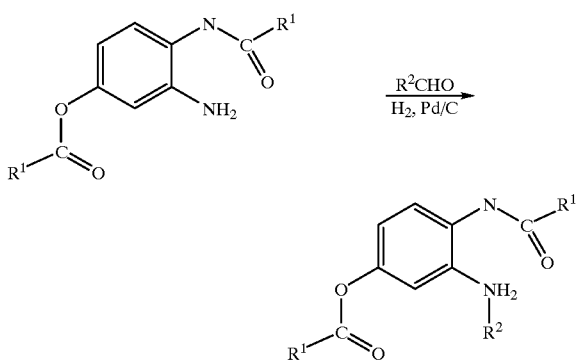

Cyclization of this substituted phenylenediamine is then performed as described supra, followed by cleavage of the ester group protecting the hydroxy group at the 6-position of the benzimidazole. Suitable cyclization catalysts include phosphorous oxychloride, thionyl chloride, phosphorous pentoxide, phosphorous pentachloride, and other like strong dehydrating agents.

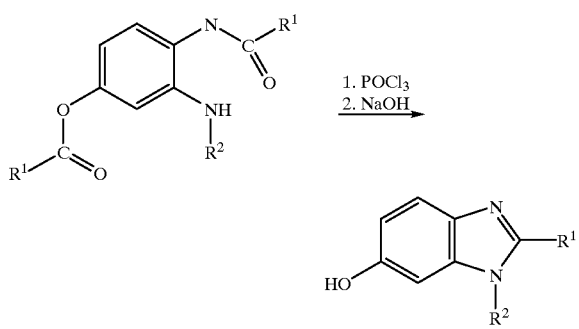

A preferred method of cleaving this ester is by incubation of the intermediate in a basic solution, such as 1N sodium hydroxide, or a weaker base such as potassium carbonate. The hydroxy group at the 6-position is then substituted using an alkyl or aryl halide, resulting in a compound of Formula I.

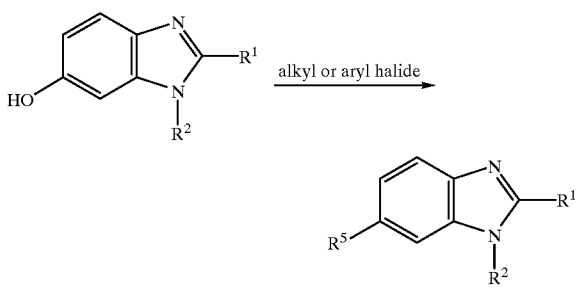

The skilled artisan understands that compounds of Formula I substituted at the 5-position of the benzimidazole can be prepared as described above by employing 3-amino-4-nitrophenol as the starting material instead of the 3-nitro-4-aminophenol shown supra.

Those compounds of Formula I wherein $R^2$ is alkyl or substituted alkyl may alternatively be prepared by the direct alkylation of a benzimidazole wherein the nitrogen at the 1-position is substituted with a hydrogen. This type of alkylation is usually performed by the reaction of the benzimidazole with an alkyl halide in the presence of a strong base, such as sodium hydride. This reaction is usually performed in a polar aprotic solvent, such as N,N-dimethylformamide, dimethyl sulfoxide, dimethylacetamide, hexamethylphosphoric triamide, and the like.

The following Examples further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofliran (THF) was obtained by distillation from sodium or sodium benzophenone ketyl prior to use.

Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz. (Unless designated otherwise, the term "NMR" as employed herein refers to proton nuclear magnetic resonance.) Free atom bombardment mass spectroscopy (FAB) was performed on a VG ZAB-2SE instrument. Field desorption mass spectroscopy (FDMS) was performed using either a VG 70SE or a Varian MAT 731 instrument.

Optical rotations were measured with a Perkin-Elmer 241 polarimeter. Chromatographic separation on a Waters Prep 500 LC was generally carried out using a linear gradient of the solvents indicated in the text unless otherwise specified.

The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 ml of 10% aqueous sulfuric acid] and then heated on a hot plate). Preparative centrifugal thin layer chromatography was performed on a Harrison Model 7924A Chromatotron using Analtech silica gel GF rotors.

Cation exchange chromatography was performed with Dowex® 50X8-100 ion exchange resin. Anion exchange chromatography was performed with Bio-Rad AG® 1-X8 anion-exchange resin (acetate form converted to hydroxide form). Flash chromatography was performed as described by Still, et al., *Journal of Organic Chemistry*, 43:2923 (1978).

Optical rotations are reported at the sodium-D-line (354 nm). Elemental analyses for carbon, hydrogen, and nitrogen were determined on a Control Equipment Corporation 440 Elemental Analyzer. Melting points were determined in open glass capillaries on a Thomas Hoover capillary melting point apparatus or a Büchi melting point apparatus, and are uncorrected.

General Procedure for Benzimidazole Synthesis

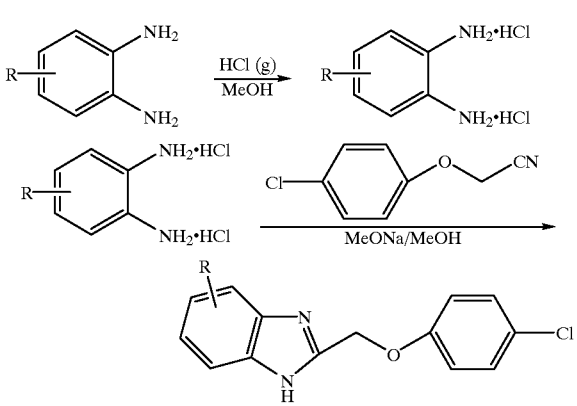

To a 0.4 M solution of the optionally substituted 1,2-diaminobenzene in methanol, anhydrous hydrogen chloride gas was bubbled until saturation. The solution was permitted to cool to room temperature. The precipitate was collected, dried and then used in the next step.

A solution of 4-chlorophenoxynitrile (1.05 eq) in dry methanol (0.3 M) was treated with sodium methoxide (1.05 eq). The mixture was stirred at room temperature. The mixture was treated with the dihydrochloride salt of the diamine (1.0 eq) and stirred at room temperature for about one hour. In most of the cases the precipitate was observed upon addition. The crude cyrstals were washed with diethyl ether and dried in vacuo.

Whne diaminotoluene was treated with 4-chlorophenoxynitrile there was no precipitate observed immediately. The reaction mixture was condensed under vacuum. The crude brownish solid was dissolved in ethyl acetate. The resulting solution was washed with water, then brine, and then dried over sodium sulfate. The solvents were then removed in vacuo to produce brown crystals with a good yield.

Preparation 1

Preparation of 2-benzylbenzimidazole

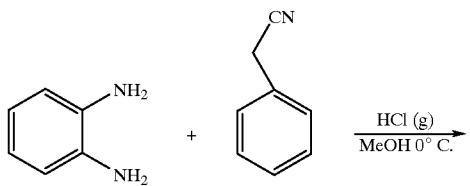

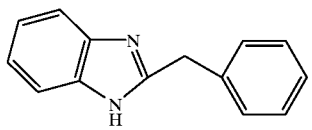

A 1 M solution of benzyl cyanide in anhydrous methanol was treated with hydrogen chloride gas at 0° C. for about thirty minutes. The mixture was stirred for two hours at 0° C. and then a 1 M solution of diaminobenzene was added and the resulting solution was stirred at 0° C. The progress of the reaction was monitored by thin layer chromatography. The reaction mixture was then poured into water. The unreacted nitrile was extracted with ethyl acetate. The aqueous layer was neutralized with 1 N sodium hydroxide. The organic fraction was extracted with ethyl acetate and condensed. The desired title product was recrystallized from methanol/water.

Preparation 2
Preparation of 2-(4-chlorophenyl)benzimidazole

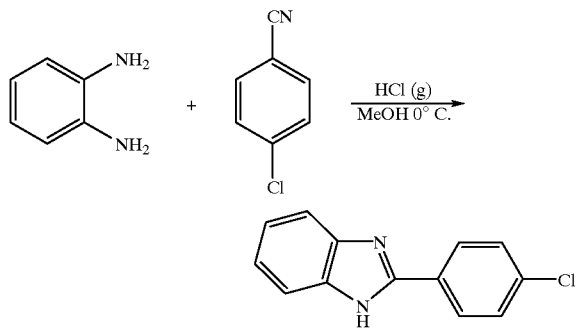

The title compound was prepared essentially as described in Preparation 1 except that an equimolar amount of 4-chlorobenzonitrile was employed instead of the benzyl cyanide employed therein.

Preparation 3
Preparation of 2-(4-chlorobenzyl)benzimidazole

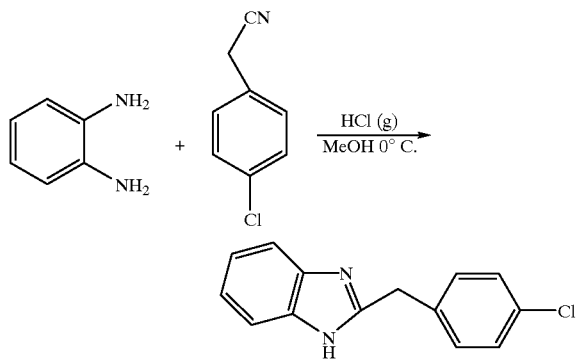

The title compound was prepared essentially as described in Preparation 1 except that an equimolar amount of 4-chlorobenzyl cyanide was employed instead of the benzyl cyanide employed therein.

Preparation 4
Preparation of 2-(benzyloxymethyl)-7-hydroxybenzimidazole

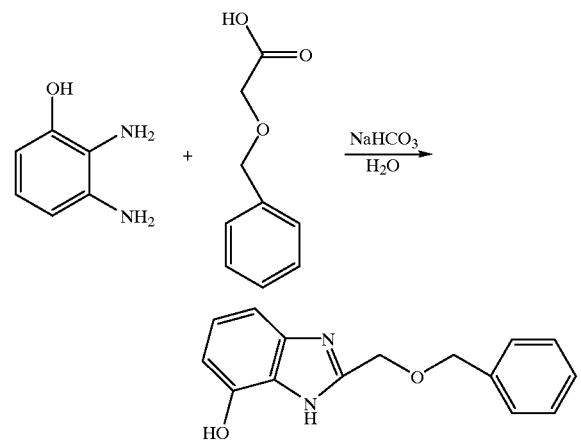

A mixture of the 2,3-diaminophenol (5 g, 40.3 mmol, 1 eq) and benzyloxyacetic acid (5.6 g, 48.3 mmol, 1.2 eq) in 40 ml of a 10% aqueous solution of sodium bicarbonate was stirred and refluxed at 140° C. for one hour. The mixture was allowed to cool down to room temperature. Ethyl acetate was poured into the mixture. The organic fraction was extracted with ethyl acetate, washed with water, and then dried over sodium sulfate. The solvents were removed in vacuo. The crude product was further purified by flash chromatography to yield 6.87 grams (67% yield) of the desired title product.

The following intermediates were prepared essentially as described above.

Preparation 5
Preparation of 6-methyl-2-(4-chlorophenoxymethyl)benzimidazole

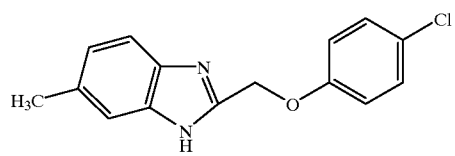

IR and NMR were consistent with the desired title product. FDMS 272 (M+).

Preparation 6
Preparation of 2-(4-chlorophenoxymethyl)benzimidazole

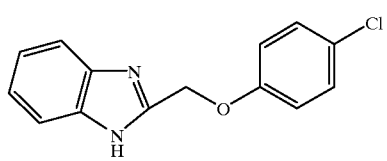

IR and NMR were consistent with the desired title product. FDMS 258 (M+).

Preparation 7
Preparation of 2-(4-chlorophenoxymethyl)-7-nitrobenzimidazole

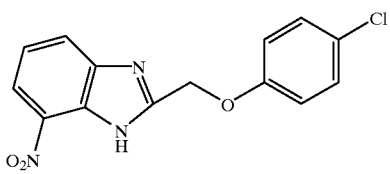

IR and NMR were consistent with the desired title product. FDMS 303 (M+).

Preparation 8
Preparation of 2-(4-chlorophenoxymethyl)-6-methoxybenzimidazole

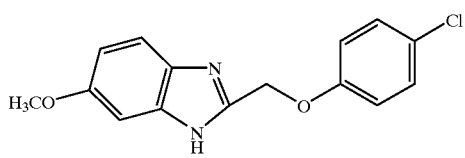

IR and NMR were consistent with the desired title product. FDMS 288 (M+).

Preparation 9
Preparation of 2-(4-chlorophenoxymethyl)-6,7-dimethylbenzimidazole

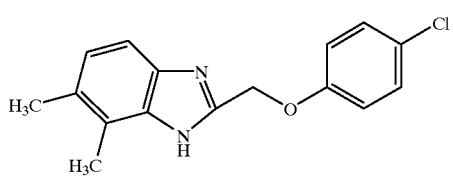

NMR was consistent with the desired title product.

Preparation 10
Preparation of 2-(4-chlorophenoxymethyl)-7-methylbenzimidazole

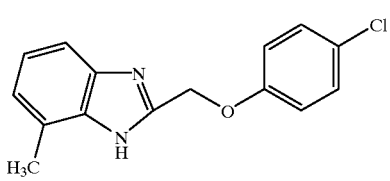

NMR was consistent with the desired title product.

Preparation 11
Preparation of 2-(4-chlorophenoxymethyl)-6-methoxycarbonylbenzimidazole

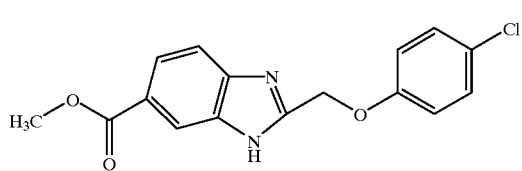

1.9 grams (57% yield).

Preparation 12
Preparation of 2-(4-chlorophenoxymethyl)-7-hydroxybenzimidazole

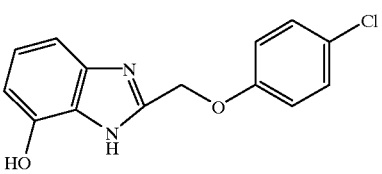

NMR was consistent with the desired title product. Yield 5.3 grams (91%).

Preparation 13
Preparation of 2-benzylbenzimidazole

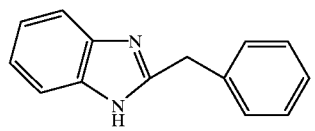

NMR was consistent with the desired title product. Yield 1.26 grams (14%).

Preparation 14
Preparation of 2-(3-chlorophenoxymethyl)benzimidazole

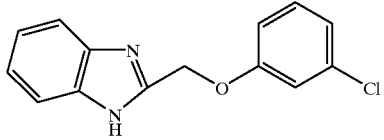

NMR was consistent with the desired title product. Yield 1.5 grams (>99%).

Preparation 15
Preparation of 2-(2-chlorophenoxymethyl)benzimidazole

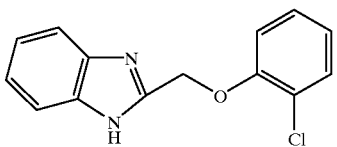

NMR was consistent with the desired title product. Yield 1.36 grams (91%).

Preparation 16
Preparation of 2-(4-chlorophenyl)benzimidazole

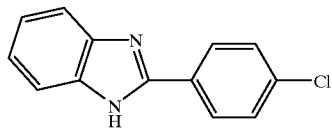

Preparation 17
Preparation of 2-(4-chlorobenzyl)benzimidazole

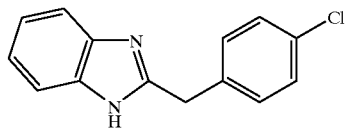

NMR was consistent with the desired title product.

Preparation 18
Preparation of 2-(phenoxymethyl)benzimidazole

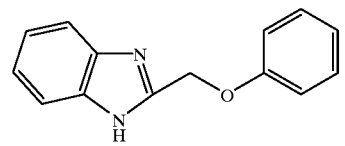

NMR was consistent with the desired title product. Yield 1.06 grams (65%).

Preparation 19
Preparation of 2-(3,5-dichlorophenoxymethyl)benzimidazole

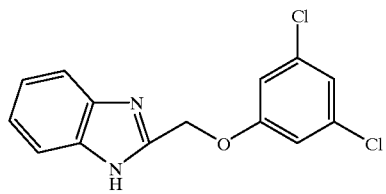

IR and NMR were consistent with the desired title product. Yield 0.28 grams (>99%). FDMS 292 (M+). Analysis for $C_{14}H_{10}Cl_2N_2O$: Theory: C, 57.36; H, 3.44; N, 9.56. Found: C, 57.45; H, 3.48; N, 9.41.

Preparation 20
Preparation of 2-(3,5-dichlorophenoxymethyl)-7-methylbenzimidazole

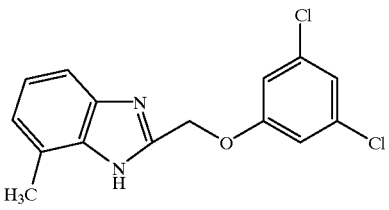

IR and NMR were consistent with the desired title product. Yield 0.448 grams (75%). FDMS 306 (M+). Analysis for $C_{15}H_{12}Cl_2N_2O$: Theory: C, 58.65; H, 3.94; N, 9.12. Found: C, 58.45; H, 3.95; N, 9.18.

Preparation 21
Preparation of 2-(3,5-dichlorophenoxymethyl)-7-hydroxybenzimidazole

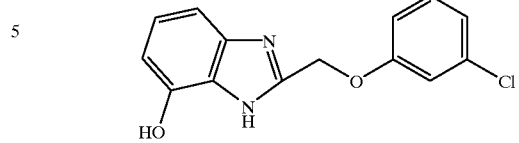

IR and NMR were consistent with the desired title product. Yield 0.46 grams (78%). FDMS 308 (M+). Analysis for $C_{14}H_{10}Cl_2N_2O_2$: Theory: C, 54.39; H, 3.26; N, 9.06. Found: C, 54.26; H, 3.22; N, 8.99.

Preparation 22
Preparation of 2-[4-(thiazol-2-yl)phenoxymethyl]-benzimidazole

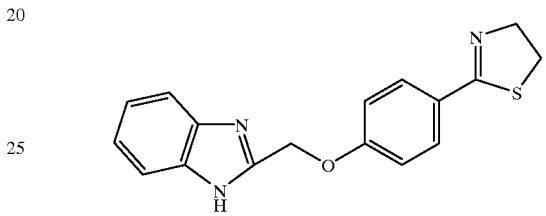

NMR was consistent with the desired title product. Yield 2.7 grams (>99%).

Preparation 23
Preparation of 2-[3-chlorophenoxymethyl]-7-methylbenzimidazole

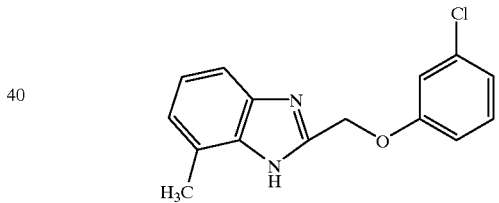

NMR was consistent with the desired title product.

Preparation 24
Preparation of 2-[3-chlorophenoxymethyl]-7-hydroxybenzimidazole

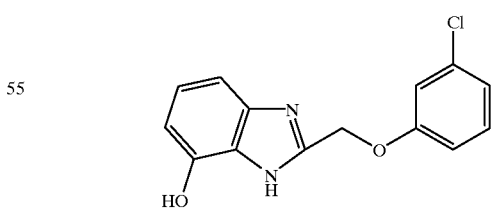

NMR was consistent with the desired title product. Yield 1.5 grams (>99%).

Preparation 25
Preparation of 2-[1,6-dichlorophenoxymethyl]benzimidazole

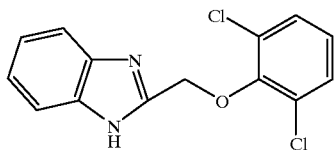

IR and NMR were consistent with the desired title product. Yield 0.27 grams (>99%). FDMS 292 (M+). Analysis for $C_{14}H_{10}Cl_2N_2O$: Theory: C, 57.36; H, 3.44; N, 9.50. Found: C, 57.50; H, 3.43; N, 9.54.

Preparation 26
Preparation of 2-[1,6-dichlorophenoxymethyl]-7-methylbenzimidazole

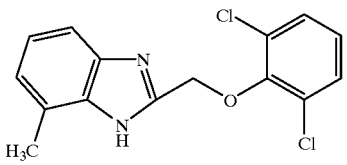

IR and NMR were consistent with the desired title product. Yield 0.5 grams (94%). FDMS 306 (M+). Analysis for $C_{15}H_{12}Cl_2N_2O$: Theory: C, 58.65; H, 3.94; N, 9.12. Found: C, 58.36; H, 3.92; N, 9.32.

Preparation 27
Preparation of 2-[1,6-dichlorophenoxymethyl]-7-hydroxybenzimidazole

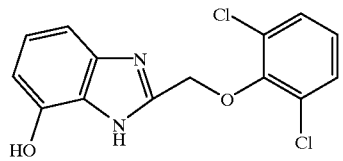

IR and NMR were consistent with the desired title product. Yield 0.52 grams (88%). FDMS 308 (M+). Analysis for $C_{14}H_{10}Cl_2N_2O_2$: Theory: C, 54.39; H, 3.26; N, 9.06. Found: C, 54.51; H, 3.22; N, 9.22.

Preparation 28
Preparation of 2-[3-trifluoromethylphenoxymethyl]-benzimidazole

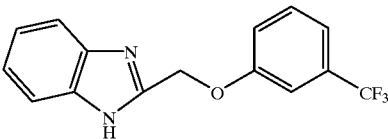

NMR was consistent with the desired title product. Yield 0.62 grams (89%).

Preparation 29
Preparation of 2-[3-trifluoromethylphenoxymethyl]-7-methylbenzimidazole

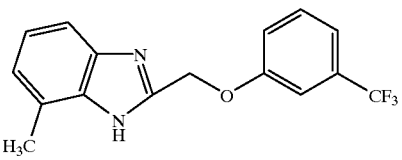

NMR was consistent with the desired title product.

Preparation 30
Preparation of 2-[4-chlorophenoxymethyl]-6-chlorobenzimidazole

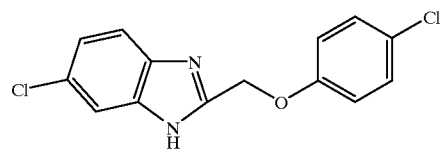

NMR and IR were consistent with the desired title product. Yield 8.20 grams (>99%). FDMS 292 (M+).

Preparation 31
Preparation of 2-[4-chlorophenoxymethyl]-5,6-dichlorobenzimidazole

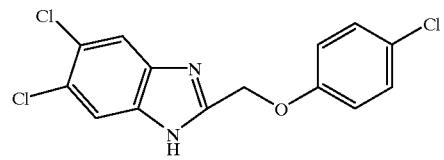

NMR and IR were consistent with the desired title product. Yield 9.20 grams (>99%). FDMS 328 (M+).

Preparation 32
Preparation of 2-[4-chlorophenoxymethyl]-5,6-dimethylbenzimidazole

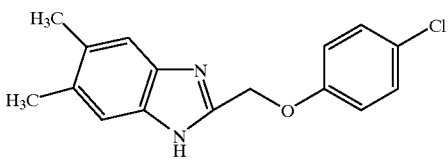

NMR and IR were consistent with the desired title product. Yield 4,4 grams (52%). FDMS 286 (M+).

Preparation 33
Preparation of 2-[4-chlorophenoxymethyl]-4,5,6,7-tetramethylbenzimidazole

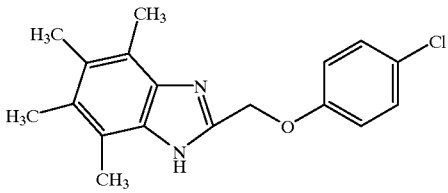

NMR was consistent with the desired title structure. Yield 0.5 grams (38%).

Preparation 33
Preparation of 2-[4-chlorophenoxymethyl]-6-(t-butyl)benzimidazole

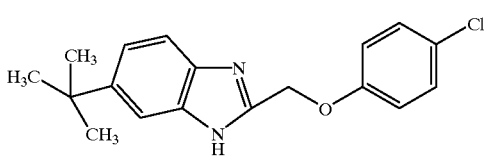

NMR was consistent with the desired title product. Yield 1.5 grams (40%).

Preparation 34
Preparation of 2-[2,4-dichlorophenoxymethyl]benzimidazole

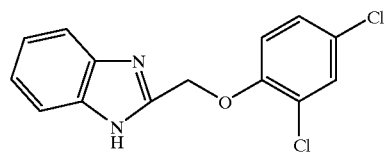

IR and NMR were consistent with the desired title product. Yield 6.7 grams (96%). FDMS 292 (M+). Analysis for $C_{14}H_{10}Cl_2N_2O$: Theory: C, 57.36; H, 3.44; N, 9.56. Found: C, 57.11; H, 3.54; N, 9.31.

Preparation 35
Preparation of 2-[2,4-dichlorophenoxymethyl]-5,6-dichlorobenzimidazole

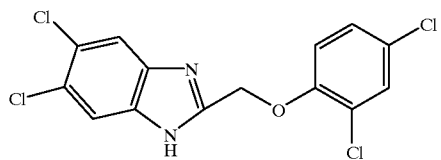

NMR and IR were consistent with the desired title product. Yield 3.2 grams (91%).

Preparation 36
Preparation of (3'R) ethyl 2-(piperidin-3-yl)acetate

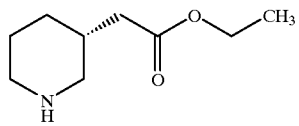

Ethyl-3-pyridylacetate (100 g, 0.606 mol) was dissolved in ethanol (1.8 liters), treated with 5% rhodium on alumina (100 g) and hydrogenated at 60° C. and 60 psi hydrogen gas overnight. The catalyst was removed by filtration and the solvent evaporated to give a brown liquid (101.4 g, 98%). The brown liquid was dissolved in ethyl acetate (600 ml) and treated with L-(+)-mandelic acid in warm ethyl acetate (600 ml). After cooling in the refrigerator for four hours, the solid was collected and the crystallization fluid reserved for processing to the other enantiomer, infra. The solid was again recrystallized from ethyl acetate (1.55–1.6 liters, overnight at ambient temperature) to give the desired title product as white needles. Yield: 81.6, 41%. O.R. (EtOH) @589 nm=+44.9°, @365 nm=+173.73°. mp 118–119° C.

Preparation 37
Preparation of (3'S) ethyl 2-(piperidin-3-yl)acetate

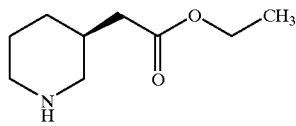

The crystallization fluid from Preparation 36, supra, was evaporated to give a dark oil (100.3 g). This was dissolved in a cold solution of potassium carbonate (52 g, 0.377 mol) in water (250 ml) and extracted with ethyl acetate (5×150 ml). The extracts were combined and dried over magnesium sulfate. The solvents were removed in vacuo to give a dark liquid (40.25 g). The dark liquid was treated with a warm solution of D-(−)-mandelic acid (36 g) in ethyl acetate (650 ml) and cooled at ambient temperatures overnight. The crystals were recrystallized twice more from ethyl acetate (1.2 liters and 1.1 liters, respectively) to give the desired title product as white needles. Yield: 48.7 g, 24.9%. O.R. (EtOH) @589 nm=−43.14°, @365 nm=−164.31°. mp 115.5–117° C.

Chiral Analytical Method

Cold aqueous potassium carbonate (0.15 g in 10 ml of water) was treated with 0.3 g of the mandelic acid salt and the mixture was extracted with ethyl acetate (3×5 ml). The combined extracts were dried over magnesium sulfate and the solvents were removed in vacuo. The residue was dissolved in diethyl ether (10 ml) and treated with S-(−)-α-methylbenzylisocyanate (0.12 ml). After 2.5 hours, the reaction was treated wtih 1 N hydrochloric acid (2 ml). The ether was separated and then washed sequentially with brine, a saturated aqueous sodium bicarbonate solution, and brine. The organic fraction was dried over magnesium sulfate and the solvents were removed by evaporation. The residue was analyzed on a CHIRACEL OJ™ high performance liquid chromatography column (4.6×250 mm), eluting with 5% ethanol in hexanes at a flow rate of 2.5 ml/minute. The slower component comes from the 1-(+)-mandelic acid salt and the faster from the d-(−)-mandelic acid salt. HPLC analysis of the final crystallization products of both enantiomers show less than three percent of the opposite enantiomer.

Preparation 38
Preparation of (3'R) ethyl 2-[N-(t-butoxycarbonyl)piperidin-3-yl]acetate

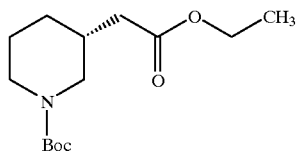

(3'R)-Ethyl-2-(piperidin-3-yl)acetate (10.9 g, 34 mmol) as prepared in Preparation 36 was dissolved in 50 ml of a 12% sodium carbonate in water solution and the resulting solution was extracted with chloroform. The extracts were dried and the solvents removed by evaporation. The residue was suspended in diethyl ether, filtered, and evaporated to give the free base (5.36 g). The liquid was dissolved in ether (50 ml) and treated dropwise with di-t-butyldicarbonate (7.9 g) in ether (10 ml). After stirring overnight, the solution was cooled in an ice water bath and treated dropwise with saturated aqueous citric acid (25 ml). The aqueous fraction was extracted with diethyl ether. The organic fractions were combined, washed with water, a saturated sodium bicarbonate solution, and then brine, and then dried over magnesium sulfate. The solvents were removed in vacuo to give the desired title product was a clear liquid. NMR was consistent with proposed title structure.

Preparation 39
Preparation of (3'S) ethyl 2-[N-(t-butoxycarbonyl)piperidin-3-yl]acetate

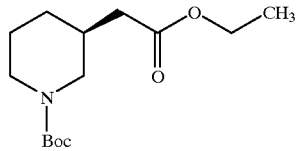

(3'S)-Ethyl-2-(piperidin-3-yl)acetate (48.6 g, 150 mmol), as prepared in Preparation 37, was treated with a solution of potassium carbonate (30 g, 0.217 mol) in water (220 ml) and the resulting solution was extracted with chloroform (3×100 ml). The extracts were dried over sodium sulfate and the solvents were removed in vacuo. The residue was mixed with diethyl ether (200 ml) and filtered to remove some suspended solids. Evaporation of the ether gave a brownish liquid (25 g, Theory=25.7 g). The residue was dissolved in diethyl ether (200 ml), cooled in an ice water bath, and a solution of di-t-butyldicarbonate (31.8 g, 0.146 mol) in ether (25 ml) was added dropwise with stirring. Cooling was removed and reaction was stirred overnight. The solution was gain cooled in ice water and a solution of saturated aqueous citric acid (100 ml) was added dropwise. The organics were washed with brine, a saturated aqueous sodium bicarbonate solution, the brine, and then dried over sodium sulfate. The solvents were removed in vacuo to give the desired title product as a clear liquid (38.6 g, >99%). NMR was consistent with desired title structure.

Preparation 40
Preparation of (RS) ethyl 3-[pyrid-3-yl]prop-2-enoate

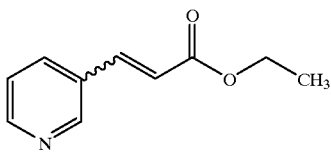

A solution of ethylphosphinoacetate (98.6 g, 0.44 mol) in dry tetrahydrofuran (1200 ml) was treated with 60% sodium hydride (17.5 g, 0.44 mol). The mixture was stirred at room temperature for two hours and was then cooled down to 0° C. To this mixture 3-pyridine carboxaldehyde (38.9 g, 0.36 mol) was added and the resulting reaction mixture was stirred for 1–2 hours while warming to room temperature. The progress of the reaction was monitored by thin layer chromatography.

Water (1000 ml) was added to the reaction mixture. The organic fraction was extracted with ethyl acetate (3×1000 ml). The organic fractions were combined, washed with water (2×1000 ml), brine (1×1000 ml), and the dried over sodium sulfate. The solvents were removed in vacuo to yield 62.5 grams (97%) of the desired title product.

Preparation 41
Preparation of (RS) ethyl 3-[piperidin-3-yl]propionoate

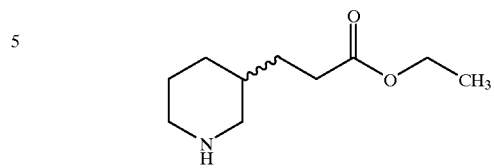

A solution of (RS) ethyl-1-[pyrid-3-yl]prop-1-enoate (60 g, 0.34 mol) in ethanol (600 ml) was treated with 5% rhodium on alumina powder (17.2 g). The mixture was placed under a hydrogen atmosphere (55 psi) for five hours at 60° C. The reaction was stopped by removing the hydrogen and the reaciton mixture was filtered through a layer of CELITE™. The residue was washed with hot ethanol. The filtrate was concentrated and purified by flash chromatography to provide 39.6 grams (63%) of the desired title product.

IR, NMR, and IR were consistent with the proposed title structure.

Preparation 42
Preparation of (3'S) ethyl 3-[piperidin-3-yl]propionoate mandelic acid salt

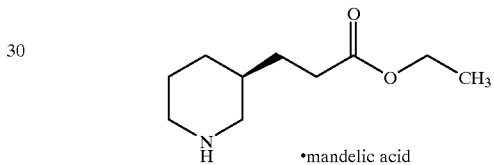

A solution of (RS) ethyl 3-[piperidin-3-yl]propionoate (52.0 g, 281 mmol) in hot ethyl acetate (300 ml) was added to the hot solution of R-(−) mandelic acid (42.7 g, 281 mmol). The resulting mixture was then filtered and the clear solution was left at room temperature overnight. The newly formed white crystals of the salt were filtered from the solution. These crystals were recrystallized twice by dissolution in hot ethyl acetate (300 ml) and letting it cool dwon to room temperature each time. The final pure crystals were dried to yield 33.1 grams (70%).

NMR and IR were consistent with the desired title product. The conformation about the chiral center was confirmed by X-ray crystallography.

Preparation 43
Preparation of (3'R) ethyl 3-[piperidin-3-yl]propionoate mandelic acid salt

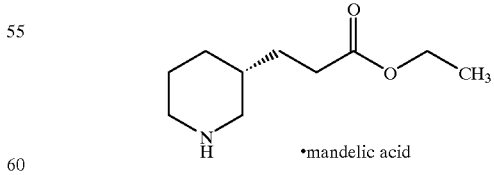

The title compound was prepared essentially as described in Preparation 42, supra, except that S-(+) mandelic acid was employed instead of the R-(−) mandelic acid employed therein.

NMR and IR were consistent with the desired title product.

Preparation 44
Preparation of (3'S) ethyl 3-[piperidin-3-yl]propionoate

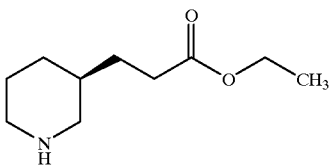

A suspension of (3'S) ethyl 3-[piperidin-3-yl]propionoate mandelic acid salt (33.1 g, 98 mmol) in ethyl acetate (500 ml) was treated with a 30% aqueous solution of potassium carbonate until all the organic layer was clear. The mixture was poured into a separatory funnel and the organic fraction was extracted with ethyl acetate (3×300 ml). The combined organic fraction was washed with water (2×300 ml), then brine (1×300 ml), and then dried over sodium sulfate. The solvents were removed in vacuo to yield an oily product in nearly 100% yield.

NMR and IR were consistent with the desired title product.

Preparation 45
Preparation of (3'R) ethyl 3-[piperidin-3-yl]propionoate

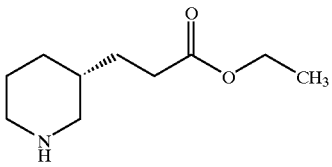

The title compound was prepared essentially as described in Preparation 44, supra, except that (3'R) ethyl 3-[piperidin-3-yl]propionoate mandelic acid salt was employed instead of the (3'S) ethyl 3-[piperidin-3-yl]propionoate mandelic acid salt therein.

NMR and IR were consistent with the desired title product.

Preparation 46
Preparation of (3'S) ethyl 3-[1-(t-butoxycarbonyl)piperidin-3-yl]propionoate

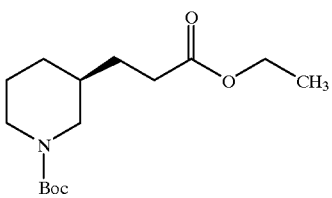

A solution of (3'S) ethyl 3-[piperidin-3-yl]propionoate (12.5 g, 67.5 mmol) in tetrahydrofuran:water (2:1, 335:168 ml) was treated with potassium carbonate (14 g, 101 mmol) and di-tert-butyl dicarbonate (17.7 g, 81 mmol). The reaction mixture was stirred at room temperature for five hours. The mixture was then poured into water (200 ml). The organic fraction was extracted with ethyl acetate (3×200 ml). The organic fractions were combined, washed with water (2×200 ml) and then brine (1×200 ml), and then dried over sodium sulfate. The solvents were removed in vacuo and the title product was further purified by flash chromatography. Yield: 19.1 grams (99.2%).

NMR and IR were consistent with the desired title product.

Preparation 47
Preparation of (3'R) ethyl 3-[1-(t-butoxycarbonyl)piperidin-3-yl]propionoate

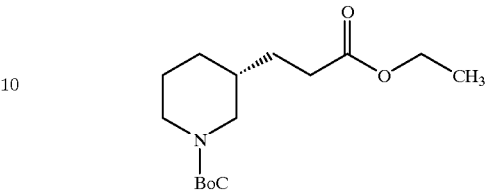

The title product was prepared essentially as described in Preparation 46, supra, except that an equimolar amount of (3'R) ethyl 3-[piperidin-3-yl]propionoate was employed instead of the (3'S) ethyl 3-[piperidin-3-yl]propionoate employed therein.

Preparation 48
Preparation of (3'S) 3-[1-(t-butoxycarbonyl)piperidin-3-yl]propanol

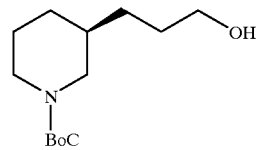

A solution of (3'S) ethyl 3-[1-(t-butoxycarbonyl) piperidin-3-yl]propionoate (17.1 g, 60 mmol) in dry diethyl acetate (600 ml) was cooled to 0° C. Lithium aluminum hydride powder (2.5 g, 65 mmol) was gradually added to the mixture. The resulting mixture was stirred at 0° C. and slowly warmed to room temperature within two hours. The reaciton was stopped by the slow addition of water (200 ml) and 15% aqueous sodium hydroxide (50 ml). The organic fraction was extracted with diethyl ether (3×300 ml). The combined layer was washed with water (2×200 ml) and then brine (1×200 ml) and then dried over sodium sulfate. The solvents were removed in vacuo to provide 13.2 grams (90% yield) of the title product.

NMR and IR were consistent with the desired title product.

Preparation 49
Preparation of (3'S) 3-[1-(t-butoxycarbonyl)piperidin-3-yl]propanol

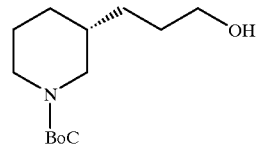

The title product was prepared essentially as described in Preparation 48, supra, except that an equimolar amount of (3'S) ethyl 3-[1-(t-butoxycarbonyl)piperidin-3-yl]propionoate was employed instead of the (3'R) ethyl 3-[1-(t-butoxycarbonyl)piperidin-3-yl]propionoate employed therein.

Preparation 50
Preparation of (3'S) 3-[1-(t-butoxycarbonyl)piperidin-3-yl]propane bromide

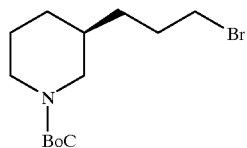

To a cold (0° C.) solution of triphenylphosphine (19.95 g, 76 mmol) in anhydrous methylene chloride (110 ml) was added bromine dropwise until the solution turned pale yellow. A few crystals of triphenylphosphine were added to the mixture to bring the color back to white. To this mixture was added a suspension of (3'S) 3-[1-(t-butoxycarbonyl) piperidin-3-yl)propanol (13.2 g, 54.4 mmol) and pyridine (8.0 g, 76 mmol) in dry methylene chloride (110 ml). The resulting mixture was stirred for five hours while warming to room temperature.

The reaction was stopped by adding water (200 ml). The organic fraction was extracted with methylene chloride (3×200 ml). The combined organic layer was washed with water (2×200 ml), then brine (1×100 ml), and then dried over sodium sulfate. The solvents were removed in vacuo to provide a light brownish crude product, which was further purified by flash chromatography to yield 11.6 grams (70%) of the desired title product.

NMR and IR were consistent with the title product.

Preparation 51

Preparation of (3'R) 3-[1-(t-butoxycarbonyl)piperidin-3-yl] propane bromide

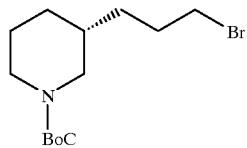

The title product was prepared essentially as described in Preparation 50, supra, except that an equimolar amount of (3'R) 3-[1-(t-butoxycarbonyl)piperidin-3-yl]propanol was employed instead of the (3'S) 3-[1-(t-butoxycarbonyl) piperidin-3-yl]propanol employed therein.

General Procedure for Preparing Compounds of the Formula

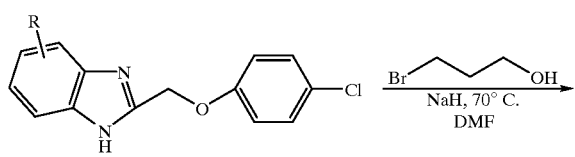

-continued

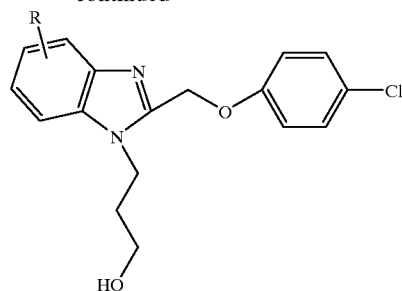

A solution of benzimidazole (1.0 g, 3.9 mmol, 1.0 eq) in anhydrous N,N-dimethylformamide (10 ml) was treated with 60% disperson of sodium hydride (0.163 g, 4.1 mmol, 1.05 eq). The reaction mixture was stirred at room temperature for about thirty minutes. Bromopropanol (0.6 g, 4.3 mmol, 1.1 eq) was added to the mixture and the resulting mixture was stirred at 70° C. for five hours. The progress of the reaction was monitored by thin layer chromatography.

The reaction mixture was poured into water (20 ml). The organic fraction was extracted wtih diethyl ether (3×50 ml). The organic fractions were combined, washed with water (2×20 ml), and then brine (1×20 ml), and then dried over sodium sulfate. The solvents were removed in vacuo to yield a white solid as a crude product. No further purification was performed on this product.

The following examples were prepared essentially as described above in the general procedure.

EXAMPLE 1

Preparation of 2-[4-chlorophenoxymethyl]-1-(3-hydroxypropyl)benzimidazole

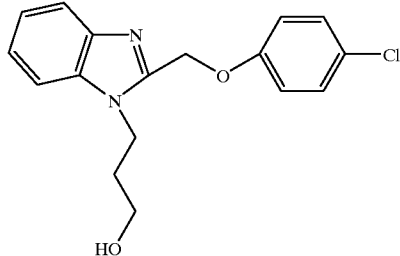

NMR was consistent with the desired title structure.

EXAMPLE 2

Preparation of 2-[4-chlorophenoxymethyl]-1-(3-hydroxypropyl)-5-chlorobenzimidazole

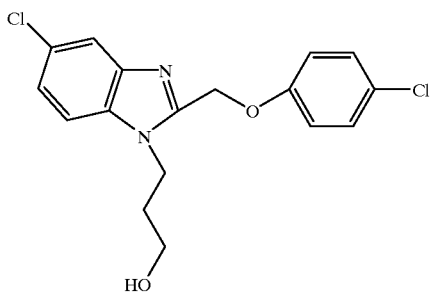

NMR was consistent with the desired title structure.

EXAMPLE 3

Preparation of 2-[4-chlorophenoxymethyl]-1-(3-hydroxypropyl)-5,6-dichlorobenzimidazole

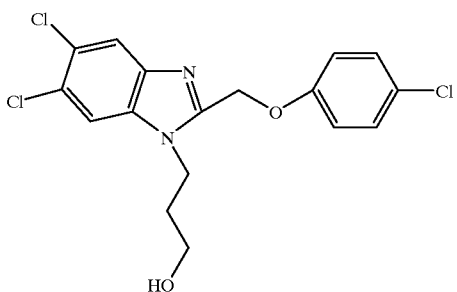

NMR was consistent with the desired title structure.

EXAMPLE 4

Preparation of 2-[4-chlorophenoxymethyl]-1-(3-hydroxypropyl)-5,6-dimethylbenzimidazole

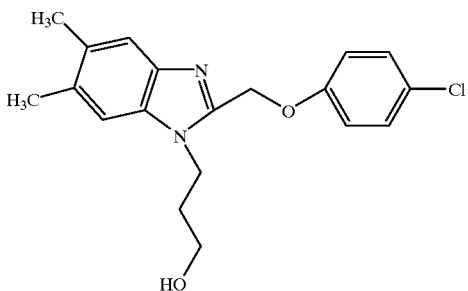

NMR was consistent with the desired title structure.

EXAMPLE 5

Preparation of 2-[4-chlorophenoxymethyl]-1-(3-hydroxypropyl)-4-methylbenzimidazole

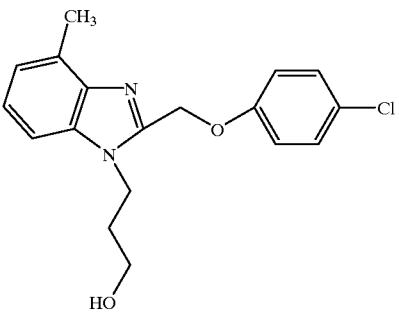

NMR was consistent with the desired title structure.

General Procedure for Preparation of Compounds of the Formula

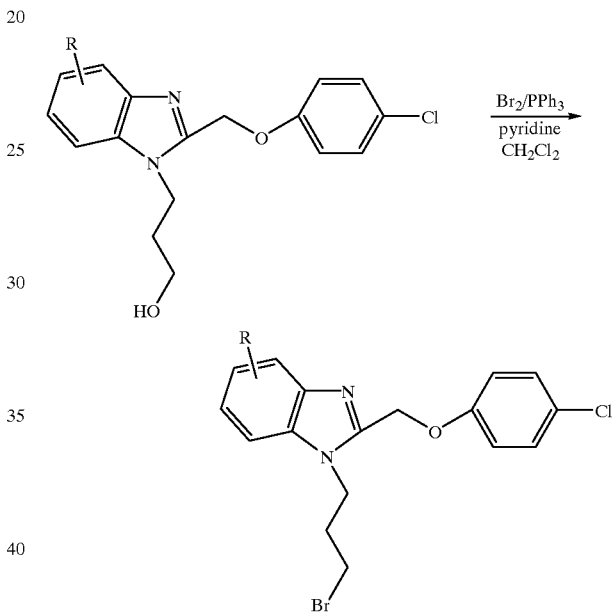

To a solution of triphenylphosphine (1.52 g, 5.8 mmol, 1.5 eq) in dry dichloromethane (10 ml) at 0° C. was added bromine solution until it was pale yellow. To the resulting mixture as added additional triphenylphosphine until the solution was white. To this mixture was then added the hydroxyalkyl-substituted benzimidazole (1.2 g, 3.9 mmol, 1.5 eq) and pyridine (0.5 ml, 5.8 mmol, 1.5 eq) in dry dichloromethane. The resulting mixture was stirred at 0° C. and then warmed to room temperature at which temperature it was maintained for about six hours. The progress of the reaction was monitored by thin layer chromatography.

White precipitate was removed by filtration, washed with dichloromethane, and dried in vacuo to provide the crude product.

The following compounds were prepared essentially as described above.

EXAMPLE 6

Preparation of 2-[4-chlorophenoxymethyl]-1-(3-bromopropyl)-benzimidazole

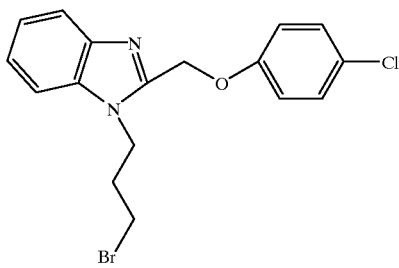

NMR and IR were consistent with the desired title structure. FDMS 380 (M+).

EXAMPLE 7

Preparation of 2-[4-chlorophenoxymethyl]-1-(3-bromopropyl)-5-chlorobenzimidazole

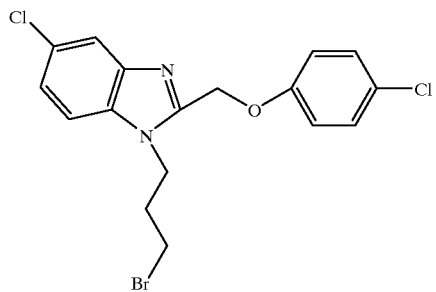

NMR was consistent with the desired title structure.

EXAMPLE 8

Preparation of 2-[4-chlorophenoxymethyl]-1-(3-bromopropyl)-5,6-dichlorobenzimidazole

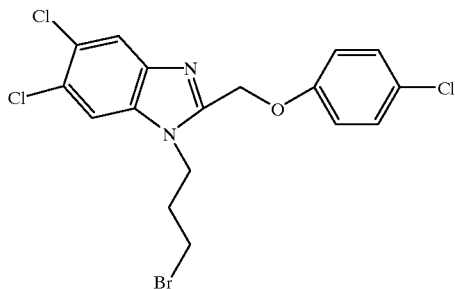

NMR was consistent with the desired title structure.

EXAMPLE 9

Preparation of 2-[4-chlorophenoxymethyl]-1-(3-bromopropyl)-5,6-dimethylbenzimidazole

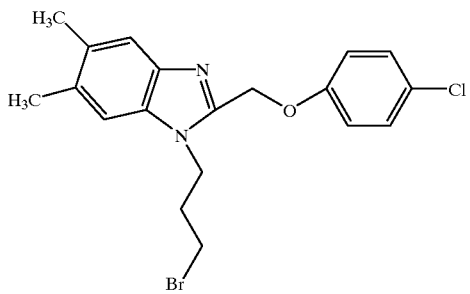

NMR was consistent with the desired title structure.

EXAMPLE 10

Preparation of 2-[4-chlorophenoxymethyl]-1-(3-bromopropyl)-4-methylbenzimidazole

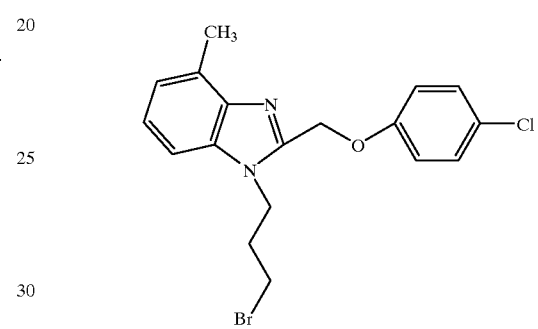

NMR was consistent with the desired title structure. FDMS 393 (M+).

General Procedure for Preparation of Compounds of the Formula

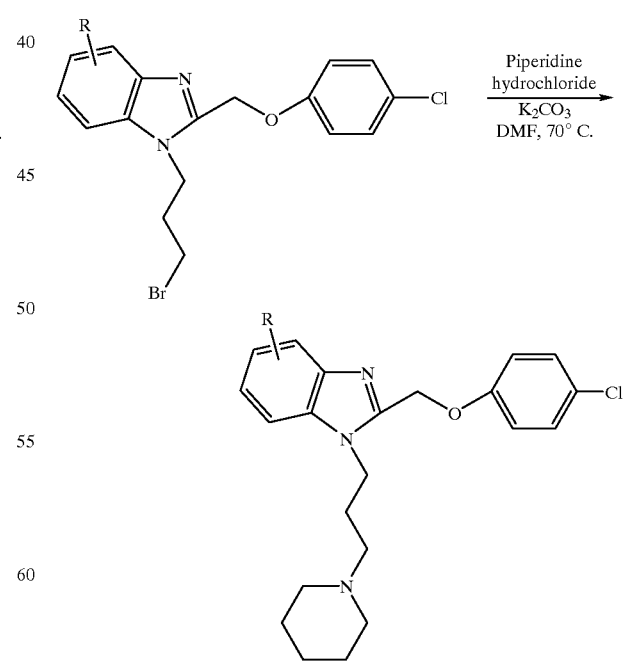

A solution of the benzimidazole (100 mg, 0.26 mmol, 1.0 eq) in anhydrous N,N-dimethylformamide (2 ml) was treated with potassium carbonate (90 mg, 0.65 mmol, 2.5 eq) and piperidine hydrochloride (35 mg, 0.29 mmol, 1.1 eq). The mixture was stirred at 70° C. for about five hours. The resulting mixture was poured into water (5 ml). The organic fraction was extracted with diethyl ether (3×10 ml). The combined ether layers were washed with water (3×5 ml), then brine, and then dried over sodium sulfate. The solvents were removed in vacuo to yield an oily crude product. The desired title product was then further purified by flash chromatography.

The following compounds were prepared essentially as described above.

EXAMPLE 11

Preparation of 2-(4-chlorophenoxymethyl)-1-[3-(piperidin-1-yl)propyl]benzimidazole

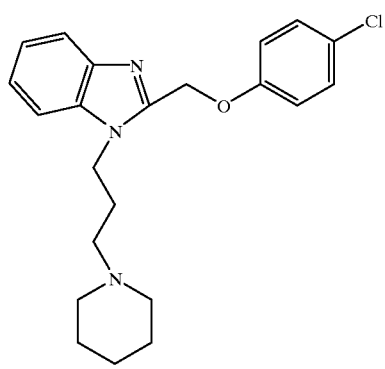

IR and NMR were consistent with the desired title product. FDMS 384 (M+). Analysis for $C_{22}H_{26}ClN_3O$: Theory: C, 68.83; H, 6.83; N, 10.94. Found: C, 68.21; H, 6.90; N, 10.98.

EXAMPLE 12

Preparation of 2-(4-chlorophenoxymethyl)-1-[3-(piperidin-1-yl)propyl]benzimidazole

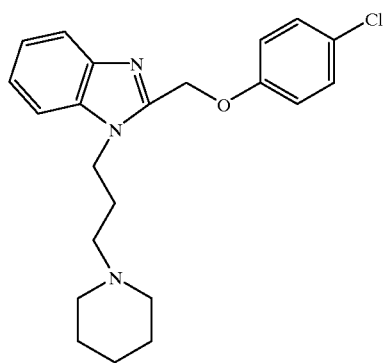

IR and NMR were consistent with the desired title product. FDMS 384 (M+). Analysis for $C_{22}H_{26}ClN_3O$: Theory: C, 68.83; H, 6.83; N, 10.94. Found: C, 68.21; H, 6.90; N, 10.98.

EXAMPLE 13

Preparation of 5-chloro-2-(4-chlorophenoxymethyl)-1-[3-(piperidin-1-yl)propyl]benzimidazole

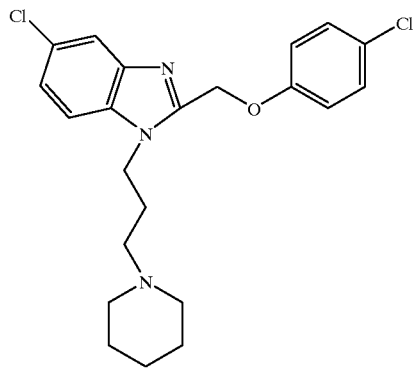

IR and NMR were consistent with the desired title product. FDMS 418 (M+).

EXAMPLE 14

Preparation of 5,6-dichloro-2-(4-chlorophenoxymethyl)-1-[3-(piperidin-1-yl)propyl]benzimidazole

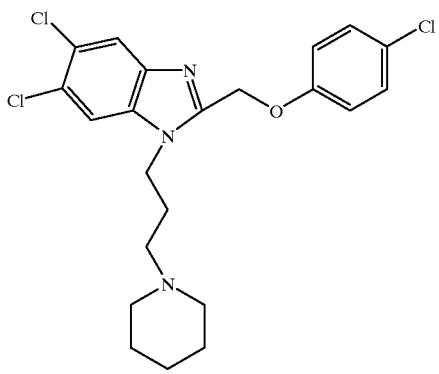

IR and NMR were consistent with the desired title product. FDMS 452 (M+).

EXAMPLE 15

Preparation of 2-(4-chlorophenoxymethyl)-5,6-dimethyl-1-[3-(piperidin-1-yl)propyl]benzimidazole

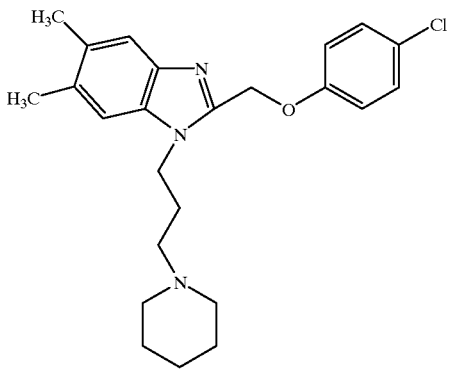

EXAMPLE 16

Preparation of 2-(4-chlorophenoxymethyl)-4-methyl-1-[3-(piperidin-1-yl)propyl]benzimidazole

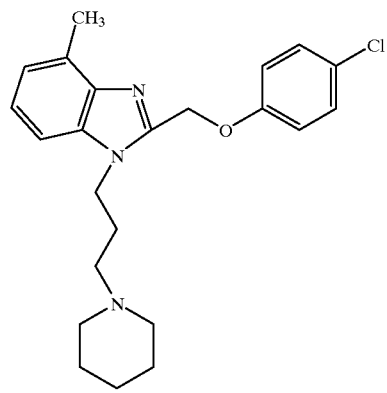

IR and NMR were consistent with the desired title product. FDMS 397 (M+).

EXAMPLE 17
Preparation of 2-(4-chlorophenoxymethyl)-5,6-dichloro-1-[3-(morpholin-1-yl)propyl]benzimidazole

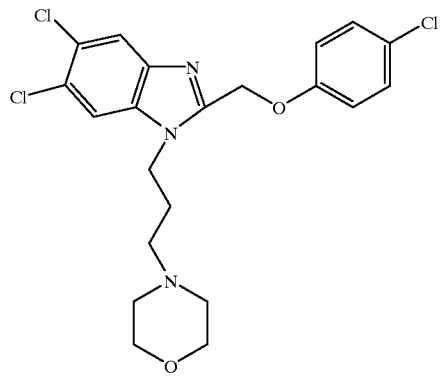

IR and NMR were consistent with the desired title product. FDMS 453, 454 (M+).

EXAMPLE 18
Preparation of 2-(4-chlorophenoxymethyl)-5-chloro-1-[3-(morpholin-1-yl)propyl]benzimidazole

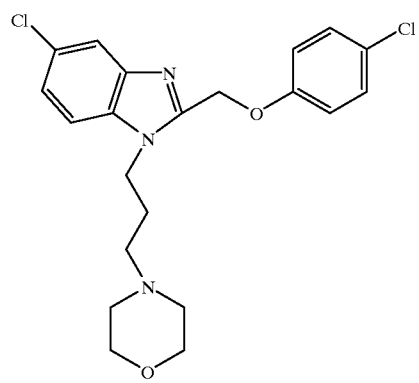

IR and NMR were consistent with the desired title product. FDMS 419, 420 (M+).

EXAMPLE 19
Preparation of 2-(4-chlorophenoxymethyl)-1-[3-(morpholin-1-yl)propyl]benzimidazole

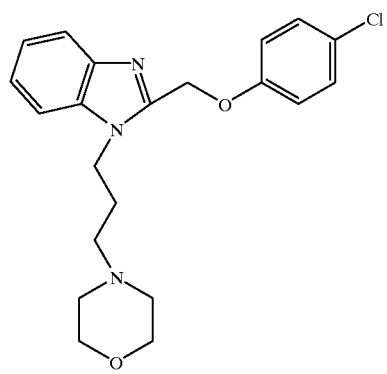

IR and NMR were consistent with the desired title product. FDMS 385, 386 (M+).

EXAMPLE 20
Preparation of 2-(4-chlorophenoxymethyl)-1-[3-(piperazin-1-yl)propyl]benzimidazole

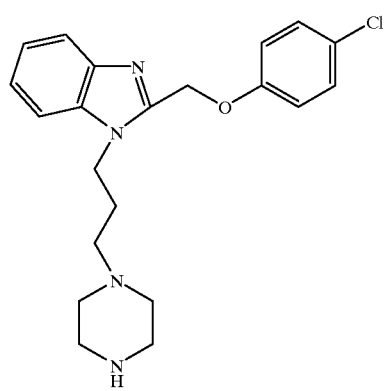

EXAMPLE 21
Preparation of 2-(4-chlorophenoxymethyl)-4-methyl-1-[3-(piperazin-1-yl)propyl]benzimidazole

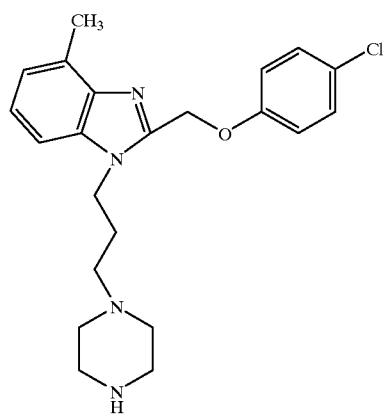

IR and NMR were consistent with the desired title product. FDMS 512 (M+).

EXAMPLE 22
Preparation of 2-(4-chlorophenoxymethyl)-4-methyl-1-[3-[4-(pyrimidin-2-yl)piperazin-1-yl]propyl]benzimidazole

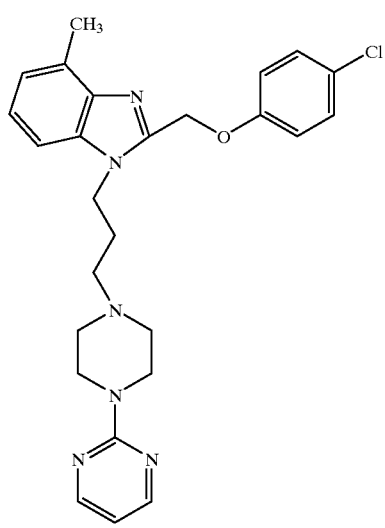

IR and NMR were consistent with the desired title product. FDMS 476.2 (M+).

EXAMPLE 22A
Preparation of 2-(4-chlorophenoxymethyl)-4-methyl-1-[3-[4-(pyrid-2-yl)piperazin-1-yl]propyl]benzimidazole

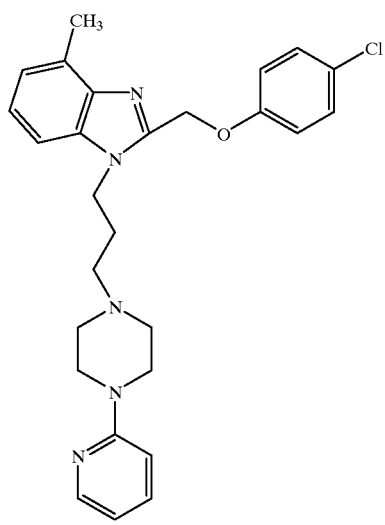

IR and NMR were consistent with the desired title product. FDMS 475.2 (M+).

EXAMPLE 23
Preparation of 2-(4-chlorophenoxymethyl)-1-[3-[4-(N,N-dimethylamino)piperidin-1-yl]propyl]benzimidazole

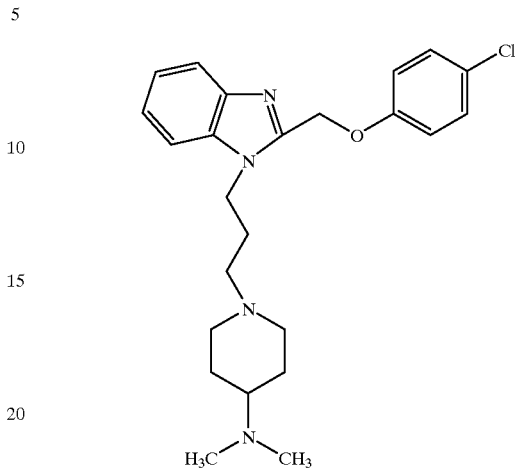

EXAMPLE 24
Preparation of 2-(4-chlorophenoxymethyl)-5,6-dichloro-1-[3-[4-(N,N-dimethylamino)piperidin-1-yl]propyl]benzimidazole

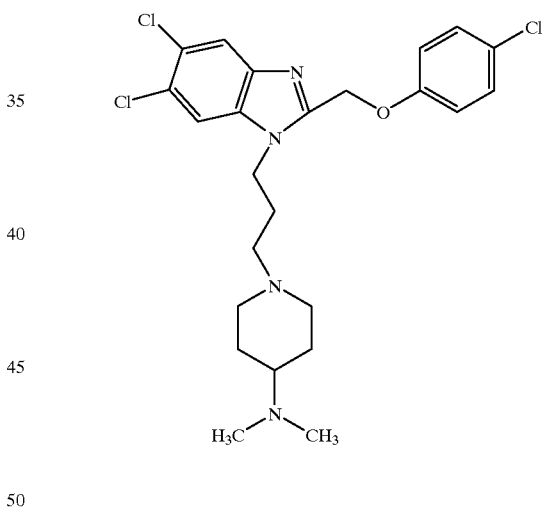

IR and NMR were consistent with the desired title product. FDMS 495.2 (M+).

EXAMPLE 25
Preparation of 2-(4-chlorophenoxymethyl)-5-chloro-1-[3-[4-(N,N-dimethylamino)piperidin-1-yl]propyl]benzimidazole

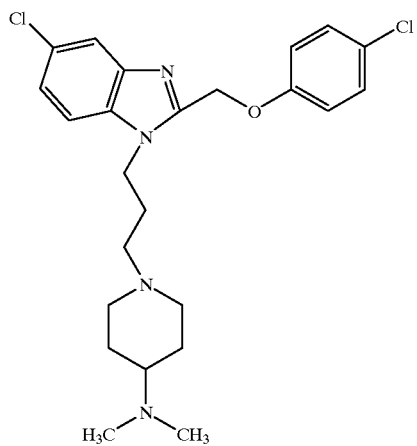

IR and NMR were consistent with the desired title product. FDMS 495.2 (M+).

EXAMPLE 26
Preparation of 2-(4-chlorophenoxymethyl)-5,6-dimethyl-1-[3-[4-(N,N-dimethylamino)piperidin-1-yl]propyl]benzimidazole

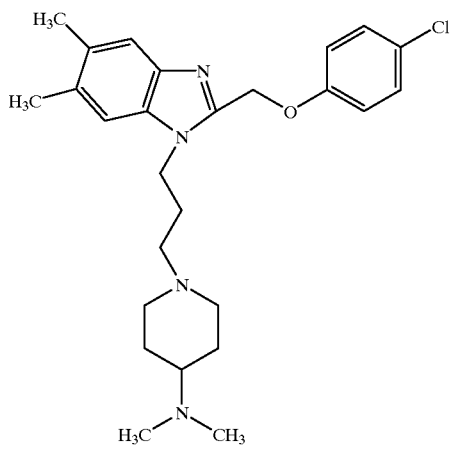

IR and NMR were consistent with the desired title product. FDMS 455.4 (M+).

EXAMPLE 27
Preparation of 2-(4-chlorophenoxymethyl)-4-methyl-1-[3-[4-(N,N-dimethylamino)piperidin-1-yl]propyl]benzimidazole

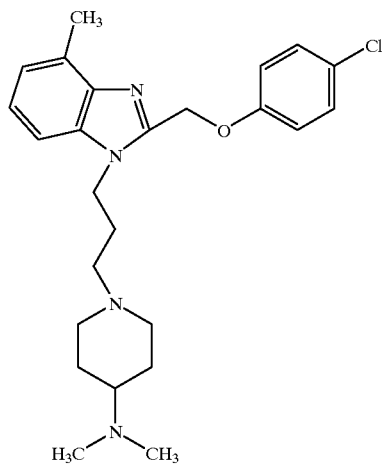

IR and NMR were consistent with the desired title product. FDMS 441 (M+).

EXAMPLE 27A
Preparation of 2-(4-chlorophenoxymethyl)-4-methyl-1-[3-[4-(piperidin-1-yl)piperidin-1-yl]propyl]benzimidazole

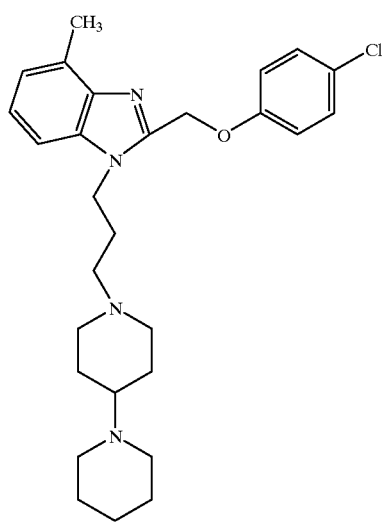

IR and NMR were consistent with the desired title product. FDMS 481 (M+).

General Procedure for Preparing Compounds of the Following Formulae

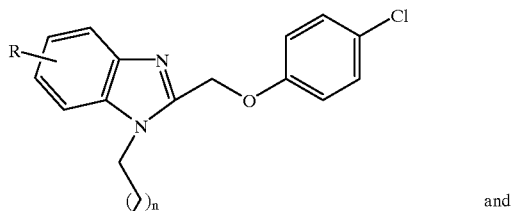

and

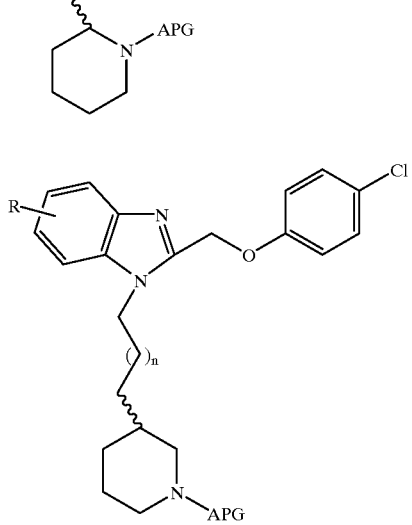

where n is 0, 1, or 2, and APG is an amino protecting group.

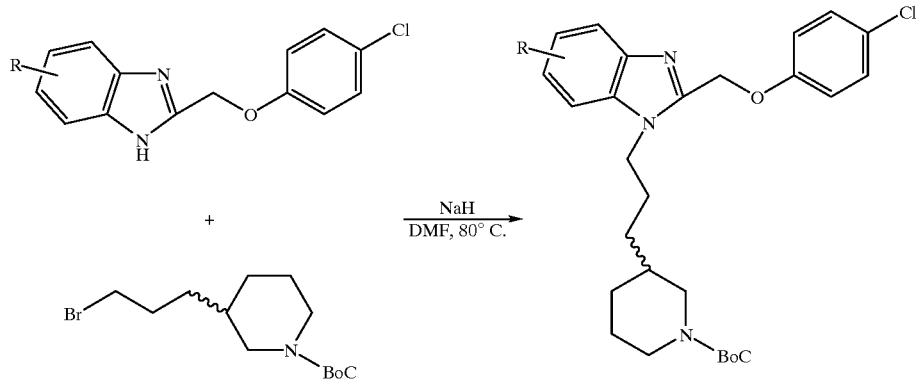

A solution of the 1-unsubstituted benzimidazole (0.77 mmol, 1.0 eq) in anhydrous N,N-dimethylformamide (3 ml) was treated with a 60% disperson of sodium hydride (33 mg, 0.80 mmol, 1.05 eq). The mixture was stirred at room temperature for thirty minutes under a stream of nitrogen. To this mixture was added [1-(t-butoxycarbonyl)piperidin-3-yl] propyl bromide (260 mg, 0.85 mmol, 1.1 eq) and the resulting mixture was stirred at 80° C. for about three hours. The progress of the reaction was monitored by thin layer chromatography.

The reaction mixture was then poured into water (10 ml). The organic fraction was extracted with diethyl ether (3×15 ml). The organic fractions were combined, washed with water (2×10 ml), brine (1×10 ml), and then dried over sodium sulfate. The solvents were removed in vacuo, leaving a light brown crude material which was further purified by flash chromatography to yield the desired title product as a white crystalline solid in 70–100% yield.

EXAMPLE 28

Preparation of 2-(4-chlorophenoxymethyl)-1-[3-[1-(t-butoxycarbonyl)piperidin-2-yl]propyl]benzimidazole

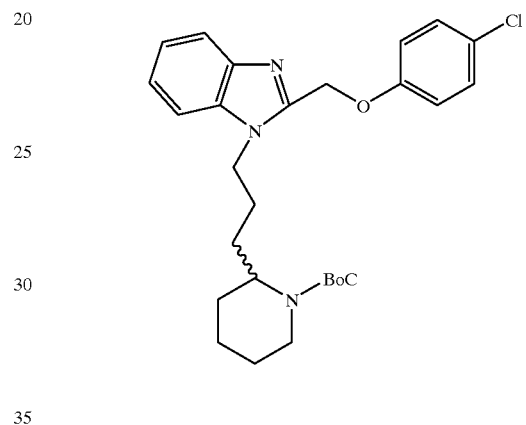

IR and NMR were consistent with the desired title product. FDMS 483, 484 (M+). Analysis for $C_{27}H_{34}ClN_3O_3$: Theory: C, 67.00; H, 7.08; N, 8.60. Found: C, 66.93; H, 7.09; N, 8.43.

EXAMPLE 29

Preparation of 2-(4-chlorophenoxymethyl)-5-methoxy-1-[3-[1-(t-butoxycarbonyl)piperidin-2-yl]propyl]benzimidazole and 2-(4-chlorophenoxymethyl)-6-methoxy-1-[3-[1-(t-butoxycarbonyl)piperidin-2-yl]propyl]benzimidazole

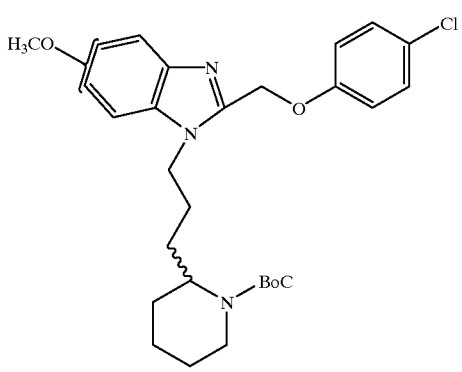

IR and NMR were consistent with the desired title products. FDMS 513, 514 (M+). Analysis for $C_{28}H_{30}ClN_3O_4$: Theory: C, 65.42; H, 7.06; N, 8.17. Found: C, 65.12; H, 6.96; N, 8.29.

EXAMPLE 30

Preparation of 2-(4-chlorophenoxymethyl)-4,5-dimethyl-1-[3-[1-(t-butoxycarbonyl)piperidin-2-yl]propyl]benzimidazole and 2-(4-chlorophenoxymethyl)-6,7-dimethyl-1-[3-[1-(t-butoxycarbonyl)piperidin-2-yl]propyl]benzimidazole

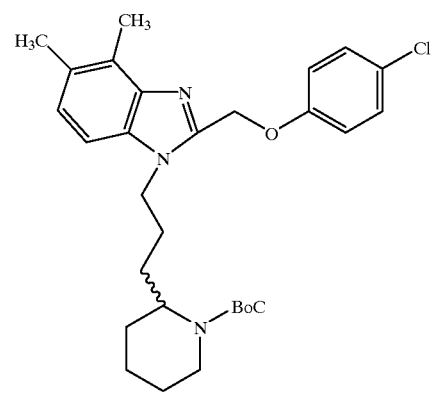

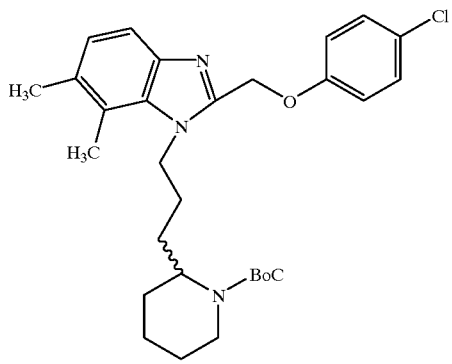

IR and NMR were consistent with the desired title products. FDMS 511, 512 (M+). Analysis for $C_{29}H_{38}ClN_3O_3$: Theory: C, 68.02; H, 7.48; N, 8.20. Found: C, 68.32; H, 7.54; N, 8.36.

EXAMPLE 31

Preparation of 2-(4-chlorophenoxymethyl)-5-methyl-1-[3-[1-(t-butoxycarbonyl)piperidin-2-yl]propyl]benzimidazole and 2-(4-chlorophenoxymethyl)-6-methyl-1-[3-[1-(t-butoxycarbonyl)piperidin-2-yl]propyl]benzimidazole

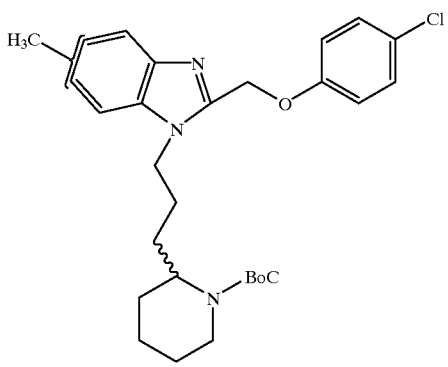

IR and NMR were consistent with the desired title products. FDMS 497, 498 (M+). 3:2 mixture of the 5-methyl isomer to the 6-methyl isomer. Analysis for $C_{28}H_{36}ClN_3O_3$: Theory: C, 67.52; H, 7.28; N, 8.44. Found: C, 68.37; H, 7.40; N, 8.60.

EXAMPLE 31A

Preparation of 2-(4-chlorophenoxymethyl)-4-methyl-1-[3-[1-(t-butoxycarbonyl)piperidin-2-yl]propyl]benzimidazole

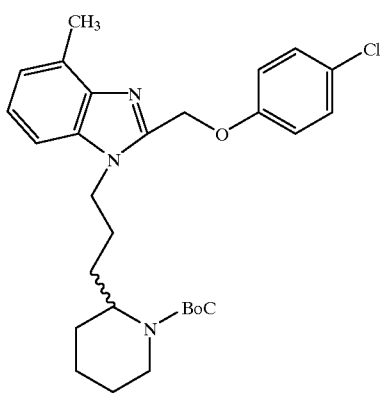

IR and NMR were consistent with the desired title product. FDMS 497, 498 (M+). Analysis for $C_{28}H_{36}ClN_3O_3$: Theory: C, 67.52; H, 7.29; N, 8.44. Found: C, 67.14; H, 7.65; N, 8.85.

EXAMPLE 32

Preparation of 2-(4-chlorophenoxymethyl)-5-benzoyl-1-[3-[1-(t-butoxycarbonyl)piperidin-2-yl]propyl]benzimidazole

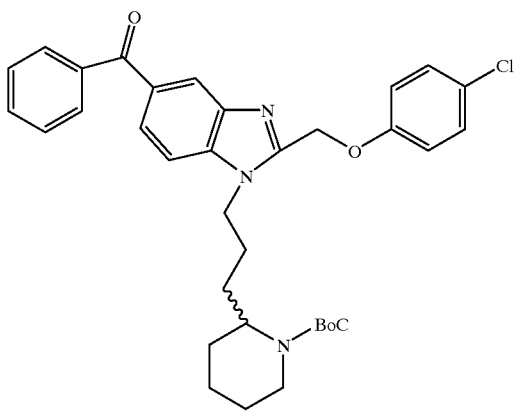

IR and NMR were consistent with the desired title product. FDMS 587, 588 (M+).

EXAMPLE 33
Preparation of 2-(4-chlorophenoxymethyl)-5,6-dichloro-1-[3-[1-(t-butoxycarbonyl)piperidin-2-yl]propyl]benzimidazole

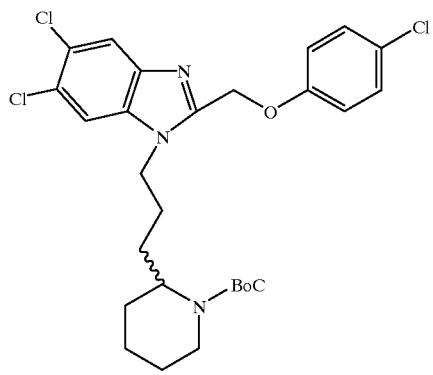

IR and NMR were consistent with the desired title product. FDMS 587, 588 (M+).

EXAMPLE 34
Preparation of 2-(2,4-dichlorophenoxymethyl)-1-[3-[1-(t-butoxycarbonyl)piperidin-2-yl]propyl]benzimidazole

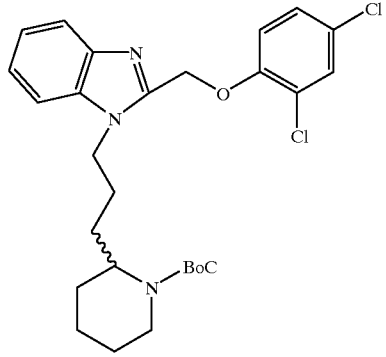

NMR was consistent with the desired title product.

EXAMPLE 35
Preparation of 2-(2,4-dichlorophenoxymethyl)-5,6-dichloro-1-[3-[1-(t-butoxycarbonyl)piperidin-2-yl]propyl]benzimidazole

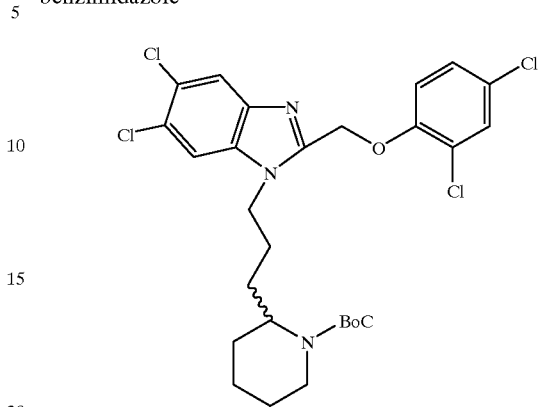

NMR and IR were consistent with the desired title product. FDMS 587 (M+). Analysis for $C_{27}H_{31}Cl_4N_3O_3$: Theory: C, 55.21; H, 5.32; N, 7.15. Found: C, 56.19; H, 5.69; N, 7.44.

EXAMPLE 36
Preparation of 2-(4-chlorophenoxymethyl)-5-methyl-1-[3-[1-(t-butoxycarbonyl)piperidin-3-yl]propyl]benzimidazole and 2-(4-chlorophenoxymethyl)-6-methyl-1-[3-[1-(t-butoxycarbonyl)piperidin-3-yl]propyl]benzimidazole

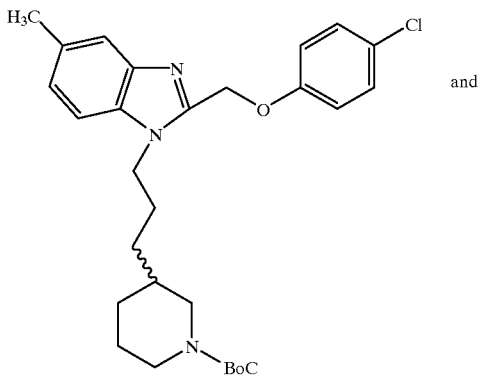

and

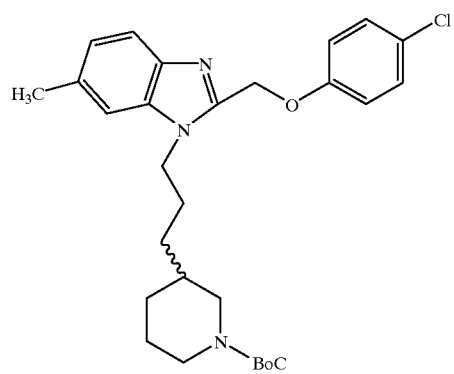

NMR and IR were consistent with the desired title products. FDMS 497, 498 (M+). Analysis for $C_{28}H_{36}ClN_3O_3$: Theory: C, 67.52; H, 7.28; N, 8.44. Found: C, 67.58; H, 7.42; N, 8.52.

EXAMPLE 37
Preparation of 2-(4-chlorophenoxymethyl)-5-methoxy-1-[3-[1-(t-butoxycarbonyl)piperidin-3-yl]propyl]benzimidazole and 2-(4-chlorophenoxymethyl)-6-methoxy-1-[3-[1-(t-butoxycarbonyl)piperidin-3-yl]propyl]benzimidazole

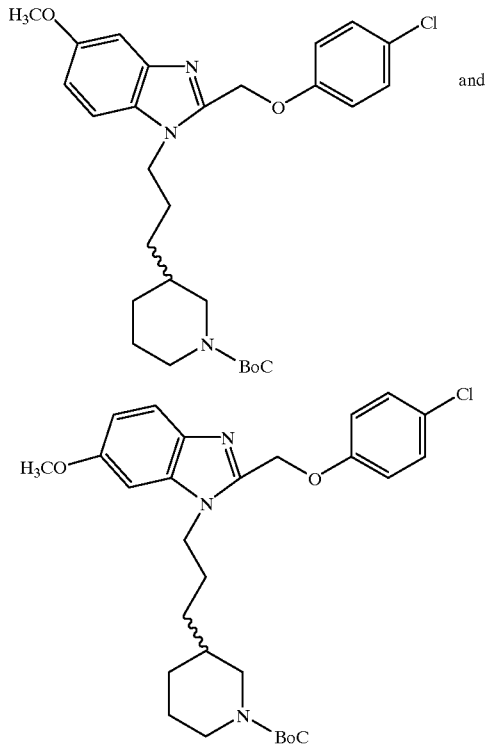

NMR and IR were consistent with the desired title products. FDMS 513, 514 (M+). Analysis for $C_{28}H_{36}ClN_3O_4$: Theory: C, 65.42; H, 7.06; N, 8.17. Found: C, 65.18; H, 7.22; N, 7.94.

EXAMPLE 38
Preparation of 2-(4-chlorophenoxymethyl)-4,5-dimethyl-1-[3-[1-(t-butoxycarbonyl)piperidin-3-yl]propyl]benzimidazole

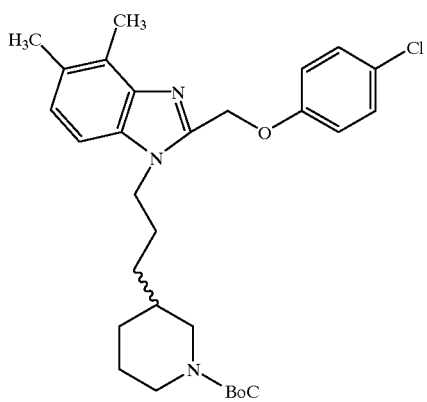

NMR and IR were consistent with the desired title product. FDMS 511, 512 (M+).

EXAMPLE 39
Preparation of 2-(4-chlorophenoxymethyl)-4-methyl-1-[3-[1-(t-butoxycarbonyl)piperidin-3-yl]propyl]benzimidazole

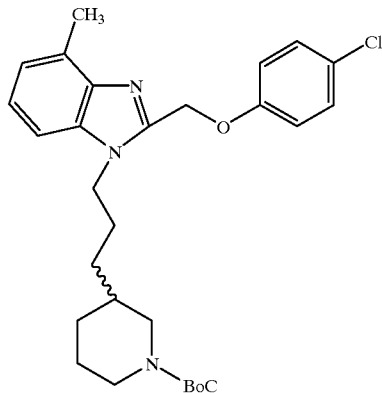

NMR and IR were consistent with the desired title product. FDMS 497, 498 (M+).

EXAMPLE 39a
Preparation of 2-(4-chlorophenoxymethyl)-4-methyl-1-[5-[1-(t-butoxycarbonyl)piperidin-3-yl]pentyl]benzimidazole

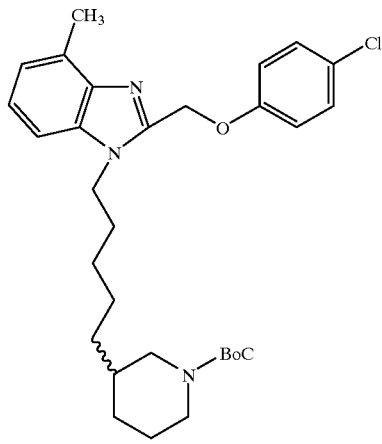

NMR was consistent with the desired title product.

EXAMPLE 40
Preparation of 2-(4-chlorophenoxymethyl)-5-benzoyl-1-[3-[1-(t-butoxycarbonyl)piperidin-3-yl]propyl]benzimidazole

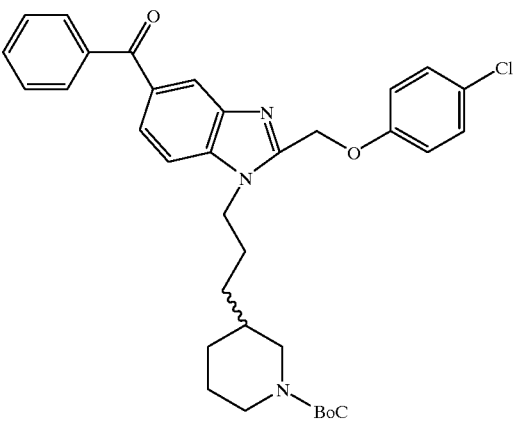

NMR and IR were consistent with the desired title product. FDMS 497, 498 (M+).

EXAMPLE 41

Preparation of 2-(4-chlorophenoxymethyl)-5,6-dichloro-1-[3-[1-(t-butoxycarbonyl)piperidin-3-yl]propyl]benzimidazole

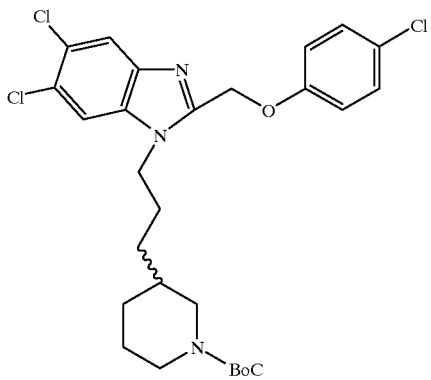

NMR and IR were consistent with the desired title product. FDMS 552.5, 554.5 (M+).

EXAMPLE 42

Preparation of 2-(4-chlorophenoxymethyl)-5-chloro-1-[3-[1-(t-butoxycarbonyl)piperidin-3-yl]propyl]benzimidazole

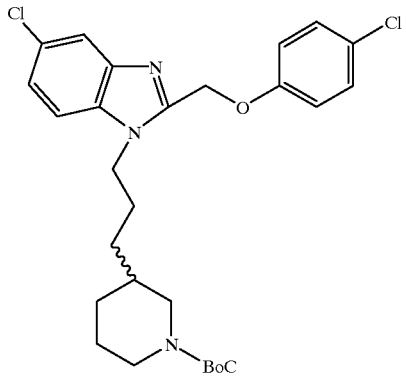

NMR and IR were consistent with the desired title product. FDMS 518 (M+).

EXAMPLE 43

Preparation of 2-(4-chlorophenoxymethyl)-5,6-dimethyl-1-[3-[1-(t-butoxycarbonyl)piperidin-3-yl]propyl]benzimidazole

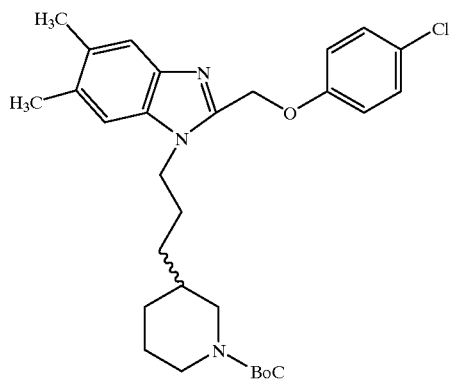

NMR and IR were consistent with the desired title product. FDMS 512.4 (M+).

EXAMPLE 44

Preparation of 2-(2,4-dichlorophenoxymethyl)-1-[3-[1-(t-butoxycarbonyl)piperidin-3-yl]propyl]benzimidazole

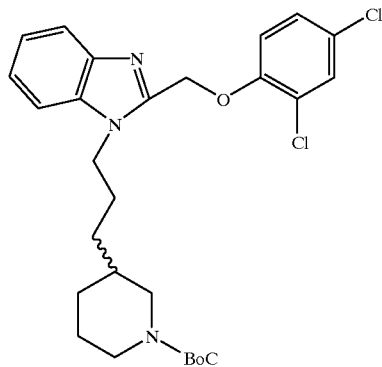

NMR and IR were consistent with the desired title product. FDMS 517, 518 (M+). Analysis for $C_{27}H_{33}Cl_2N_3O_3$: Theory: C, 62.58; H, 6.41; N, 8.10. Found: C, 62.54; H, 6.39; N, 8.20.

EXAMPLE 45

Preparation of 2-(2,4-dichlorophenoxymethyl)-5,6-dichloro-1-[3-[1-(t-butoxycarbonyl)piperidin-3-yl]propyl]benzimidazole

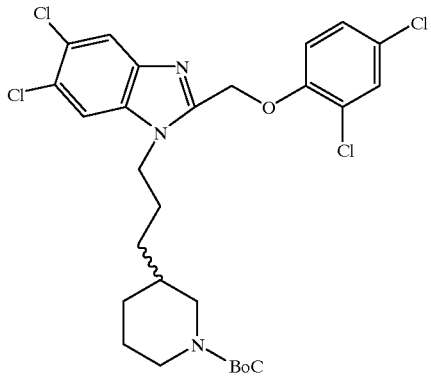

NMR and IR were consistent with the desired title product. FDMS 587 (M+).

EXAMPLE 46

Preparation of 2-(4-chlorophenoxymethyl)-4,5-dimethyl-1-[3-[1-(t-butoxycarbonyl)piperidin-4-yl]propyl]benzimidazole

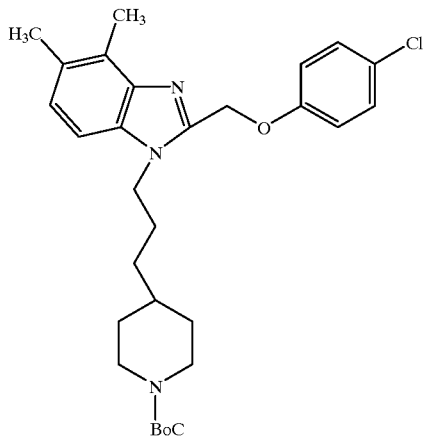

EXAMPLE 47

Preparation of 2-(4-chlorophenoxymethyl)-1-[3-[1-(t-butoxycarbonyl)piperidin-4-yl]propyl]benzimidazole

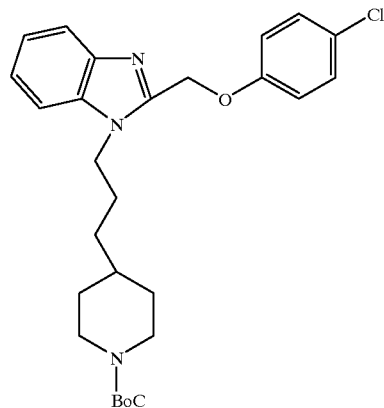

NMR and IR were consistent with the desired title product. FDMS 484 (M+).

EXAMPLE 48

Preparation of 2-(4-chlorophenoxymethyl)-4,5,6,7-tetramethyl-1-[3-[1-(t-butoxycarbonyl)piperidin-4-yl]propyl]benzimidazole

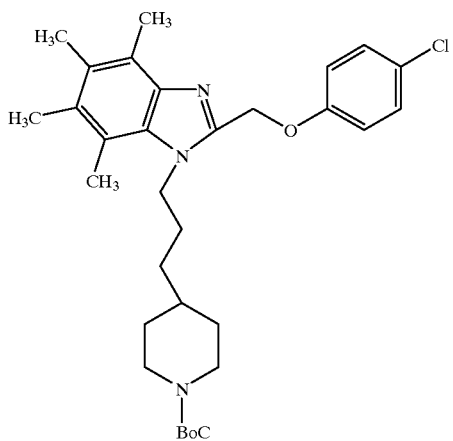

EXAMPLE 49

Preparation of 2-(4-chlorophenoxymethyl)-5-methoxycarbonyl-1-[3-[1-(t-butoxycarbonyl)piperidin-4-yl]propyl]benzimidazole and 2-(4-chlorophenoxymethyl)-6-methoxycarbonyl-1-[3-[1-(t-butoxycarbonyl)piperidin-4-yl]propyl]benzimidazole

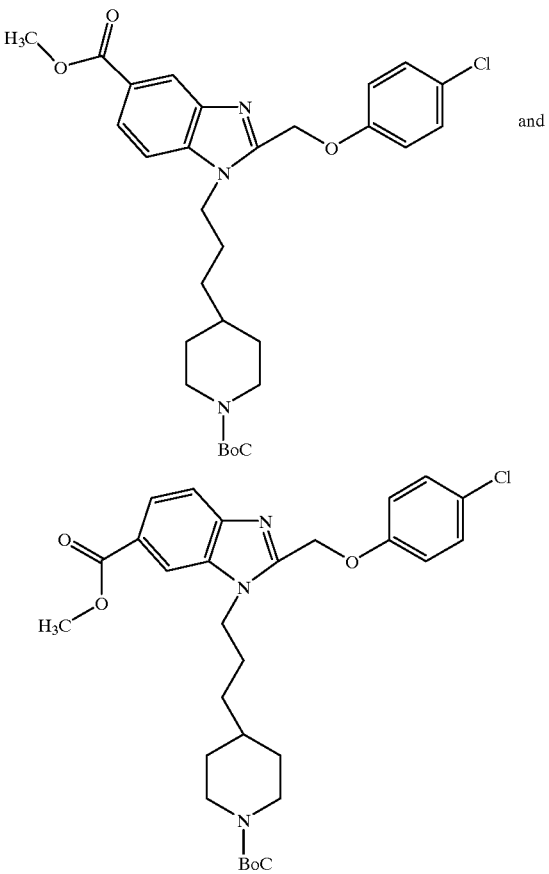

NMR and IR were consistent with the desired title products. FDMS 541 (M+). Analysis for $C_{29}H_{36}ClN_3O_5$: Theory: C, 64.26; H, 6.69; N, 7.75. Found: C, 64.07; H, 6.63; N, 7.95.

EXAMPLE 50

Preparation of 2-(4-chlorophenoxymethyl)-4-methyl-1-[3-[1-(t-butoxycarbonyl)piperidin-4-yl]propyl]benzimidazole

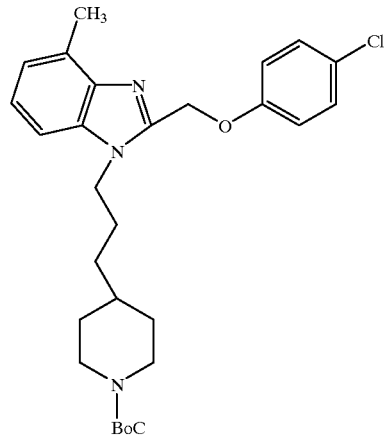

NMR and IR were consistent with the desired title product. FDMS 497, 498 (M+).

EXAMPLE 50a

Preparation of 2-(4-chlorophenoxymethyl)-4-methyl-1-[5-[1-(t-butoxycarbonyl)piperidin-4-yl]pentyl]benzimidazole

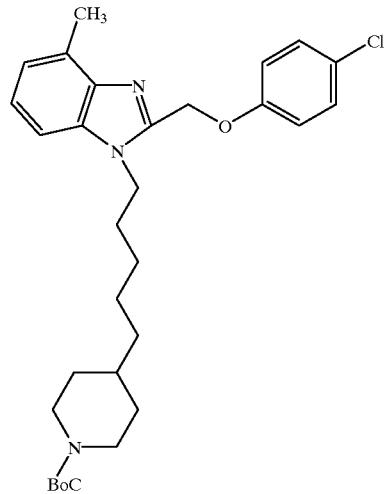

NMR was consistent with the desired title product.

EXAMPLE 51

Preparation of 2-(4-chlorophenoxymethyl)-4-(t-butyl)-1-[3-[1-(t-butoxycarbonyl)piperidin-4-yl]propyl]benzimidazole and 2-(4-chlorophenoxymethyl)-7-(t-butyl)-1-[3-[1-(t-butoxycarbonyl)piperidin-4-yl]propyl]benzimidazole

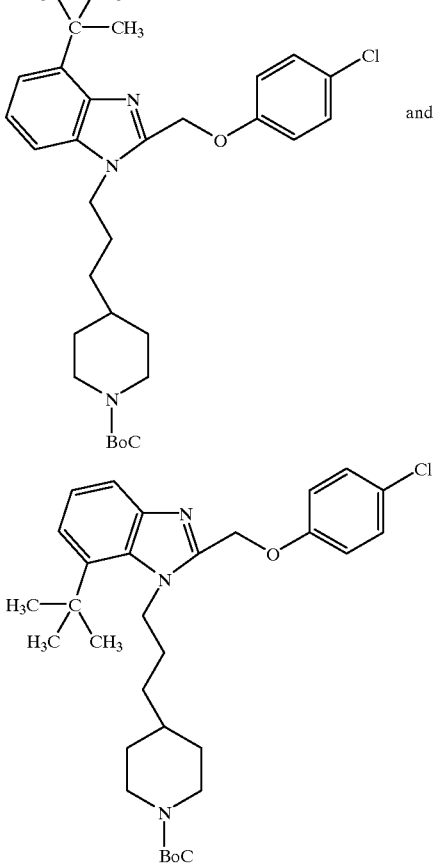

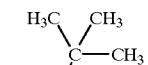 and

NMR and IR were consistent with the desired title products. FDMS 539, 540 (M+).

EXAMPLE 52

Preparation of 2-(4-chlorophenoxymethyl)-4-methyl-1-[4-[1-(t-butoxycarbonyl)piperidin-4-yl]butyl]benzimidazole

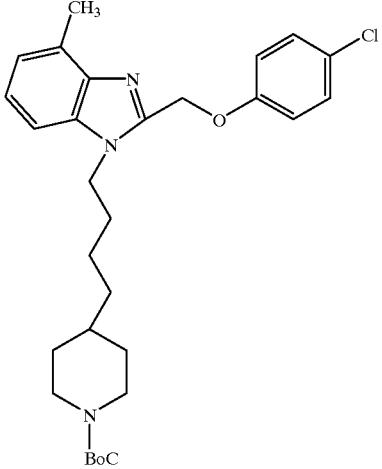

NMR and IR were consistent with the desired title product. FDMS 511 (M+).

EXAMPLE 53

Preparation of 2-(4-chlorophenoxymethyl)-5,6-dimethyl-1-[4-[1-(t-butoxycarbonyl)piperidin-4-yl]butyl]benzimidazole

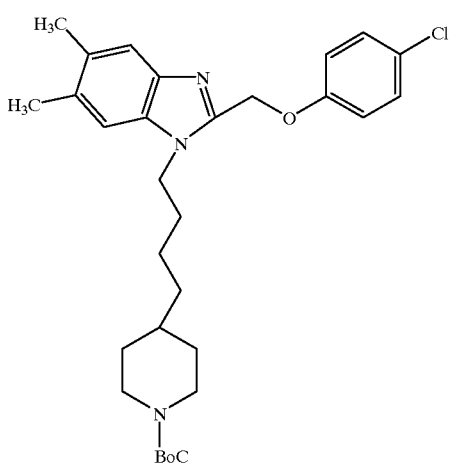

NMR and IR were consistent with the desired title product. FDMS 526 (M+).

EXAMPLE 54
Preparation of 2-(4-chlorophenoxymethyl)-4,5-dimethyl-1-[4-[1-(t-butoxycarbonyl)piperidin-4-yl]butyl]benzimidazole and 2-(4-chlorophenoxymethyl)-6,7-dimethyl-1-[4-[1-(t-butoxycarbonyl)piperidin-4-yl]butyl]benzimidazole

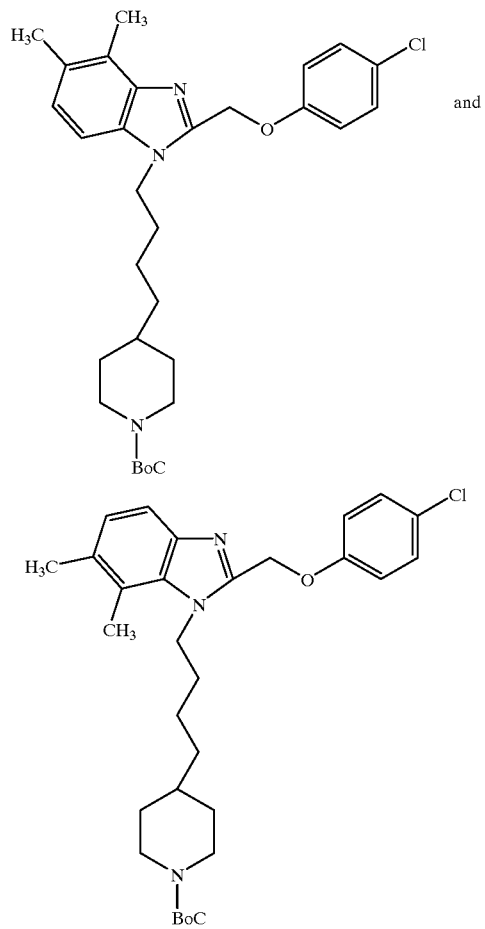

NMR and IR were consistent with the desired title products.

EXAMPLE 55
Preparation of 2-benzyl-1-[3-[1-(t-butoxycarbonyl)piperidin-3-yl]propyl]benzimidazole

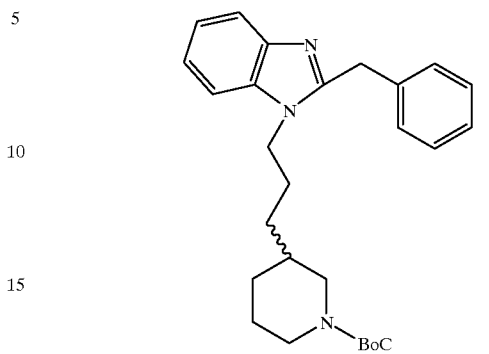

NMR and IR were consistent with the desired title product. FDMS 433 (M+).

EXAMPLE 56
Preparation of 2-(4-chlorophenyl)-1-[3-[1-(t-butoxycarbonyl)piperidin-3-yl]propyl]benzimidazole

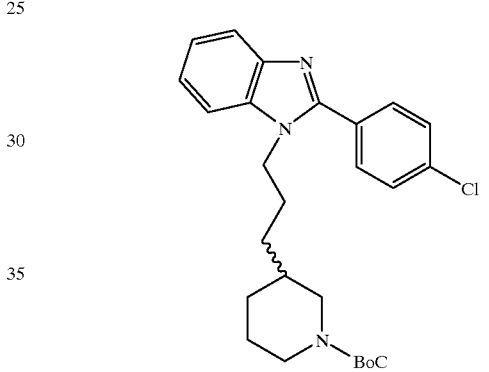

NMR and IR were consistent with the desired title product. FDMS 453 (M+). Analysis for $C_{26}H_{32}ClN_3O_2$: Theory: C, 68.78; H, 7.10; N, 9.25. Found: C, 68.56; H, 7.03; N, 9.54.

EXAMPLE 57
Preparation of 2-(2-chlorophenoxymethyl)-1-[3-[1-(t-butoxycarbonyl)piperidin-3-yl]propyl]benzimidazole

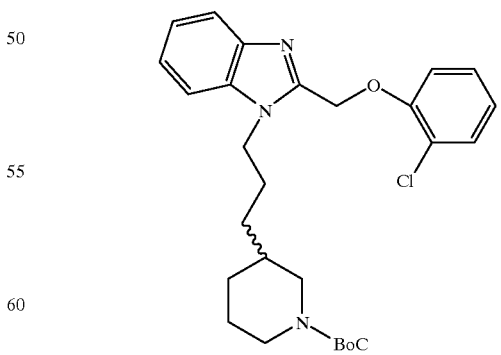

NMR and IR were consistent with the desired title product. FDMS 483 (M+). Analysis for $C_{27}H_{34}ClN_3O_3$: Theory: C, 67.00; H, 7.08; N, 8.08. Found: C, 67.25; H, 7.27; N, 8.81.

EXAMPLE 58
Preparation of 2-(3-chlorophenoxymethyl)-1-[3-[1-(t-butoxycarbonyl)piperidin-3-yl]propyl]benzimidazole

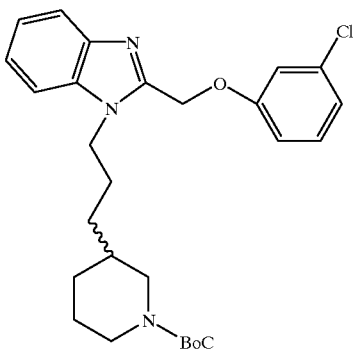

NMR and IR were consistent with the desired title product. FDMS 483 (M+).

EXAMPLE 59
Preparation of 2-(4-chlorobenzyl)-1-[3-[1-(t-butoxycarbonyl)piperidin-3-yl]propyl]benzimidazole

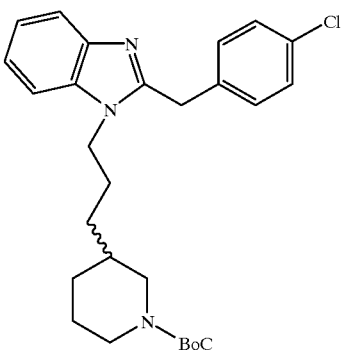

NMR and IR were consistent with the desired title product. FDMS 467 (M+). Analysis for $C_{27}H_{34}ClN_3O_2$: Theory: C, 69.30; H, 7.32; N, 9.98. Found: C, 69.54; H, 7.49; N, 9.08.

EXAMPLE 60
Preparation of 2-(phenoxymethyl)-1-[3-[1-(t-butoxycarbonyl)piperidin-3-yl]propyl]benzimidazole

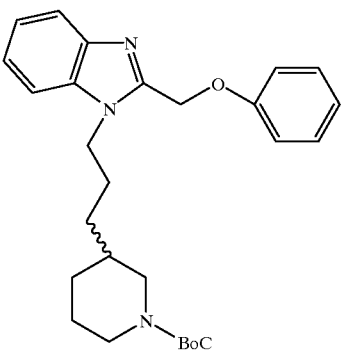

NMR and IR were consistent with the desired title product. FDMS 449 (M+). Analysis for $C_{27}H_{35}N_3O_3$: Theory: C, 72.13; H, 7.85; N, 9.35. Found: C, 71.85; H, 7.81; N, 9.25.

EXAMPLE 61
Preparation of 2-(3,5-dichlorophenoxymethyl)-1-[3-[1-(t-butoxycarbonyl)piperidin-3-yl]propyl]benzimidazole

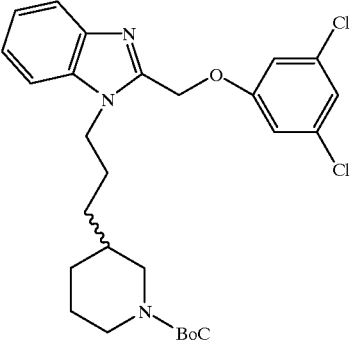

NMR and IR were consistent with the desired title product. FDMS 517 (M+). Analysis for $C_{27}H_{33}Cl_2N_3O_3$: Theory: C, 62.55; H, 6.41; N, 8.10. Found: C, 62.33; H, 6.35; N, 8.12.

EXAMPLE 62
Preparation of 2-[4-(4,5-dihydrothiazol-2-yl)phenoxymethyl]-1-[3-[1-(t-butoxycarbonyl)piperidin-3-yl]propyl]benzimidazole

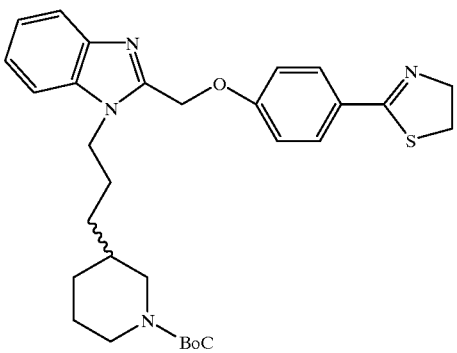

NMR and IR were consistent with the desired title product. FDMS 534 (M+). Analysis for $C_{30}H_{38}N_4O_3S$: Theory: C, 67.38; H, 7.16; N, 10.48. Found: C, 66.78; H, 7.09; N, 10.00.

EXAMPLE 63
Preparation of 2-(2,6-dichlorophenoxymethyl)-1-[3-[1-(t-butoxycarbonyl)piperidin-3-yl]propyl]benzimidazole

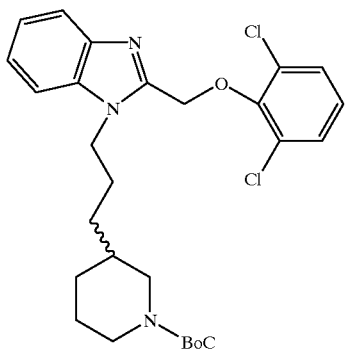

NMR and IR were consistent with the desired title product. FDMS 517 (M+). Analysis for $C_{27}H_{33}Cl_2N_3O_3$: Theory: C, 62.55; H, 6.41; N, 8.10. Found: C, 62.76; H, 6.44; N, 8.33.

EXAMPLE 64

Preparation of 2-(3-trifluoromethylphenoxymethyl)-1-[3-[1-(t-butoxycarbonyl)piperidin-3-yl]propyl]benzimidazole

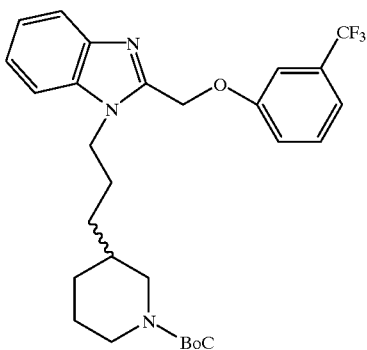

NMR and IR were consistent with the desired title product. FDMS 517 (M+). Analysis for $C_{28}H_{34}F_3N_3O_3$: Theory: C, 64.98; H, 6.42; N, 8.12. Found: C, 64.89; H, 6.48; N, 8.31.

EXAMPLE 65

Preparation of 2-(4-chlorophenoxymethyl)-4-methyl-1-(3-phenylpropyl)benzimidazole

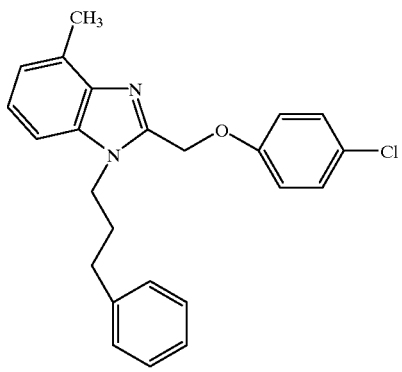

NMR and IR were consistent with the desired title product. FDMS 390 (M+). Analysis for $C_{24}H_{23}ClN_2O$: Theory: C, 73.74; H, 5.93; N, 7.17. Found: C, 73.87; H, 5.99; N, 7.27.

EXAMPLE 66

Preparation of 2-(4-chlorophenoxymethyl)-4-methyl-1-(3-cyclohexylpropyl)benzimidazole

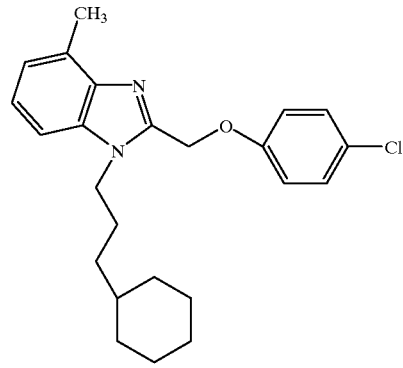

NMR and IR were consistent with the desired title product. FDMS 390 (M+).

EXAMPLE 67

Preparation of 2-(4-chlorophenoxymethyl)-4-methyl-1-[3-(pyrid-3-yl)propyl]benzimidazole and 2-(4-chlorophenoxymethyl)-7-methyl-1-[3-(pyrid-3-yl)propyl]benzimidazole

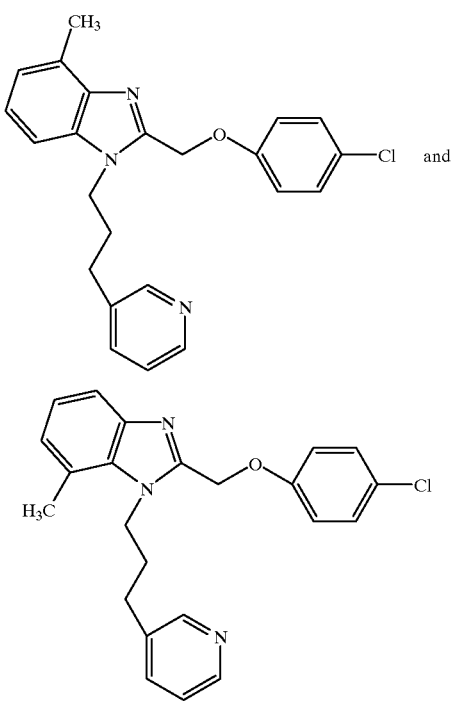

NMR and IR were consistent with the desired title products. Analysis for $C_{23}H_{22}ClN_3O$: Theory: C, 70.49; H, 5.66; N, 10.72. Found: C, 70.20; H, 5.76; N, 10.50.

General Procedure for Removal of the t-Butoxycarbonyl Protecting Group

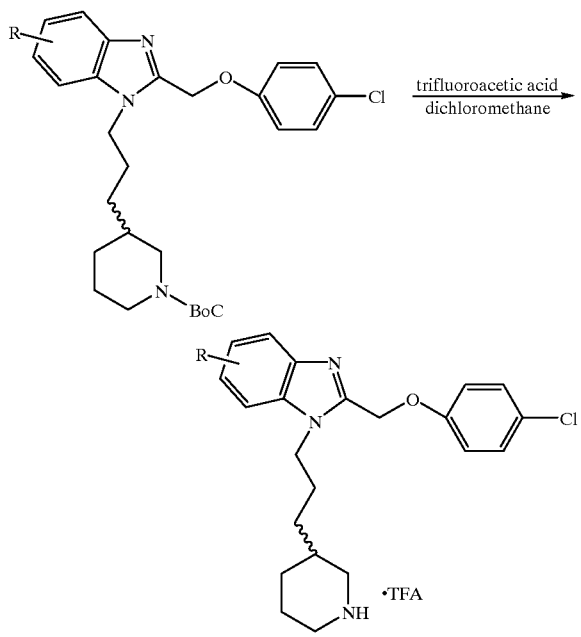

To the amino-protected benzimidazole was added a 1:1 mixture of trifluoroacetic acid in dichloromethane. The resulting mixture was stirred at room temperature for about one hour. The progress of the reaction was monitored by thin layer chromatography. The solvents were removed in vacuo and the residue was triturated with diethyl ether (3×10 ml) and dried under vacuum to yield white crystalline hydroscopic solids.

EXAMPLE 68

Preparation of 2-(4-chlorophenoxymethyl)-1-[3-(piperidin-3-yl)propyl]benzimidazole trifluoroacetate salt

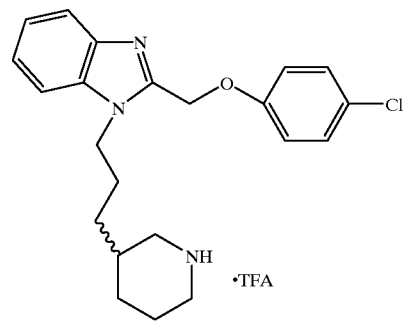

NMR and IR were consistent with the desired title product. FDMS 383, 384 (M+).

EXAMPLE 69

Preparation of 2-(4-chlorophenoxymethyl)-5-methoxy-1-[3-(piperidin-3-yl)propyl]benzimidazole trifluoroacetate salt

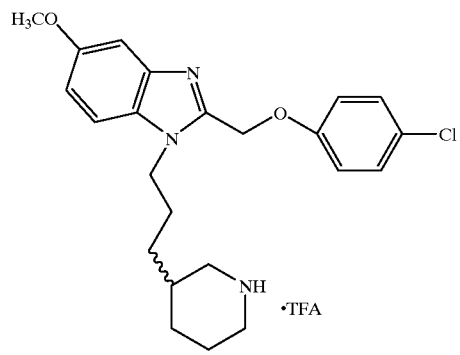

NMR and IR were consistent with the desired title product. FDMS 413, 414 (M+). Analysis for $C_{23}H_{28}ClN_3O_3$: Theory: C, 56.87; H, 5.54; N, 7.96. Found: C, 55.93; H, 5.31; N, 8.01.

EXAMPLE 70

Preparation of 2-(4-chlorophenoxymethyl)-4,5-dimethyl-1-[3-(piperidin-3-yl)propyl]benzimidazole trifluoroacetate salt

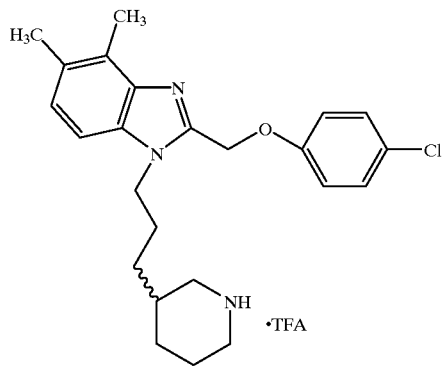

NMR and IR were consistent with the desired title product. FDMS 411, 412 (M+).

EXAMPLE 71

Preparation of 2-(4-chlorophenoxymethyl)-5-methyl-1-[3-(piperidin-3-yl)propyl]benzimidazole trifluoroacetate salt and 2-(4-chlorophenoxymethyl)-6-methyl-1-[3-(piperidin-3-yl)propyl]benzimidazole trifluoroacetate salt

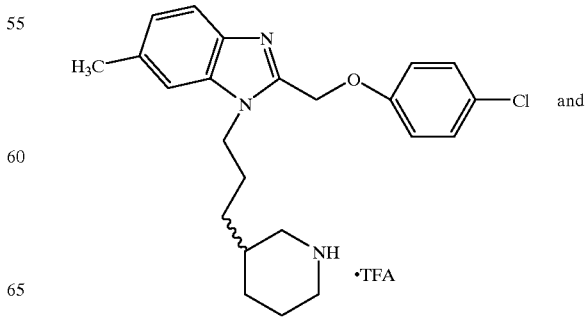

-continued

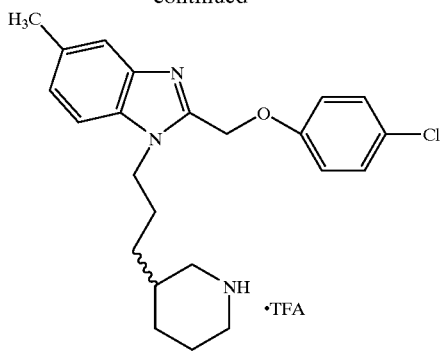

NMR and IR were consistent with the desired title products. FDMS 397 (M+). Analysis for $C_{23}H_{28}ClN_3O$: Theory: C, 58.65; H, 5.54; N, 7.96. Found: C, 58.26; H, 5.56; N, 9.17.

EXAMPLE 72

Preparation of 2-(4-chlorophenoxymethyl)-4-methyl-1-[3-(piperidin-2-yl)propyl]benzimidazole trifluoroacetate salt

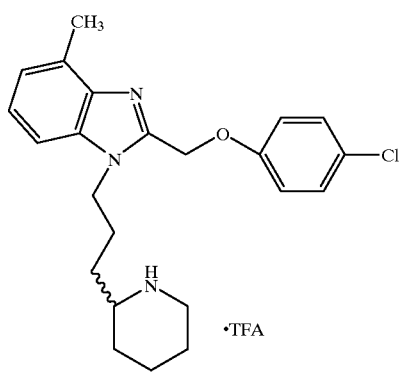

NMR and IR were consistent with the desired title product. FDMS 397, 398 (M+).

EXAMPLE 72a

Preparation of 2-(4-chlorophenoxymethyl)-4-methyl-1-[5-(piperidin-3-yl)pentyl]benzimidazole

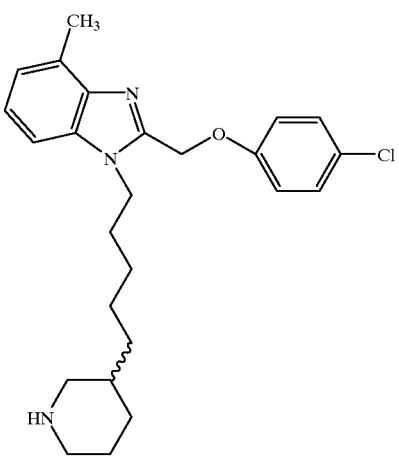

NMR and IR were consistent with the desired title product. FDMS 427 (M+). Analysis for $C_{25}H_{32}ClN_3O$: Theory: C, 60.05; H, 6.16; N, 7.78. Found: C, 59.75; H, 6.11; N, 7.78.

EXAMPLE 73

Preparation of 2-(4-chlorophenoxymethyl)-5-benzoyl-1-[3-(piperidin-2-yl)propyl]benzimidazole trifluoroacetate salt

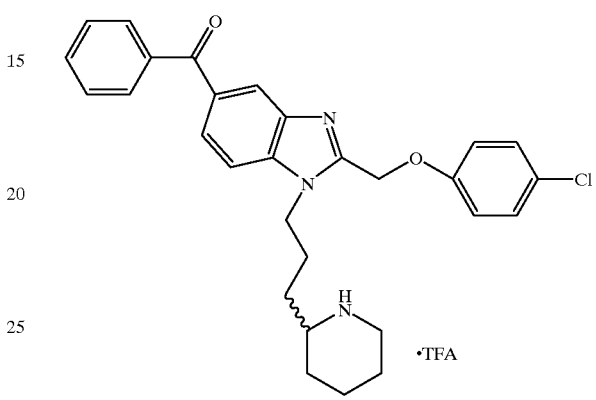

NMR and IR were consistent with the desired title product. FDMS 487, 488 (M+).

EXAMPLE 74

Preparation of 2-(4-chlorophenoxymethyl)-5,6-dichloro-1-[3-(piperidin-3-yl)propyl]benzimidazole trifluoroacetate salt

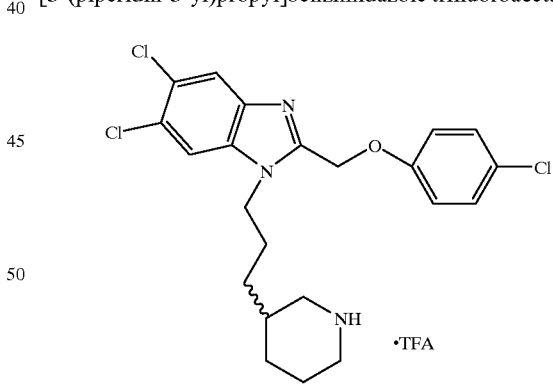

NMR and IR were consistent with the desired title product. FDMS 451, 452 (M+).

EXAMPLE 75

Preparation of 2-(2,4-dichlorophenoxymethyl)-5,6-dichloro-1-[3-(piperidin-2-yl)propyl]benzimidazole trifluoroacetate salt

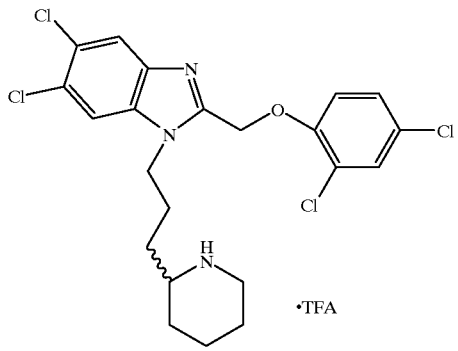

NMR and IR were consistent with the desired title product. FDMS 487 (M+).

EXAMPLE 76

Preparation of 2-(2,4-dichlorophenoxymethyl)-1-[3-(piperidin-2-yl)propyl]benzimidazole trifluoroacetate salt

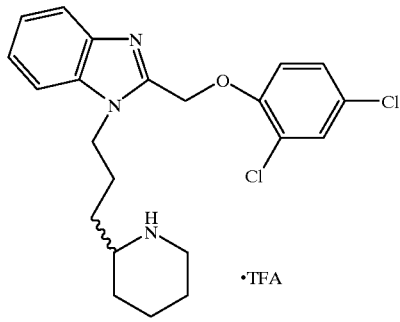

NMR and IR were consistent with the desired title product. FDMS 418 (M+).

EXAMPLE 78

Preparation of 2-(4-chlorophenoxymethyl)-5-methoxy-1-[3-(piperidin-3-yl)propyl]benzimidazole

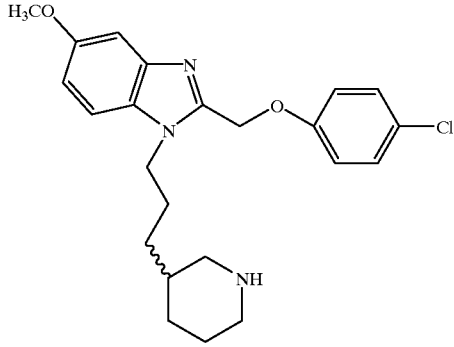

NMR and IR were consistent with the desired title product. FDMS 413 (M+).

EXAMPLE 79

Preparation of 2-(4-chlorophenoxymethyl)-6-methoxy-1-[3-(piperidin-3-yl)propyl]benzimidazole

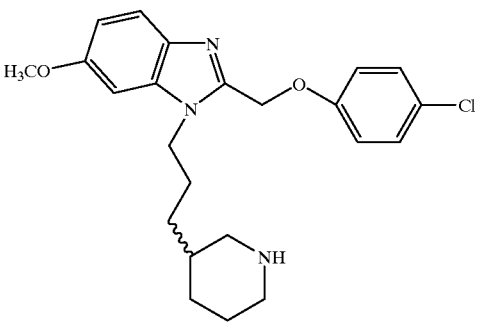

NMR and IR were consistent with the desired title product. FDMS 413 (M+).

EXAMPLE 80

Preparation of 2-(4-chlorophenoxymethyl)-4,5-dimethyl-1-[3-(piperidin-3-yl)propyl]benzimidazole

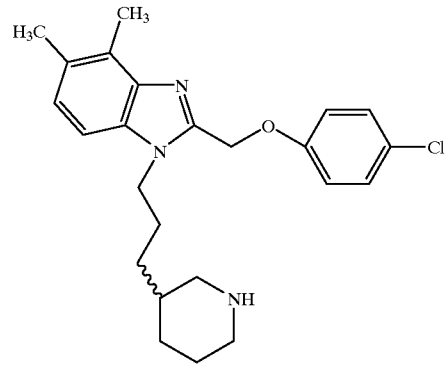

NMR and IR were consistent with the desired title product. FDMS 411, 412 (M+).

EXAMPLE 81

Preparation of 2-(4-chlorophenoxymethyl)-4-methyl-1-[3-(piperidin-3-yl)propyl]benzimidazole and 2-(4-chlorophenoxymethyl)-7-methyl-1-[3-(piperidin-3-yl)propyl]benzimidazole

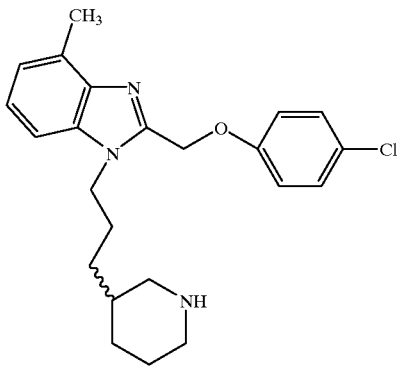

and

-continued

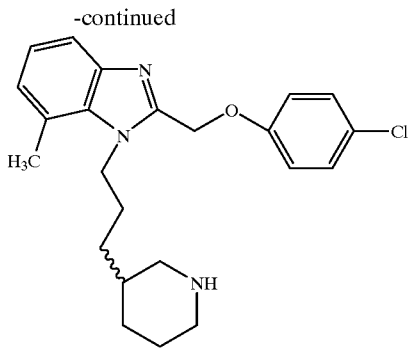

NMR and IR were consistent with the desired title products. FDMS 397, 398 (M+).

EXAMPLE 82
Preparation of 2-(4-chlorophenoxymethyl)-5-benzoyl-1-[3-(piperidin-3-yl)propyl]benzimidazole

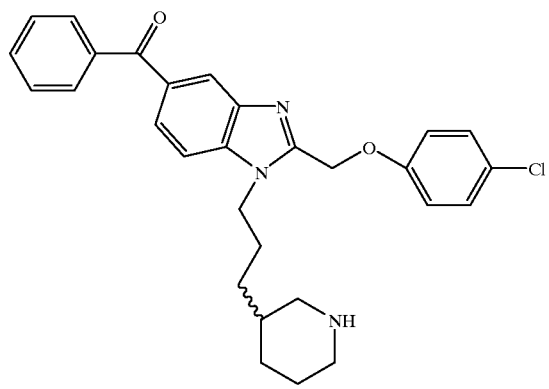

NMR and IR were consistent with the desired title product. FDMS 487, 488 (M+).

EXAMPLE 83
Preparation of 2-(4-chlorophenoxymethyl)-5,6-dichloro-1-[3-(piperidin-3-yl)propyl]benzimidazole

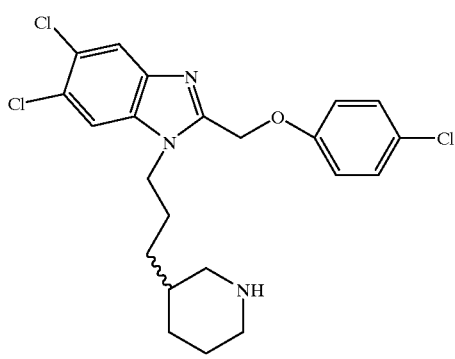

NMR and IR were consistent with the desired title product. FDMS 452.2 (M+).

EXAMPLE 84
Preparation of 2-(4-chlorophenoxymethyl)-5-chloro-1-[3-(piperidin-3-yl)propyl]benzimidazole

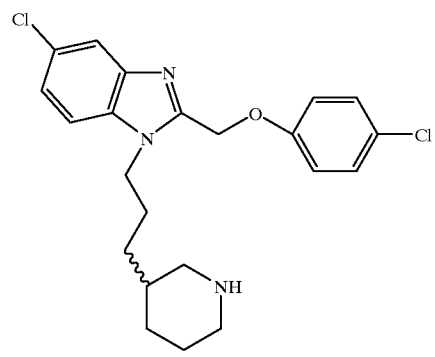

NMR and IR were consistent with the desired title product. FDMS 418.2 (M+).

EXAMPLE 85
Preparation of 2-(4-chlorophenoxymethyl)-5,6-dimethyl-1-[3-(piperidin-3-yl)propyl]benzimidazole

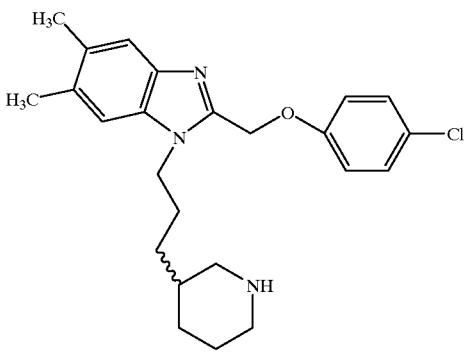

NMR and IR were consistent with the desired title product. FDMS 418.2 (M+).

EXAMPLE 86
Preparation of 2-(2,4-dichlorophenoxymethyl)-1-[3-(piperidin-3-yl)propyl]benzimidazole

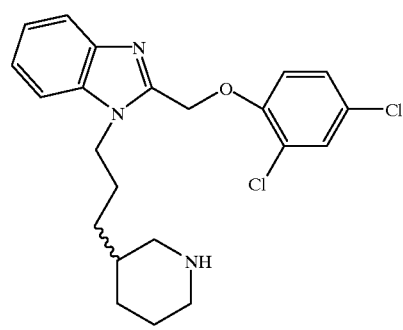

NMR and IR were consistent with the desired title product. FDMS 417, 418 (M+). Analysis for $C_{22}H_{25}Cl_2N_3O$: Theory: C, 53.14; H, 4.92; N, 7.89. Found: C, 53.02; H, 4.74; N, 7.59.

EXAMPLE 87
Preparation of 2-(2,4-dichlorophenoxymethyl)-5,6-dichloro-1-[3-(piperidin-3-yl)propyl]benzimidazole

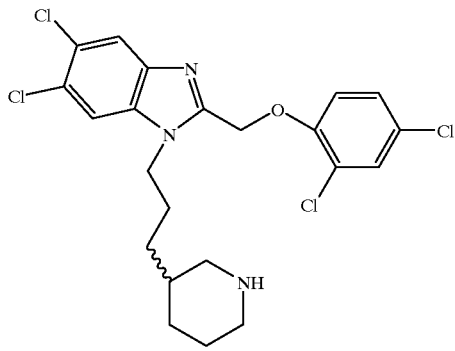

NMR and IR were consistent with the desired title product. FDMS 487 (M+).

EXAMPLE 88
Preparation of 2-(4-chlorophenoxymethyl)-4,5-dimethyl-1-[3-(piperidin-4-yl)propyl]benzimidazole

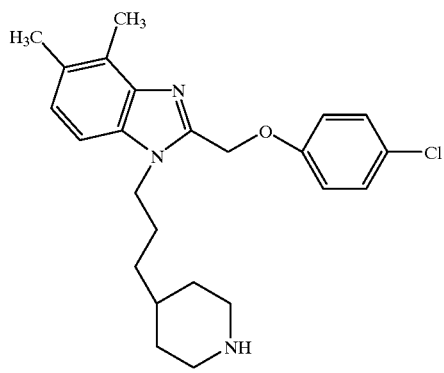

NMR and IR were consistent with the desired title product. FDMS 411 (M+).

EXAMPLE 89
Preparation of 2-(4-chlorophenoxymethyl)-1-[3-(piperidin-4-yl)propyl]benzimidazole

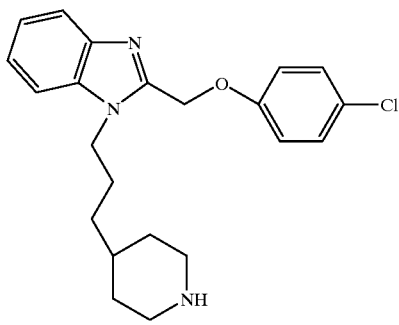

NMR and IR were consistent with the desired title product. FDMS 383 (M+). Analysis for $C_{22}H_{26}ClN_3O$: Theory: C, 57.89; H, 5.46; N, 8.44. Found: C, 57.06; H, 5.44; N, 8.31.

EXAMPLE 90
Preparation of 2-(4-chlorophenoxymethyl)-4,5,6,7-tetramethyl-1-[3-(piperidin-4-yl)propyl]benzimidazole

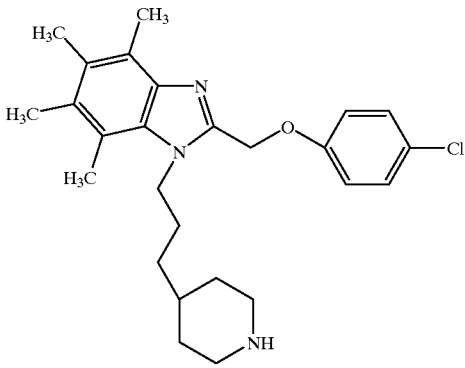

NMR and IR were consistent with the propsoed title structure.

EXAMPLE 91
Preparation of 2-(4-chlorophenoxymethyl)-5-methoxycarbonyl-1-[3-(piperidin-4-yl)propyl]benzimidazole and 2-(4-chlorophenoxymethyl)-6-methoxycarbonyl-1-[3-(piperidin-4-yl)propyl]benzimidazole

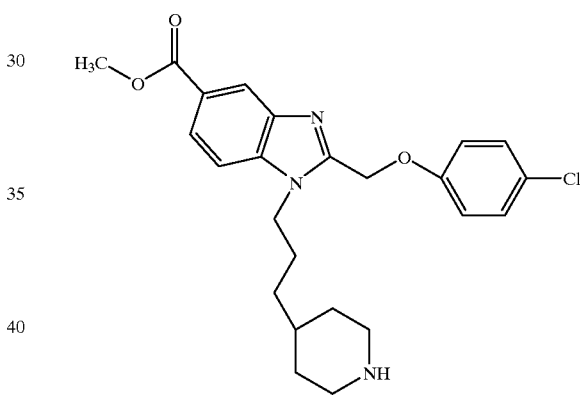

and

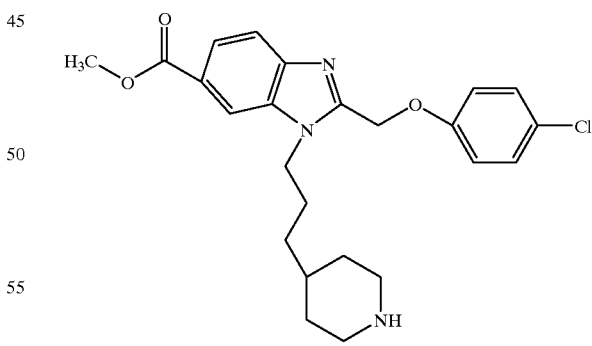

NMR and IR were consistent with the desired title products. FDMS 541 (M+). Analysis for $C_{24}H_{28}ClN_3O$: Theory: C, 56.17; H, 5.26; N, 7.50. Found: C, 55.91; H, 5.32; N, 7.58.

EXAMPLE 92
Preparation of 2-(4-chlorophenoxymethyl)-4-methyl-1-[3-(piperidin-4-yl)propyl]benzimidazole

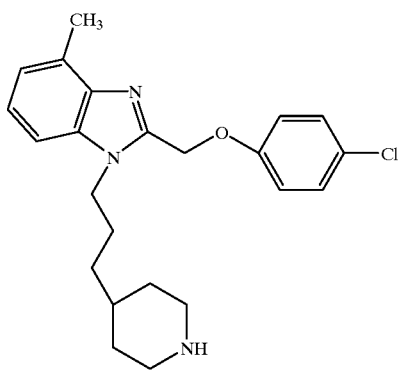

IR and NMR were consistent with the desired title structure. FDMS 397 (M+).

EXAMPLE 92a

Preparation of 2-(4-chlorophenoxymethyl)-4-methyl-1-[5-(piperidin-4-yl)pentyl]benzimidazole

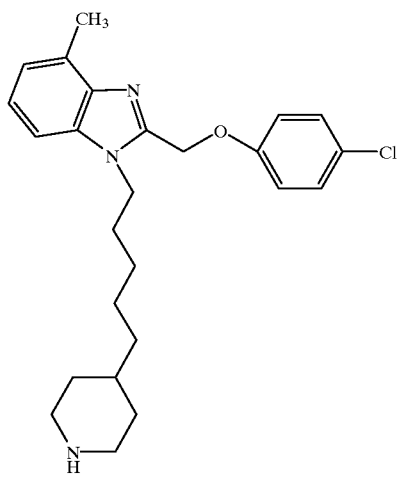

IR and NMR were consistent with the desired title structure. FDMS 426 (M+). Analysis for $C_{25}H_{32}ClN_3O$: Theory: C, 60.05; H, 6.16; N, 7.78. Found: C, 60.30; H, 6.19; N, 7.65.

EXAMPLE 93

Preparation of 2-(4-chlorophenoxymethyl)-4-(t-butyl)-1-[3-(piperidin-4-yl)propyl]benzimidazole and 2-(4-chlorophenoxymethyl)-7-(t-butyl)-1-[3-(piperidin-4-yl)propyl]benzimidazole

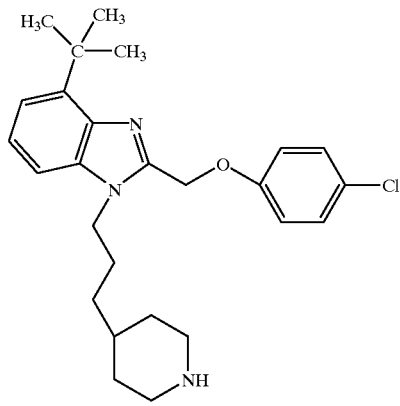

and

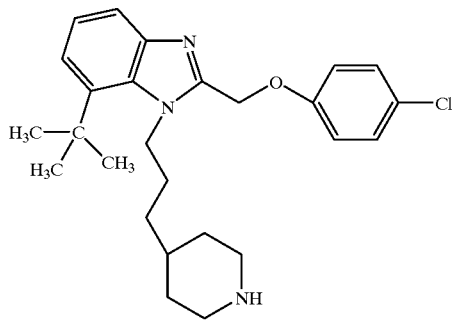

IR and NMR were consistent with the desired title structures. FDMS 439 (M+).

EXAMPLE 94

Preparation of 2-(4-chlorophenoxymethyl)-4-methyl-1-[4-(piperidin-4-yl)butyl]benzimidazole

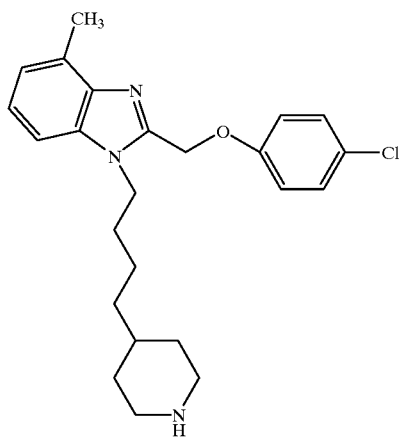

IR and NMR were consistent with the desired title structure. FDMS 411 (M+).

EXAMPLE 95

Preparation of 2-(4-chlorophenoxymethyl)-5,6-dimethyl-1-[4-(piperidin-4-yl)butyl]benzimidazole

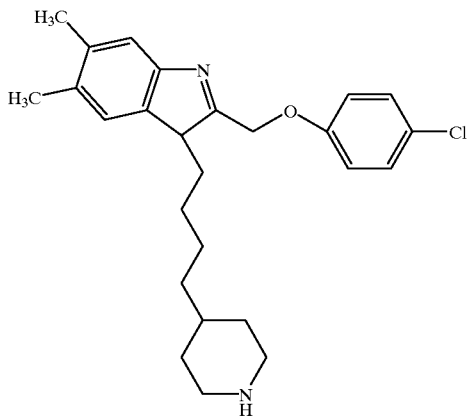

IR and NMR were consistent with the desired title structure. FDMS 425 (M+).

EXAMPLE 96
Preparation of 2-(4-chlorophenoxymethyl)-4,5-dimethyl-1-[4-(piperidin-4-yl)butyl]benzimidazole and 2-(4-chlorophenoxymethyl)-6,7-dimethyl-1-[4-(piperidin-4-yl)butyl]benzimidazole

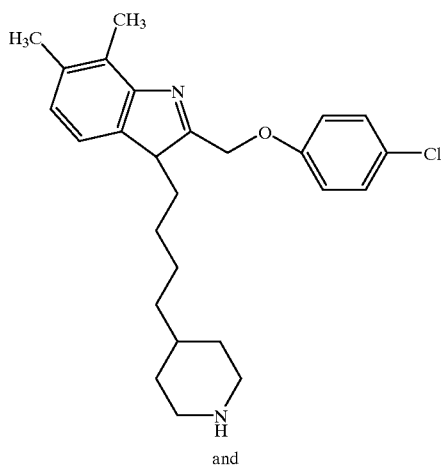

and

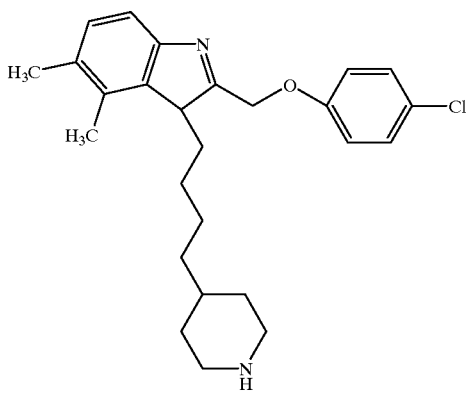

IR and NMR were consistent with the desired title structures. FDMS 425 (M+).

EXAMPLE 97
Preparation of 2-benzyl-1-[3-(piperidin-3-yl)propyl]benzimidazole

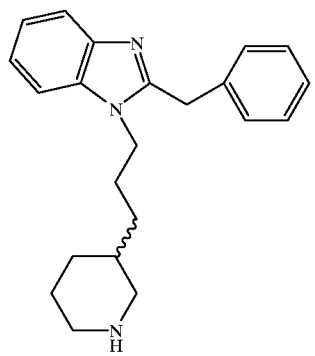

IR and NMR were consistent with the desired title structure. FDMS 344 (M+).

EXAMPLE 98
Preparation of 2-(4-chlorophenyl)-1-[3-(piperidin-3-yl)propyl]benzimidazole

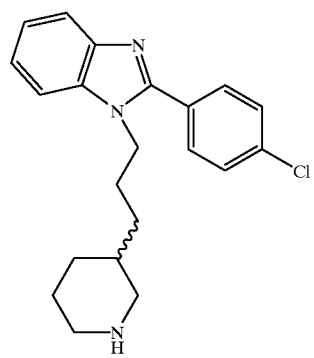

IR and NMR were consistent with the desired title structure. FDMS 354 (M+).

EXAMPLE 99
Preparation of 2-(2-chlorophenoxymethyl)-1-[3-(piperidin-3-yl)propyl]benzimidazole

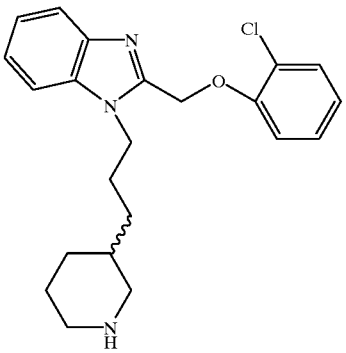

IR and NMR were consistent with the desired title structure. FDMS 384 (M+).

EXAMPLE 100
Preparation of 2-(3-chlorophenoxymethyl)-1-[3-(piperidin-3-yl)propyl]benzimidazole

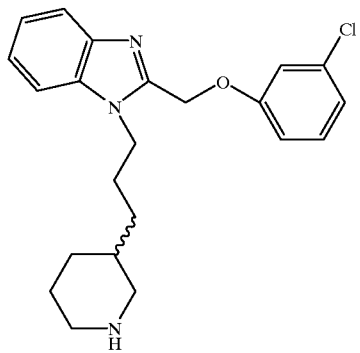

IR and NMR were consistent with the desired title structure. FDMS 384 (M+).

EXAMPLE 101
Preparation of 2-(4-chlorobenzyl)-1-[3-(piperidin-3-yl)propyl]benzimidazole

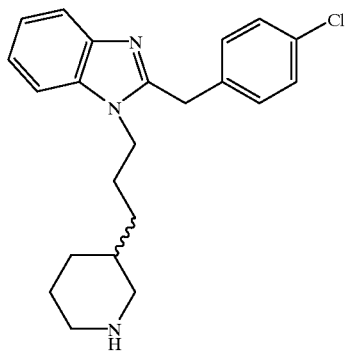

IR and NMR were consistent with the desired title structure. FDMS 368 (M+).

EXAMPLE 102
Preparation of 2-(phenoxymethyl)-1-[3-(piperidin-3-yl)propyl]benzimidazole

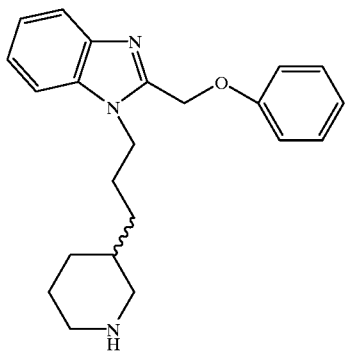

IR and NMR were consistent with the desired title structure. FDMS 349 Analysis for $C_{22}H_{27}N_3O$: Theory: C, 62.19; H, 6.09; N, 9.07. Found: C, 61.08; H, 6.01; N, 9.01.

EXAMPLE 103
Preparation of 2-(3,5-dichlorophenoxymethyl)-1-[3-(piperidin-3-yl)propyl]benzimidazole

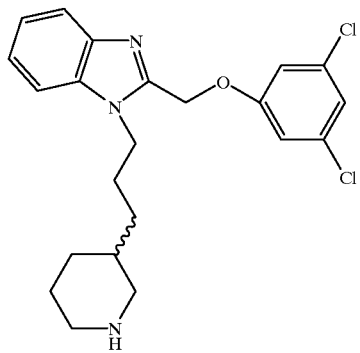

IR and NMR were consistent with the desired title structure. FDMS 417 (M+). Analysis for $C_{22}H_{25}Cl_2N_3O$: Theory: C, 54.14; H, 4.92; N, 7.89. Found: C, 54.05; H, 4.87; N, 7.82.

EXAMPLE 104
Preparation of 2-[4-(4,5-dihydrothiazol-2-yl)phenoxymethyl]-1-[3-(piperidin-3-yl)propyl]benzimidazole

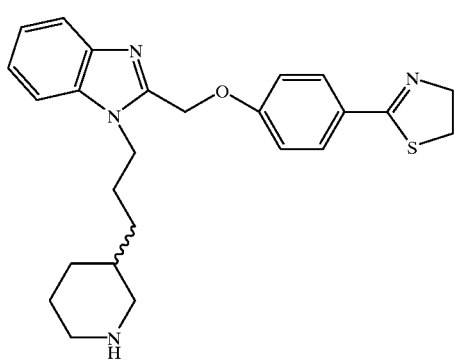

IR and NMR were consistent with the desired title structure. FDMS 435 (M+).

EXAMPLE 105
Preparation of 2-(2,6-dichlorophenoxymethyl)-1-[3-(piperidin-3-yl)propyl]benzimidazole

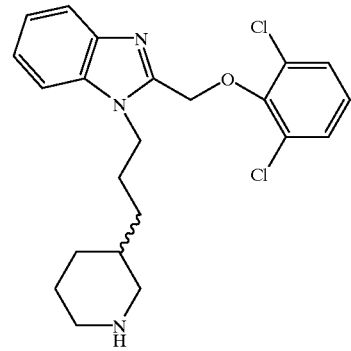

IR and NMR were consistent with the desired title structure. FDMS 420 (M+).

EXAMPLE 106
Preparation of 2-(3-trifluoromethylphenoxymethyl)-1-[3-(piperidin-3-yl)propyl]benzimidazole

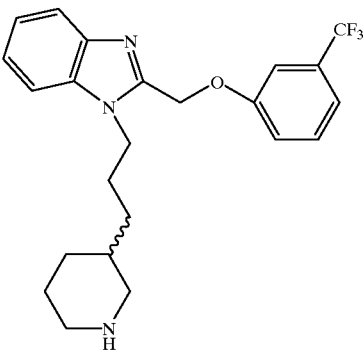

IR and NMR were consistent with the desired title structure. FDMS 418 (M+). Analysis for $C_{23}H_{26}F_3N_3O$: Theory: C, 56.50; H, 5.12; N, 7.91. Found: C, 55.49; H, 5.03; N, 7.64.

EXAMPLE 107

Preparation of 2-(4-chlorophenoxymethyl)-4-methyl-1-[4-[3-(piperidin-1-yl)propylamino]-3-methylbutyl]benzimidazole

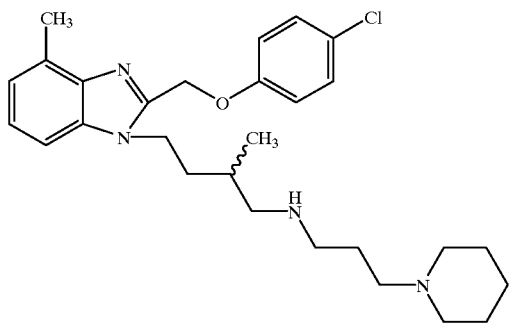

EXAMPLE 108

Preparation of 2-(4-chlorophenoxymethyl)-4-methyl-1-[4-amino-3-methylbutyl]benzimidazole

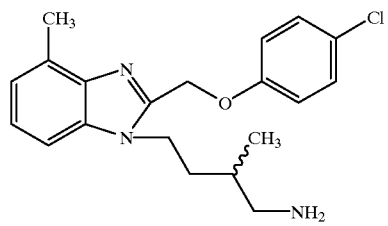

EXAMPLE 109

Preparation of 2-(4-chlorophenoxymethyl)-4-methyl-1-[4-dimethylamino-3-methylbutyl]benzimidazole

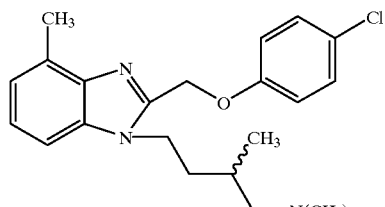

EXAMPLE 110

Preparation of 2-(4-chlorophenoxymethyl)-4-methyl-1-[4-(1,2,3,4-tetrahydroisoquinolin-2-yl)-3-methylbutyl]benzimidazole

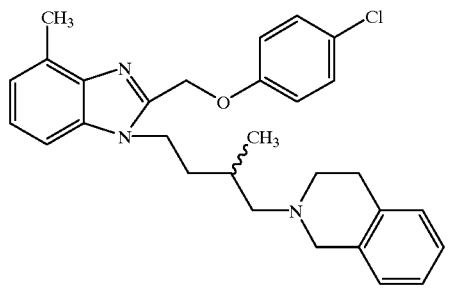

EXAMPLE 111

Preparation of 2-(4-chlorophenoxymethyl)-4-methyl-1-[3-[2-[2-(piperidin-1-yl)ethyl]piperidin-1-yl]carbonyl]butyl]benzimidazole

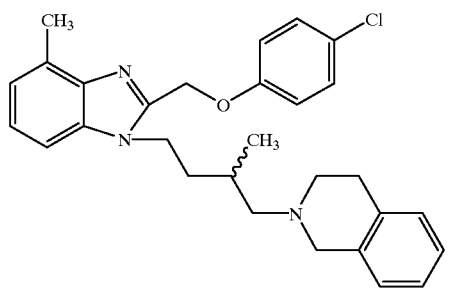

EXAMPLE 112

Preparation of 2-(4-chlorophenoxymethyl)-4-methyl-1-{4-[2-[2-(piperidin-1-yl)ethyl]piperidin-1-yl]-3-methylbutyl}benzimidazole

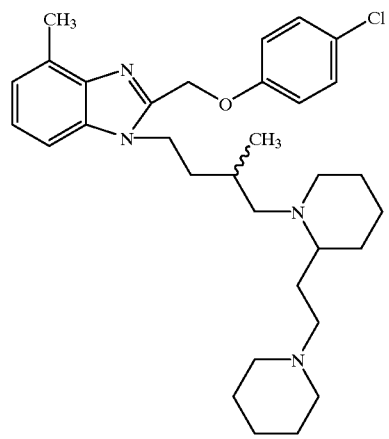

EXAMPLE 113
Preparation of 2-(4-chlorophenoxymethyl)-4-methyl-1-{4-[(1,2,3,4-tetrahydronaphth-1-yl)amino]-3-methylbutyl}benzimidazole

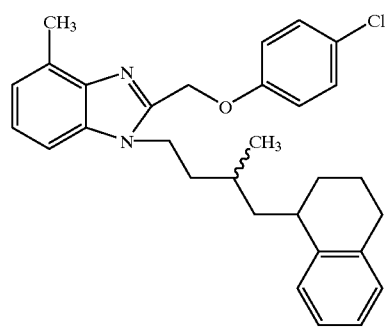

EXAMPLE 114
Preparation of 2-(4-chlorophenoxymethyl)-4-methyl-1-{3-[3-[(2-methylpiperidin-1-yl)propylamino]carbonyl]-3-methylpropyl}benzimidazole

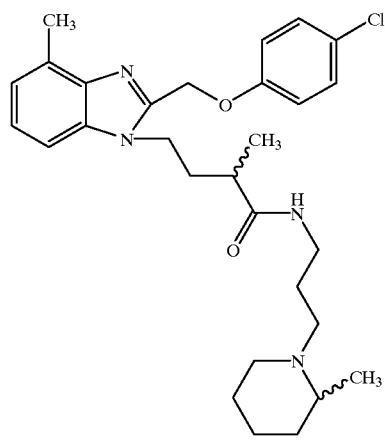

EXAMPLE 115
Preparation of 2-(4-chlorophenoxymethyl)-4-methyl-1-{4-[3-(2-methylpiperidin-1-yl)propylamino]-3-methylbutyl}benzimidazole

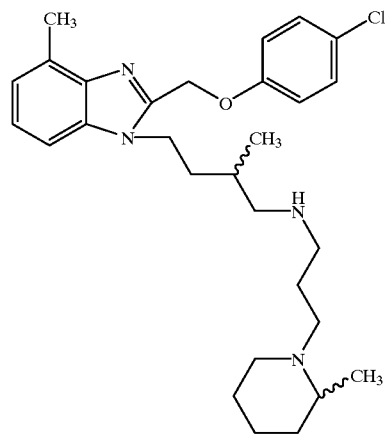

EXAMPLE 116
Preparation of 2-(4-chlorophenoxymethyl)-4-methyl-1-{3-[1-(3-ethoxycarbonylbutyl)piperidin-3-yl]propyl}benzimidazole

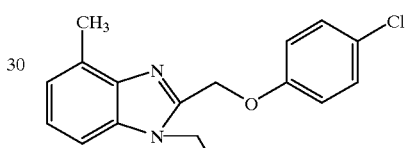

EXAMPLE 117
Preparation of 2-(4-chlorophenoxymethyl)-4-methyl-1-{3-[1-(3-ethoxycarbonyl-4-phenylbutyl)piperidin-3-yl]propyl}benzimidazole

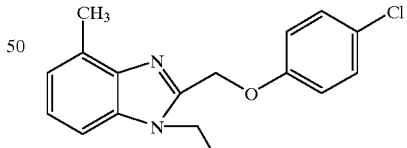

EXAMPLE 118
Preparation of 2-(4-chlorophenoxymethyl)-4-methyl-1-{3-[1-(2-ethoxycarbonyl-4-phenylbutyl)piperidin-3-yl]propyl}benzimidazole

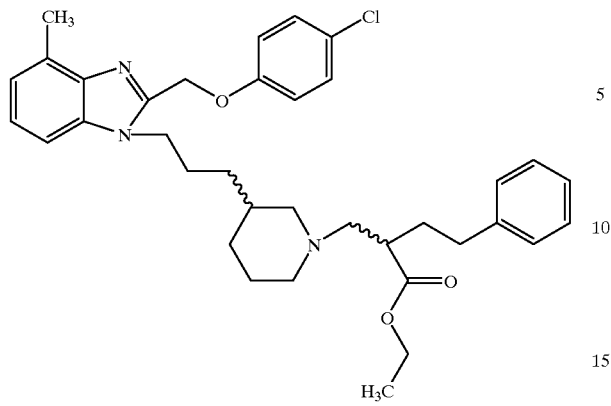

EXAMPLE 119

Preparation of 2-(4-chlorophenoxymethyl)-4-methyl-1-{3-[1-(3-carboxybutyl)piperidin-3-yl]propyl}benzimidazole

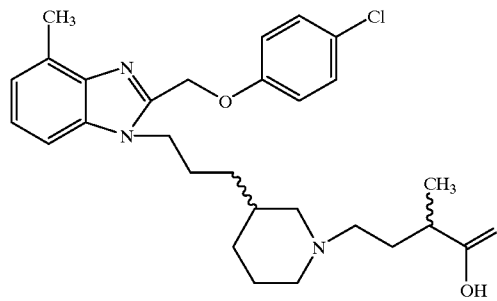

EXAMPLE 120

Preparation of 2-(4-chlorophenoxymethyl)-4-methyl-1-[4-[2-[2-(piperidin-1-yl)ethyl]piperidin-1-yl]-3-methyl]butyl]benzimidazole

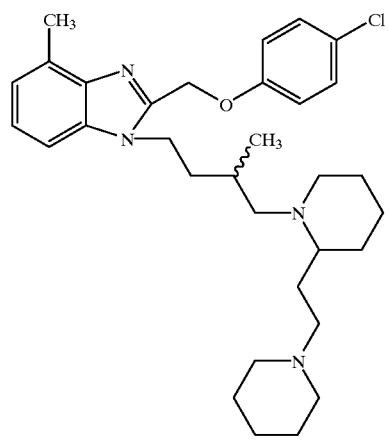

EXAMPLE 121

Preparation of 2-(4-chlorophenoxymethyl)-4-methyl-1-[3-[1-(3-phenyl-3-carboxypropyl)piperidin-3-yl]propyl]benzimidazole

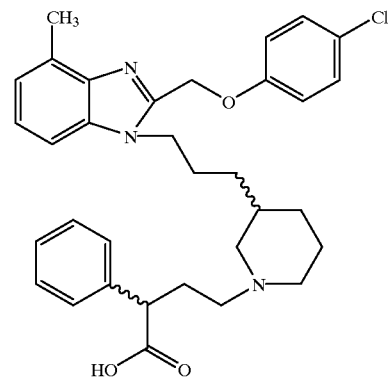

EXAMPLE 122

Preparation of 2-(4-chlorophenoxymethyl)-4-methyl-1-[3-[1-(4-phenyl-3-carboxybutyl)piperidin-3-yl]propyl]benzimidazole

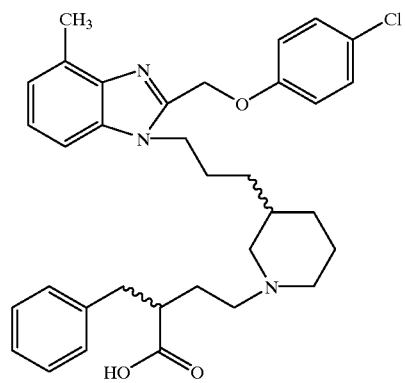

EXAMPLE 123

Preparation of 2-(4-chlorophenoxymethyl)-4-methyl-1-[3-[1-(3-benzoylbutyl)piperidin-3-yl]propyl]benzimidazole

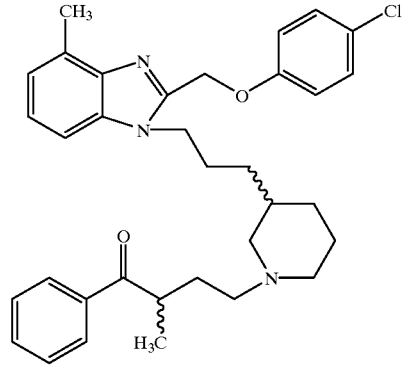

EXAMPLE 124

Preparation of 2-(4-chlorophenoxymethyl)-4-methyl-1-[3-[1-(3-benzoyl-3-phenylpropyl)piperidin-3-yl]propyl]benzimidazole

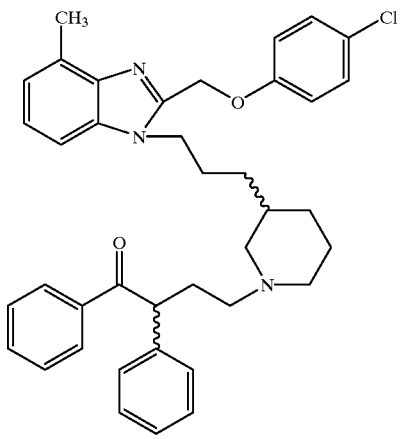

EXAMPLE 125

Preparation of 2-(4-chlorophenoxymethyl)-4-methyl-1-[3-[1-(3-benzoyl-3-phenylpropyl)piperidin-3-yl]propyl]benzimidazole

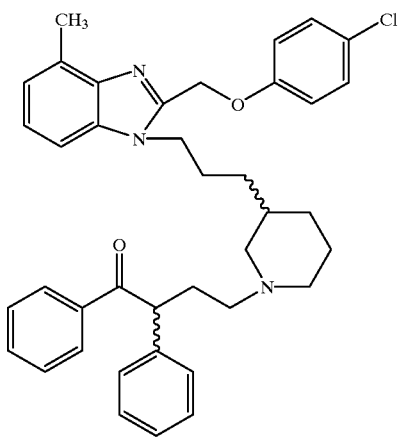

EXAMPLE 126

Preparation of 2-(4-chlorophenoxymethyl)-4-methyl-1-[3-[1-(3-benzoyl-3-benzylpropyl)piperidin-3-yl]propyl]benzimidazole

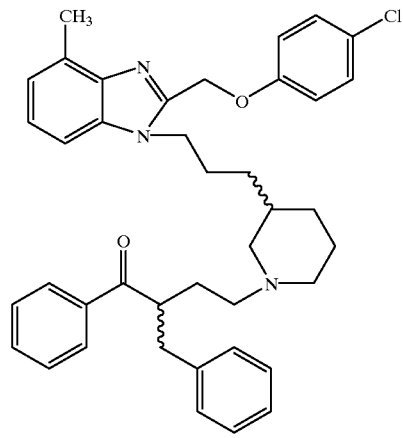

EXAMPLE 127

Preparation of 2-(4-chlorophenoxymethyl)-4-methyl-1-[3-[1-[4-(piperidin-1-yl)-3-methylbutyl]piperidin-3-yl]propyl]benzimidazole

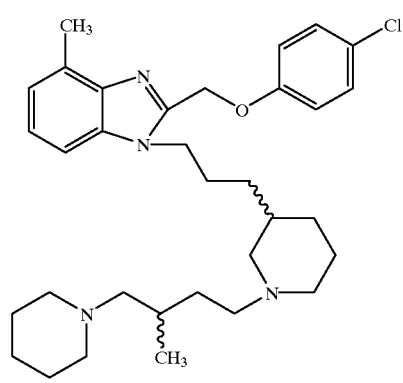

EXAMPLE 128

Preparation of 2-(4-chlorophenoxymethyl)-4-methyl-1-[3-[1-[4-(piperidin-1-yl)-3-phenylbutyl]piperidin-3-yl]propyl]benzimidazole

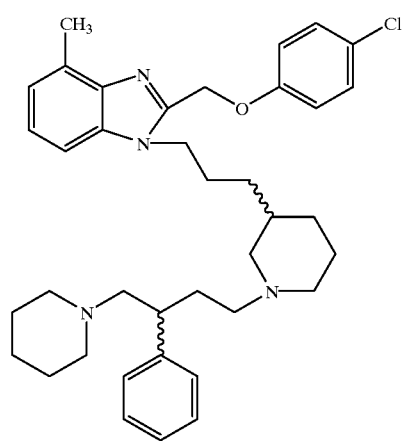

EXAMPLE 130

Preparation of 2-(4-chlorophenoxymethyl)-4-methyl-1-[3-[1-[4-(piperidin-1-yl)-3-benzylbutyl]piperidin-3-yl]propyl]benzimidazole

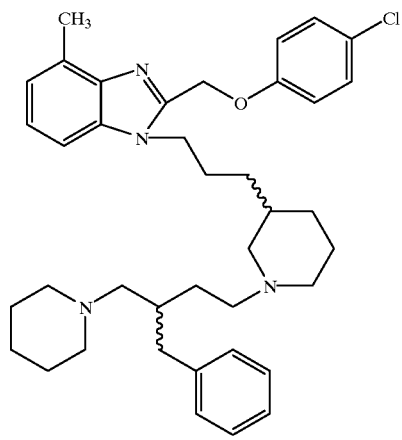

EXAMPLE 131

Preparation of 2-(4-chlorophenoxymethyl)-4-methyl-1-[3-[1-(3-ethoxycarbonyl-4-phenylbutyl)piperidin-3-yl]propyl]benzimidazole

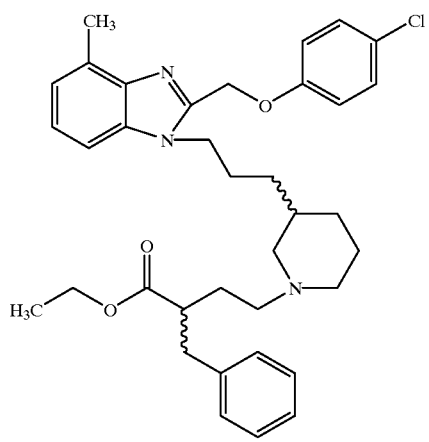

EXAMPLE 132

Preparation of 2-(4-chlorophenoxymethyl)-4-methyl-1-[3-[1-(3-carboxy-4-phenylbutyl)piperidin-4-yl]propyl]benzimidazole

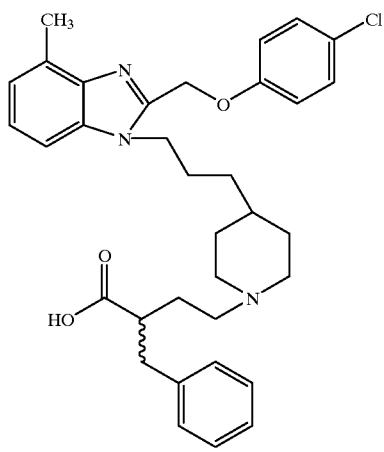

EXAMPLE 133

Preparation of 2-(4-chlorophenoxymethyl)-4-methyl-1-[3-[1-[3-(piperidin-1-ylcarbonyl)-4-phenylbutyl]piperidin-4-yl]propyl]benzimidazole

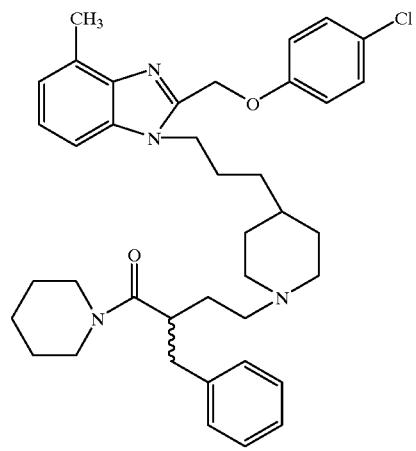

EXAMPLE 134

Preparation of 2-(4-chlorophenoxymethyl)-4-methyl-1-[3-[1-[3-(piperidin-1-ylmethyl)-4-phenylbutyl]piperidin-4-yl]propyl]benzimidazole

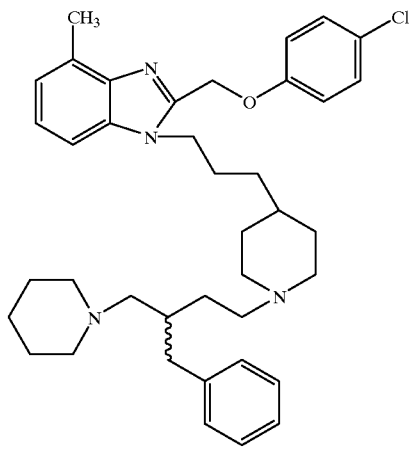

EXAMPLE 135

Preparation of 2-(4-chlorophenoxymethyl)-4-methyl-1-[3-[1-[3-(ethoxycarbonyl)butyl]piperidin-4-yl]propyl]benzimidazole

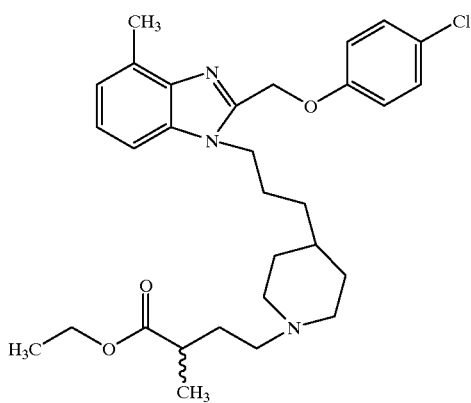

EXAMPLE 136

Preparation of 2-(4-chlorophenoxymethyl)-4-methyl-1-[3-[1-[3-(ethoxycarbonyl)propyl]piperidin-4-yl]propyl]benzimidazole

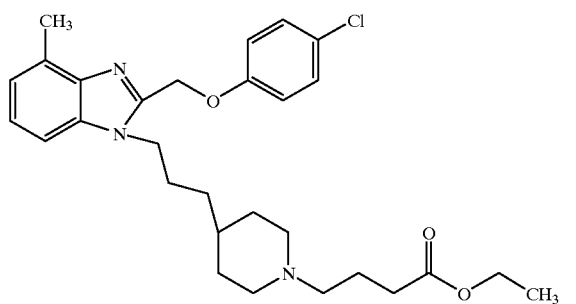

EXAMPLE 137

Preparation of 2-(4-chlorophenoxymethyl)-4-methyl-1-[3-[1-[3-(carboxy)butyl]piperidin-4-yl]propyl]benzimidazole

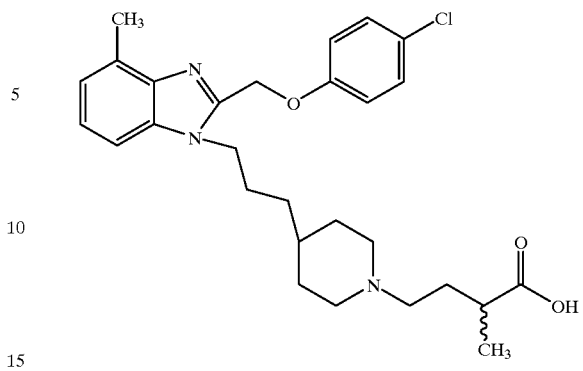

EXAMPLE 138

Preparation of 2-(4-chlorophenoxymethyl)-4-methyl-1-[3-[1-(3-carboxypropyl)piperidin-4-yl]propyl]benzimidazole

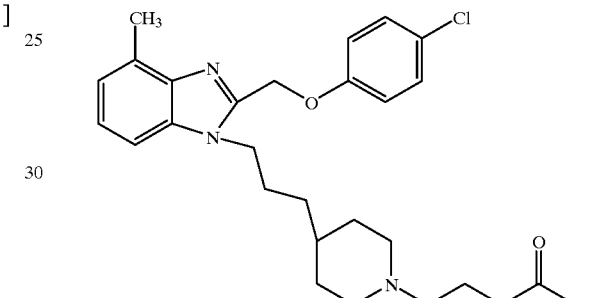

EXAMPLE 139

Preparation of 2-(4-chlorophenoxymethyl)-4-methyl-1-[3-[1-[3-(piperidin-1-ylcarbonyl)butyl]piperidin-4-yl]propyl]benzimidazole

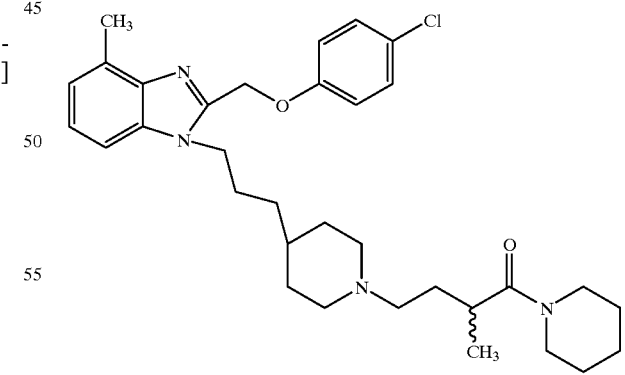

EXAMPLE 140

Preparation of 2-(4-chlorophenoxymethyl)-4-methyl-1-[3-[1-[3-(piperidin-1-ylcarbonyl)propyl]piperidin-4-yl]propyl]benzimidazole

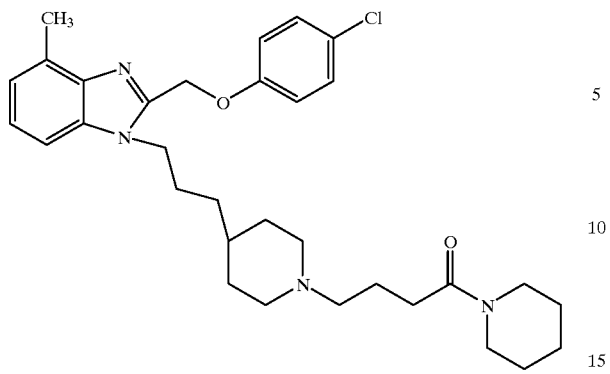

EXAMPLE 141

Preparation of 2-(4-chlorophenoxymethyl)-4-methyl-1-[3-[1-[3-methyl-4-(piperidin-1-yl)butyl]piperidin-4-yl]propyl]benzimidazole

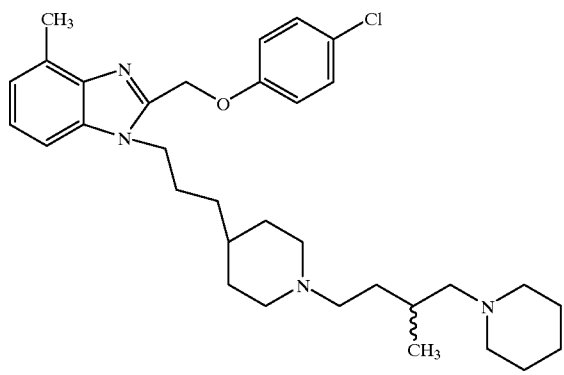

EXAMPLE 142

Preparation of 2-(4-chlorophenoxymethyl)-4-methyl-1-[3-[1-[4-(piperidin-1-yl)butyl]piperidin-4-yl]propyl]benzimidazole

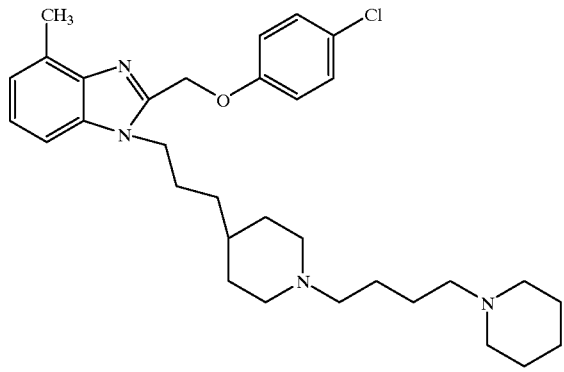

EXAMPLE 143

Preparation of 2-(4-chlorophenoxymethyl)-4-methyl-1-[3-[1-(ethoxycarbonyl)piperidin-4-yl]propyl]benzimidazole

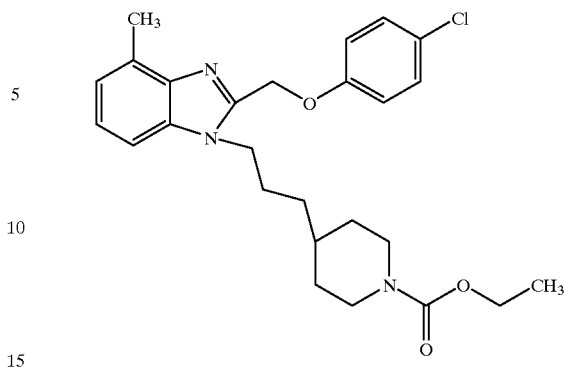

EXAMPLE 144

Preparation of 2-(4-chlorophenoxymethyl)-4-methyl-1-[3-[1-[3-(aminocarbonyl)propyl]piperidin-4-yl]propyl]-benzimidazole

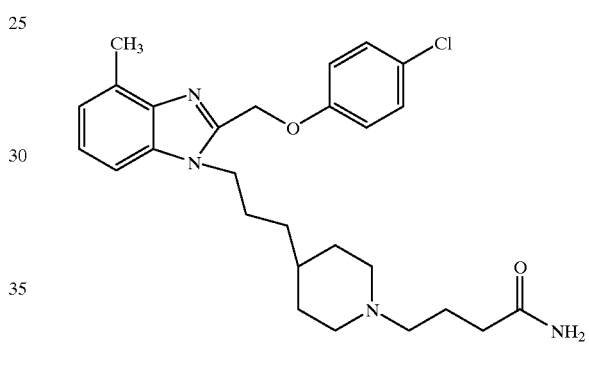

EXAMPLE 145

Preparation of 2-(4-chlorophenoxymethyl)-4-methyl-1-[3-[4-[3-(benzylamino)propyl]piperidin-1-yl]propyl]-benzimidazole

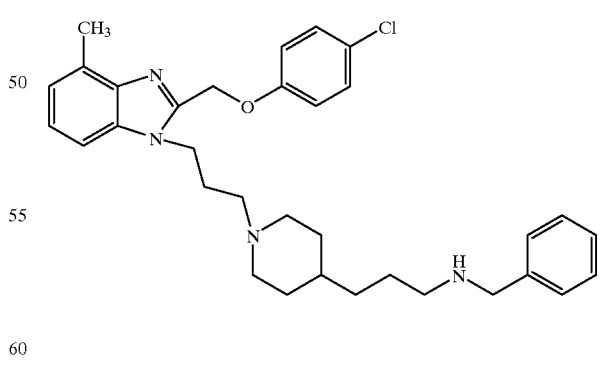

EXAMPLE 146

Preparation of 2-(4-chlorophenoxymethyl)-4-methyl-1-[3-[4-[2-[(benzylamino)carbonyl]ethyl]piperidin-1-yl]propyl]-benzimidazole

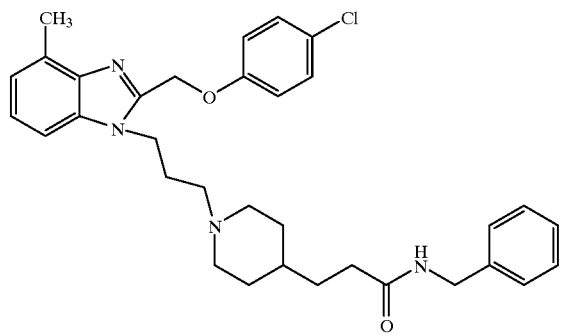

EXAMPLE 147

Preparation of 2-(4-chlorophenoxymethyl)-4-methyl-1-[3-[4-[2-[(4-methoxybenzylamino)carbonyl]ethyl]piperidin-1-yl]propyl]-benzimidazole

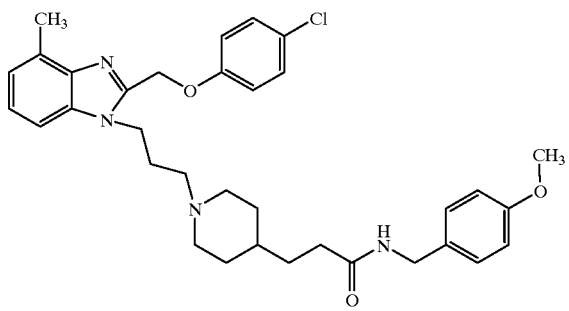

EXAMPLE 147

Preparation of 2-(4-chlorophenoxymethyl)-4-methyl-1-[3-[4-[2-(benzyloxycarbonylamino)ethyl]piperidin-1-yl]propyl]-benzimidazole

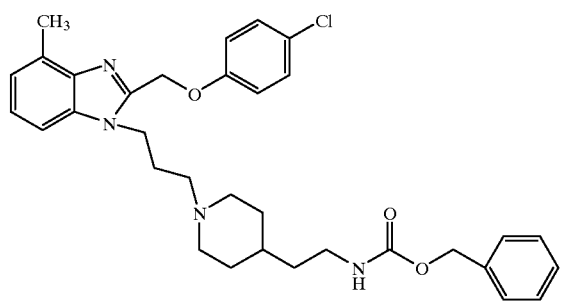

EXAMPLE 148

Preparation of 2-(4-chlorophenoxymethyl)-4-methyl-1-[4-(4-phenylpiperidin-1-yl)butyl]benzimidazole

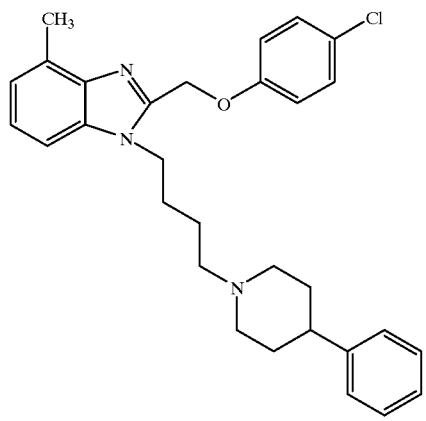

EXAMPLE 149

Preparation of 2-(4-chlorophenoxymethyl)-4-methyl-1-[3-methyl-4-[4-phenyl-4-(acetamidomethyl)piperidin-1-yl]butyl]benzimidazole

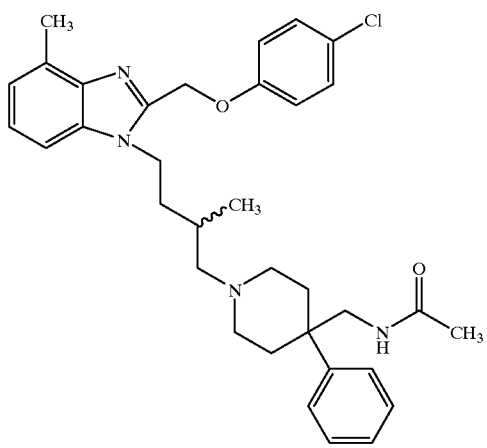

EXAMPLE 150

Preparation of 2-(4-chlorophenoxymethyl)-4-methyl-1-[3-[4-(propylaminocarbonylethyl)piperidin-1-yl]propyl]benzimidazole

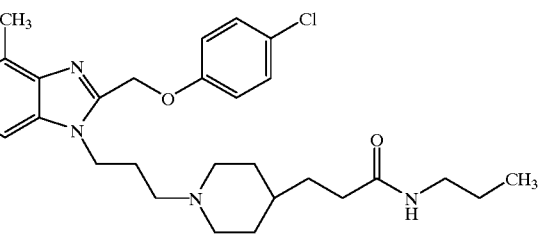

EXAMPLE 151

Preparation of 2-(4-chlorophenoxymethyl)-4-methyl-1-[3-[3-(piperidin-1-yl)propylamino]propyl]benzimidazole

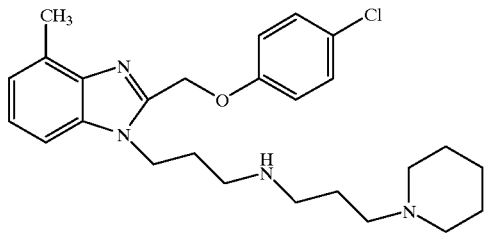

EXAMPLE 152
Preparation of 2-(4-chlorophenoxymethyl)-4-methyl-1-[3-(4-phenylpiperidin-1-yl)propyl]benzimidazole

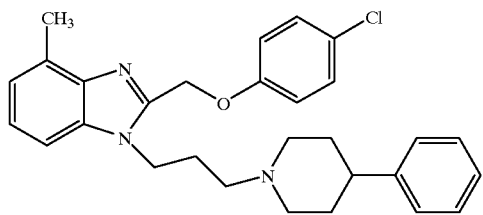

EXAMPLE 153
Preparation of 2-(4-chlorophenoxymethyl)-4-methyl-1-[4-phenyl-4-(4-phenyl-4-methylaminocarbonylpiperidin-1-yl)butyl]benzimidazole

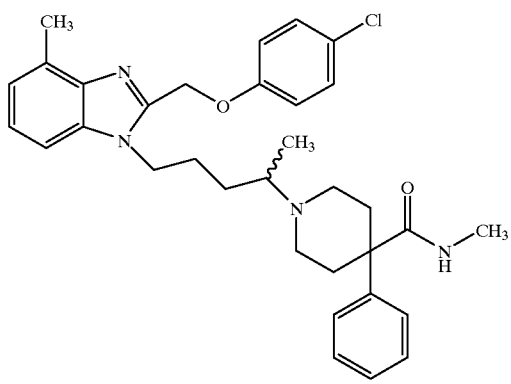

EXAMPLE 154
Preparation of 2-(4-chlorophenoxymethyl)-4-methyl-1-[3-[3-(piperidin-1-yl)propylamino]propyl]benzimidazole

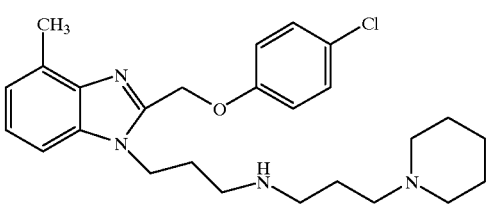

EXAMPLE 155
Preparation of 2-(4-chlorophenoxymethyl)-4-methyl-1-[3-(4-benzylpiperidin-1-yl)propyl]benzimidazole

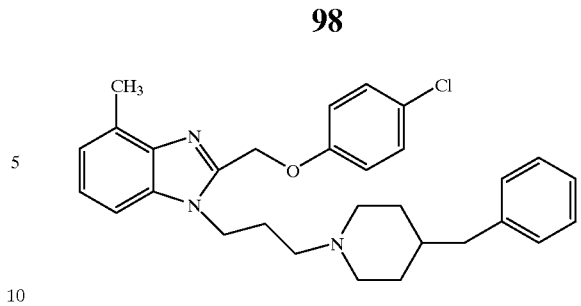

EXAMPLE 156
Preparation of 2-(4-chlorophenoxymethyl)-4-methyl-1-{3-[N-benzoyl-N-[3-(piperdin-1-yl)propyl]amino]propyl}benzimidazole

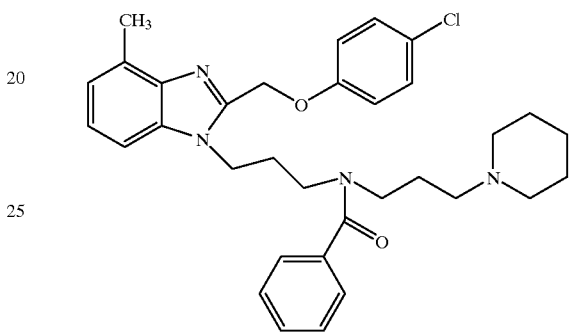

EXAMPLE 157
Preparation of 2-(4-chlorophenoxymethyl)-4-methyl-1-{3-[4-(ethoxycarbonylethyl)piperidin-1-yl]propyl}benzimidazole

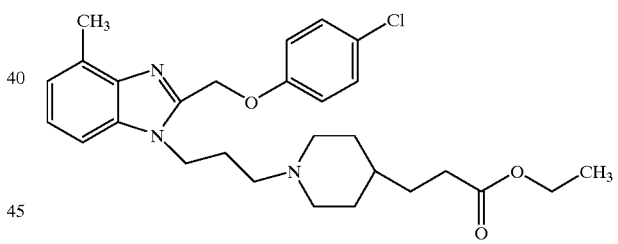

EXAMPLE 158
Preparation of 2-(4-chlorophenoxymethyl)-4-methyl-1-{3-[4-hydroxy-4-benzylpiperidin-1-yl]propyl}benzimidazole

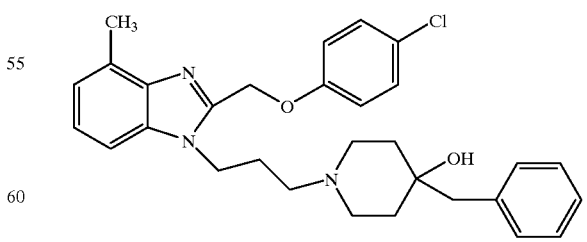

EXAMPLE 159
Preparation of 2-(4-chlorophenoxymethyl)-4-methyl-1-{4-(1,2,3,4-tetrahydroisoquinolin-1-yl)butyl}benzimidazole

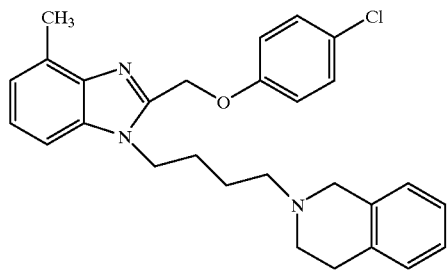

EXAMPLE 160

Preparation of 2-(4-chlorophenoxymethyl)-4-methyl-1-{4-(4-propoxy-4-phenylpiperidin-1-yl)pentyl}benzimidazole

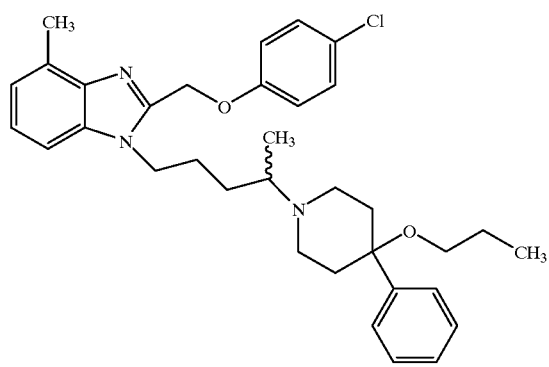

EXAMPLE 161

Preparation of 2-(4-chlorophenoxymethyl)-4-methyl-1-{3-[N-benzyl-N-(3-piperidin-1-ylpropyl)amino]propyl}benzimidazole

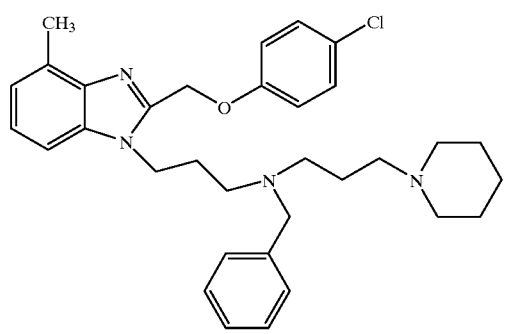

EXAMPLE 162

Preparation of 2-(4-chlorophenoxymethyl)-4-methyl-1-{3-[N-(benzyloxycarbonylmethyl)-N-(3-piperidin-1-ylpropyl)amino]propyl}benzimidazole

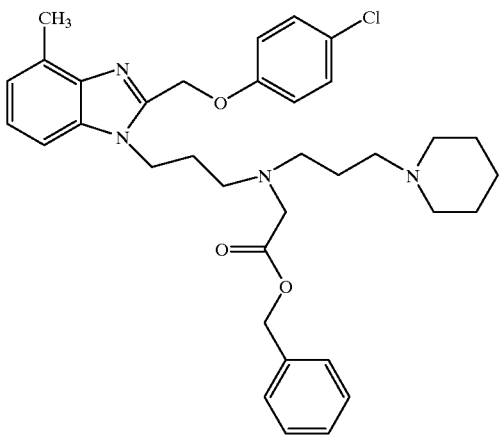

EXAMPLE 163

Preparation of 2-(4-chlorophenoxymethyl)-4-methyl-1-{3-methyl-4-[4-phenyl-4-(ethoxycarbonyl)piperidin-1-yl]butyl}benzimidazole

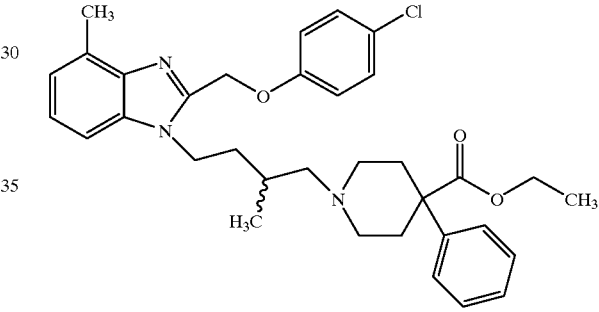

EXAMPLE 164

Preparation of 2-(4-chlorophenoxymethyl)-4-methyl-1-{3-[(1,2,3,4-tetrahydronaphth-1-yl)amino]propyl}benzimidazole

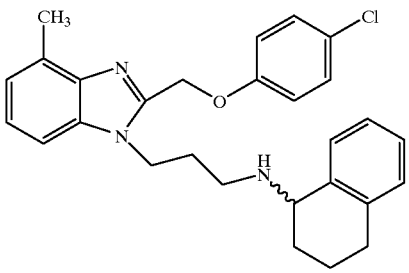

EXAMPLE 165

Preparation of 2-(4-chlorophenoxymethyl)-4-methyl-1-[3-(benzylamino)propyl]benzimidazole

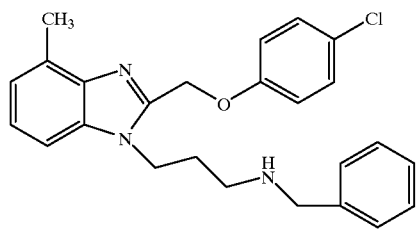

EXAMPLE 166

Preparation of 2-(4-chlorophenoxymethyl)-4-methyl-1-[3-[4-(piperidin-1-ylcarbonylethyl)piperidin-1-yl]propyl] benzimidazole

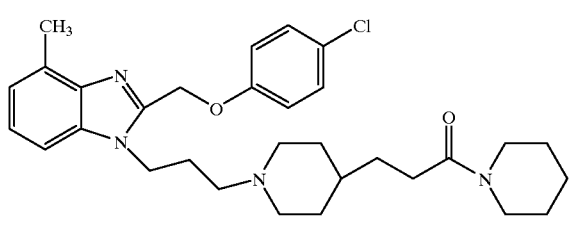

EXAMPLE 167

Preparation of 2-(4-chlorophenoxymethyl)-4-methyl-1-[3-(piperidin-1-yl)propyl]benzimidazole

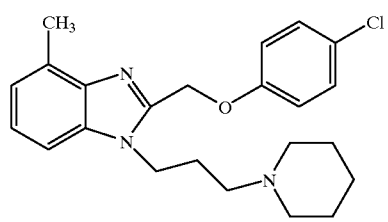

EXAMPLE 168

Preparation of 2-(4-chlorophenoxymethyl)-4-methyl-1-[3-(4-phenyl-1,2,5,6-tetrahydropyridin-1-yl)propyl] benzimidazole

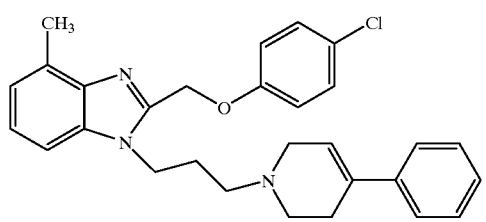

EXAMPLE 169

Preparation of 2-(4-chlorophenoxymethyl)-4-methyl-1-[3-(4-phenyl-4-ethoxycarbonylpiperidin-1-yl)propyl] benzimidazole

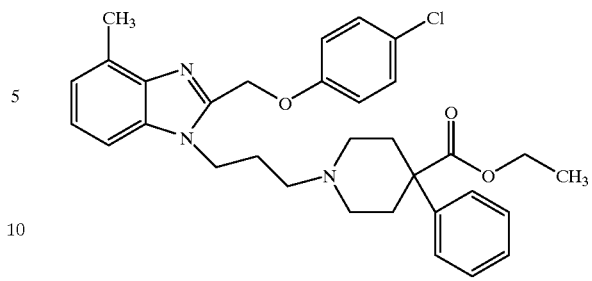

EXAMPLE 170

Preparation of 2-(4-chlorophenoxymethyl)-1-[2-(4-dimethylaminopiperidin-1-yl)ethyl]benzimidazole

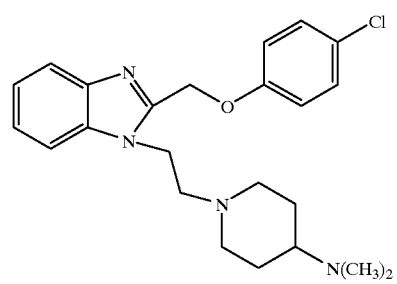

EXAMPLE 171

Preparation of 2-(4-chlorophenoxymethyl)-4-methyl-1-(3-hydroxypropyl)benzimidazole

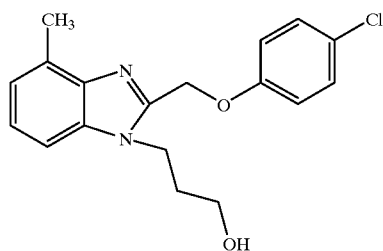

EXAMPLE 172

Preparation of 2-(4-chlorophenoxymethyl)-4-methyl-1-(3-cyanopropyl)benzimidazole

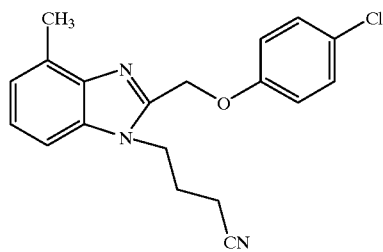

mp 112°. NMR, IR and UV were consistent with the desired title structure. FDMS 339 (M+). Analysis calculated for $C_{19}H_{18}ClN_3O$: Theory: C, 67.16; H, 5.34; N, 12.37. Found: C, 66.95; H, 5.26; N, 12.16.

EXAMPLE 173

Preparation of 2-(4-chlorophenoxymethyl)-4-methyl-1-(3-azidopropyl)benzimidazole

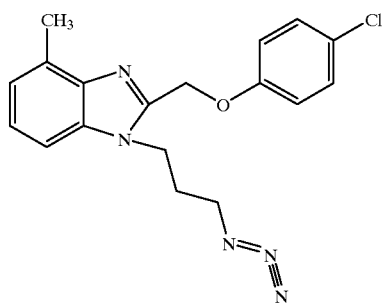

mp 68°. NMR, IR and UV were consistent with the desired title structure. FDMS 355 (M+). Analysis calculated for $C_{18}H_{18}N_5O_3$: Theory: C, 60.76; H, 5.10; N, 19.68. Found: C, 61.00; H, 5.13; N, 19.70.

EXAMPLE 174

Preparation of 2-(4-chlorophenoxymethyl)-4-methyl-1-[3-[N-methyl-N-(7-dimethylaminoheptyl)amino]propyl]benzimidazole

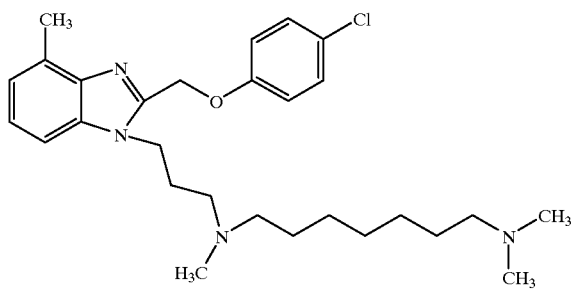

EXAMPLE 175

Preparation of 2-(4-chlorophenoxymethyl)-4-methyl-1-[3-[4-(2-phenylethyl)piperazin-1-yl]propyl]benzimidazole

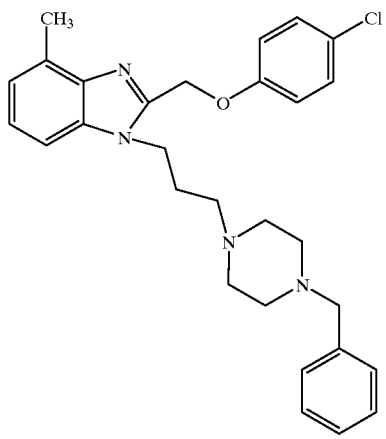

EXAMPLE 176

Preparation of 2-(4-chlorophenoxymethyl)-4-methyl-1-[3-[(4-cyclohexylpiperazin-1-yl)acetoxy]propyl]benzimidazole

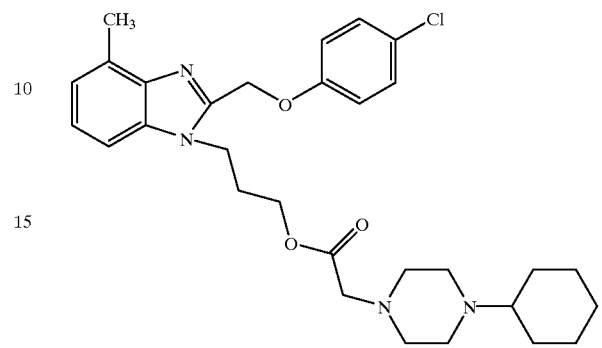

NMR was consistent with the the desired title structure. FAB exact mass calculated for $C_{30}H_{40}ClN_4O_3$: Theory: 539.2803 Found: 539.2789

EXAMPLE 177

Preparation of (RS) 2-(4-chlorophenoxyethyl)-4-methyl-1-[3-(pyrrolidin-3-yloxy)propyl]benzimidazole.

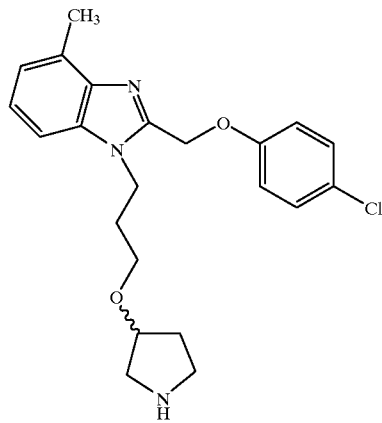

NMR was consistent with the desired title structure. FDMS 399 (M+). FAB exact mass calculated for $C_{22}H_{27}ClN_3O_2$: Theory: 400.1792 Found: 400.1805

EXAMPLE 178

Preparation of 2-(4-chlorophenoxymethyl)-4-methyl-1-[3-[1-[3-(1-benzoyl)propyl]piperidin-4-yl]propyl]benzimidazole

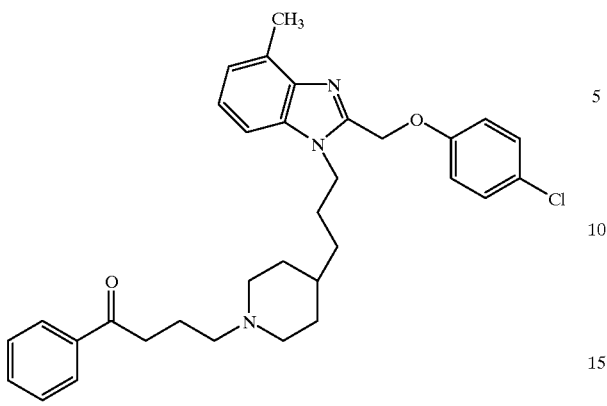

NMR, IR and UV were consistent with the desired title structure. FDMS 544 (M+). Analysis calculated for $C_{33}H_{38}ClN_3O_2$: Theory: C, 72.84; H, 7.04; N, 7.72. Found: C, 72.58; H, 7.22: N, 7.72.

EXAMPLE 179

Preparation of 2-(4-chlorophenoxymethyl)-4-methyl-1-[3-[[4-2-phenylethyl)piperazin-1-yl]carbonyl]butyl]benzimidazole

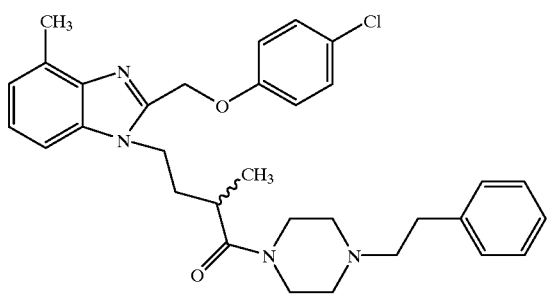

EXAMPLE 180

Preparation of 2-(4-chlorophenoxymethyl)-4-methyl-1-[3-methyl-4-[4-(2-phenylethyl)piperazin-1-yl]butyl]benzimidazole

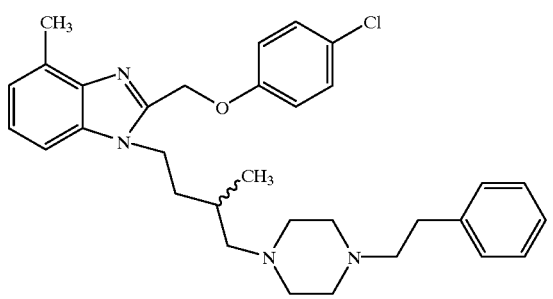

EXAMPLE 181

Preparation of 2-(4-chlorophenoxymethyl)-4-methyl-1-[3-(1-benzylpiperidin-4-yl)propyl]benzimidazole

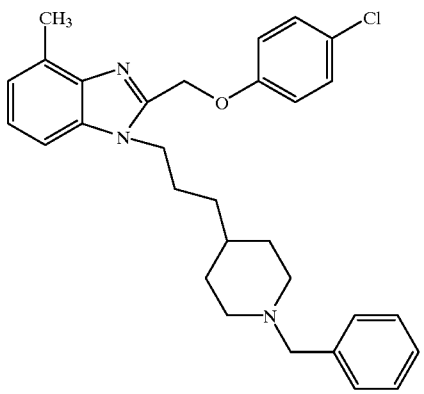

EXAMPLE 182

Preparation of 2-(4-chlorophenoxymethyl)-4-methyl-1-[3-[1-(2-phenylethyl)piperidin-4-yl]propyl]benzimidazole

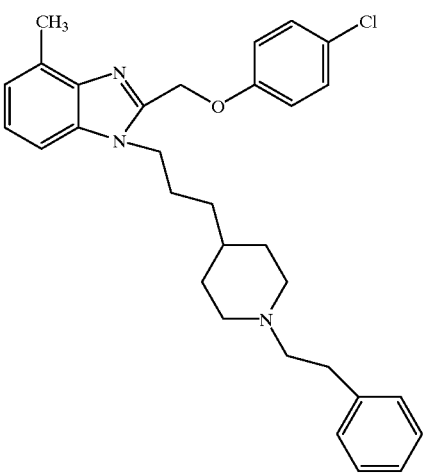

EXAMPLE 183

Preparation of 2-(4-chlorophenoxymethyl)-4-methyl-1-[3-[1-(3-phenylpropyl)piperidin-4-yl]propyl]benzimidazole

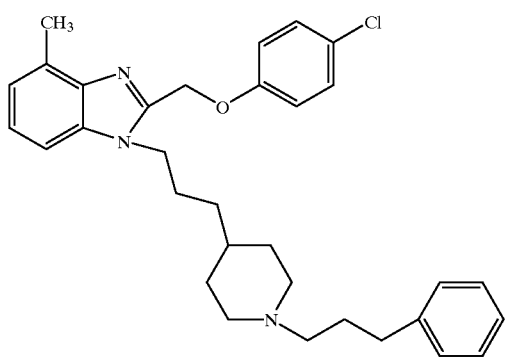

MP 59°. NMR was consistent with the desired title structure. FDMS 515 (M+). Analysis calculated for $C_{32}H_{38}ClN_3O$: Theory: C, 74.47; H, 7.42; N, 8.14. Found: C, 74.20; H, 7.23; N, 8.17.

EXAMPLE 184

Preparation of 2-(4-chlorophenoxymethyl)-4-methyl-1-[3-[1-(benzoylmethyl)piperidin-4-yl]propyl]benzimidazole

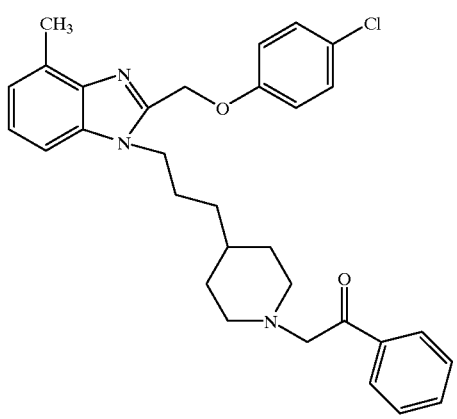

NMR and IR were consistent with the desired title structure. Analysis calculated for $C_{31}H_{34}ClN_3O_2$: Theory: C, 72.15; H, 6.64; N, 8.14. Found: C, 72.35; H, 6.61; N, 8.34.

EXAMPLE 185

Preparation of 2-(4-chlorophenoxymethyl)-4-methyl-1-[3-[1-(2-benzoylethyl)piperidin-4-yl]propyl]benzimidazole

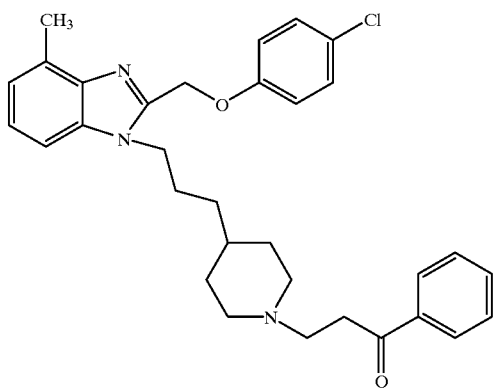

NMR was consistent with the desired title structure. FAB exact mass calculated for $C_{32}H_{37}ClN_3O_2$: Theory: 530.2574 Found: 530.2584

EXAMPLE 186

Preparation of 2-(4-chlorophenoxymethyl)-4-methyl-1-[3-[1-(3-hydroxy-3-phenylpropyl)piperidin-4-yl]propyl]benzimidazole

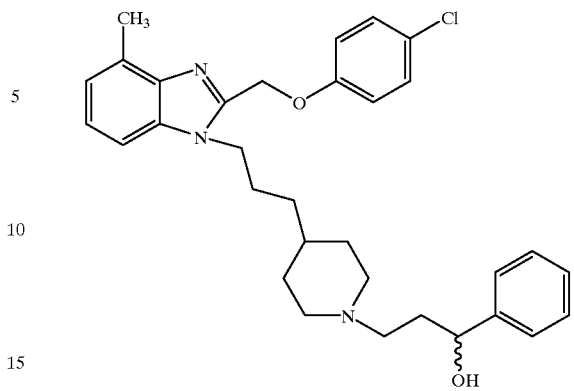

NMR was consistent with the desired title structure. FAB exact mass calculated for $C_{32}H_{39}ClN_3O_2$: Theory: 532.2731 Found: 532.2738

EXAMPLE 187

Preparation of 2-(4-chlorophenoxymethyl)-4-methyl-1-[2-formylethyl]benzimidazole

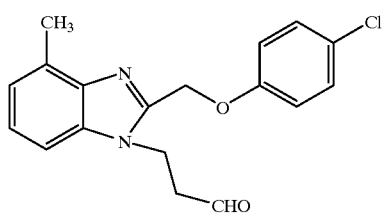

EXAMPLE 188

Preparation of 2-(4-chlorophenoxymethyl)-4-methyl-1-(prop-1-en-3-yl)benzimidazole

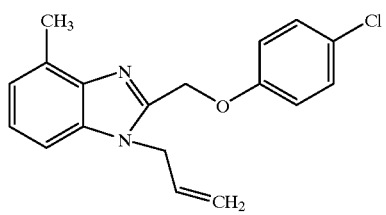

EXAMPLE 189

Preparation of 2-(4-chlorophenoxymethyl)-7-methyl-1-(prop-1-en-3-yl)benzimidazole

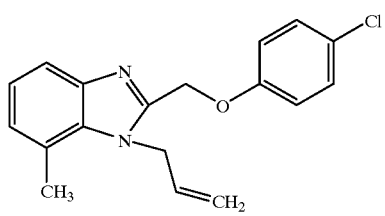

EXAMPLE 190

Preparation of 2-(4-chlorophenoxymethyl)-4-methyl-1-[3-[4-phenyl-4-acetamidomethyl)piperidin-1-yl]propyl]benzimidazole

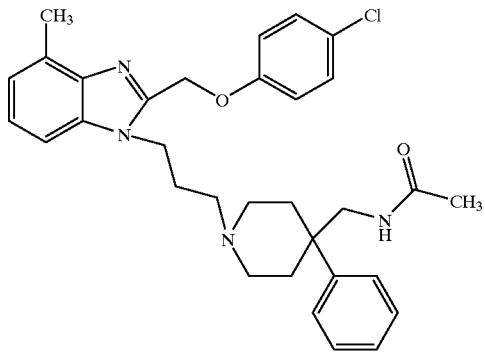

EXAMPLE 191

Preparation of 2-(4-chlorophenoxymethyl)-4-methyl-1-(4-aminobutyl)benzimidazole

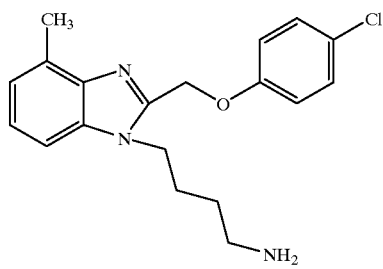

EXAMPLE 192

Preparation of 2-(4-chlorophenoxymethyl)-4-methyl-1-[3-(piperidin-1-yl)propyl)benzimidazole

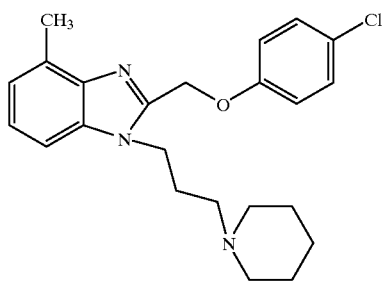

EXAMPLE 193

Preparation of 2-(4-chlorophenoxymethyl)-4-methyl-1-[3-[[2-(phenylethylcarbamoyl)ethyl]piperidin-1-yl]propyl]benzimidazole

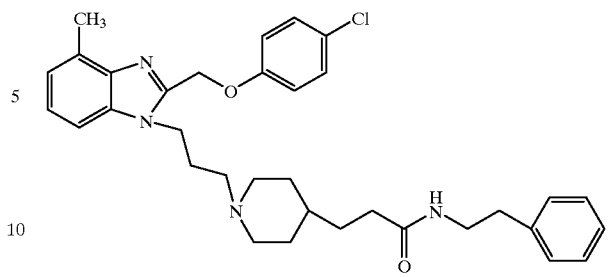

EXAMPLE 194

Preparation of 2-(4-chlorophenoxymethyl)-4-methyl-1-[3-[[N-[3-(piperidin-1-yl)propyl]-N-2-phenylethyl]amino]propyl]benzimidazole

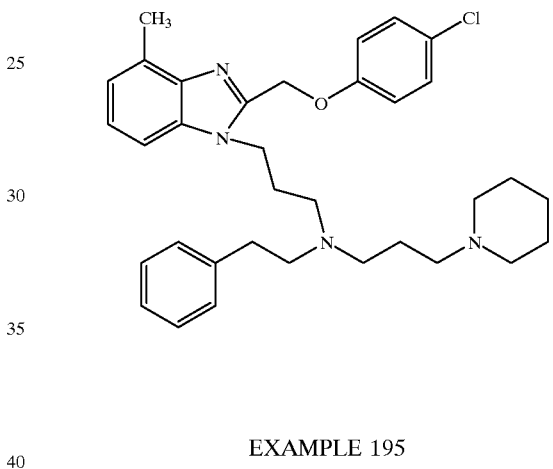

EXAMPLE 195

Preparation of 2-(4-chlorophenoxymethyl)-4-methyl-1-[3-[N-[3-(piperidin-1-yl)propyl]-N-(2-phenylethyl)amino]propyl]benzimidazole

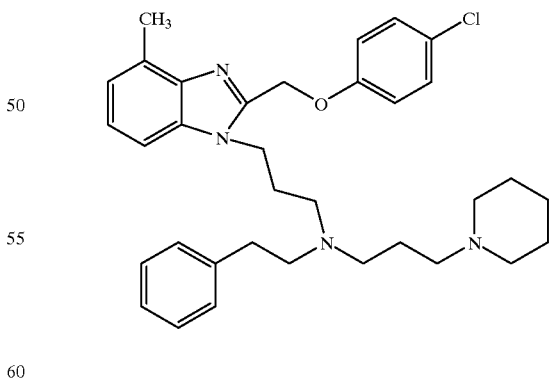

EXAMPLE 196

Preparation of 2-(4-chlorophenoxymethyl)-4-methyl-1-[3-[N-(2-phenylethyl)amino]propyl]benzimidazole

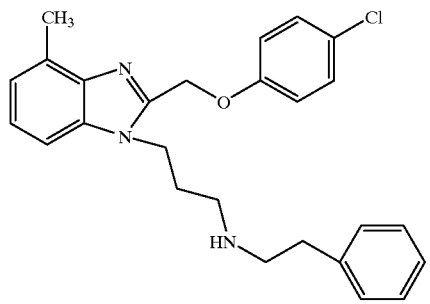

EXAMPLE 197

Preparation of 2-(4-chlorophenoxymethyl)-4-methyl-1-[3-(1,2,3,4-tetrahydroisoquinolin-1-yl)propyl]benzimidazole

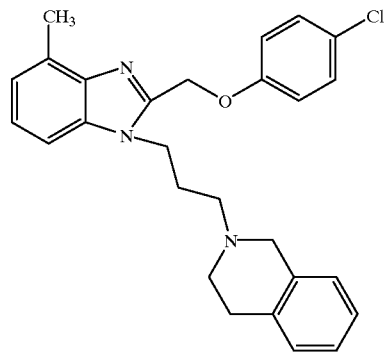

EXAMPLE 198

Preparation of 2-(4-chlorophenoxymethyl)-4-methyl-1-[3-(4-phenylpiperazin-1-yl)propyl]benzimidazole

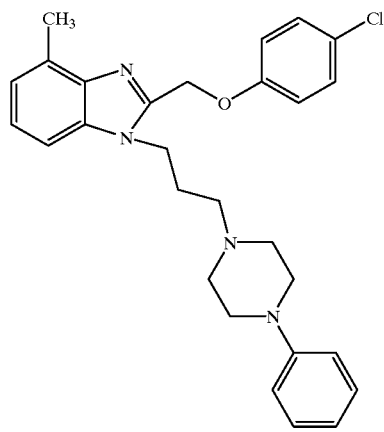

EXAMPLE 199

Preparation of 2-(4-chlorophenoxymethyl)-4-methyl-1-[3-[N-[3-(piperidin-1-yl)propyl]-N-(biphenylacetyl)amino]propyl]benzimidazole

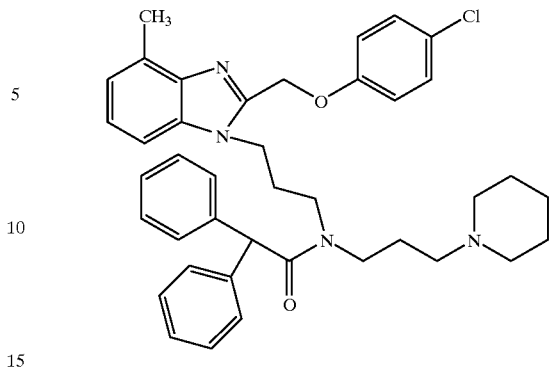

EXAMPLE 200

Preparation of 2-(4-chlorophenoxymethyl)-4-methyl-1-[3-[N-[3-(piperidin-1-yl)propyl]-N-(biphenylacetyl)amino]propyl]benzimidazole

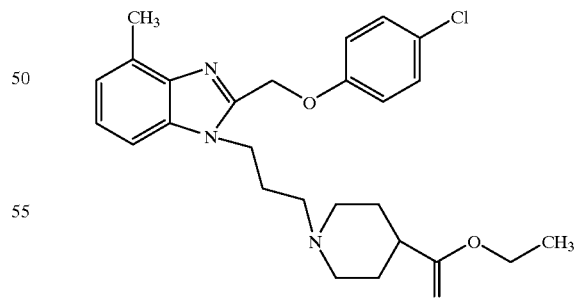

EXAMPLE 201

Preparation of 2-(4-chlorophenoxymethyl)-4-methyl-1-[3-(4-ethoxycarbonylpiperidin-1-yl)propyl]benzimidazole

EXAMPLE 202

Preparation of 2-(4-chlorophenoxymethyl)-4-methyl-1-(3-aminopropyl)benzimidazole

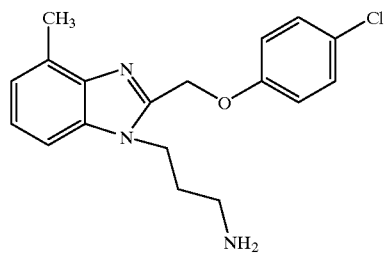

EXAMPLE 203
Preparation of 2-(4-chlorophenoxymethyl)-4-methyl-1-(4-hydroxybutyl)benzimidazole

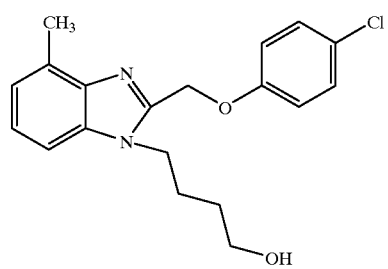

EXAMPLE 204
Preparation of 2-(4-chlorophenoxymethyl)-5-[2-(piperidin-1-yl)ethylcarbamoyl]-1-[3-(piperidin-4-yl)propyl]benzimidazole

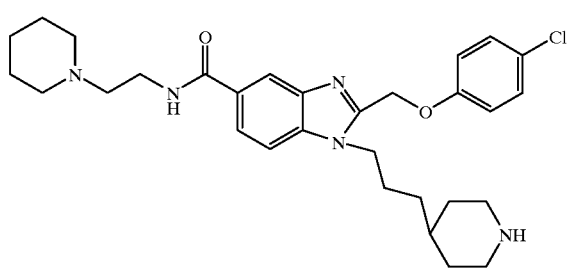

EXAMPLE 205
Preparation of 2-(4-chlorophenoxymethyl)-4-methyl-1-(3-bromopropyl)benzimidazole

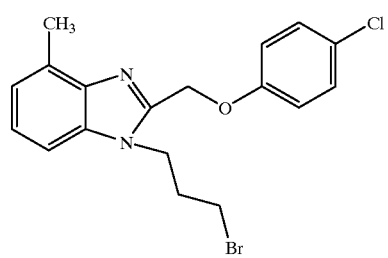

EXAMPLE 206
Preparation of 2-(4-chlorophenoxymethyl)-4-methyl-1-[3-(ethoxycarbonyl)propyl]benzimidazole

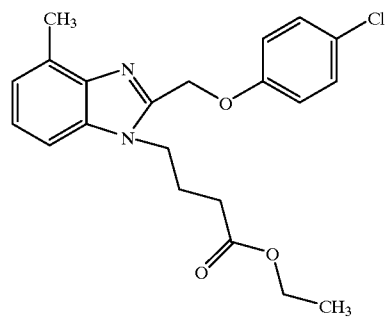

EXAMPLE 207
Preparation of 2-(4-chlorophenoxymethyl)-4-methyl-1-(3-hydroxypropyl)benzimidazole

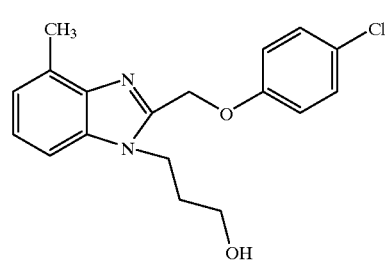

EXAMPLE 208
Preparation of 2-(4-chlorophenoxymethyl)-4-methyl-1-{3-[N-ethyl-N-(3-piperidin-1-ylpropyl)amino]propyl}benzimidazole

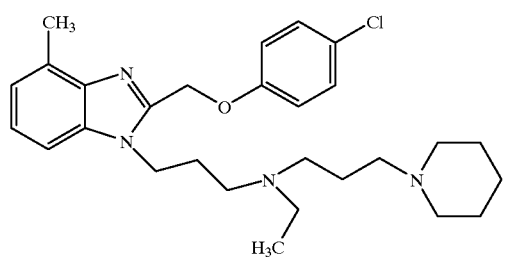

EXAMPLE 209
Preparation of 2-(4-chlorophenoxymethyl)-4-methyl-1-{3-[N-acetyl-N-(3-piperidin-1-ylpropyl)amino]propyl}benzimidazole

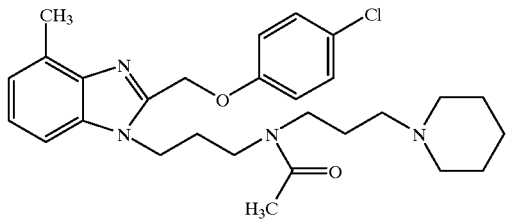

EXAMPLE 210
Preparation of 2-(4-chlorophenoxymethyl)-4-methyl-1-{3-[N-(benzoylmethyl)-N-(3-piperidin-1-ylpropyl)amino]propyl}benzimidazole

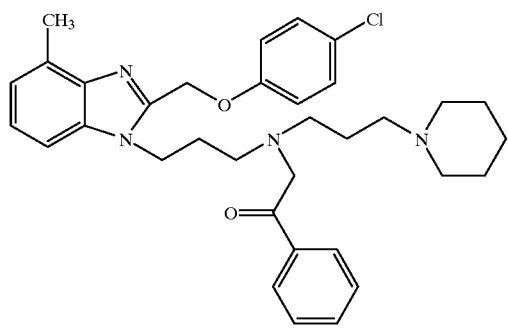

EXAMPLE 211

Preparation of 2-(4-chlorophenoxymethyl)-4-methyl-1-{3-[N-(benzyloxycarbonylmethyl)-N-(3-piperidin-1-ylpropyl)amino]propyl}benzimidazole

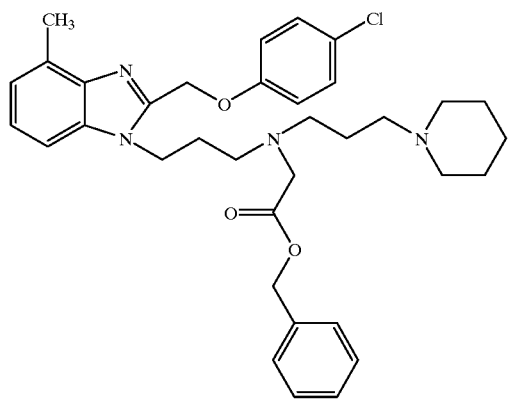

EXAMPLE 212

Preparation of 2-(4-chlorophenoxymethyl)-4-methyl-1-{3-[4-benzoylpiperidin-1-yl]propyl}benzimidazole

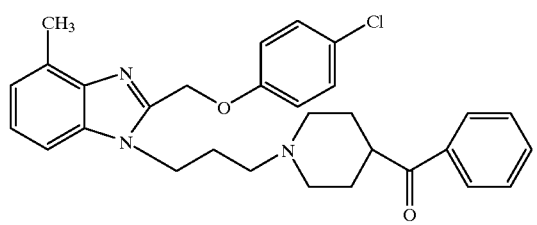

EXAMPLE 212A

Preparation of 2-(4-chlorophenoxymethyl)-4-methyl-1-{3-[2-(piperidin-1-ylethyl)piperidin-1-yl]propyl}benzimidazole

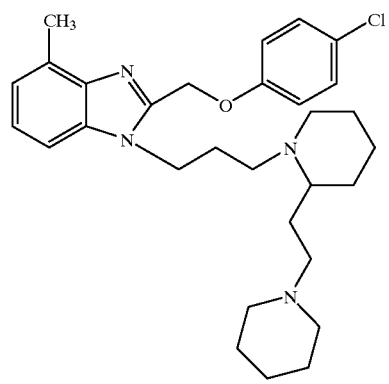

EXAMPLE 213

Preparation of 2-(4-chlorophenoxymethyl)-4-methyl-1-{3-[4-(propylcarbamoylethyl)piperidin-1-yl]propyl}benzimidazole

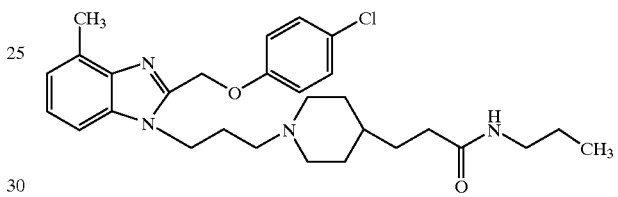

EXAMPLE 214

Preparation of 2-(4-chlorophenoxymethyl)-4-methyl-1-{3-[4-[2-(phenylethylcarbamoyl)ethyl]piperidin-1-yl]propyl}benzimidazole

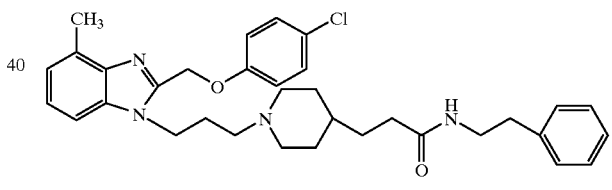

EXAMPLE 215

Preparation of 2-(4-chlorophenoxymethyl)-4-methyl-1-(4-methylamino-3-methylbutyl)benzimidazole

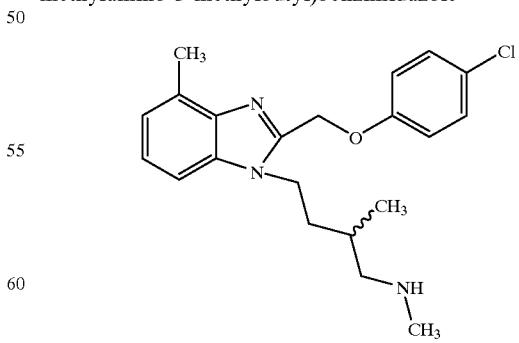

EXAMPLE 216

Preparation of 2-(4-chlorophenoxymethyl)-4-methyl-1-(4-methylamino-3-benzylbutyl)benzimidazole

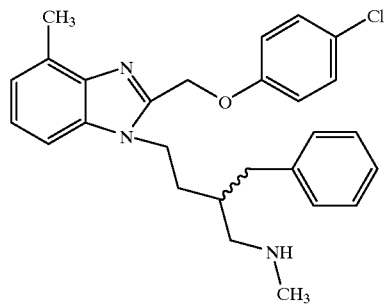

EXAMPLE 217

Preparation of 2-(4-chlorophenoxymethyl)-4-methyl-1-[4-(piperidin-1-yl)-3-methylbutyl]benzimidazole

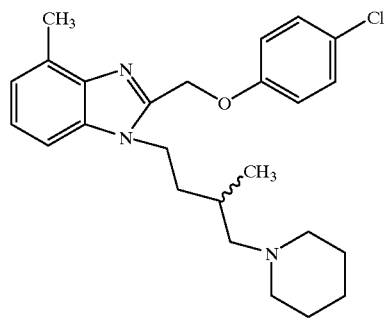

EXAMPLE 218

Preparation of 2-(4-chlorophenoxymethyl)-4-methyl-1-[4-(piperidin-1-yl)-3-benzylbutyl]benzimidazole

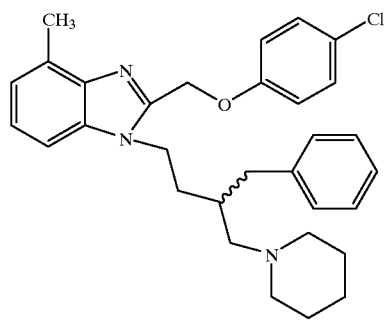

EXAMPLE 219

Preparation of 2-(4-chlorophenoxymethyl)-4-methyl-1-[3-[3-[(piperidin-1-yl)amino]carbonyl]-3-methylpropyl]benzimidazole

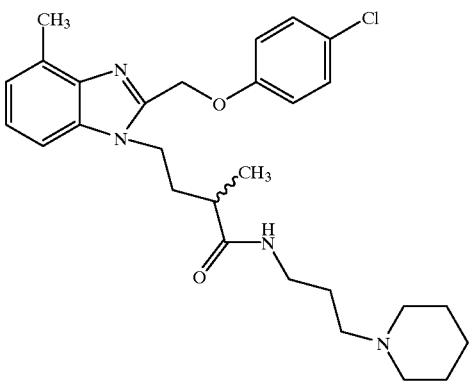

EXAMPLE 220

Preparation of 2-(4-chlorophenoxymethyl)-4-methyl-1-[3-[3-[(piperidin-1-yl)amino]carbonyl]-3-benzylpropyl]benzimidazole

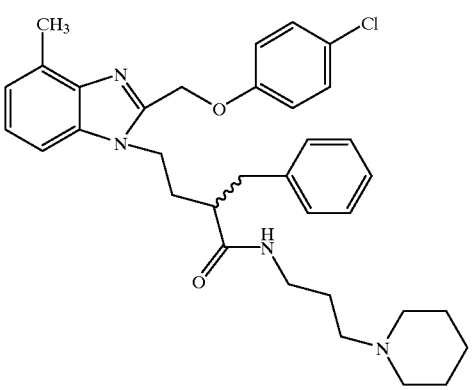

EXAMPLE 221

Preparation of 2-(4-nitrophenoxymethyl)-4-methyl-1-[3-[1-(t-butoxycarbonyl)piperidin-3-yl]propyl]benzimidazole

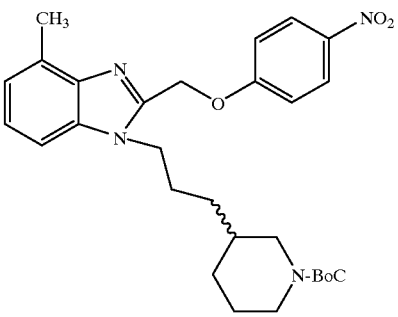

NMR and IR were consistent with the desired title product. FDMS 508 (M+). Analysis for $C_{28}H_{36}N_4O_5$: Theory: C, 66.12; H, 7.13; N, 11.01. Found: C, 65.86; H, 7.09; N, 10.98.

EXAMPLE 222

Preparation of 2-(4-aminophenoxymethyl)-4-methyl-1-[3-[1-(t-butoxycarbonyl)piperidin-3-yl]propyl]benzimidazole

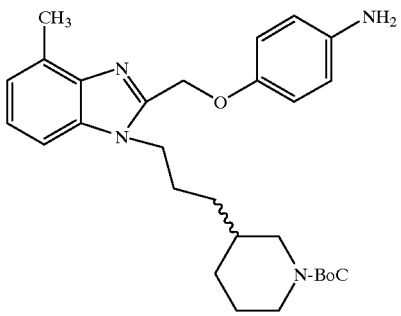

A mixture of 2-(4-nitrophenoxymethyl)-4-methyl-1-[3-[1-(t-butoxycarbonyl)piperidin-3-yl]propyl]benzimidazole (395 mg, 0.78 mmol) and 10% palladium on activated carbon (400 mg) in 10 ml of ethanol was stirred under a hydrogen atmosphere at room temperature. After two hours, the reaction mixture was filtered through a CELITE™ cake. The filtrate was condensed on a rotoevaporator to yield 310 mg (83%) of the desired title product.

NMR and IR were consistent with the desired title product. FDMS 478 (M+). Analysis for $C_{28}H_{38}N_4O_3$: Theory: C, 70.26; H, 8.00; N, 11.70. Found: C, 70.00; H, 7.97; N, 11.60.

EXAMPLE 223

Preparation of 2-[4-(t-butoxycarbonylamino) phenoxymethyl]-4-methyl-1-[3-[1-(t-butoxycarbonyl) piperidin-3-yl]propyl]benzimidazole

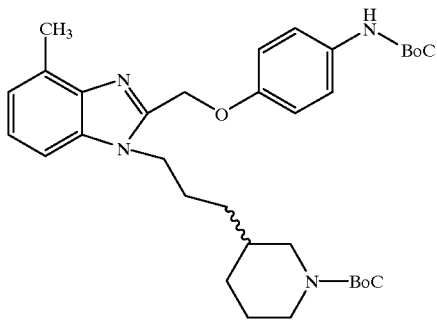

A solution of 2-(4-aminophenoxymethyl)-4-methyl-1-[3-[1-(t-butoxycarbonyl)piperidin-3-yl]propyl]benzimidazole (160 mg, 0.33 mmol, 1.0 eq.) in a 1:1 mixture of anhydrous tetrahydrofuran and water (2 ml total) was treated wtih potassium carbonate (56 mg, 0.4 mmol, 1.2 eq.) and di-t-butyl dicarbonate (90 mg, 0.4 mmol, 1.2 eq.). The mixture was stirred at room temperature for two hours. Water (10 ml) was added to the mixture. The organic fraction was extracted with ethyl acetate (3×10 ml). The combined organic fraction was washed with water (10 ml), brine (1×10 ml), and then dried over sodium sulfate. The solvents were removed in vacuo. The title product was further purified by flash chromatography. Yield: 190 mg (>99%).

Preparation 52

Preparation of α-benzyl-γ-butyrolactone (3-benzyl-3,4-dihydrofuran-2-one)

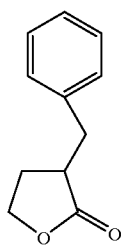

To a solution of diisopropylamine (15.18 g, 0.15 mol) in dry tetrahydrofuran (200 ml) at −78° C. under a nitrogen atmosphere, n-butyllithium (1.6 M in hexanes, 94 ml, 0.15 mol) was added dropwise. After twenty minutes of stirring at −78° C., γ-butyrolactone (12.91 g, 0.15 mol) was added dropwise, such that the reaction temperature was maintained below −70° C. After twenty minutes of stirring at −78° C., a mixture of benzyl bromide (25.65 g, 0.15 mol) and hexamethylphosphoramide (26.85 g, 0.15 mol) was added dropwise to the reaction mixture. The reaction mixture was then permitted to warm to −30° C. and stirred at this temperature for two hours.

The reaction mixture was partitioned between a saturated ammonium chloride solution (500 ml) and diethyl ether (500 ml). The organic fraction was dried over potassium carbonate and the solvents were removed in vacuo to yield 36.13 grams of the desired intermediates as a dark yellow oil.

The crude material was further purified by flash silica gel chromatography eluting with a solvent gradient beginning at 19:1 hexanes/ethyl acetate and ending with 3:1 hexanes/ethyl acetate. The fractions containing desired product were combined and concentrated under reduced pressure to yield 20.1 grams (76%) as a pale yellow oil.

IR and NMR were consistent with the proposed title structure. FDMS 177 (M+1). Analysis for $C_{11}H_{12}O_2$: Theory: C, 74.98; H, 6.86. Found: C, 74.76; H, 6.73.

Preparation 53

Preparation of ethyl 2-benzyl-4-bromobutanoate

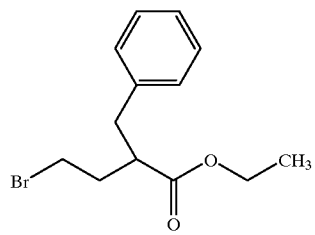

In absolute ethanol (78 ml), α-benzyl-γ-butyrolactone (14 g, 80 mmol) was added and then saturated for thirty minutes with gaseous hydrogen bromide, maintaining the temperature below 50° C. The reaction was then heated to 45° C. and stirred at this temperature for 16 hours. The solution was concentrated under reduced pressure and the resulting oil was taken into ethyl acetate (500 ml), washed once with water, and then dried over magnesium sulfate. The solvents were removed in vacuo to yield 15.13 grams of tan oil.

The crude mixture was further purified by flask silica gel chromatography, eluting with a gradient solvent of hexanes to a 1:1 mixture of hexanes/methylene chloride. The fractions containing the desired intermediate were combined and concentrated under reduced pressure to yield 13.47 grams (67%).

IR and NMR were consistent with the proposed title structure. FDMS 286.1 (M+1). Analysis for $C_{13}H_{17}O_2Br$: Theory: C, 54.75; H, 6.01. Found: C, 54.99; H, 6.02.

Preparation 54
Preparation of ethyl 2-methyl-4-bromobutanoate

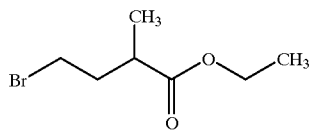

In absolute ethanol (78 ml), α-methyl-γ-butyrolactone (8 g, 8 mmol) was added and then saturated for thirty minutes with gaseous hydrogen bromide, maintaining the temperature below 50° C. The reaction was then heated to 45° C. and stirred at this temperature for 16 hours. The solution was concentrated under reduced pressure and the resulting oil was taken into ethyl acetate (500 ml), washed once with water, and then dried over magnesium sulfate. The solvents were removed in vacuo.

The crude mixture was further purified by flask silica gel chromatography, eluting with a gradient solvent of hexanes to a 1:1 mixture of hexanes/methylene chloride. The fractions containing the desired intermediate were combined and concentrated under reduced pressure to yield 7.1 grams (44%).

IR and NMR were consistent with the proposed title structure. FDMS 208, 209, 210; Analysis for $C_7H_{13}O_2Br$: Theory: C, 40.21; H, 6.27. Found: C, 39.24; H, 6.19.

Preparation 55
Preparation of (RS) ethyl 2-phenyl-4-chlorobutanoate

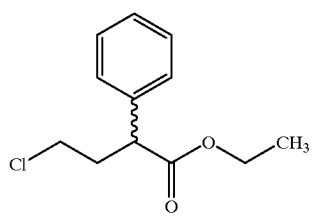

To a solution of diisopropylamine (23 ml, 0.16 mol) in dry tetrahydrofuran (100 ml) at −78° C., under a nitrogen atmosphere, was added dropwise n-butyllithium (100 ml of a 1.6 M solution, 160 mmol). After stirring for thirty minutes at −78° C., ethyl phenylacetate (25 g, 0.15 mol) in dry tetrahydrofuran (172 ml) was added dropwise to the reaction mixture. The resulting mixture was permitted to warm to −30° C. After stirring for fifteen minutes at −30° C., N,N'-dimethylpropylene urea (18 ml, 0.15 mol) in dry tetrahydrofuran (30 ml) was added dropwise and the resulting mixture was stirred for ten minutes.

The reaction mixture was added via cannula under nitrogen atmosphere into a flask containing 1-bromo-2-chloroethane (63 ml, 0.75 mol) in diethyl ether (200 ml) at −15° C. This reaction mixture was then stirred at −15° C. for three hours. The reaction mixture was partitioned between a saturated ammonium chloride in water solution (500 ml) and diethyl ether (1 L). The organic fraction was dried over potassium carbonate and the solvents were removed in vacuo to yield 41.37 grams of oil.

The crude material was further purified by flask solica gel chromatography, eluting with a solvent gradient of hexanes to 1:1 hexanes:methylene chloride. Fractions containing the desired title product were combined and concentrated under reduced pressure to yield 15.0 grams (44%) as a clear oil.

NMR was consistent with the proposed title structure. FDMS 226.1 (M+). Analysis for $C_{12}H_{15}O_2Cl$: Theory: C, 63.58; H, 6.67. Found: C, 63.29; H, 6.80.

Preparation 56
Preparation of 4-(cyclohexyl)piperidine and 4-phenylpiperidine

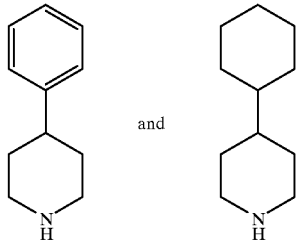

3-Phenylpyridine (25 g, 0.16 mol) was placed in ethanol (470 ml) along with rhodium (5% on alumina, 5.0 g) and was subjected to hydrogenation at room temperature for four hours at 60 psi. The resulting solution was then filtered, and the resulting oil was taken into ethyl acetate (500 ml), washed with water, and then dired over potassium carbonate. The solvents were removed in vacuo to yield 24.41 grams of a tan oil. The mixture of compounds was further purifed by flash chromatography, eluting with methanol. The fractions containing the desired title intermediates were combined and concentrated in vacuo to yield 22.41 grams (86%) of a clear oil.

NMR and FDMS were consistent with the proposed title structures.

Preparation 57
Preparation of 4-(cyclohexylmethyl)piperidine and 4-benzylpiperidine

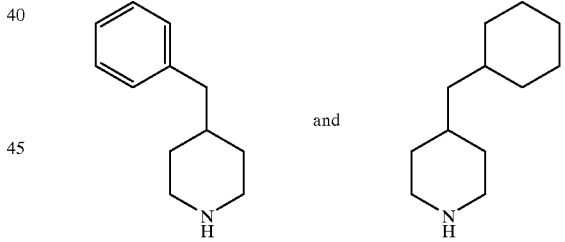

3-Benzylpyridine (5 g, 0.029 mol) was placed in ethanol (145 ml) along with rhodium (5% on alumina, 0.125 g) and was subjected to hydrogenation at room temperature for four hours at 60 psi. The resulting solution was then filtered, and the resulting oil was taken into ethyl acetate (500 ml), washed with water, and then dired over potassium carbonate. The solvents were removed in vacuo to yield 4.71 grams of a tan oil. The mixture of compounds was further purifed by flash chromatography, eluting with methanol. The fractions containing the desired title intermediates were combined and concentrated in vacuo to yield 3.64 grams (71%) of a clear oil.

NMR and FDMS were consistent with the proposed title structures.

EXAMPLE 224
Preparation of 1-[3-(ethoxycarbonyl)butyl]-2-[(4-chlorophenoxy)methyl]-4-methylbenzimidazole

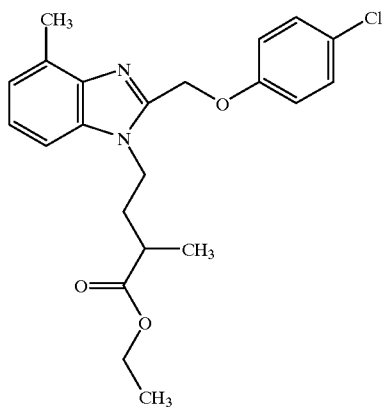

A sodium hydride solution (60% in oil, 810 mg, 20.3 mmol) was washed with hexanes (2×50 ml) and then diluted with N,N-dimethylformamide (100 ml). At room temperature, under a nitrogen atmosphere, 2-[(4-chlorophenoxy)methyl]-4-methylbenzimidazole (5 g, 18.3 mmol) was then added in one portion. The resulting mixture was then stirred at room temperature for thirty minutes, and then 3-(ethoxycarbonyl)butyl bromide (4.25 g, 20.3 mmol) in N,N-dimethylformamide (10 ml) was added dropwise. Upon completion of this addition, the reaction mixture was stirred for about six hours at a temperature of 70–80° C. The reaction mixture was then cooled to room temperature, poured into water (500 ml), and then extracted with ethyl acetate (500 ml). The organic fraction was washed once with water (500 ml) and then dried over potassium carbonate. The solvents were removed in vacuo, yielding 8.01 grams of a dark oil. The crude material was further purified by flash silica gel chromatography, eluting with a gradient solvent of methylene chloride to 3:1 methylene chloride:ethyl acetate. The fractions containing the desired title product were combined and concentrated in vacuo to yield 7.21 grams (98%) of a viscous yellow oil.

NMR and IR were consistent with the proposed title structure. FDMS 401 (M+). Analysis for $C_{22}H_{25}N_2O_3Cl$: Theory: C, 65.91; H, 6.29; N, 6.99. Found: C, 66.13; H, 6.50; N, 7.11.

EXAMPLE 225
Preparation of 1-[3-(ethoxycarbonyl)-4-phenylbutyl]-2-[(4-chlorophenoxy)methyl]-4-methylbenzimidazole

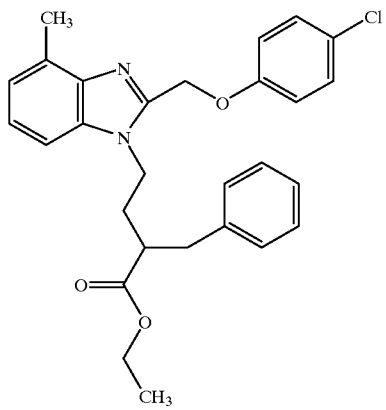

A sodium hydride solution (60% in oil, 810 mg, 20.3 mmol) was washed with hexanes (2×50 ml) and then diluted with N,N-dimethylformamide (100 ml). At room temperature, under a nitrogen atmosphere, 2-[(4-chlorophenoxy)methyl]-4-methylbenzimidazole (5.0 g, 18.3 mmol) was then added in one portion. The resulting mixture was then stirred at room temperature for thirty minutes, and then 3-(ethoxycarbonyl)-4-phenylbutyl bromide (5.79 g, 20.3 mmol) in N,N-dimethylformamide (10 ml) was added dropwise. Upon completion of this addition, the reaction mixture was stirred for about six hours at a temperature of 70–80° C. The reaction mixture was then cooled to room temperature, poured into water (500 ml), and then extracted with ethyl acetate (500 ml). The organic fraction was washed once with water (500 ml) and then dried over potassium carbonate. The solvents were removed in vacuo, yielding 10.28 grams of a dark oil. The crude material was further purified by flash silica gel chromatography, eluting with a gradient solvent of methylene chloride to 9:1 methylene chloride:ethyl acetate. The fractions containing the desired title product were combined and concentrated in vacuo to yield 8.08 grams (93%) of a viscous yellow oil.

NMR and IR were consistent with the proposed title structure. FDMS 476,477 (M+). Analysis for $C_{28}H_{29}N_2O_3Cl$: Theory: C, 70.50; H, 6.13; N, 5.87. Found: C, 67.56; H, 6.22; N, 6.37.

EXAMPLE 226
Preparation of 1-[3-(ethoxycarbonyl)propyl]-2-[(4-chlorophenoxy)methyl]-4-methylbenzimidazole

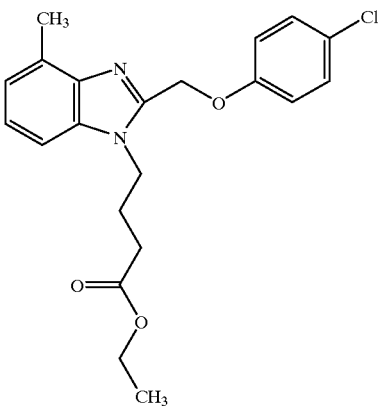

A sodium hydride solution (60% in oil, 325 mg, 8.1 mmol) was washed with hexanes (2×50 ml) and then diluted with N,N-dimethylformamide (100 ml). At room temperature, under a nitrogen atmosphere, 2-[(4-chlorophenoxy)methyl]-4-methylbenzimidazole (2.0 g, 7.3 mmol) was then added in one portion. The resulting mixture was then stirred at room temperature for thirty minutes, and then 3-(ethoxycarbonyl)propyl bromide (1.58 g, 8.1 mmol) in N,N-dimethylformamide (10 ml) was added dropwise. Upon completion of this addition, the reaction mixture was stirred for about six hours at a temperature of 70–80° C. The reaction mixture was then cooled to room temperature, poured into water (500 ml), and then extracted with ethyl acetate (500 ml). The organic fraction was washed once with water (500 ml) and then dried over potassium carbonate. The solvents were removed in vacuo, yielding 3.16 grams of a semi-solid material. The crude material was firther purified by flash silica gel chromatography, eluting with a gradient solvent of methylene chloride to 1:1 methylene chloride:ethyl acetate. The fractions containing the desired title product were combined and concentrated in vacuo to yield 2.21 grams (78%) of a viscous yellow oil.

mp 78.5–80° C.; NMR was consistent with the proposed title structure. FDMS 386 (M+). Analysis for $C_{21}H_{23}N_2O_3Cl$: Theory: C, 65.20; H, 5.99; N, 7.24. Found: C, 64.97; H, 6.05; N, 7.23.

EXAMPLE 227

Preparation of 1-(3-carboxybutyl)-2-[(4-chlorophenoxy)methyl]-4-methylbenzimidazole

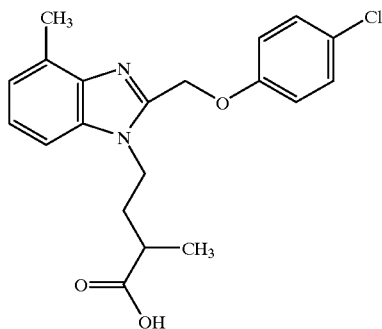

To a mixture of tetrahydrofuran (42 ml), methanol (14 ml), and water (14 ml), were added 1-[3-(ethoxycarbonyl)butyl]-2-[(4-chlorophenoxy)methyl]-4-methylbenzimidazole (1.3 g, 3.2 mmol) and lithium hydroxide (403 mg, 3 eq.). The resulting mixture was stirred overnight at room temperature and was then concentrated in vacuo to yield a white solid. This residue was taken into 250 ml of a 3:1 butanol:toluene solution. The organic fraction was washed once with 200 ml of water and then dried over magnesium sulfate. The solvents were removed in vacuo to yield 1.22 grams of tan solid, which was further purified by flash chromatography, eluting with a gradient solvent of 19:1 ethyl acetate:methanol to 9:1 ethyl acetate:methanol. The fractions containing the desired material were combined and concentrated under reduced pressure to yield 1.12 grams (94%) of the desired title product as a white solid.

mp 149–151° C.; NMR and IR were consistent with the proposed title structure. FDMS 373 (M+). Analysis for $C_{20}H_{21}N_2O_3Cl$: Theory: C, 64.43; H, 5.68; N, 7.51. Found: C, 64.62; H, 5.91; N, 7.26.

EXAMPLE 228

Preparation of 1-(4-phenyl-3-carboxybutyl)-2-[(4-chlorophenoxy)methyl]-4-methylbenzimidazole

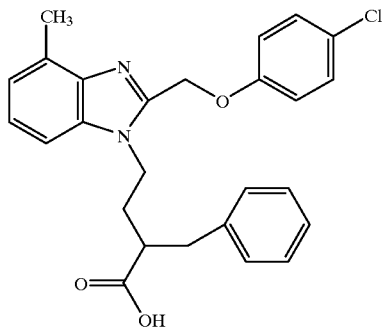

To a mixture of tetrahydrofuran (84 ml), methanol (28 ml), and water (28 ml), were added 1-[3-(ethoxycarbonyl)-4-phenylbutyl]-2-[(4-chlorophenoxy)methyl]-4-methylbenzimidazole (3.05 g, 6.4 mmol) and lithium hydroxide (788 mg, 3 eq.). The resulting mixture was stirred overnight at room temperature and was then concentrated in vacuo to yield a white solid. This residue was taken into 250 ml of a 3:1 butanol:toluene solution. The organic fraction was washed once with 200 ml of water and then dried over magnesium sulfate. The solvents were removed in vacuo to yield 4.17 grams of tan solid, which was further purified by flash chromatography, eluting with a gradient solvent of 19:1 ethyl acetate:methanol to 9:1 ethyl acetate:methanol. The fractions containing the desired material were combined and concentrated under reduced pressure to yield 2.71 grams (94%) of the desired title product as a white solid.

mp 190–191.5° C.; NMR and IR were consistent with the proposed title structure. FDMS 448 (M+). Analysis for $C_{26}H_{25}N_2O_3Cl$: Theory: C, 69.56; H, 5.61; N, 6.24. Found: C, 69.77; H, 5.68; N, 6.46.

EXAMPLE 229

Preparation of 1-(3-carboxypropyl)-2-[(4-chlorophenoxy)methyl]-4-methylbenzimidazole

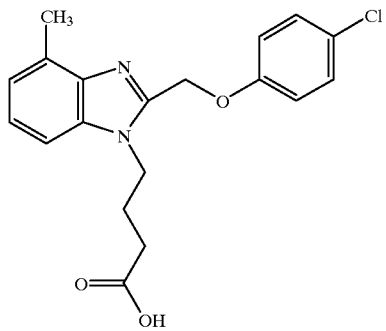

To a mixture of tetrahydrofuran (72 ml), methanol (24 ml), and water (24 ml), were added 1-[3-(ethoxycarbonyl)propyl]-2-[(4-chlorophenoxy)methyl]-4-methylbenzimidazole (2.0 g, 5.2 mmol) and lithium hydroxide (642 mg, 3 eq.). The resulting mixture was stirred overnight at room temperature and was then concentrated in vacuo to yield a white solid. This residue was taken into 250 ml of a 3:1 butanol:toluene solution. The organic fraction was washed once with 200 ml of water and then dried over magnesium sulfate. The solvents were removed in vacuo to yield 1.56 grams of tan solid, which was further purified by flash chromatography, eluting with a gradient solvent of 19:1 ethyl acetate:methanol to 9:1 ethyl acetate:methanol. The fractions containing the desired material were combined and concentrated under reduced pressure to yield 1.31 grams (70%) of the desired title product as a white solid.

NMR was consistent with the proposed title structure. FDMS 359 (M+). Analysis for $C_{19}H_{19}N_2O_3Cl$: Theory: C, 63.60; H, 5.34; N, 7.81. Found: C, 63.32; H, 5.26; N, 7.82.

EXAMPLE 230

Preparation of 1-[3-(N-methylcarbamoyl)butyl]-2-[(4-chlorophenoxy)methyl]-4-methylbenzimidazole

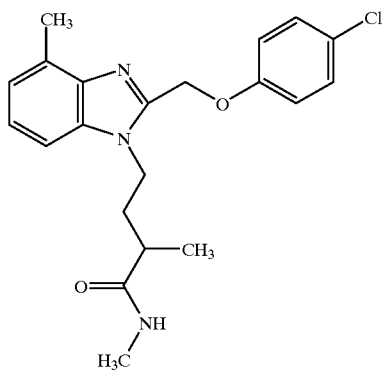

In methylamine (40% in water, 20 ml), 1-[3-(ethoxycarbonyl)butyl]-2-[(4-chlorophenoxy)methyl]-4-methylbenzimidazole (1.50 g, 3.7 mmol) was placed. To this mixture 10 ml of methanol were added, to enhance solubility. The resulting mixture was stirred at room temperature for about 64 hours, after which time the reaction mixture was concentrated in vacuo. The residue was taken up in 200 ml of methylene chloride. The organic fraction was washed once with 200 ml of water. The organic fraction was dried over potassium carbonate and the solvents were removed in vacuo to yield 1.61 grams of a dark oil. The crude material was further purified by flash silica gel chromatography, eluting with a gradient of methylene chlor ide to a 1:1 methylene chloride:ethyl acetate mixture. The fractions containing the desired material were combined and concentrated under reduced pressure to yield 510 mg (36%) of the desired title product as a white solid.

mp 167.5–168.5° C.; NMR and IR were consistent with the proposed title structure. FDMS 386 (M+). Analysis for $C_{21}H_{24}N_3O_2Cl$: Theory: C, 65.36; H, 6.27; N, 10.89. Found: C, 65.10; H, 6.46; N, 10.96.

EXAMPLE 231
Preparation of 1-[3-(N-methylcarbamoyl)-4-phenylbutyl]-2-[(4-chlorophenoxy)methyl]-4-methylbenzimidazole

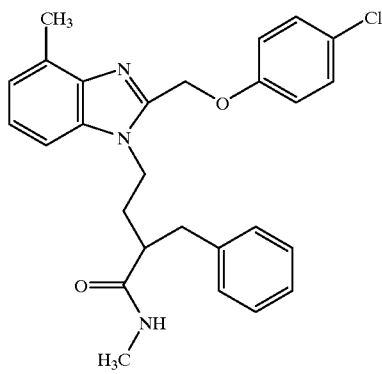

In methylamine (40% in water, 10 ml), 1-[3-(ethoxycarbonyl)-4-phenylbutyl]-2-[(4-chlorophenoxy)methyl]-4-methylbenzimidazole (1.0 g, 2.5 mmol) was placed. To this mixture 10 ml of methanol were added, to enhance solubility. The resulting mixture was stirred at room temperature for about 64 hours, after which time the reaction mixture was concentrated in vacuo. The residue was taken up in 200 ml of methylene chloride. The organic fraction was washed once with 200 ml of water. The organic fraction was dried over potassium carbonate and the solvents were removed in vacuo to yield 0.967 grams of a viscous oil. The crude material was further purified by flash silica gel chromatography, eluting with a gradient of methylene chloride to a 1:1 methylene chloride:ethyl acetate mixture. The fractions containing the desired material were combined and concentrated under reduced pressure to yield 305 mg (26%) of the desired title product as a crystalline material.

mp 169–170.5° C.; NMR and IR were consistent with the proposed title structure. FDMS 461, 462 (M+). Analysis for $C_{27}H_{28}N_3O_2Cl$: Theory: C, 70.20; H, 6.11; N, 9.09. Found: C, 69.91; H, 5.85; N, 9.09.

EXAMPLE 232

Preparation of 1-[3-(chlorocarbonyl)butyl]-2-[(4-chlorophenoxy)methyl]-4-methylbenzimidazole

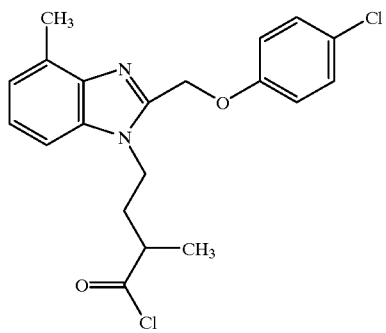

Under a nitrogen atmosphere at room temperature 1-[3-(carboxy)butyl]-2-[(4-chlorophenoxy)methyl]-4-methylbenzimidazole (1.2 g, 3.2 mmol) was added in one portion to oxalyl chloride (5 ml) in methylene chloride (150 ml). After the material solubilized, one drop of N,N-dimethylformamide was added to initiate the reaction. Bubbling of the solution began and was visible for approximately fifteen minutes. The reaction mixture was stirred at room temperature for two hours. The reaction mixture was then concentrated under reduced pressure, reuslting in the formation of a white solid. The solid was triturated in 100 ml of hexanes, filtered and dried in a vacuum oven at 50° C. for one hours to yield the title product (1.3 g, 91%) as a white solid.

mp 140–142° C.; NMR was consistent with the proposed title structure. FDMS 390, 391 (M+). Analysis for $C_{20}H_{20}N_2O_2Cl$: Theory: C, 61.39; H, 5.15; N, 7.16. Found: C, 56.11; H, 5.00; N, 6.61.

EXAMPLE 233

Preparation of 1-[3-(carbamoyl)butyl]-2-[(4-chlorophenoxy)methyl]-4-methylbenzimidazole

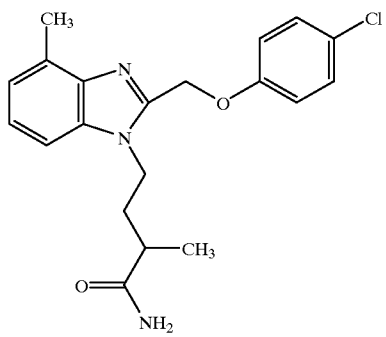

In an ammonium hydroxide solution (28%, 10 ml) was placed 1-[3-(chlorocarbonyl)butyl]-2-[(4-chlorophenoxy)methyl]-4-methylbenzimidazole (400 mg, 1.0 mmol). To this mixture 10 ml of methanol were added, to enhance solubility and the mixture was stirred for about 64 hours at room temperature. The reaction mixture was then concentrated under reduced pressure to produce a tan foam. The crude material was further purified by flash silica gel chromatography, eluting with a gradient solvent of 19:1 ethyl acetate:methanol to 9:1 ethyl acetate:methanol. The fractions containing the desired material were combined and concentrated in vacuo to yield 300 mg (73%) of the desired title compound as a white foam.

NMR was consistent with the proposed title structure. FDMS 371.3 (M+).

EXAMPLE 234

Preparation of 1-[3-(N,N-dimethylcarbamoyl)butyl]-2-[(4-chlorophenoxy)methyl]-4-methylbenzimidazole

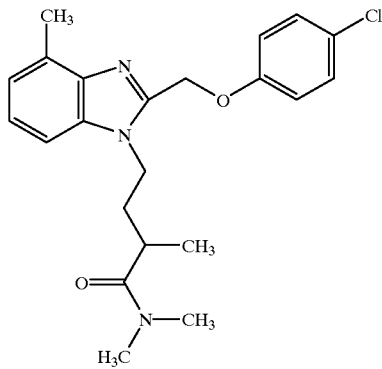

In an dimethylamine (40% in water, 10 ml) was placed 1-[3-(chlorocarbonyl)butyl]-2-[(4-chlorophenoxy)methyl]-4-methylbenzimidazole (600 mg, 1.5 mmol). To this mixture 10 ml of methanol were added, to enhance solubility and the mixture was stirred for about 64 hours at room temperature. The reaction mixture was then concentrated under reduced pressure to produce 600 mg as a tan foam. The crude material was further purified by flash silica gel chromatography, eluting with a gradient solvent of 19:1 ethyl acetate:methanol to 9:1 ethyl acetate:methanol. The fractions containing the desired material were combined and concentrated in vacuo to yield 375 mg (63%) of the desired title compound as a white foam.

NMR was consistent with the proposed title structure.

EXAMPLE 235

Preparation of 1-[4-(methylamino)-3-methylbutyl]-2-[(4-chlorophenoxy)methyl]-4-methylbenzimidazole dihydrochloride salt monohydrate

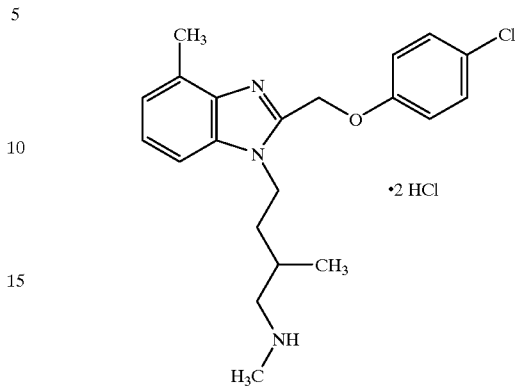

Under a nitrogen atmosphere 1-[3-[(methylamino)carbonyl]butyl]-2-[(4-chlorophenoxy)methyl]-4-methylbenzimidazole (100 mg, 0.26 mmol) was added via spatual to a solution of RED-AL™ (2 ml) in 10 ml dry toluene at room temperature. The reaction mixture was then heated to 55° C. for fifteen minutes. The reaction mixture was cooled to room temperature and poured into 100 ml of water, and was then extracted with 200 ml ethyl acetate. The organic fraction was washed once with water, and then dried over potassium carbonate. The solvents were removed in vacuo to yield 107 mg of a viscous oil. The crude material was further purified by flash chromatography, eluting with 2% ethylamine in methanol. The fractions containing the desired title product were combined and concentrated under reduced pressure to yield 30 mg of a viscous oil (Yield 31%).

The title desired product was converted to the dihydrochloride salt by placing the free base in 10 ml ethyl acetate and adding a saturated solution of hydrochloric acid in diethyl ether, until solution turned congo red litmus slightly blue. The solvents were removed in vacuo and the resulting white residue was triturated in diethyl ether. Drying at 60° C. for one hour yield 32 mg of the dihydrochloride salt as a white solid.

mp 79–81° C.; FDMS 371 (M+). Analysis for $C_{21}H_{28}N_3OCl.2HCl.H_2O$: Theory: C, 54.49; H, 6.53; N, 9.08. Found: C, 54.55; H, 6.23; N, 8.97.

EXAMPLE 236

Preparation of 1-[4-(methylamino)-3-benzylbutyl]-2-[(4-chlorophenoxy)methyl]-4-methylbenzimidazole dihydrochloride salt

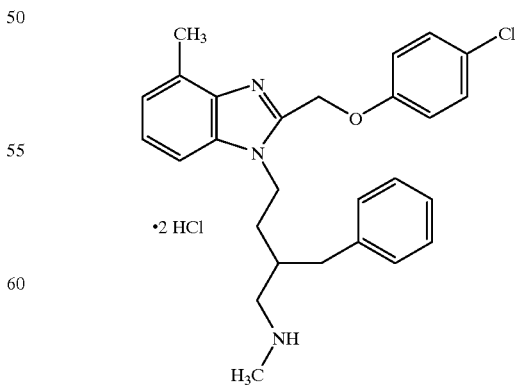

Under a nitrogen atmosphere 1-[3-[(methylamino)carbonyl]-4-phenylbutyl]-2-[(4-chlorophenoxy)methyl]-4- methylbenzimidazole (470 mg, 0.87 mmol) was added via spatual to a solution of RED-AL™ (3 ml) in 10 ml dry toluene at room temperature. The reaction mixture was then heated to 55° C. for fifteen minutes. The reaction mixture was cooled to room temperature and poured into 100 ml of water, and was then extracted with 200 ml ethyl acetate. The organic fraction was washed once with water, and then dried over potassium carbonate. The solvents were removed in vacuo to yield 161 mg of a viscous oil. The crude material was further purified by flash chromatography, eluting with 2% ethylamine in methanol. The fractions containing the desired title product were combined and concentrated under reduced pressure to yield 117 mg of a viscous oil (Yield 30%).

The title desired product was converted to the dihydrochloride salt by placing the free base in 10 ml ethyl acetate and adding a saturated solution of hydrochloric acid in diethyl ether, until solution turned congo red litmus slightly blue. The solvents were removed in vacuo and the resulting white residue was triturated in diethyl ether. Drying at 60° C. for one hour yield 104 mg of the dihydrochloride salt as a white solid.

mp 106–109° C.; NMR was consistent with the proposed title structure. FDMS 448 (M+). Analysis for $C_{27}H_{32}N_3OCl.2HCl$: Theory: C, 62.25; H, 6.19; N, 8.07. Found: C, 63.77; H, 6.33; N, 8.30.

EXAMPLE 237

Preparation of 1-[4-(piperidin-1-yl)-3-methylbutyl]-2-[(4-chlorophenoxy)methyl]-4-methylbenzimidazole dihydrochloride salt

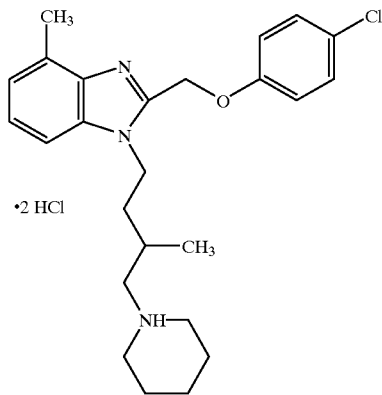

Under a nitrogen atmosphere 1-[3-[(piperidin-1-yl)carbonyl]butyl]-2-[(4-chlorophenoxy)methyl]-4-methylbenzimidazole (800 mg, 1.80 mmol) was added via spatual to a solution of RED-AL™ (5 ml) in 10 ml dry toluene at room temperature. The reaction mixture was then heated to 55° C. for fifteen minutes. The reaction mixture was cooled to room temperature and poured into 100 ml of water, and was then extracted with 200 ml ethyl acetate. The organic fraction was washed once with water, and then dried over potassium carbonate. The solvents were removed in vacuo to yield 700 mg of a viscous oil. The crude material was further purified by flash chromatography, eluting with 2% ethylamine in methanol. The fractions containing the desired title product were combined and concentrated under reduced pressure to yield 200 mg of a light yellow oil (Yield 27%).

The title desired product was converted to the dihydrochloride salt by placing the free base in 10 ml ethyl acetate and adding a saturated solution of hydrochloric acid in diethyl ether, until solution turned congo red litmus slightly blue. The solvents were removed in vacuo and the resulting white residue was triturated in diethyl ether. Drying at 60° C. for one hour yielded the dihydrochloride salt as a white solid.

mp 98–102° C.; NMR was consistent with the proposed title structure. FDMS 425, 426 (M+). Analysis for $C_{25}H_{34}N_3OCl.2HCl$: Theory: C, 60.19; H, 6.87; N, 8.42. Found: C, 60.33; H, 6.88; N, 8.69.

EXAMPLE 238

Preparation of 1-[3-[(piperidin-1-yl)carbonyl]-4-phenylbutyl]-2-[(4-chlorophenoxy)methyl]-4-methylbenzimidazole

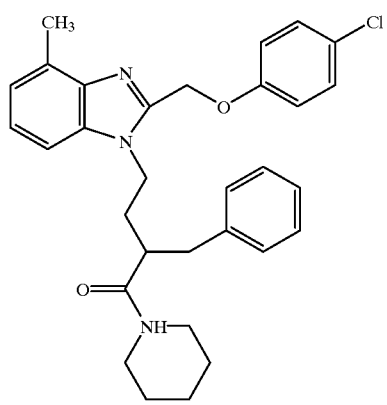

To a stirring solution of 1-[3-carboxy-4-phenylbutyl]-2-[(4-chlorophenoxy)methyl]-4-methylbenzimidazole (1.0 g, 2.2 mmol) in N,N-dimethylformamide (75 ml) were added sequentially piperidine (206 mg, 1.1 eq), 1-hydroxybenzotriazole (327 mg, 1.1 eq), and dicyclohexylcarbodiimide (500 mg, 1.1 eq). The resulting mixture was then stirred under a nitrogen atmosphere at room temperature for 64 hours. The reaction mixture was then filtered and the resulting filtrate was concntrated under reduced pressure. This residue was taken into ethyl acetate (200 ml) and washed once with water (200 ml), dried over potassium carbonate. The solvents were removed in vacuo to yield 1.84 grams of a tan foam.

This crude material was purified by flash silica gel chromatography, eluting with a gradient solvent of 9:1 hexanes:ethyl acetate to 1:1 hexanes:ethyl acetate. The fractions containing the desired material were combined and concentrated under reduced pressure to yield 880 mg (77%) of the desired title product as a viscous oil. The slowly crystallizing oil was recrystallized from 10: hexanes:ethyl acetate to yield 710 mg as a white solid.

mp 93.5–95° C.; NMR and IR were consistent with the proposed title structure. FDMS 515, 516 (M+). Analysis for $C_{31}H_{34}N_3O_2Cl$: Theory: C, 72.15; H, 6.64; N, 8.14. Found: C, 71.88; H, 6.73; N, 7.98.

EXAMPLE 239

Preparation of 1-[3-[(piperidin-1-yl)carbonyl]butyl]-2-[(4-chlorophenoxy)methyl]-4-methylbenzimidazole

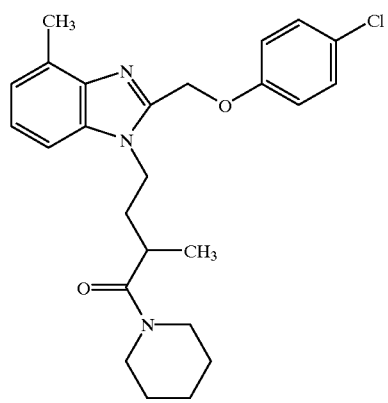

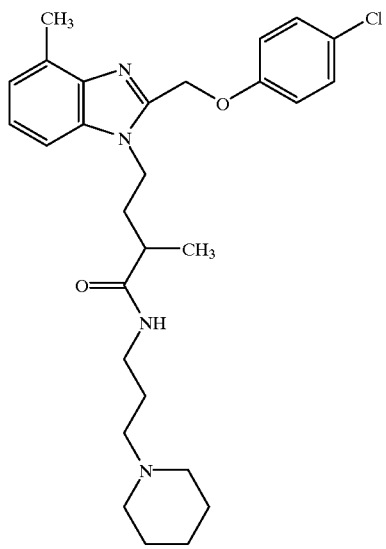

To a stirring solution of 1-[3-carboxybutyl]-2-[(4-chlorophenoxy)methyl]-4-methylbenzimidazole (1.2 g, 3.2 mmol) in N,N-dimethylformamide (75 ml) were added sequentially piperidine (299 mg, 1.1 eq), 1-hydroxybenzotriazole (475 mg, 1.1 eq), and dicyclohexylcarbodiimide (726 mg, 1.1 eq). The resulting mixture was then stirred under a nitrogen atmosphere at room temperature for 64 hours. The reaction mixture was then filtered and the resulting filtrate was concntrated under reduced pressure. This residue was taken into ethyl acetate (200 ml) and washed once with water (200 ml), dried over potassium carbonate. The solvents were removed in vacuo to yield 1.78 grams of a tan foam.

This crude material was purified by flash silica gel chromatography, eluting with a gradient solvent of 1:1 hexanes:ethyl acetate to ethyl acetate. The fractions containing the desired material were combined and concentrated under reduced pressure to yield 910 mg (65%) of the desired title product as a white foam.

NMR was consistent with the proposed title structure. FDMS 439.3 (M+). Analysis for $C_{25}H_{30}N_3O_2Cl$: Theory: C, 68.25; H, 6.87; N, 9.55. Found: C, 68.54; H, 6.97; N, 9.52.

EXAMPLE 240

Preparation of 1-[3-[3-(piperidin-1-yl)propylcarbamoyl]butyl]-2-[(4-chlorophenoxy)methyl]-4-methylbenzimidazole To a stirring solution of 1-[3-carboxybutyl]-2-[(4-chlorophenoxy)methyl]-4-methylbenzimidazole (1.2 g, 3.2 mmol) in N,N-dimethylformamide (75 ml) were added sequentially 1-amino-3-(piperidin-1-yl)propane (500 mg, 1.1 eq), 1-hydroxybenzotriazole (475 mg, 1.1 eq), and dicyclohexylcarbodiimide (726 mg, 1.1 eq). The resulting mixture was then stirred under a nitrogen atmosphere at room temperature for 64 hours. The reaction mixture was then filtered and the resulting filtrate was concntrated under reduced pressure. This residue was taken into ethyl acetate (200 ml) and washed once with water (200 ml), dried over potassium carbonate. The solvents were removed in vacuo to yield 2.00 grams of a semi-solid material.

This crude material was purified by flash silica gel chromatography, eluting with a gradient solvent of 9:1 hexanes:ethyl acetate to 1:1 hexanes:ethyl acetate. The fractions containing the desired material were combined and concentrated under reduced pressure to yield 1.04 g (65%) of the desired title product as a white foam. The title product was recrystallized from a 9:1 hexanes:ethyl acetate mixture to yield 800 mg as crystals.

mp 102–103° C.; NMR and IR were consistent with the proposed title structure. FDMS 496, 497 (M+). Analysis for $C_{28}H_{37}N_4O_2Cl$: Theory: C, 67.66; H, 7.50; N, 11.27. Found: C, 67.41; H, 7.79; N, 11.22.

EXAMPLE 241

Preparation of 1-[3-[3-(piperidin-1-yl)propylcarbamoyl]-4-phenylbutyl]-2-[(4-chlorophenoxy)methyl]-4-methylbenzimidazole

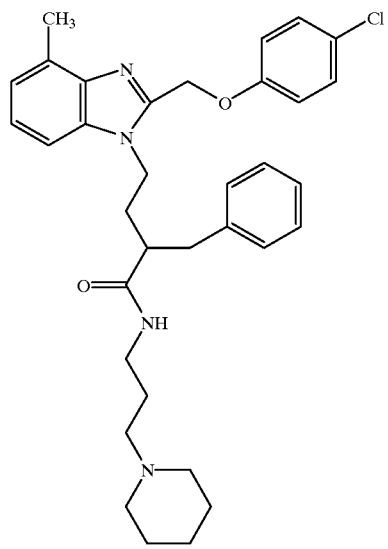

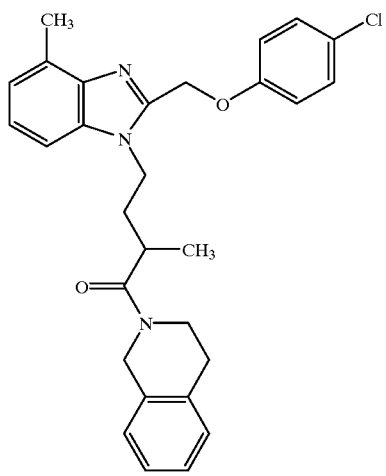

To a stirring solution of 1-[3-carboxy-4-phenylbutyl]-2-[(4-chlorophenoxy)methyl]-4-methylbenzimidazole (1.0 g, 2.2 mmol) in N,N-dimethylformamide (75 ml) were added sequentially 1-amino-3-(piperidin-1-yl)propane (345 mg, 1.1 eq), 1-hydroxybenzotriazole (327 mg, 1.1 eq), and dicyclohexylcarbodiimide (500 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 1.35 grams of an orange foam.

This crude material was purified by flash silica gel chromatography, eluting with a gradient solvent of 19:1 ethyl acetate:methanol to ethyl acetate:methanol. The fractions containing the desired material were combined and concentrated under reduced pressure to yield 950 mg (75%) of the desired title product as a slowly crystallizing oil. The title product was recrystallized from a 19:1 hexanes:ethyl acetate mixture to yield 800 mg as crystals.

mp 91–93° C.; NMR and IR were consistent with the proposed title structure. FDMS 572–573 (M+). Analysis for $C_{34}H_{41}N_4O_2Cl$: Theory: C, 71.25; H, 7.21; N, 9.78. Found: C, 71.15; H, 7.39; N, 9.67.

EXAMPLE 242

Preparation of 1-[3-[(1,2,3,4-tetrahydroisoquinolin-1-yl)carbonyl]butyl]-2-[(4-chlorophenoxy)methyl]-4-methylbenzimidazole To a stirring solution of 1-[3-carboxybutyl]-2-[(4-chlorophenoxy)methyl]-4-methylbenzimidazole (0.800 g, 2.2 mmol) in N,N-dimethylformamide (50 ml) were added sequentially 1,2,3,4-tetrahydroisoquinoline (322 mg, 1.1 eq), 1-hydroxybenzotriazole (327 mg, 1.1 eq), and dicyclohexylcarbodiimide (500 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to Yield 1.24 grams of a dark oil.

This crude material was purified by flash silica gel chromatography, eluting with a gradient solvent of 1:1 hexanes:ethyl acetate to ethyl acetate. The fractions containing the desired material were combined and concentrated under reduced pressure to yield 1.04 g of the desired title product as a white foam. The title product was recrystallized from a 9:1 hexanes:ethyl acetate mixture to yield 734 mg (69%) as a white foam.

NMR was consistent with the proposed title structure. FDMS 487, 488 (M+). Analysis for $C_{29}H_{30}N_3O_2Cl$: Theory: C, 71.37; H, 6.20; N, 8.61. Found: C, 70.97; H, 6.20; N, 8.52.

EXAMPLE 243

Preparation of 1-[3-[(1,2,3,4-tetrahydronaphth-1-ylamino)carbonyl]butyl]-2-[(4-chlorohenoxy)methyl]-4-methylbenzimidazole

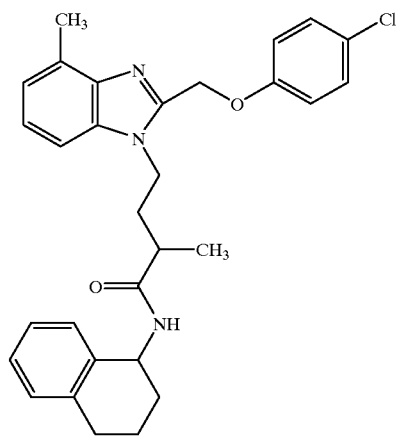

To a stirring solution of 1-[3-carboxybutyl]-2-[(4-chlorophenoxy)methyl]-4-methylbenzimidazole (0.800 g, 2.2 mmol) in N,N-dimethylformamide (50 ml) were added sequentially 1,2,3,4-tetrahydronaphthalene (356 mg, 1.1 eq), 1-hydroxybenzotriazole (327 mg, 1.1 eq), and dicyclohexylcarbodiimide (500 mg, 1.1 eq). The resulting mixture was then stirred under a nitrogen atmosphere at room temperature for 64 hours. The reaction mixture was then filtered and the resulting filtrate was concntrated under reduced pressure. This residue was taken into ethyl acetate (200 ml) and washed once with water (200 ml), dried over potassium carbonate. The solvents were removed in vacuo to yield 1.3 grams of a semi-solid. This crude material was purified by recrystallization from 9:1 ethyl acetate:ethanol to yield 741 mg (67%) as a white solid.

mp 192–194° C.; NMR was consistent with the proposed title structure. FDMS 501, 502 (M+). Analysis for $C_{30}H_{32}N_3O_2Cl$: Theory: C, 71.77; H, 6.43; N, 8.37. Found: C, 71.43; H, 6.52; N, 8.22.

EXAMPLES 244 AND 245

Preparation of (R) 1-[3-[[2-[(2-piperidin-1-yl)ethyl] piperidin-1-yl]carbonyl]butyl]-2-[(4-chlorophenoxy) methyl]-4-methylbenzimidazole dihydrochloride salt monohydrate[A] and (S) 1-[3-[[2-[(2-piperidin-1-yl)ethyl] piperidin-1-yl]carbonyl]butyl]-2-[(4-chlorophenoxy) methyl]-4-methylbenzimidazole dihydrochloride salt [B]

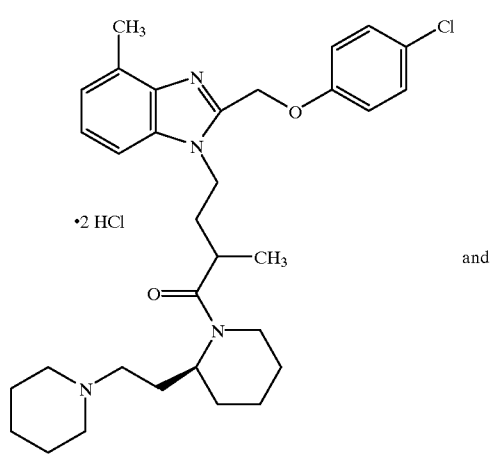

and

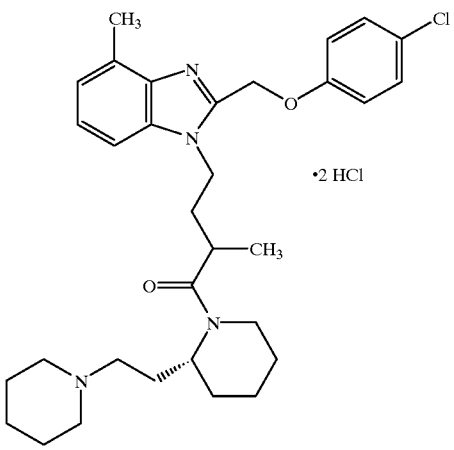

To a stirring solution of 1-[3-carboxybutyl]-2-[(4-chlorophenoxy)methyl]-4-methylbenzimidazole (0.800 g, 2.2 mmol) in N,N-dimethylformamide (50 ml) were added sequentially (RS) 2-[(piperidin-1-yl)ethyl]piperidine (475 mg, 1.1 eq), 1-hydroxybenzotriazole (327 mg, 1.1 eq), and dicyclohexylcarbodiimide (500 mg, 1.1 eq). The resulting mixture was then stirred under a nitrogen atmosphere at room temperature for 64 hours. The reaction mixture was then filtered and the resulting filtrate was concntrated under reduced pressure. This residue was taken into ethyl acetate (200 ml) and washed once with water (200 ml), dried over potassium carbonate. The solvents were removed in vacuo to yield 1.3 grams of the racemate as a yellow foam.

The isomers were separated and purified by flash silica gel chromatography, eluting with a solvent gradient of 9:1 ethyl acetaet:methanol to 1:1 ethyl acetate:methanol. Fractions containing each isomer were then concentrated under reduced pressure and converted to the dihydrochloride salt as a white solid.

Yield: (R) isomer—335 mg; (S) isomer 164 mg. [A]; mp 106–109° C.; NMR was consistent with the proposed title structure. FDMS 550, 551 (M+). Analysis for $C_{32}H_{43}N_4O_2Cl.2HCl,.H_2O$: Theory: C, 59.85; H, 7.38; N, 8.73. Found: C, 59.89; H, 7.32; N, 9.11.

[B]; mp>146° C.; NMR was consistent with the proposed title structure. FDMS 551 (M+). Analysis for $C_{32}H_{43}N_4O_2Cl.2HCl$: Theory: C, 61.59; H, 7.27; N, 8.98. Found: C, 61.39; H, 7.05; N, 8.78.

EXAMPLE 246

Preparation of (RS) 1-[3-[[3-(2-methylpiperidin-1-yl) propylamino]carbonyl]butyl]-2-[(4-chlorophenoxy) methyl]-4-methylbenzimidazole dihydrochloride salt monohydrate

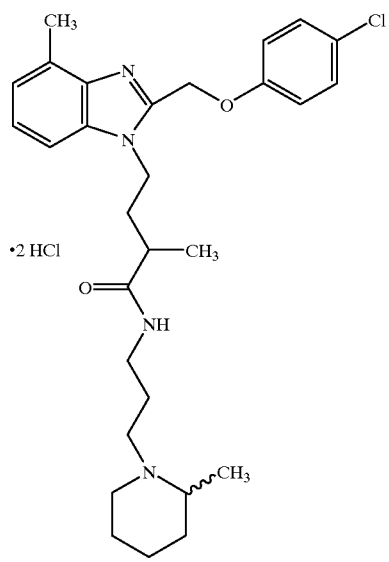

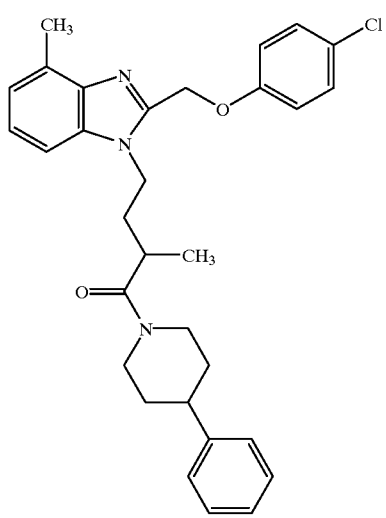

To a stirring solution of 1-[3-carboxybutyl]-2-[(4-chlorophenoxy)methyl]-4-methylbenzimidazole (1.00 g, 2.7 mmol) in N,N-dimethylformamide (60 ml) were added sequentially (RS) 3-(2-methylpiperidin-1-yl)propylamine (464 mg, 1.1 eq), 1-hydroxybenzotriazole (402 mg, 1.1 eq), and dicyclohexylcarbodiimide (615 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 1.17 grams of the racemate as an orange solid.

The material was further purified by flash silica gel chromatography, eluting with a solvent gradient of 1:1 ethyl acetaet:methanol to methanol. Fractions containing the desired title product were then concentrated under reduced pressure and converted to the dihydrochloride salt as a white solid.

Yield: 500 mg of the free base (36%) mp 85–87.5° C.; NMR was consistent with the proposed title structure. FDMS 510, 511 (M+). Analysis for $C_{32}H_{43}N_4O_2Cl.2HCl.H_2O$: Theory: C, 57.85; H, 7.20; N, 9.31. Found: C, 58.01; H, 7.15; N, 9.02.

EXAMPLE 247

Preparation of 1-[3-[4-phenylpiperidin-1-yl]carbonyl]butyl]-2-[(4-chlorophenoxy)methyl]-4-methylbenzimidazole hemihydrate To a stirring solution of 1-[3-carboxybutyl]-2-[(4-chlorophenoxy)methyl]-4-methylbenzimidazole (0.800 g, 2.2 mmol) in N,N-dimethylformamide (50 ml) were added sequentially 4-phenylpiperidine (390 mg, 1.1 eq), 1-hydroxybenzotriazole (327 mg, 1.1 eq), and dicyclohexylcarbodiimide (500 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 1.04 grams of the title product as an orange foam.

The material was further purified by flash silica gel chromatography, eluting with a solvent gradient of 9:1 ethyl acetate:methanol to 1:1 ethyl acetate:methanol. Fractions containing the desired title product were then concentrated under reduced pressure.

Yield: 641 mg (56%); NMR was consistent with the proposed title structure. FDMS 515, 516 (M+). Analysis for $C_{31}H_{34}N_3O_2Cl.½H_2O$: Theory: C, 70.90; H, 6.70; N, 8.00. Found: C, 70.43; H, 6.96; N, 7.75.

EXAMPLE 248

Preparation of 1-[3-[[3-(piperidin-1-yl)propylamino]carbonyl]propyl]-2-[(4-chlorophenoxy)methyl]-4-methylbenzimidazole dihydrochloride salt

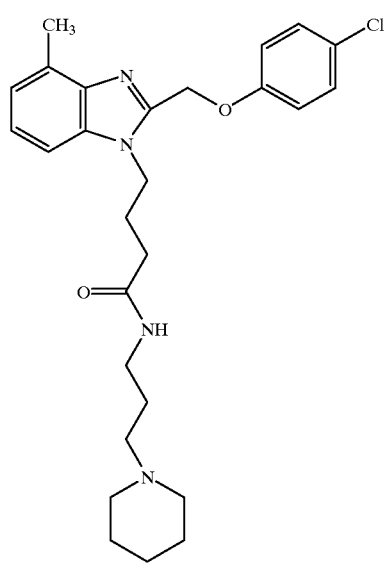

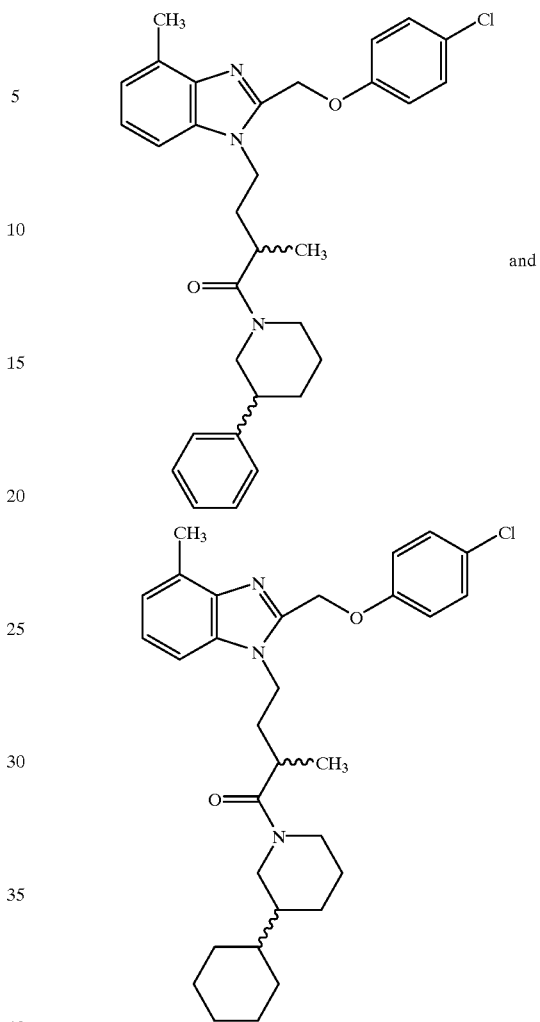

and

To a stirring solution of 1-[3-carboxypropyl]-2-[(4-chlorophenoxy)methyl]-4-methylbenzimidazole (0.540 g, 1.5 mmol) in N,N-dimethylformamide (60 ml) were added sequentially 3-(piperidin-1-yl)propylamine (235 mg, 1.1 eq), 1-hydroxybenzotriazole (223 mg, 1.1 eq), and dicyclohexylcarbodiimide (340 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 0.731 grams of the title compound as an orange solid.

The material was further purified by flash silica gel chromatography, eluting with methanol. Fractions containing the desired title product were then concentrated under reduced pressure to yield a slowly crystallizing oil.

Yield: 471 mg (65%); mp 92–94° C.; NMR was consistent with the proposed title structure. FDMS 482, 483 (M+). Analysis for $C_{27}H_{35}N_4O_2Cl$: Theory: C, 67.14; H, 7.30; N, 11.60. Found: C, 66.94; H, 7.23; N, 11.37.

EXAMPLES 249 AND 250

Preparation of (RS) 1-[3-[[3-phenylpiperidin-1-yl]carbonyl]butyl]-2-[(4-chlorophenoxy)methyl]-4-methylbenzimidazole and (RS) 1-[3-[[3-cyclohexylpiperidin-1-yl]carbonyl]butyl]-2-[(4-chlorophenoxy)methyl]-4-methylbenzimidazole To a stirring solution of 1-[3-carboxybutyl]-2-[(4-chlorophenoxy)methyl]-4-methylbenzimidazole (1.00 g, 2.7 mmol) in N,N-dimethylformamide (50 ml) were added sequentially a 50:50 mixture of 3-phenylpiperidine and 3-cyclohexylpiperidine (496 mg total, 1.1 eq), 1-hydroxybenzotriazole (402 mg, 1.1 eq), and dicyclohexylcarbodiimide (615 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 1.43 grams of approximately a 50:50 mixture of the title products.

Separation and purification of this mix was attempted using a chromatotron with a 4000 micron rotor and eluting with a gradient solvent of hexanes to 1:1 ethyl acetate:hexanes. Early fractions containing an 80:20 mixture of the 3-cyclohexyl derivatives:3-phenyl derivatives were then concentrated under reduced pressure, yielding 641 mg. Later fractions containing substantially purified 3-phenyl derivatives were combined and concentrated under reduced pressure to yield 200 mg as a white foam.

NMR was consistent with the proposed title structures.

EXAMPLES 251 AND 252

Preparation of (RS) 1-[3-[[4-benzylpiperidin-1-yl]carbonyl]butyl]-2-[(4-chlorophenoxy)methyl]-4-methylbenzimidazole and (RS) 1-[3-[[4-(cyclohexylmethyl)piperidin-1-yl]carbonyl]butyl]-2-[(4-chlorophenoxy)methyl]-4-methylbenzimidazole

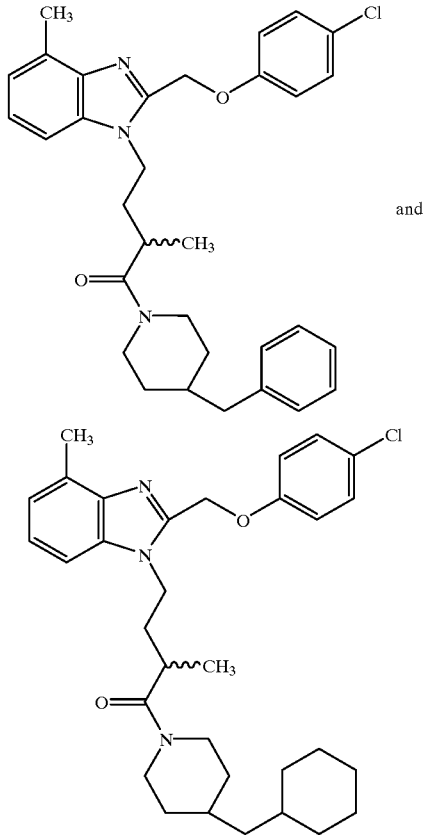

To a stirring solution of 1-[3-carboxybutyl]-2-[(4-chlorophenoxy)methyl]-4-methylbenzimidazole (1.00 g, 2.7 mmol) in N,N-dimethylformamide (50 ml) were added sequentially a 50:50 mixture of 4-benzylpiperidine and 4-(cyclohexylmethyl)piperidine (520 mg total, 1.1 eq), 1-hydroxybenzotriazole (402 mg, 1.1 eq), and dicyclohexylcarbodiimide (615 mg, 1.1 eq). The resulting mixture was then stirred under a nitrogen atmosphere at room temperature for 64 hours. The reaction mixture was then filtered and the resulting filtrate was concntrated under reduced pressure. This residue was taken into ethyl acetate (200 ml) and washed once with water (200 ml), dried over potassium carbonate. The solvents were removed in vacuo to yield 1.51 grams of approximately a 50:50 mixture of the title products.

Separation and purification of this mix was attempted using a chromatotron with a 4000 micron rotor and eluting with a gradient solvent of hexanes to 2:1 ethyl acetate:hexanes. Early fractions containing substantially purified the 4-benzyl derivatives were then concentrated under reduced pressure, yielding 481 mg as a white foam. Later fractions containing substantially purified 4-cyclohexylmethyl derivatives were combined and concentrated under reduced pressure to yield 356 mg as a white foam.

NMR was consistent with the proposed title structures.

EXAMPLE 253

Preparation of (RS) 1-[3-[2-phenylethylamino]carbonyl]butyl]-2-[(4-chlorophenoxy)methyl]-4-methylbenzimidazole

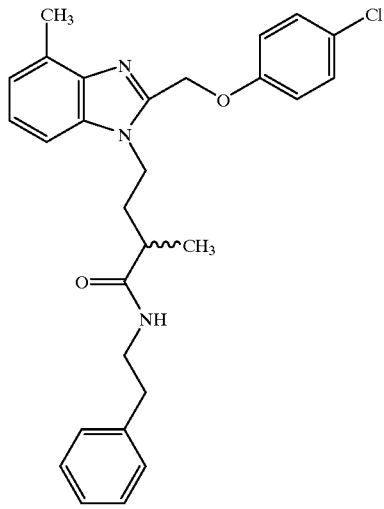

To a stirring solution of (RS) 1-[3-carboxybutyl]-2-[(4-chlorophenoxy)methyl]-4-methylbenzimidazole (0.500 g, 1.4 mmol) in N,N-dimethylformamide (40 ml) were added sequentially 2-phenylethylamine (187 mg, 1.1 eq), 1-hydroxybenzotriazole (208 mg, 1.1 eq), and dicyclohexylcarbodiimide (317 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 0.731 grams of the title product as a white foam.

The material was further purified by flash silica gel chromatography, eluting with a solvent gradient of 1:1 ethyl acetate:hexanes to ethyl acetate. Fractions containing the desired title product were then concentrated under reduced pressure, yielding 581 mg (80%) as a white solid.

EXAMPLE 254

Preparation of (RS) 1-[3-[[benzylaminoamino]carbonyl]butyl]-2-[(4-chlorophenoxy)methyl]-4-methylbenzimidazole

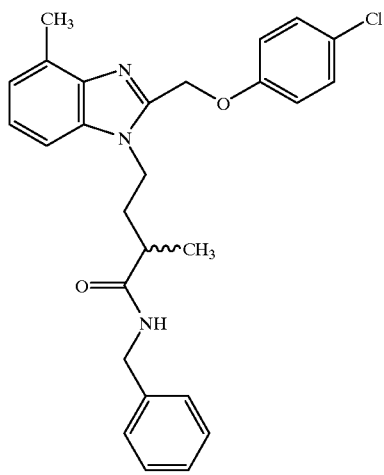

To a stirring solution of (RS) 1-[3-carboxybutyl]-2-[(4-chlorophenoxy)methyl]-4-methylbenzimidazole (0.500 g, 1.4 mmol) in N,N-dimethylformamide (40 ml) were added sequentially benzylamine (165 mg, 1.1 eq), 1-hydroxybenzotriazole (208 mg, 1.1 eq), and dicyclohexylcarbodiimide (317 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 0.714 grams of the title product as a white foam.

The material was further purified by flash silica gel chromatography, eluting with a solvent gradient of hexanes to 1:1 ethyl acetate:hexanes. Fractions containing the desired title product were then concentrated under reduced pressure, yielding 437 mg (68%) as a white solid.

mp 145–146° C.; NMR was consistent with the proposed title structure. FDMS 461, 462 (M+). Analysis for $C_{27}H_{28}N_3O_2Cl$: Theory: C, 70.20; H, 6.11; N, 9.10. Found: C, 70.44; H, 6.33; N, 8.7881

EXAMPLE 255

Preparation of (RS) 1-[3-[(pyrrolidin-1-yl)carbonyl]butyl]-2-[(4-chlorophenoxy)methyl]-4-methylbenzimidazole

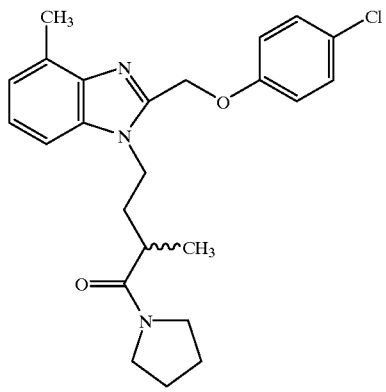

To a stirring solution of (RS) 1-[3-carboxybutyl]-2-[(4-chlorophenoxy)methyl]-4-methylbenzimidazole (0.700 g, 1.9 mmol) in N,N-dimethylformamide (40 ml) were added sequentially pyrroldine (155 mg, 1.1 eq), 1-hydroxybenzotriazole (282 mg, 1.1 eq), and dicyclohexylcarbodiimide (431 mg, 1.1 eq). The resulting mixture was then stirred under a nitrogen atmosphere at room temperature for 64 hours. The reaction mixture was then filtered and the resulting filtrate was concentrated under reduced pressure. This residue was taken into ethyl acetate (200 ml) and washed once with water (200 ml), dried over potassium carbonate. The solvents were removed in vacuo to yield 0.835 grams of the title product as a white foam.

The material was further purified by flash silica gel chromatography, eluting with a solvent gradient of 1:1 ethyl acetate:hexanes to ethyl acetate. Fractions containing the desired title product were then concentrated under reduced pressure, yielding 560 mg (69%) as a white solid.

mp 140–142° C.; NMR was consistent with the proposed title structure. FDMS 425 (M+). Analysis for $C_{24}H_{28}N_3O_2Cl$: Theory: C, 67.67; H, 6.63; N, 9.87. Found: C, 67.76; H, 6.73; N, 9.84.

EXAMPLE 256

Preparation of (RS) 1-[3-(methyl)-4-[3-(piperidin-1-yl)propylamine]butyl]-2-[(4-chlorophenoxy)methyl]-4-methylbenzimidazole trihydrochloride salt monohydrate

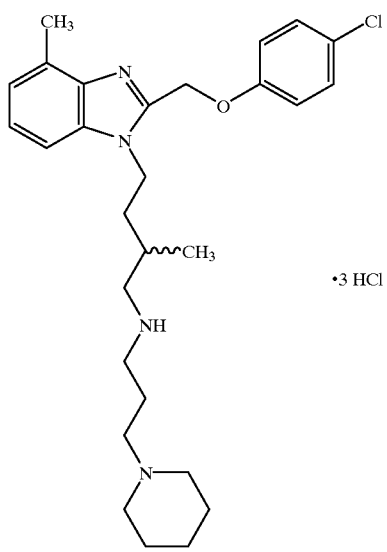

A solution of 1-[3-[3-(piperidin-1-yl)propylcarbamoyl]butyl]-2-[(4-chlorophenoxy)methyl]-4-methylbenzimidazole (300 mg, 0.6 mmol) in dry tetrahydrofuran (5 ml) was stirred at room temperature under a nitrogen atmosphere. To this solution borane-tetrahydrofuran complex (3.8 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 200 mg of a viscous oil. This oil was further purified using a chromatotron with a 2000 micron rotor, eluting with a gradient solvent of 9:1 ethyl acetate:methanol (with 1% ammonium hydroxide) to 1:1 ethyl acetate:methanol (with 1% ammonium hydroxide). Fractions containing the desired title product (170 mg, 59%) were collected and the compound was converted to the tri-hydrochloride salt, yielding a white solid.

mp 98–100.5° C.; NMR was consistent with the proposed title structure. FDMS 483 (M+). Analysis for $C_{28}H_{39}N_4OCl.3HCl.H_2O$: Theory: C, 55.09; H, 7.26; N, 9.18. Found: C, 55.47; H, 7.12; N, 9.33.

EXAMPLE 257

Preparation of (RS) 1-[3-(benzyl)-4-[3-(piperidin-1-yl)propylamine]butyl]-2-[(4-chlorophenoxy)methyl]-4-methylbenzimidazole trihydrochloride salt monohydrate

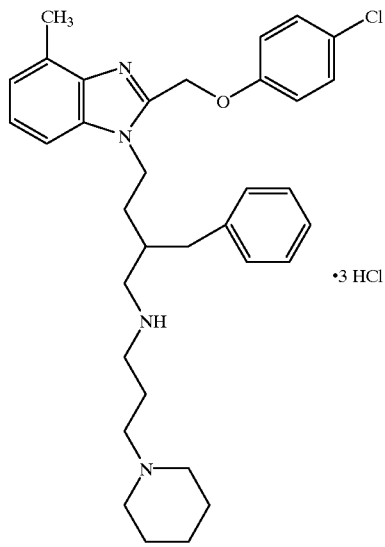

•3 HCl

A solution of 1-[4-phenyl-3-[3-(piperidin-1-yl) propylcarbamoyl]butyl]-2-[(4-chlorophenoxy)methyl]-4-methylbenzimidazole (450 mg, 0.78 mmol) in dry tetrahydrofuran (5 ml) was stirred at room temperature under a nitrogen atmosphere. To this solution borane-tetrahydrofuran complex (4.7 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 200 mg of a viscous oil. This oil was further purified using a chromatotron with a 2000 micron rotor, eluting with a 9:1 ethyl acetate:methanol (with 1% ammonium hydroxide) solution. Fractions containing the desired title product (185 mg, 42%) were collected and the compound was converted to the tri-hydrochloride salt, yielding a white solid.

mp 96–98° C.; NMR was consistent with the proposed title structure. FDMS 559.1 (M+). Analysis for $C_{34}H_{43}N_4OCl.3HCl.H_2O$: Theory: C, 59.47; H, 7.04; N, 8.16. Found: C, 59.39; H, 6.87; N, 8.12.

EXAMPLE 258

Preparation of (RS) 1-[3-benzyl-4-(piperidin-1-yl)butyl]-2-[(4-chlorophenoxy)methyl]-4-methylbenzimidazole trihydrochloride salt

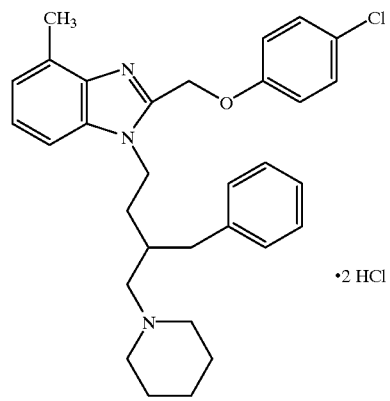

•2 HCl

A solution of 1-[4-phenyl-3-[(piperidin-1-yl)carbonyl] butyl]-2-[(4-chlorophenoxy)methyl]-4-methylbenzimidazole (400 mg, 0.7 mmol) in dry tetrahydrofuran (5 ml) was stirred at room temperature under a nitrogen atmosphere. To this solution borane-tetrahydrofuran complex (4.5 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 350 mg of a viscous oil. This oil was further purified using a chromatotron with a 2000 micron rotor, eluting with a gradient solvent of 9:1 ethyl acetate::methanol (with 1% ammonium hydroxide) to 1:1 ethyl acetate:methanol (with 1% ammonium hydroxide). Fractions containing the desired title product (195 mg, 56%) were collected and the compound was converted to the di-hydrochloride salt, yielding a white solid.

mp 120–123° C.; NMR was consistent with the proposed title structure. FDMS 501, 502 (M+). Analysis for $C_{31}H_{36}N_3OCl.2HCl$: Theory: C, 64.75; H, 6.66; N, 7.31. Found: C, 64.50; H, 6.36; N, 7.31.

EXAMPLE 259

Preparation of (RS) 1-[3-(methyl)-4-aminobutyl]-2-[(4-chlorophenoxy)methyl]-4-methylbenzimidazole dihydrochloride salt monohydrate

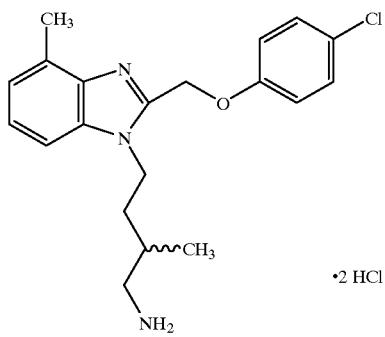

·2 HCl

A solution of 1-[3-carbamoylbutyl]-2-[(4-chlorophenoxy)methyl]-4-methylbenzimidazole (350 mg, 0.94 mmol) in dry tetrahydrofuran (5 ml) was stirred at room temperature under a nitrogen atmosphere. To this solution borane-tetrahydrofuran complex (5.7 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 260 mg of a viscous oil. This oil was further purified using a chromatotron with a 2000 micron rotor, eluting with a gradient solvent of 1:1 ethyl acetate-:methanol to methanol. Fractions containing the desired title product (69 mg, 21%) were collected and the compound was converted to the dihydrochloride salt, yielding a white solid.

mp>150° C.; NMR was consistent with the proposed title structure. FDMS 357.2 (M+). Analysis for C$_{20}$H$_{24}$N$_3$OCl.2HCl. H$_2$O: Theory: C, 53.51; H, 6.29; N, 9.36. Found: C, 53.22; H, 6.10; N, 9.28.

EXAMPLE 260

Preparation of (RS) 1-[3-(methyl)-4-dimethylaminobutyl]-2-[(4-chlorophenoxy)methyl]-4-methylbenzimidazole

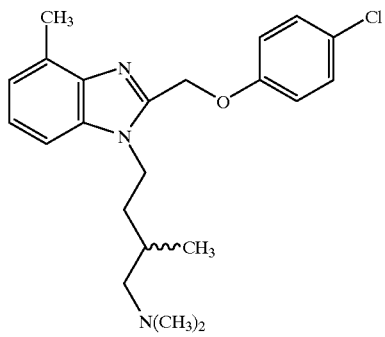

A solution of 1-[3-[(N,N-dimethylamino)carbonyl]butyl]-2-[(4-chlorophenoxy)methyl]-4-methylbenzimidazole (350 mg, 0.88 mmol) in dry tetrahydrofuran (5 ml) was stirred at room temperature under a nitrogen atmosphere. To this solution borane-tetrahydrofuran complex (5.3 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 295 mg of a viscous oil. This oil was further purified using a chromatotron with a 2000 micron rotor, eluting with a gradient solvent of 19:1 ethyl acetate-:methanol to 1:1 ethyl acetate:methanol. Fractions containing the desired title product (200 mg, 21%) were collected.

mp 80–82° C.; NMR was consistent with the proposed title structure. FDMS 385.2 (M+). Analysis for C$_{22}$H$_{28}$N$_3$OCl: Theory: C, 68.47; H, 7.31; N, 10.89. Found: C, 68.51; H, 7.45; N, 11.07.

EXAMPLE 261

Preparation of (R) 1-[4-[2-[(2-piperidin-1-yl)ethyl]piperidin-1-yl]-3-methylbutyl]-2-[(4-chlorophenoxy)methyl]-4-methylbenzimidazole trihydrochloride salt hemihydrate

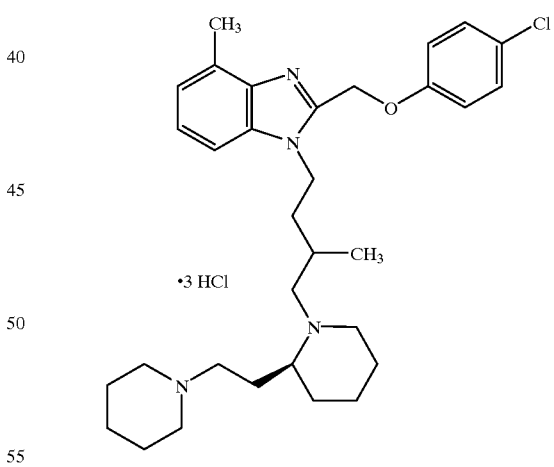

·3 HCl

A solution of (R) 1-[4-[[2-[(2-piperidin-1-yl)ethyl]piperidin-1-yl]carbonyl]butyl]-2-[(4-chlorophenoxy)methyl]-4-methylbenzimidazole dihydrochloride salt monohydrate (135 mg, 0.25 mmol) in dry tetrahydrofuran (5 ml) was stirred at room temperature under a nitrogen atmosphere. To this solution borane-tetrahydrofuran complex (1.8 ml of a 1M solution in tetrafiran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 105 mg of a viscous oil. This oil was further purified using a chromatotron with a 2000 micron rotor, eluting with methanol. Fractions containing the desired title product (73 mg, 55%) were collected and converted to the trihydrochloride salt, yielding a white solid.

mp 103–106° C.; NMR was consistent with the proposed title structure. FDMS 537 (M+). Analysis for $C_{32}H_{45}N_4OCl \cdot 3HCl \cdot \frac{1}{2}H_2O$: Theory: C, 58.62; H, 7.53; N, 8.55. Found: C, 58.32; H, 7.22; N, 7.93.

Analysis for $C_{32}H_{45}N_4OCl$: Theory: C, 71.55; H, 8.44; N, 10.43. Found: C, 71.25; H, 8.49; N, 10.19.

EXAMPLE 262

Preparation of (S) 1-[4-[2-[(2-piperidin-1-yl)ethyl] piperidin-1-yl]-3-methylbutyl]-2-[(4-chlorophenoxy) methyl]-4-methylbenzimidazole trihydrochloride salt hemihydrate

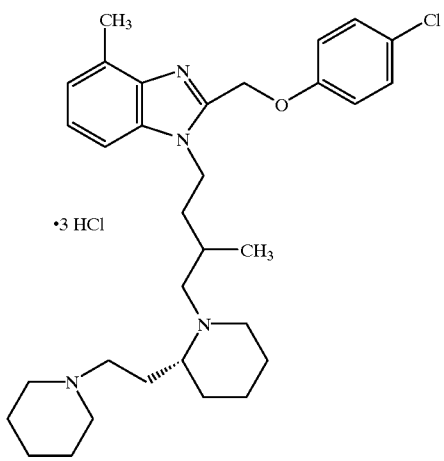

The title compound was prepared essentially as described for the R siomer, except that (S) 1-[4-[[2-[(2-piperidin-1-yl) ethyl]piperidin-1-yl]carbonyl]butyl]-2-[(4-chlorophenoxy) methyl]-4-methylbenzimidazole dihydrochloride salt monohydrate was employed as a starting material.

EXAMPLE 263

Preparation of (RS) 1-[3-(methyl)-4-(1,2,3,4-tetrahydroisoquinolin-1-yl)butyl]-2-[(4-chlorophenoxy) methyl]-4-methylbenzimidazole

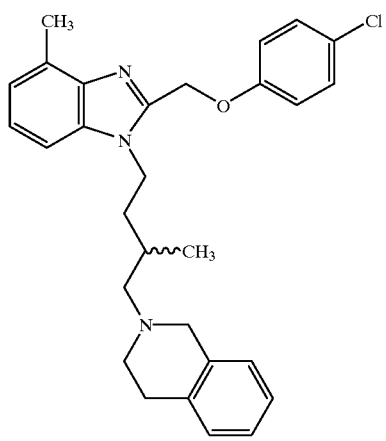

A solution of 1-[3-[(1,2,3,4-tetrahydroisoquinolin-1-yl) carbonyl]butyl]-2-[(4-chlorophenoxy)methyl]-4-methylbenzimidazole (375 mg, 0.76 mmol) in dry tetrahydrofuran (5 ml) was stirred at room temperature under a nitrogen atmosphere. To this solution borane-tetrahydrofuran complex (4.5 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 340 mg of a slowly crystallizing viscous oil. This oil was further purified by recrystallization from ethyl acetate to yield the desired title product (183 mg, 52%) as white crystals.

mp 114.5–116° C.; NMR was consistent with the proposed title structure. FDMS 474 (M+). Analysis for $C_{29}H_{32}N_3OCl$: Theory: C, 73.48; H, 6.80; N, 8.86. Found: C, 73.18; H, 6.82; N, 8.67.

EXAMPLE 264

Preparation of (RS) 1-[3-(methyl)-4-(1,2,3,4-tetrahydronaphth-1-yl)butyl]-2-[(4-chlorophenoxy)methyl]-4-methylbenzimidazole dihydrochloride salt

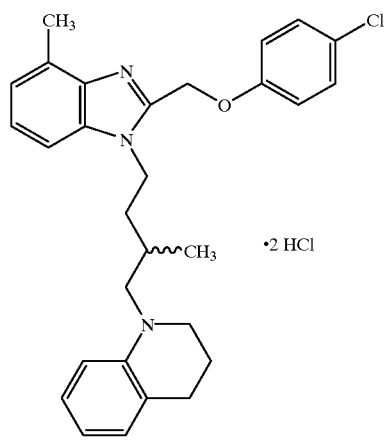

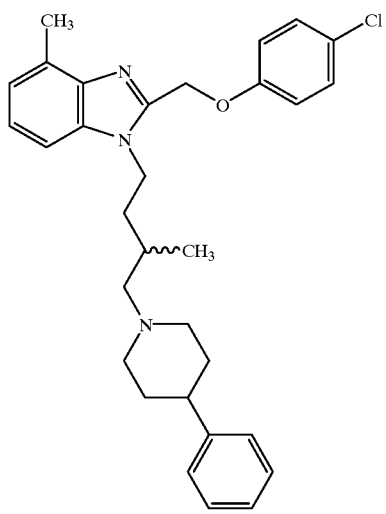

A solution of 1-[3-[(1,2,3,4-tetrahydronaphth-1-yl)carbonyl]butyl]-2-[(4-chlorophenoxy)methyl]-4-methylbenzimidazole (525 mg, 1.05 mmol) in dry tetrahydrofuran (5 ml) was stirred at room temperature under a nitrogen atmosphere. To this solution borane-tetrahydrofuran complex (6.3 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 487 mg of a viscous oil. This oil was further purified via a chromatotron using a 4000 micron rotor, eluting with ethyl acetate to yield the desired title product (325 mg, 64%) as a clear viscous oil. The title product was then converted to the dihydrochloride salt, yielding a white solid.

mp 116–118.5° C.; NMR was consistent with the proposed title structure. FDMS 487, 488 (M+). Analysis for $C_{30}H_{34}N_3OCl\cdot 2HCl$: Theory: C, 64.23; H, 6.47; N, 7.49. Found: C, 64.04; H, 6.35; N, 7.35.

A solution of 1-[3-[(4-phenylpiperidin-1-yl)carbonyl]butyl]-2-[(4-chlorophenoxy)methyl]-4-methylbenzimidazole (550 mg, 1.07 mmol) in dry tetrahydrofuran (5 ml) was stirred at room temperature under a nitrogen atmosphere. To this solution borane-tetrahydrofuran complex (6.7 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 531 mg of a a white solid. This material was further purified by recrystallization from 5:1 hexanes-:ethyl acetate, yielding a white solid (385 mg, 72%).

mp 124–125° C.; NMR was consistent with the proposed title structure. FDMS 501, 502 (M+). Analysis for $C_{31}H_{36}N_3OCl$: Theory: C, 74.16; H, 7.23; N, 8.37. Found: C, 74.42; H, 7.35; N, 8.41.

EXAMPLE 265

Preparation of (RS) 1-[3-(methyl)-4-(4-phenylpiperidin-1-yl)butyl]-2-[(4-chlorophenoxy)methyl]-4-methylbenzimidazole dihydrochloride salt

EXAMPLE 266

Preparation of (RS) 1-[3-(methyl)-4-(3-phenylpiperidin-1-yl)butyl]-2-[(4-chlorophenoxy)methyl]-4-methylbenzimidazole dihydrochloride salt

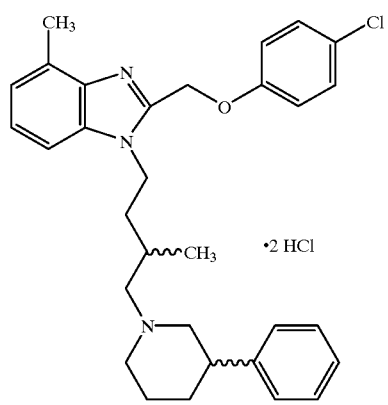

A solution of 1-[3-[(3-phenylpiperidin-1-yl)carbonyl]butyl]-2-[(4-chlorophenoxy)methyl]-4-methylbenzimidazole (200 mg, 0.380 mmol) in dry tetrahydrofuran (5 ml) was stirred at room temperature under a nitrogen atmosphere. To this solution borane-tetrahydrofuran complex (6.3 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 176 mg of a yellow oil. This oil was further purified via a chromatotron using a 2000 micron rotor, eluting with ethyl acetate to yield the desired title product (113 mg, 59%) as a clear viscous oil. The title product was then converted to the dihydrochloride salt, yielding a white solid.

mp 84–86.5° C.; NMR was consistent with the proposed title structure. FDMS 501, 502 (M+). Analysis for $C_{31}H_{36}N_3OCl \cdot 2HCl \cdot 1\frac{1}{2}H_2O$: Theory: C, 61.83; H, 6.86; N, 6.98. Found: C, 61.98; H, 6.46; N, 6.81.

EXAMPLE 267

Preparation of (RS) 1-[3-(methyl)-4-(2-phenylethylamino)butyl]-2-[(4-chlorophenoxy)methyl]-4-methylbenzimidazole dihydrochloride salt

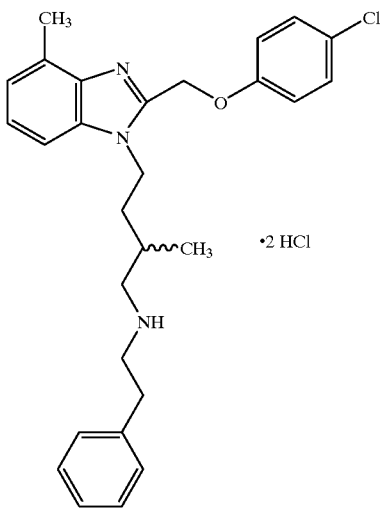

A solution of 1-[3-[(2-phenylethylamino)carbonyl]butyl]-2-[(4-chlorophenoxy)methyl]-4-methylbenzimidazole (525 mg, 1.05 mmol) in dry tetrahydrofuran (5 ml) was stirred at room temperature under a nitrogen atmosphere. To this solution borane-tetrahydrofuran complex (6.3 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 370 mg of a viscous oil. This oil was further purified via a chromatotron using a 2000 micron rotor, eluting with ethyl acetate to yield the desired title product (150 mg, 31%) as a clear viscous oil. The title product was then converted to the dihydrochloride salt, yielding a white solid.

mp 84–87.5° C.; NMR was consistent with the proposed title structure. FDMS 462 (M+). Analysis for $C_{28}H_{32}N_3OCl \cdot 2HCl \cdot \frac{1}{2}H_2O$: Theory: C, 61.81; H, 6.49; N, 7.72. Found: C, 61.98; H, 6.35; N, 7.79.

EXAMPLE 268

Preparation of (RS) 1-[3-(methyl)-4-(3-(piperidin-1-yl)propylamino)butyl]-2-[(4-chlorophenoxy)methyl]-4-methylbenzimidazole trihydrochloride salt

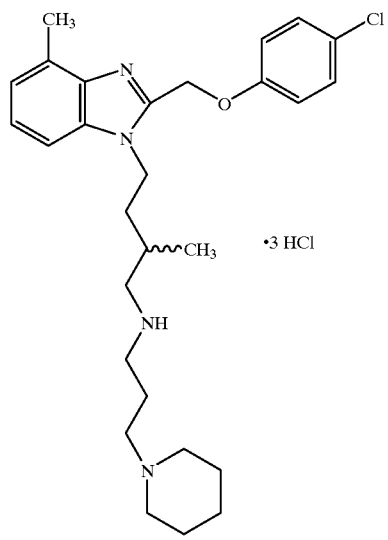

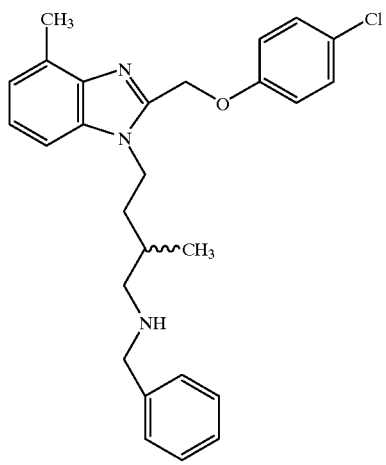

A solution of 1-[3-[(3-(piperidin-1-yl)propylamino)carbonyl]butyl]-2-[(4-chlorophenoxy)methyl]-4-methylbenzimidazole (400 mg, 0.85 mmol) in dry tetrahydrofuran (5 ml) was stirred at room temperature under a nitrogen atmosphere. To this solution borane-tetrahydrofuran complex (6.3 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 380 mg of a viscous oil. This oil was further purified via a chromatotron using a 2000 micron rotor, eluting with a gradient of ethyl acetate to 1:1 ethyl acetate:methanol (with 1% ammonium hydroxide) to yield the desired title product (113 mg, 28%) as a clear viscous oil. The title product was then converted to the trihydrochloride salt, yielding a white solid.

NMR was consistent with the proposed title structure. FDMS 469 (M+). Analysis for $C_{27}H_{37}N_4OCl \cdot 3HCl \cdot \frac{1}{2}H_2O$: Theory: C, 67.82; H, 8.01; N, 11.72. Found: C, 67.73; H, 8.20; N, 11.59.

EXAMPLE 269

Preparation of (RS) 1-[3-(methyl)-4-(benzylamino)butyl]-2-[(4-chlorophenoxy)methyl]-4-methylbenzimidazole A solution of 1-[3-[(benzylamino)carbonyl]butyl]-2-[(4-chlorophenoxy)methyl]-4-methylbenzimidazole (500 mg, 1.05 mmol) in dry tetrahydrofuran (5 ml) was stirred at room temperature under a nitrogen atmosphere. To this solution borane-tetrahydrofuran complex (6.0 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 315 mg of a semi-solid. This oil was further purified via a chromatotron using a 2000 micron rotor, eluting with ethyl acetate to yield the desired title product (190 mg, 40%) as a slowly crystallizing oil.

mp 84.5–87° C.; NMR was consistent with the proposed title structure. FDMS 447, 448 (M+). Analysis for $C_{27}H_{30}N_3OCl$: Theory: C, 72.37; H, 6.75; N, 9.38. Found: C, 72.67; H, 6.75; N, 9.25.

EXAMPLE 270

Preparation of (RS) 1-[3-(methyl)-4-(pyrrolidin-1-yl)butyl]-2-[(4-chlorophenoxy)methyl]-4-methylbenzimidazole

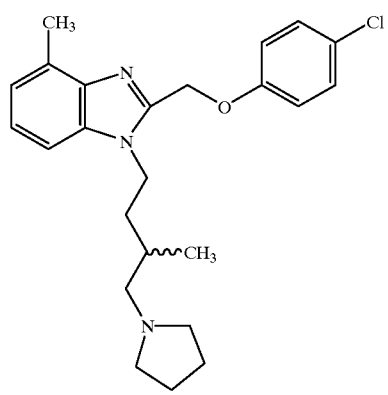

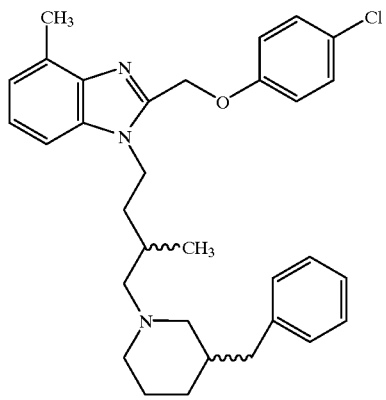

A solution of 1-[3-[(pyrrolidin-1-yl)carbonyl]butyl]-2-[(4-chlorophenoxy)methyl]-4-methylbenzimidazole (500 mg, 1.17 mmol) in dry tetrahydrofuran (5 ml) was stirred at room temperature under a nitrogen atmosphere. To this solution borane-tetrahydrofuran complex (6.2 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 326 mg of a semi-solid. This oil was further purified via a chromatotron using a 2000 micron rotor, eluting with a gradient of ethyl acetate to 1:1 ethyl acetate:methanol to yield the desired title product (225 mg, 47%) as a white solid.

mp 85–87° C.; NMR was consistent with the proposed title structure. FDMS 411 (M+). Analysis for $C_{24}H_{30}N_3OCl$: Theory: C, 69.97; H, 7.34; N, 10.20. Found: C, 69.78; H, 7.29; N, 10.31.

EXAMPLE 271

Preparation of (RS) 1-[3-(methyl)-4-(3-benzylpiperidin-1-yl)butyl]-2-[(4-chlorophenoxy)methyl]-4-methylbenzimidazole dihydrochloride salt A solution of 1-[3-[(3-benzylpiperidin-1-yl)carbonyl]butyl]-2-[(4-chlorophenoxy)methyl]-4-methylbenzimidazole (360 mg, 0.68 mmol) in dry tetrahydrofuran (5 ml) was stirred at room temperature under a nitrogen atmosphere. To this solution borane-tetrahydrofuran complex (4.1 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 330 mg of a viscous oil. This oil was further purified via a chromatotron using a 2000 micron rotor, eluting with ethyl acetate to yield the desired title product (250 mg, 71%) as a slowly crystallizing oil.

mp 95–97° C.; NMR was consistent with the proposed title structure. FDMS 515, 516 (M+). Analysis for $C_{32}H_{38}N_3OCl$: Theory: C, 74.46; H, 7.42; N, 8.14. Found: C, 74.74; H, 7.62; N, 8.03.

EXAMPLE 272

Preparation of (RS) 1-[3-(methyl)-4-(3-cyclohexylmethylpiperidin-1-yl)butyl]-2-[(4-chlorophenoxy)methyl]-4-methylbenzimidazole dihydrochloride salt trihydrate

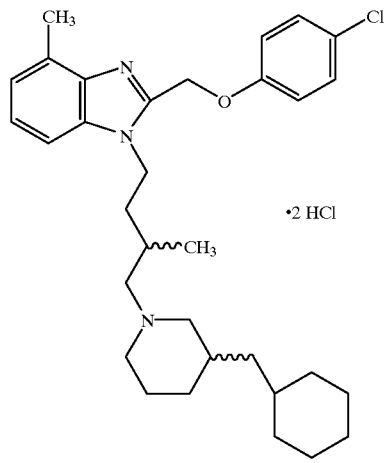

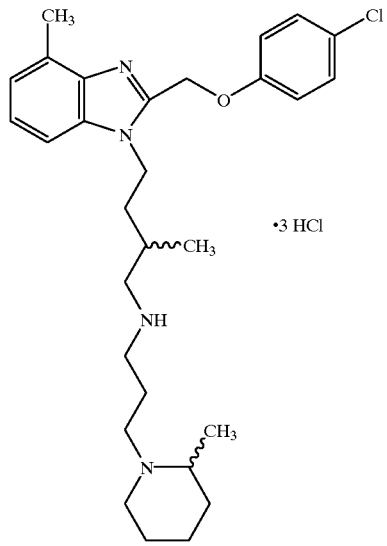

A solution of 1-[3-[(3-cyclohexylmethylpiperidin-1-yl)carbonyl]butyl]-2-[(4-chlorophenoxy)methyl]-4-methylbenzimidazole (350 mg, 0.67 mmol) in dry tetrahydrofuran (5 ml) was stirred at room temperature under a nitrogen atmosphere. To this solution borane-tetrahydrofuran complex (4.0 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 232 mg of a viscous oil. This oil was further purified via a chromatotron using a 2000 micron rotor, eluting with ethyl acetate to yield the desired title product (160 mg, 46%) as a clear viscous oil. The title product was then converted to the dihydrochloride salt, yielding a white solid.

mp 52–56° C.; NMR was consistent with the proposed title structure. FDMS 521, 522 (M+). Analysis for $C_{32}H_{44}N_3OCl \cdot 2HCl \cdot 3H_2O$: Theory: C, 59.20; H, 8.08; N, 6.47. Found: C, 59.43; H, 7.50; N, 6.37.

Analysis for $C_{32}H_{44}N_3OCl \cdot \frac{1}{2}H_2O$: Theory: C, 72.35; H, 8.54; N, 7.91. Found: C, 72.75; H, 8.57; N, 7.86.

A solution of 1-[3-[3-(2-methylpiperidin-1-yl)propylamino]butyl]-2-[(4-chlorophenoxy)methyl]-4-methylbenzimidazole (350 mg, 0.69 mmol) in dry tetrahydrofuran (5 ml) was stirred at room temperature under a nitrogen atmosphere. To this solution borane-tetrahydrofuran complex (4.3 ml of a 1M solution in tetrafuran, 6 eq) was syringed dropwise over a two minute period. The solution was then stirred overnight at room temperature. To the reaction mixture was then slowly added, by syringe, a 1:1 solution of tetrahydrofuran and methanol. After the foaming subsided, 5 N sodium hydroxide (2 ml) was then added by syrine and the resulting mixture was stirred for about sixteen hours under a nitrogen atmosphere at 50–60° C. The reaction mixture was cooled to room temperature and was then diluted with methylene chloride (10 ml).

The organic fraction was separated and concentrated in vacuo to yield a semi-solid. This residue was taken up into ethyl acetate (50 ml), washed once with water, and then dried over potassium carbonate. The solvents were removed in vacuo, yielding 320 mg of a viscous oil. This oil was further purified via a chromatotron using a 2000 micron rotor, eluting with 1:1 ethyl acetate:methanol (with 1% ammonium hydroxide) to yield the desired title product (151 mg, 44%) as a clear viscous oil. The title product was then converted to the trihydrochloride salt, yielding a white solid.

NMR was consistent with the proposed title structure. FDMS 497 (M+). Analysis for $C_{29}H_{44}N_4OCl \cdot 3HCl \cdot H_2O$: Theory: C, 55.76; H, 7.42; N, 8.97. Found: C, 55.70; H, 7.21; N, 9.04.

EXAMPLE 273

Preparation of (RS) 1-[3-(methyl)-4-[3-(2-methylpiperidin-1-yl)propylamino]butyl]-2-[(4-chlorophenoxy)methyl]-4-methylbenzimidazole trihydrochloride salt monohydrate

EXAMPLE 274

Preparation of 2-(4-chlorophenoxymethyl)-4-[3-[1-(t-butoxycarbonyl)piperidin-4-yl]propoxy]-1-[3-[1-(t-butoxycarbonyl)piperidin-4-yl]propyl]benzimidazole

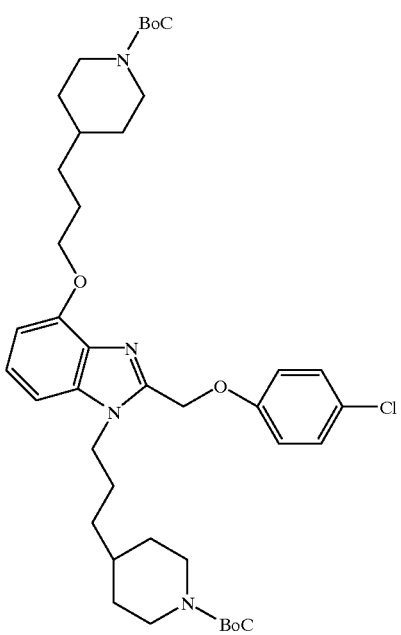

A solution of 4-hydroxy-2-(4-chlorophenoxymethyl) benzimidazole (500 mg, 1.82 mmol) in dry N,N-dimethylformamide (8 ml) was treated with sodium hydride (60% in mineral oil, 162 mg, 4.0 mmol, 2.2 eq). The resulting mixture was stirred at room temperature under a stream of nitrogen for about one hour. To this reaction mixture 3-[1-(t-butoxycarbonyl)piperidin-4-yl]propyl bromide (4.0 mmol, 2.2 eq) was added and the resulting mixture was stirred for three hours at 70° C. The reaction was quenched by the addition of 10 ml of water. The aqueous fraction was extracted with ethyl acetate (3×10 ml). The organic fractions were combined and washed with water (2×10 ml), and then brine (1×10 ml), and then dried over magnesium sulfate. The solvents were removed in vacuo to yield a light brownish crude material. The desired title product was further purified by flash chromatography. There is some substitution at the 7-position of the benzimidazole present, although the 4-substituted is the major isomer.

NMR was consistent with the proposed title structure. FDMS (M+) 725.

EXAMPLE 275

Preparation of 2-(4-chlorophenoxymethyl)-4-[3-(piperidin-4-yl)propoxy]-1-[3-(piperidin-4-yl)propyl]benzimidazole

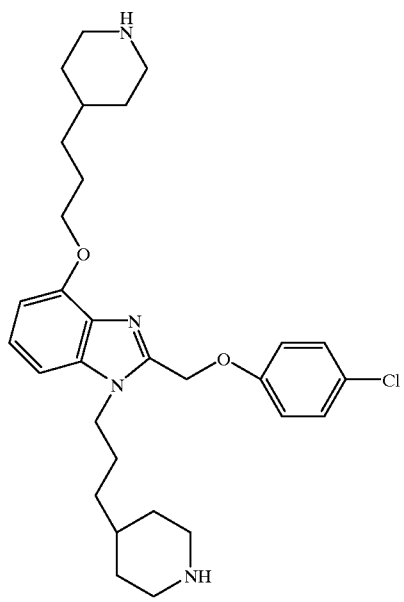

The title compound is prepared from 2-(4-chlorophenoxymethyl)-4-[3-[1-(t-butoxycarbonyl)piperidin-4-yl]propoxy]-1-[3-[1-(t-butoxycarbonyl)piperidin-4-yl]propyl]benzimidazole by standard deprotection techniques using trifluoroacetic acid.

NMR and IR were consistent with the proposed title structure. FDMS (M+) 525; Analysis for $C_{30}H_{41}ClN_4O_2$: Theory: C, 54.22; H, 5.75; N, 7.44. Found: C, 53.97; H, 5.48; N, 7.26.

EXAMPLE 276

Preparation of (RS) 2-(4-chlorophenoxymethyl)-4-[3-[1-(t-butoxycarbonyl)piperidin-3-yl]propoxy]-1-[3-[1-(t-butoxycarbonyl)piperidin-3-yl]propyl]benzimidazole

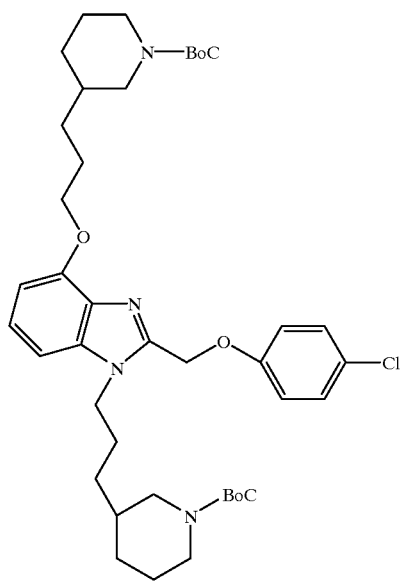

A solution of 4-hydroxy-2-(4-chlorophenoxymethyl) benzimidazole (500 mg, 1.82 mmol) in dry N,N-dimethylformamide (8 ml) was treated with sodium hydride (60% in mineral oil, 162 mg, 4.0 mmol, 2.2 eq). The resulting mixture was stirred at room temperature under a stream of nitrogen for about one hour. To this reaction mixture (RS) 3-[1-(t-butoxycarbonyl)piperidin-3-yl)propyl bromide (4.0 mmol, 2.2 eq) was added and the resulting mixture was stirred for three hours at 70° C. The reaction was quenched by the addition of 10 ml of water. The aqueous fraction was extracted with ethyl acetate (3×10 ml). The organic fractions were combined and washed with water (2×10 ml), and then brine (1×10 ml), and then dried over magnesium sulfate. The solvents were removed in vacuo to yield a light brownish crude material. The desired title product was further purified by flash chromatography.

NMR and IR were consistent with the proposed title structure. FDMS (M+) 724. Analysis for $C_{40}H_{57}ClN_4O_6$: Theory: C, 66.23; H, 7.92; N, 7.72. Found: C, 66.49; H, 8.04; N, 7.79.

EXAMPLE 277

Preparation of (RS) 2-(4-chlorophenoxymethyl)-4-[3-(piperidin-3-yl)propoxy]-1-[3-(piperidin-3-yl)propyl]benzimidazole

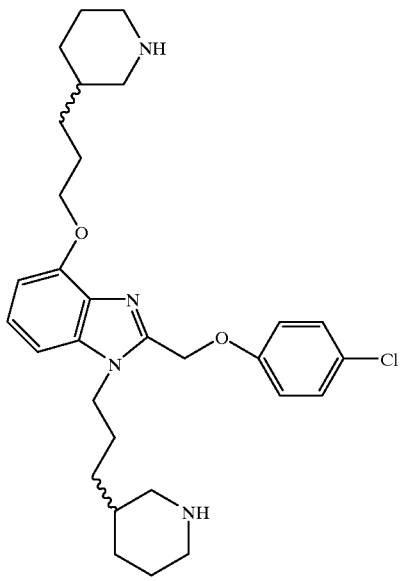

The title compound is prepared from (RS) 2-(4-chlorophenoxymethyl)-4-[3-[1-(t-butoxycarbonyl)piperidin-3-yl]propoxy]-1-[3-[1-(t-butoxycarbonyl)piperidin-3-yl]propyl]benzimidazole by standard deprotection techniques using trifluoroacetic acid.

NMR and IR were consistent with the proposed title structure. FDMS (M+) 525; Analysis for $C_{30}H_{41}ClN_4O_2$: Theory: C, 54.22; H, 5.75; N, 7.44. Found: C, 53.97; H, 5.48; N, 7.26.

EXAMPLE 278

Preparation of (R) 2-(4-chlorophenoxymethyl)-4-[3-[1-(t-butoxycarbonyl)piperidin-3-yl]propoxy]-1-[3-[1-(t-butoxycarbonyl)piperidin-3-yl]propyl]benzimidazole

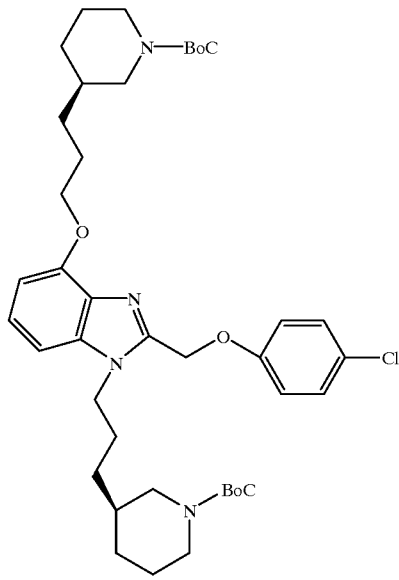

A solution of 4-hydroxy-2-(4-chlorophenoxymethyl) benzimidazole (500 mg, 1.82 mmol) in dry N,N-dimethylformamide (8 ml) was treated with sodium hydride (60% in mineral oil, 162 mg, 4.0 mmol, 2.2 eq). The resulting mixture was stirred at room temperature under a stream of nitrogen for about one hour. To this reaction mixture (R) 3-[1-(t-butoxycarbonyl)piperidin-3-yl)propyl bromide (4.0 mmol, 2.2 eq) was added and the resulting mixture was stirred for three hours at 70° C. The reaction was quenched by the addition of 10 ml of water. The aqueous fraction was extracted with ethyl acetate (3×10 ml). The organic fractions were combined and washed with water (2×10 ml), and then brine (1×10 ml), and then dried over magnesium sulfate. The solvents were removed in vacuo to yield a light brownish crude material. The desired title product was further purified by flash chromatography.

NMR and IR were consistent with the proposed title structure. FDMS (M+) 724. Analysis for $C_{40}H_{57}ClN_4O_6$: Theory: C, 66.23; H, 7.92; N, 7.72. Found: C, 66.23; H, 7.86; N, 7.69.

EXAMPLE 279

Preparation of (R) 2-(4-chlorophenoxymethyl)-4-[3-(piperidin-3-yl)propoxy]-1-[3-(piperidin-3-yl)propyl]benzimidazole

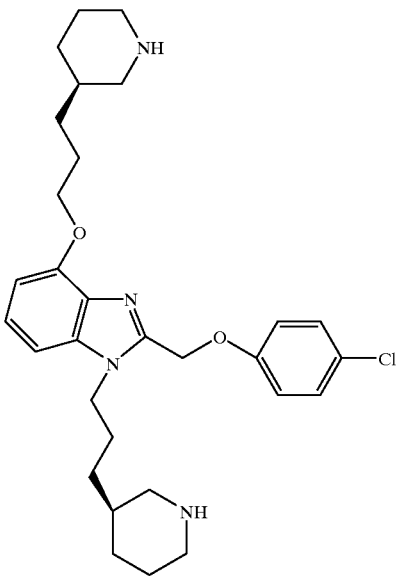

The title compound is prepared from (R) 2-(4-chlorophenoxymethyl)-4-[3-[1-(t-butoxycarbonyl)piperidin-3-yl]propoxy]- 1-[3-[1-(t-butoxycarbonyl)piperidin-3-yl]propyl]benzimidazole by standard deprotection techniques using trifluoroacetic acid.

NMR and IR were consistent with the proposed title structure. FDMS (M+) 525; Analysis for $C_{30}H_{41}ClN_4O_2$: Theory: C, 54.22; H, 5.75; N, 7.44. Found: C, 54.12; H, 5.86; N, 7.47.

EXAMPLE 280

Preparation of (S) 2-(4-chlorophenoxymethyl)-4-[3-[1-(t-butoxycarbonyl)piperidin-3-yl]propoxy]-1-[3-[1-(t-butoxycarbonyl)piperidin-3-yl]propyl]benzimidazole

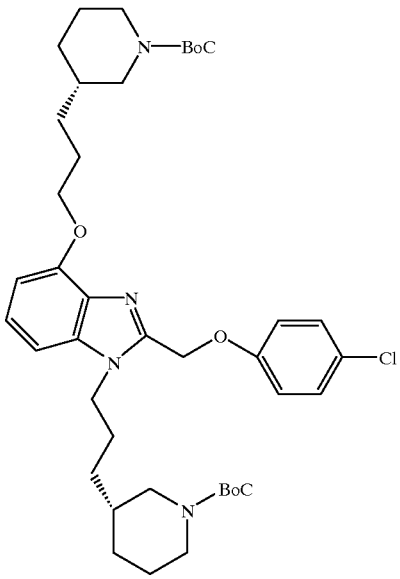

A solution of 4-hydroxy-2-(4-chlorophenoxymethyl)benzimidazole (500 mg, 1.82 mmol) in dry N,N-dimethylformamide (8 ml) was treated with sodium hydride (60% in mineral oil, 162 mg, 4.0 mmol, 2.2 eq). The resulting mixture was stirred at room temperature under a stream of nitrogen for about one hour. To this reaction mixture (S) 3-[1-(t-butoxycarbonyl)piperidin-3-yl)propyl bromide (4.0 mmol, 2.2 eq) was added and the resulting mixture was stirred for three hours at 70° C. The reaction was quenched by the addition of 10 ml of water. The aqueous fraction was extracted with ethyl acetate (3×10 ml). The organic fractions were combined and washed with water (2×10 ml), and then brine (1×10 ml), and then dried over magnesium sulfate. The solvents were removed in vacuo to yield a light brownish crude material. The desired title product was further purified by flash chromatography.

NMR and IR were consistent with the proposed title structure. FDMS (M+) 724. Analysis for $C_{40}H_{57}ClN_4O_6$: Theory: C, 66.23; H, 7.92; N, 7.72. Found: C, 65.51; H, 7.94; N, 7.80.

EXAMPLE 281

Preparation of (S) 2-(4-chlorophenoxymethyl)-4-[3-(piperidin-3-yl)propoxy]-1-[3-(piperidin-3-yl)propyl]benzimidazole

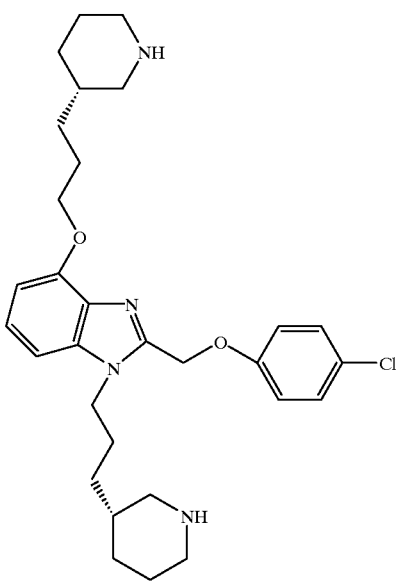

The title compound is prepared from (S) 2-(4-chlorophenoxymethyl)-4-[3-[1-(t-butoxycarbonyl)piperidin-3-yl]propoxy]-1-[3-[1-(t-butoxycarbonyl)piperidin-3-yl]propyl]benzimidazole by standard deprotection techniques using trifluoroacetic acid.

NMR and IR were consistent with the proposed title structure. FDMS (M+) 525; Analysis for $C_{30}H_{41}ClN_4O_2$: Theory: C, 54.22; H, 5.75; N, 7.44. Found: C, 53.96; H, 5.74; N, 7.40.

EXAMPLE 282

Preparation of 2-(4-chlorophenoxymethyl)-4-[5-[1-(t-butoxycarbonyl)piperidin-4-yl]pentoxy]-1-[5-[1-(t-butoxycarbonyl)piperidin-4-yl]pentyl]benzimidazole

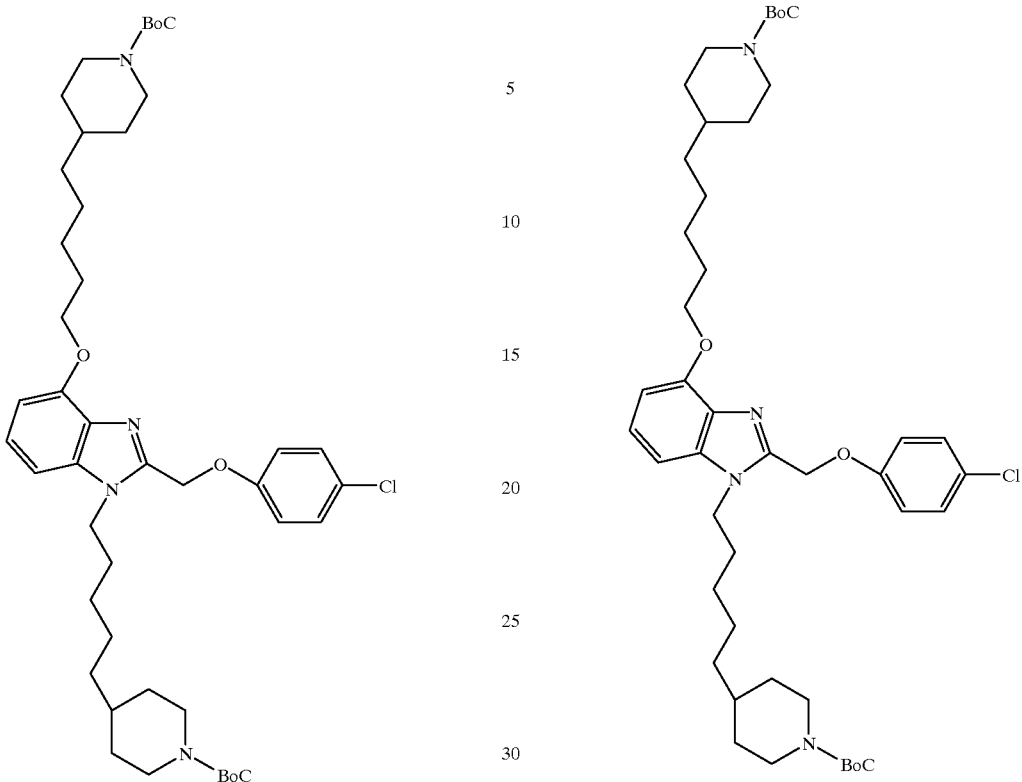

A solution of 4-hydroxy-2-(4-chlorophenoxymethyl) benzimidazole (500 mg, 1.82 mmol) in dry N,N-dimethylformamide (8 ml) was treated with sodium hydride (60% in mineral oil, 162 mg, 4.0 mmol, 2.2 eq). The resulting mixture was stirred at room temperature under a stream of nitrogen for about one hour. To this reaction mixture 5-[1-(t-butoxycarbonyl)piperidin-4-yl)pentyl bromide (4.0 mmol, 2.2 eq) was added and the resulting mixture was stirred for three hours at 70° C. The reaction was quenched by the addition of 10 ml of water. The aqueous fraction was extracted with ethyl acetate (3×10 ml). The organic fractions were combined and washed with water (2×10 ml), and then brine (1×10 ml), and then dried over magnesium sulfate. The solvents were removed in vacuo to yield a light brownish crude material. The desired title product was further purified by flash chromatography. There is some substitution at the 7-position of the benzimidazole present, although the 4-substituted is the major isomer.

NMR was consistent with the proposed title structure. FDMS (M+) 781.

EXAMPLE 283

Preparation of 2-(4-chlorophenoxymethyl)-4-[5-(piperidin-4-yl)pentoxy]-1-[5-(piperidin-4-yl]pentyl]benzimidazole The title compound is prepared from 2-(4-chlorophenoxymethyl)-4-[5-[1-(t-butoxycarbonyl) piperidin-4-yl]pentoxy]-1-[5-[1-(t-butoxycarbonyl) piperidin-4-yl]pentyl]benzimidazole by standard deprotection techniques using trifluoroacetic acid.

NMR and IR were consistent with the proposed title structure. FDMS (M+) 581; Analysis for $C_{34}H_{49}ClN_4O_2$: Theory: C, 56.40; H, 6.35; N, 6.92. Found: C, 56.22; H, 6.37; N, 6.90.

Preparation 58

Preparation of 2-(4-chlorophenoxymethyl)-4-benzyloxy-benzimidazole

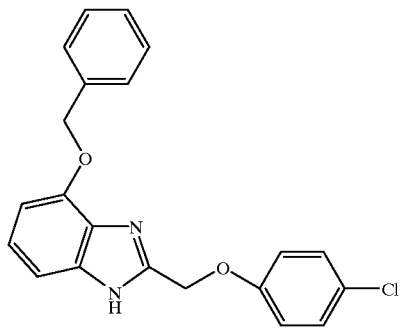

A solution of 4-hydroxybenzimidazole (7.28 mmol, 1.0 eq) and triphenylphosphine (2.30 mg, 8,74 mmol, 1.2 eq) in dry tetrahydrofuran (72 ml, 0.1 M) was treated with a solution of benzyl alcohol (0.9 ml, 8.74 mmol, 1.2 eq) and diethyl azodicarboxylate (1.4 ml, 8.74 mmol, 1.2 eq). The resulting mixture was stirred at 0° C. and was then warmed

EXAMPLE 284
Preparation of 2-(4-chlorophenoxymethyl)-4-benzyloxy-1-[3-[1-(t-butoxycarbonyl )piperidin-4-yl]propyl]-benzimidazole to room temperature. After five hours, the tetrahydrofuran was removed in vacuo. The residue was further purified using flash chromatography to provide the title intermediate in 55–70% yield.

NMR and IR were consistent with the proposed title structure. FDMS 364(M+). Analysis for $C_{21}H_{16}ClN_2O$: Theory: C, 69.14; H, 4.70; N, 7.68. Found: C, 69.35; H, 4.89; N, 7.74.

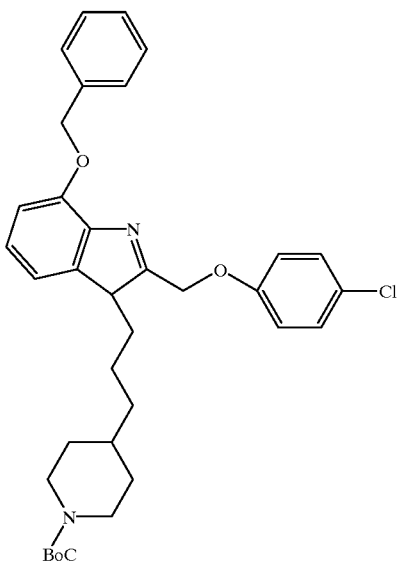

A solution of 2-(4-chlorophenoxymethyl)-4-benzyloxy-benzimidazole (720 mg, 1.97 mmol, 1.0 eq) in dry N,N-dimethylformamide (8 ml, 0.25 M) was treated with sodium hydride (60% in mineral oil, 57 mg, 2.30 mmol, 1.2 eq). The resulting mixture was stirred at room temperature for thirty minutes and then 3-[1-(t-butoxycarbonyl)piperidin-4-yl]propyl bromide (7.24 mg, 2.36 mmol, 1.2 eq) was added to the reaction mixture. The resulting mixture was stirred at 70° C. for three hours. The reaction was quenched by the addition of water (1×30 ml). The aqueous fraction was extracted with diethyl ether (1×30 ml). The organic fractions were combined, washed with water (1×30 ml), then brine (1×30 ml), and then dried over sodium sulfate. The solvents were removed in vacuo. The desired title product was further purified by flash chromatography to provide a white foam in 38% yield.

NMR and IR were consistent with the proposed title structure. FDMS 589 (M+).

EXAMPLE 285
Preparation of (RS) 2-(4-chlorophenoxymethyl)-4-benzyloxy-1-[3-[1-(t-butoxycarbonyl)piperidin-3-yl]propyl]-benzimidazole

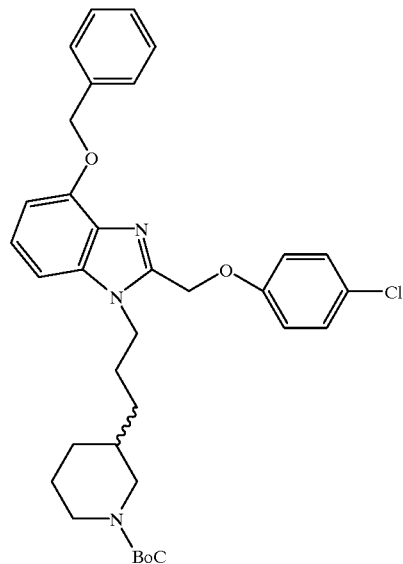

A solution of 2-(4-chlorophenoxymethyl)-4-benzyloxy-benzimidazole (720 mg, 1.97 mmol, 1.0 eq) in dry N,N-dimethylformamide (8 ml, 0.25 M) was treated with sodium hydride (60% in mineral oil, 57 mg, 2.30 mmol, 1.2 eq). The resulting mixture was stirred at room temperature for thirty minutes and then (RS) 3-[1-(t-butoxycarbonyl)piperidin-3-yl]propyl bromide (7.24 mg, 2.36 mmol, 1.2 eq) was added to the reaction mixture. The resulting mixture was stirred at 70° C. for three hours. The reaction was quenched by the addition of water (1×30 ml). The aqueous fraction was extracted with diethyl ether (1×30 ml). The organic fractions were combined, washed with water (1×30 ml), then brine (1×30 ml), and then dried over sodium sulfate. The solvents were removed in vacuo. The desired title product was further purified by flash chromatography to provide a white foam in 38% yield.

NMR and IR were consistent with the proposed title structure. FDMS 589 (M+). Analysis for $C_{34}H_{40}ClN_3O_4$: Theory: C, 69.20; H, 6.83; N, 7.12. Found: C, 69.20; H, 6.90; N, 7.28.

EXAMPLE 286
Preparation of (R) 2-(4-chlorophenoxymethyl)-4-benzyloxy-1-[3-[1-(t-butoxycarbonyl)piperidin-3-yl]propyl]-benzimidazole

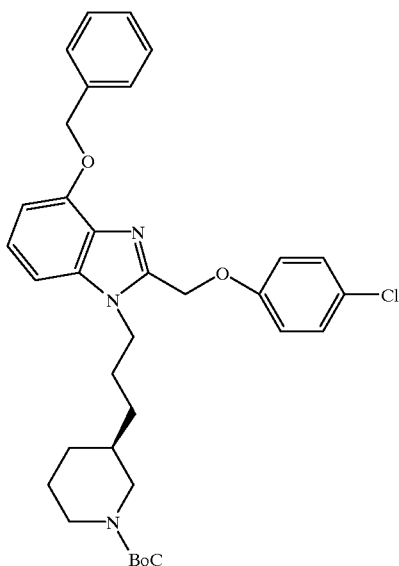

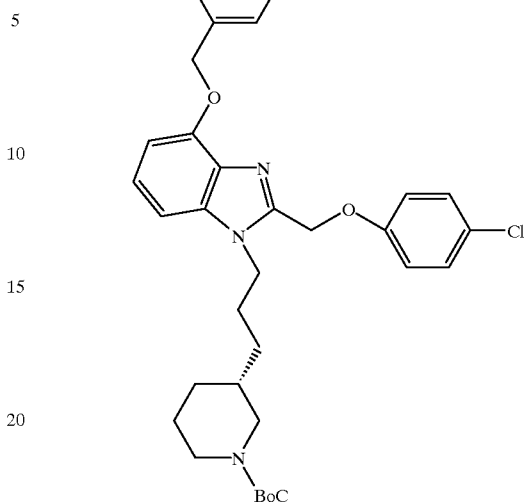

A solution of 2-(4-chlorophenoxymethyl)-4-benzyloxy-benzimidazole (720 mg, 1.97 mmol, 1.0 eq) in dry N,N-dimethylformamide (8 ml, 0.25 M) was treated with sodium hydride (60% in mineral oil, 57 mg, 2.30 mmol, 1.2 eq). The resulting mixture was stirred at room temperature for thirty minutes and then (R) 3-[1-(t-butoxycarbonyl)piperidin-3-yl]propyl bromide (7.24 mg, 2.36 mmol, 1.2 eq) was added to the reaction mixture. The resulting mixture was stirred at 70° C. for three hours. The reaction was quenched by the addition of water (1×30 ml). The aqueous fraction was extracted with diethyl ether (1×30 ml). The organic fractions were combined, washed with water (1×30 ml), then brine (1×30 ml), and then dried over sodium sulfate. The solvents were removed in vacuo. The desired title product was further purified by flash chromatography to provide a white foam in 38% yield.

IR was consistent with the proposed title structure. FDMS 589 (M+). Analysis for $C_{34}H_{40}ClN_3O_4$: Theory: C, 69.20; H, 6.83; N, 7.12. Found: C, 70.15; H, 7.17; N, 7.07.

EXAMPLE 287

Preparation of (S) 2-(4-chlorophenoxymethyl)-4-benzyloxy-1-[3-[1-(t-butoxycarbonyl)piperidin-3-yl]propyl]-benzimidazole A solution of 2-(4-chlorophenoxymethyl)-4-benzyloxy-benzimidazole (720 mg, 1.97 mmol, 1.0 eq) in dry N,N-dimethylformamide (8 ml, 0.25 M) was treated with sodium hydride (60% in mineral oil, 57 mg, 2.30 mmol, 1.2 eq). The resulting mixture was stirred at room temperature for thirty minutes and then (S) 3-[1-(t-butoxycarbonyl)piperidin-3-yl]propyl bromide (7.24 mg, 2.36 mmol, 1.2 eq) was added to the reaction mixture. The resulting mixture was stirred at 70° C. for three hours. The reaction was quenched by the addition of water (1×30 ml). The aqueous fraction was extracted with diethyl ether (1×30 ml). The organic fractions were combined, washed with water (1×30 ml), then brine (1×30 ml), and then dried over sodium sulfate. The solvents were removed in vacuo. The desired title product was further purified by flash chromatography to provide a white foam in 38% yield.

IR was consistent with the proposed title structure. FDMS 589 (M+). Analysis for $C_{34}H_{40}ClN_3O_4$: Theory: C, 69.20; H, 6.83; N, 7.12. Found: C, 68.25; H, 7.01; N, 7.25.

EXAMPLE 288

Preparation of (R) 2-(4-chlorophenoxymethyl)-4-benzyloxy-1-[2-[1-(t-butoxycarbonyl)piperidin-3-yl]ethyl]-benzimidazole

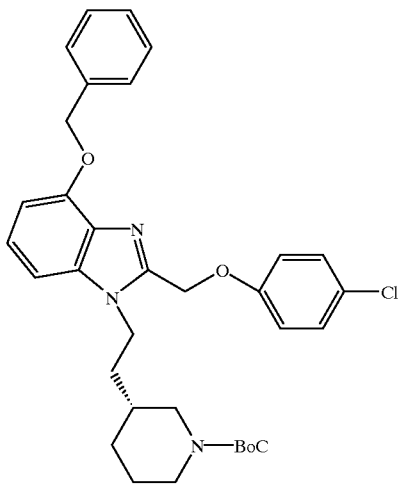

A solution of 2-(4-chlorophenoxymethyl)-4-benzyloxy-benzimidazole (720 mg, 1.97 mmol, 1.0 eq) in dry N,N-dimethylformamide (8 ml, 0.25 M) was treated with sodium hydride (60% in mineral oil, 57 mg, 2.30 mmol, 1.2 eq). The resulting mixture was stirred at room temperature for thirty minutes and then (R) 2-[1-(t-butoxycarbonyl)piperidin-3-yl] ethyl bromide (2.36 mmol, 1.2 eq) was added to the reaction mixture. The resulting mixture was stirred at 70° C. for three hours. The reaction was quenched by the addition of water (1×30 ml). The aqueous fraction was extracted with diethyl ether (1×30 ml). The organic fractions were combined, washed with water (1×30 ml), then brine (1×30 ml), and then dried over sodium sulfate. The solvents were removed in vacuo. The desired title product was further purified by flash chromatography to provide a white foam in 40–50% yield.

IR and NMR were consistent with the proposed title structure. FDMS 575 (M+). Analysis for $C_{33}H_{38}ClN_3O_4$: Theory: C, 68.80; H, 6.65; N, 7.29. Found: C, 68.35; H, 7.47; N, 8.08.

EXAMPLE 289
Preparation of (S) 2-(4-chlorophenoxymethyl)-4-benzyloxy-1-[2-[1-(t-butoxycarbonyl)piperidin-3-yl]ethyl]-benzimidazole

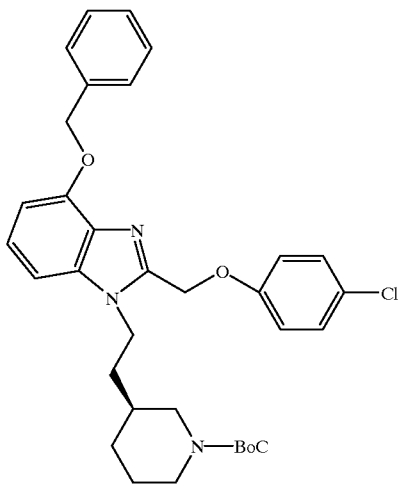

A solution of 2-(4-chlorophenoxymethyl)-4-benzyloxy-benzimidazole (720 mg, 1.97 mmol, 1.0 eq) in dry N,N-dimethylformamide (8 ml, 0.25 M) was treated with sodium hydride (60% in mineral oil, 57 mg, 2.30 mmol, 1.2 eq). The resulting mixture was stirred at room temperature for thirty minutes and then (S) 2-[1-(t-butoxycarbonyl)piperidin-3-yl] ethyl bromide (2.36 mmol, 1.2 eq) was added to the reaction mixture. The resulting mixture was stirred at 70° C. for three hours. The reaction was quenched by the addition of water (1×30 ml). The aqueous fraction was extracted with diethyl ether (1×30 ml). The organic fractions were combined, washed with water (1×30 ml), then brine (1×30 ml), and then dried over sodium sulfate. The solvents were removed in vacuo. The desired title product was further purified by flash chromatography to provide a white foam in 40–50% yield.

IR and NMR were consistent with the proposed title structure. FDMS 575 (M+). Analysis for $C_{33}H_{38}ClN_3O_4$: Theory: C, 68.80; H, 6.65; N, 7.29. Found: C, 68.03; H, 7.39; N, 7.86.

EXAMPLE 290

Preparation of (RS) 2-(4-chlorophenoxymethyl)-4-hydroxy-1-[3-[1-(t-butoxycarbonyl)piperidin-3-yl]propyl]-benzimidazole

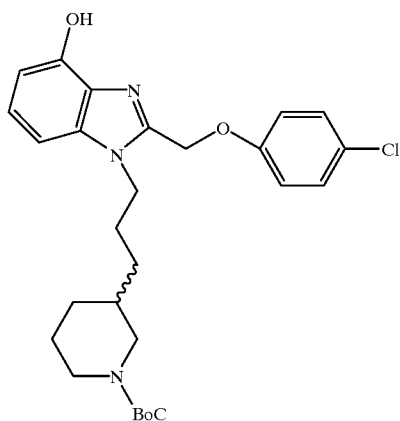

A solution of (RS) 2-(4-chlorophenoxymethyl)-4-benzyloxy-1-[3-[1-(t-butoxycarbonyl)piperidin-3-yl]propyl]-benzimidazole (245 mg, 0.42 mmol, 1.0 eq) in ethyl acetate (4.2 ml) was degassed and then treated with 5% palladium on carbon (250 mg). The resulting mixture was stirred under a hydrogen atmosphere. The reaction mixture was then filtered through a CELITE™ cake layer. The catalyst was washed thoroughly with ethyl acetate and ethanol. The filtrate was condensed on a rotoevaporator to yield the desired title product in 78% yield.

NMR was consistent with the proposed title structure. FDMS 589 (M+).

EXAMPLE 291

Preparation of (RS) 2-(4-chlorophenoxymethyl)-4-[2-[1-(t-butoxycarbonyl)piperidin-3-yl]ethoxy]-1-[3-[1-(t-butoxycarbonyl)piperidin-3-yl]propyl]-benzimidazole

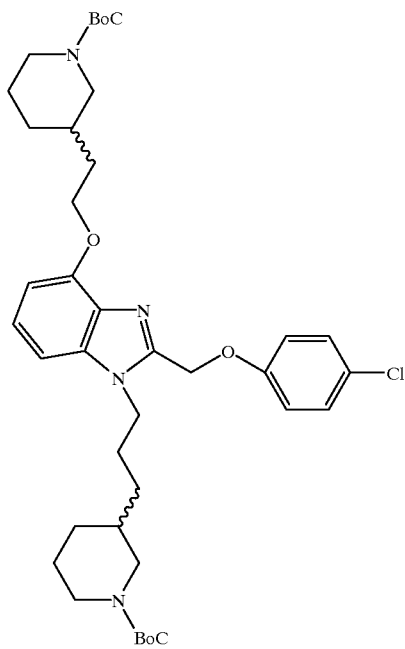

A solution of (RS) 2-(4-chlorophenoxymethyl)-4-hydroxy-1-[3-[1-(t-butoxycarbonyl)piperidin-3-yl]propyl]benzimidazole (75 mg, 0.15 mmol, 1.0 eq) in dry N,N-dimethylformamide (1.0 ml) was treated with sodium hydride (60% in oil, 7.5 mg, 0.18 mmol, 1.20 eq). The resulting mixture was stirred at room temperature for thirty minutes, after which time 2-[1-(t-butoxycarbonyl)piperidin-3-yl]ethyl bromide (0.18 mmol, 1.2 eq) was added. The resulting mixture was stirred for three hours at 70° C. The reaction was quenched by the addition of water (10 ml). The aqueous fraction was extracted with diethyl ether (3×10 ml). The organic fractions were combined, washed with water (2×10 ml), then brine (1×10 ml), and then dried over sodium sulfate. The solvents were removed in vacuo to give a crude product. The title product was further purified by flash chromatography to provide a crystalline product. Yield: 92%

NMR was consistent with the proposed title structure. FDMS 711 (M+).

EXAMPLE 292
Preparation of (RS) 2-(4-chlorophenoxymethyl)-4-[[1-(t-butoxycarbonyl)piperidin-3-yl]methoxy]-1-[3-[1-(t-butoxycarbonyl)piperidin-3-yl]propyl]-benzimidazole

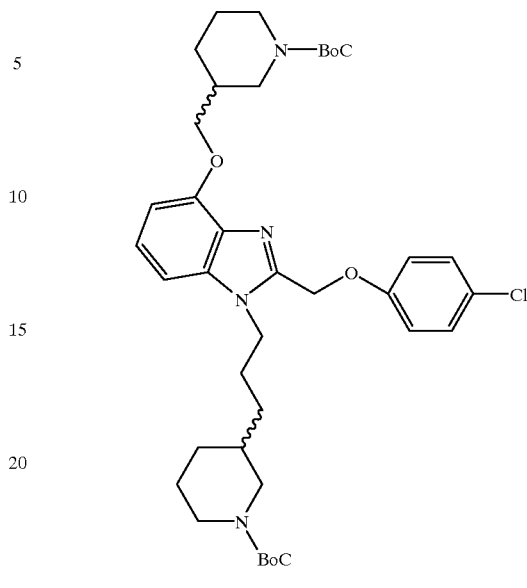

A solution of (RS) 2-(4-chlorophenoxymethyl)-4-hydroxy-1-[3-[1-(t-butoxycarbonyl)piperidin-3-yl]propyl] benzimidazole (75 mg, 0.15 mmol, 1.0 eq) in dry N,N-dimethylformamide (1.0 ml) was treated with sodium hydride (60% in oil, 7.5 mg, 0.18 mmol, 1.20 eq). The resulting mixture was stirred at room temperature for thirty minutes, after which time 1-(t-butoxycarbonyl)piperidin-3-yl)methyl bromide (0.18 mmol, 1.2 eq) was added. The resulting mixture was stirred for three hours at 70° C. The reaction was quenched by the addition of water (10 ml). The aqueous fraction was extracted with diethyl ether (3×10 ml). The organic fractions were combined, washed with water (2×10 ml), then brine (1×10 ml), and then dried over sodium sulfate. The solvents were removed in vacuo to give a crude product. The title product was further purified by flash chromatography to provide a crystalline product.

NMR and IR were consistent with the proposed title structure. FDMS 696 (M+).

EXAMPLE 293
Preparation of (RS) 2-(4-chlorophenoxymethyl)-4-[(piperidin-3-yl)methoxy]-1-[3-[1-(t-butoxycarbonyl)piperidin-3-yl]propyl]-benzimidazole

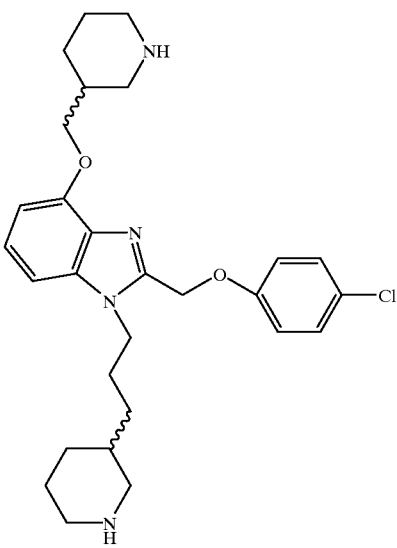

The title product is prepared from (RS) 2-(4-chlorophenoxymethyl)-4-[[1-(t-butoxycarbonyl)piperidin-3-yl]methoxy]-1-[3-[1-(t-butoxycarbonyl)piperidin-3-yl]propyl]-benzimidazole using a standard trifluoroacetic acid deprotection protocol.

NMR and IR were consistent with the proposed title structure. FDMS 497 (M+).

EXAMPLE 294

Preparation of (RS) 2-(4-chlorophenoxymethyl)-4-[3-[1-(t-butoxycarbonyl)piperidin-4-yl]propoxy]-1-[3-[1-(t-butoxycarbonyl)piperidin-3-yl]propyl]-benzimidazole

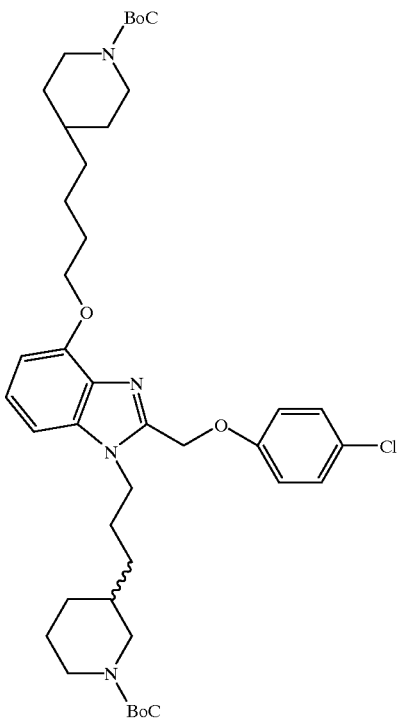

A solution of (RS) 2-(4-chlorophenoxymethyl)-4-hydroxy-1-[3-[1-(t-butoxycarbonyl)piperidin-3-yl]propyl]benzimidazole (75 mg, 0.15 mmol, 1.0 eq) in dry N,N-dimethylformamide (1.0 ml) was treated with sodium hydride (60% in oil, 7.5 mg, 0.18 mmol, 1.20 eq). The resulting mixture was stirred at room temperature for thirty minutes, after which time 3-[1-(t-butoxycarbonyl)piperidin-4-yl)]propyl bromide (0.18 mmol, 1.2 eq) was added. The resulting mixture was stirred for three hours at 70° C. The reaction was quenched by the addition of water (10 ml). The aqueous fraction was extracted with diethyl ether (3×10 ml). The organic fractions were combined, washed with water (2×10 ml), then brine (1×10 ml), and then dried over sodium sulfate. The solvents were removed in vacuo to give a crude product. The title product was further purified by flash chromatography to provide a crystalline product.

NMR and IR were consistent with the proposed title structure. FDMS 724 (M+). Analysis for $C_{40}H_{57}ClN_4O_6$: Theory: C, 66.23; H, 7.92; N, 7.72. Found: C, 66.51; H, 7.99; N, 7.52.

EXAMPLE 295

Preparation of (RS) 2-(4-chlorophenoxymethyl)-4-[3-[1-(t-butoxycarbonyl)piperidin-4-yl]propoxy]-1-[3-[1-(t-butoxycarbonyl)piperidin-3-yl]propyl]-benzimidazole

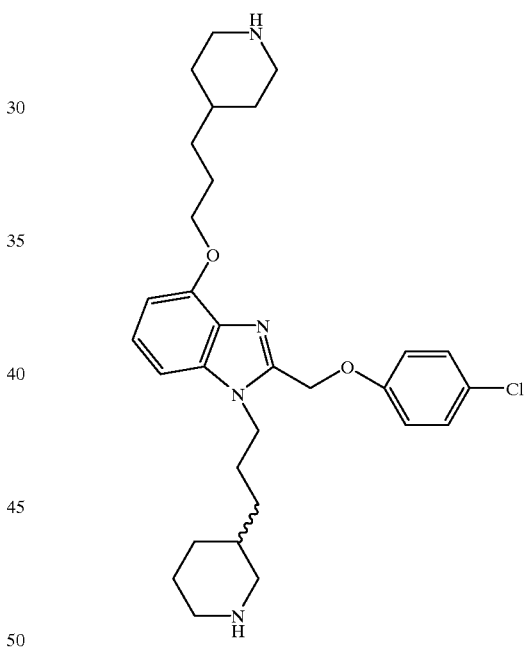

The title product is prepared from (RS) 2-(4-chlorophenoxymethyl)-4-[3-[1-(t-butoxycarbonyl)piperidin-4-yl]propoxy]-1-[3-[1-(t-butoxycarbonyl)piperidin-3-yl]propyl]benzimidazole using a standard trifluoroacetic acid deprotection protocol.

NMR and IR were consistent with the proposed title structure. FDMS 511.4 (M+). Analysis for $C_{29}H_{39}ClN_4O_2$: Theory: C, 53.62; H, 5.59; N, 7.58. Found: C, 53.38; H, 5.64; N, 7.63.

EXAMPLE 296

Preparation of (RS) 2-(4-chlorophenoxymethyl)-4-[5-[1-(t-butoxycarbonyl)piperidin-4-yl]pentoxy]-1-[3-[1-(t-butoxycarbonyl)piperidin-3-yl]propyl]-benzimidazole

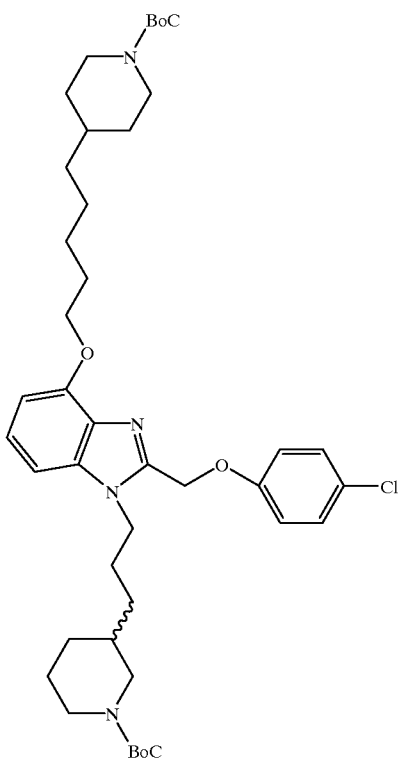

A solution of (RS) 2-(4-chlorophenoxymethyl)-4-hydroxy-1-[3-[1-(t-butoxycarbonyl)piperidin-3-yl]propyl] benzimidazole (75 mg, 0.15 mmol, 1.0 eq) in dry N,N-dimethylformamide (1.0 ml) was treated with sodium hydride (60% in oil, 7.5 mg, 0.18 mmol, 1.20 eq). The resulting mixture was stirred at room temperature for thirty minutes, after which time 5-[1-(t-butoxycarbonyl)piperidin-4-yl)]pentyl bromide (0.18 mmol, 1.2 eq) was added. The resulting mixture was stirred for three hours at 70° C. The reaction was quenched by the addition of water (10 ml). The aqueous fraction was extracted with diethyl ether (3×10 ml). The organic fractions were combined, washed with water (2×10 ml), then brine (1×10 ml), and then dried over sodium sulfate. The solvents were removed in vacuo to give a crude product. The title product was further purified by flash chromatography to provide a crystalline product.

NMR and IR were consistent with the proposed title structure. FDMS 752 (M+).

EXAMPLE 297

Preparation of (RS) 2-(4-chlorophenoxymethyl)-4-[5-(piperidin-4-yl)pentoxy]-1-[3-(piperidin-3-yl)propyl]-benzimidazole

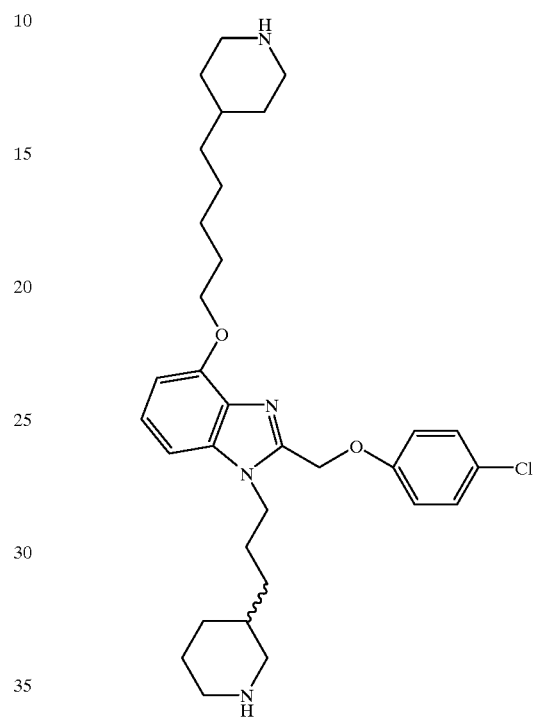

The title product is prepared from (RS) 2-(4-chlorophenoxymethyl)-4-[5-[1-(t-butoxycarbonyl) piperidin-4-yl]pentoxy]-1-[3-[1-(t-butoxycarbonyl) piperidin-3-yl]propyl]benzimidazole using a standard trifluoroacetic acid deprotection protocol.

NMR and IR were consistent with the proposed title structure. FDMS 555 (M+1).

EXAMPLE 298

Preparation of (RS) 2-(4-chlorophenoxymethyl)-4-[5-[1-(t-butoxycarbonyl)piperidin-3-yl]pentoxy]-1-[3-[1-(t-butoxycarbonyl)piperidin-3-yl]propyl]-benzimidazole

183

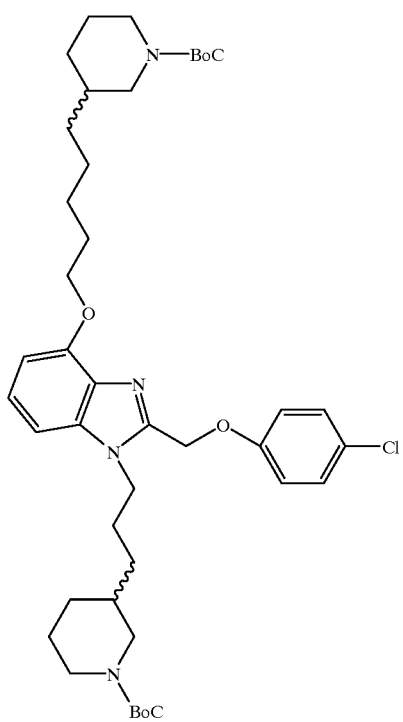

A solution of (RS) 2-(4-chlorophenoxymethyl)-4-hydroxy-1-[3-[1-(t-butoxycarbonyl)piperidin-3-yl]propyl] benzimidazole (75 mg, 0.15 mmol, 1.0 eq) in dry N,N-dimethylformamide (1.0 ml) was treated with sodium hydride (60% in oil, 7.5 mg, 0.18 mmol, 1.20 eq). The resulting mixture was stirred at room temperature for thirty minutes, after which time 5-[1-(t-butoxycarbonyl)piperidin-3-yl)]pentyl bromide (0.18 mmol, 1.2 eq) was added. The resulting mixture was stirred for three hours at 70° C. The reaction was quenched by the addition of water (10 ml). The aqueous fraction was extracted with diethyl ether (3×10 ml). The organic fractions were combined, washed with water (2×10 ml), then brine (1×10 ml), and then dried over sodium sulfate. The solvents were removed in vacuo to give a crude product. The title product was further purified by flash chromatography to provide a crystalline product.

NMR and IR were consistent with the proposed title structure. FDMS 753 (M+).

EXAMPLE 299

Preparation of (RS) 2-(4-chlorophenoxymethyl)-4-[5-(piperidin-3-yl)pentoxy]-1-[3-(piperidin-3-yl)propyl]-benzimidazole

184

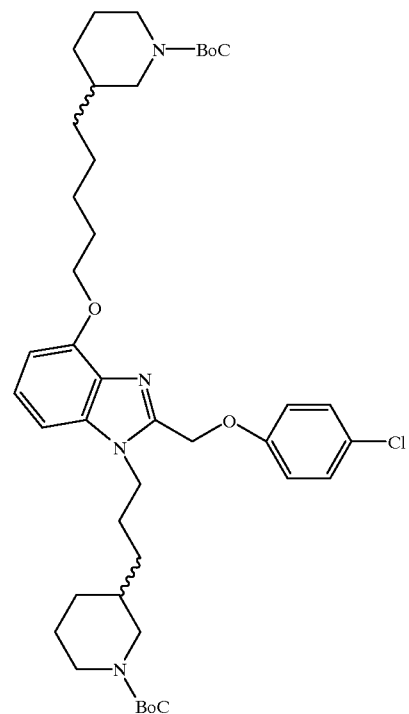

The title product is prepared from (RS) 2-(4-chlorophenoxymethyl)-4-[5-[1-(t-butoxycarbonyl) piperidin-3-yl]pentoxy]-1-[3-[1-(t-butoxycarbonyl) piperidin-3-yl]propyl]benzimidazole using a standard trifluoroacetic acid deprotection protocol.

NMR and IR were consistent with the proposed title structure. FDMS 555 (M+1).

Preparation 59

Preparation of 2,3-diaminophenol dihydrochloride salt

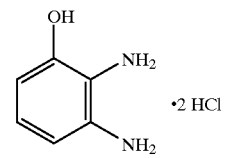

In a 250 ml single neck round bottom flask was added 2,3-diaminophenol (10 g, 80.55 mmol) to ethanol (100 ml). This mixture was heated to 50° C. to achieve dissolution. The resulting solution is cooled to −5 to 0° C. and an excess of anhydrous hydrogen chloride gas was added to form a viscous slurry. The resulting mixture was stirred for two hours at ~0° C., then filtered, and rinsed with chilled methanol (30 ml). The solvents were removed in vacuo and the residue was dried overnight.

Yield: 15.29 g (96.3%).

Preparation 60

Preparation of 4-hydroxy-2-[(4-chlorophenoxy)methyl] benzimidazole

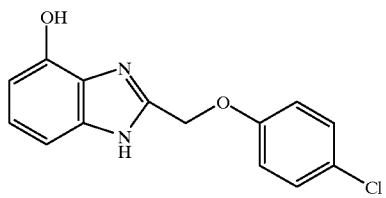

In a 50 ml single neck round bottom flask, under a nitrogen atmosphere, 4-chlorophenoxyacetonitrile (0.46 g, 2.79 mmol) was admixed in methanol (11 ml). The contents were stirred to achieve dissolution. To this solution were added sodium methoxide (0.164 g, 3.0 mmol). The resulting mixture was stirred for about 40 minutes. To this mixture was added 2,3-diaminophenol dihydrochloride salt (0.5 g, 2.5 mmol) and the resulting mixture was stirred for two hours at room temperature. The reaction mixture was filtered and the filtrate was added to 60 ml of water. A light brown precipitate formed and this precipitate is removed by filtration, and washed with 20 ml of water. The solid was dried in a vacuum oven overnight.

NMR was consistent with the proposed title structure. Yield: 0.60 grams (86.1%).

Preparation 61

Preparation of 4-hydroxy-2-[(4-methylphenoxy)methyl]benzimidazole

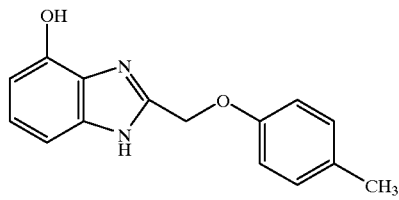

In a 50 ml single neck round bottom flask, under a nitrogen atmosphere, 4-methylphenoxyacetonitrile (2.79 mmol) was admixed in methanol (11 ml). The contents were stirred to achieve dissolution. To this solution were added sodium methoxide (0.164 g, 3.0 mmol). The resulting mixture was stirred for about 40 minutes. To this mixture was added 2,3-diaminophenol dihydrochloride salt (0.5 g, 2.5 mmol) and the resulting mixture was stirred for two hours at room temperature. The reaction mixture was filtered and the filtrate was added to 60 ml of water. A light brown precipitate formed and this precipitate is removed by filtration, and washed with 20 ml of water. The solid was dried in a vacuum oven overnight.

Preparation 62

Preparation of 4-benzyloxy-2-[(4-methylphenoxy)methyl]benzimidazole

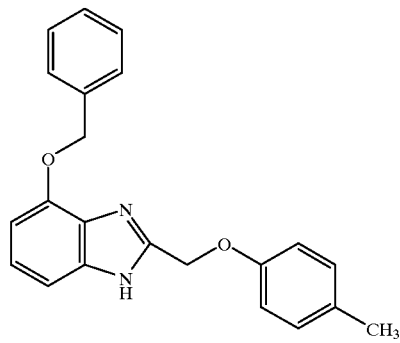

In a 500 ml single neck round bottom flask, under a nitrogen atmosphere, 4-benzyloxy-2-[(4-methylphenoxy)methyl]benzimidazole (7.0 g, 27.5 mmol) and triphenylphosphine (9.31 g, 35.5 mmol) were admixed. To this was added anhydrous tetrahydrofuran (275 ml). The resulting mixture was stirred for five minute to achieve a dark red solution, after which time benzyl alcohol (3.79 ml, 36.6 mmol) and diethyl azodicarboxylate (5.9 ml, 37.5 mmol) were added. The resulting mixture was stirred at room temperature overnight. The reaction mixture was extracted with ethyl acetate (500 ml). The organic fraction was washed with water (2×500 ml). The organic fraction was dried over sodium sulfate and the solvents were removed in vacuo. The residue was then redissolved in methylene chloride (110 ml) and further purified by chromatography. The desired fractions were collected and the title product was recrystallized from 80:20 hexanes:diethyl ether.

NMR was consistent with the proposed title structure.

EXAMPLE 300

Preparation of 4-trifluoromethanesulfonyloxy-2-[(4-chlorophenoxy)methyl]-1-trifluoromethanesulfonylbenzimidazole

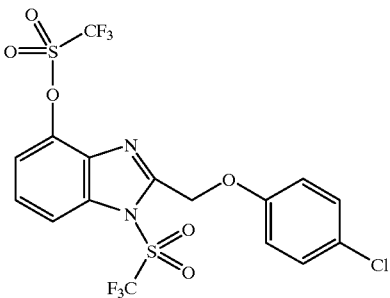

In a 500 ml flask, under a nitrogen atmosphere, were added 4-hydroxy-2-[(4-chlorophenoxy)methyl]benzimidazole (9.10 g, 33.1 mmol) and pyridine (300 ml). The contents were then chilled to 0° C. and trifluoromethanesulfonic anhydride (23.36 g, 82.8 mmol) was then added by syringe. The resulting mixture was stirred at 0° C. for two hours and then stirred at room temperature overnight. The progress of the reaction was monitored by thin layer chromatography. The solvents were then removed in vacuo. The residue was redissolved in ethyl acetate (500 ml) and washed with water (3×500 ml). The organic fraction was dried over sodium sulfate and the solvents were removed in vacuo. Yield: 14.64 g (82.0%).

IR was concistent with the proposed title structure. FDMS 537.95 (M+). Analysis for $C_{16}H_9ClF_6N_2O_6S_2$: Theory: C, 35.76; H, 1.68; N, 5.20. Found: C, 34.83; H, 1.56; N, 5.15.

EXAMPLE 301
Preparation of 4-(prop-2-enyl)-2-[(4-chlorophenoxy)methyl]-1-trifluoromethanesulfonylbenzimidazole

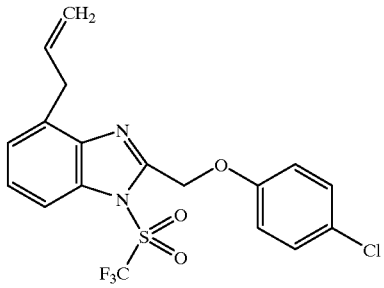

In a 250 ml single neck round bottom flask, under a nitrogen atmosphere, were added 4-trifluoromethanesulfonyloxy-2-[(4-chlorophenoxy)methyl]-1-trifluoromethanesulfonylbenzimidazole (4.97 g, 9.22 mmol), lithium chloride (1.17 g, 27.65 mmol), allyltributyltin (4.27 g, 12.90 mmol), and bis(triphenylphosphine)palladium(II) chloride (301.03 mg, 0.369 mmol) in anhydrous tetrahydrofuran (99 ml). The resulting mixture was stirred for five hours at reflux, followed by the addition of an additional 0.15 mg of the palladium catalyst. The contents were then stirred overnight. The progress of the reaction was monitored by thin layer chromatography. The desired title product was further purified by flash chromatography.

Yield: 3.97 g (35.8%); NMR was consistent with the proposed title structure.

EXAMPLE 302
Preparation of 4-(ethenyl)-2-[(4-chlorophenoxy)methyl]-1-trifluoromethanesulfonylbenzimidazole

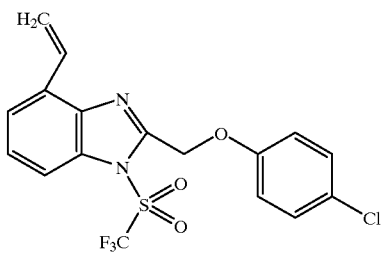

In a 250 ml single neck round bottom flask, under a nitrogen atmosphere, were added 4-trifluoromethanesulfonyloxy-2-[(4-chlorophenoxy)methyl]-1-trifluoromethanesulfonylbenzimidazole (5.00 g, 9.28 mmol), lithium chloride (1.18 g, 27.84 mmol), vinyltributyltin (4.12 g, 12.99 mmol), and bis(triphenylphosphine)palladium(II) chloride (303 mg, 0.371 mmol) in anhydrous tetrahydrofuran (99 ml). The resulting mixture was stirred for five hours at reflux, followed by the addition of an additional 0.15 mg of the palladium catalyst. The contents were then stirred overnight. The progress of the reaction was monitored by thin layer chromatography. An additional 0.15 mg of the palladium catalyst and 0.5 ml of vinyltributyltin were added to the reaction mixture and it was refluxed for five hours. The desired title product was further purified by flash chromatography.

Yield: 3.87 g (33.6%)

EXAMPLE 303
Preparation of 4-(ethenyl)-2-[(4-chlorophenoxy)methyl]-1-trifluoromethanesulfonylbenzimidazole

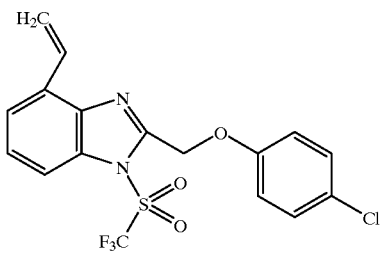

To a 250 ml round bottom flask were added 4-trifluoromethanesulfonyloxy-2-[(4-chlorophenoxy)methyl]-1-trifluoromethanesulfonylbenzimidazole (5.00 g, 9.28 mmol), palladium tetrakis(triphenylphosphine) (428 mg, 0.371 mmol), lithium chloride (2.95 g, 69.6 mmol) and vinyltributyltin (2.94 g, 9.28 mmol) to anhydrous tetrahydrofuran. The reaction mixture was heated to reflux and maintained at this temperature overnight. The progress of the reaction was monitored by thin layer chromatography. An additional 428 mg of the palladium catalyst was added and the resulting mixture was refluxed an additional three hours. To the reaction mixture was added cuprous iodide (35.3 mg, 0.02 eq) and the reaction mixture was refluxed overnight. The solvents were removed in vacuo. The residue was redissolved in ethyl acetate (500 ml) and was washed with 1:1 water:28% aqueous ammonium hydroxide (3×). The organic fraction was dried over sodium sulfate. The desired title product was further purified by column chromatography.

Yield: 3.87 g (48.4%); IR was consistent with the proposed title structure. FDMS 416.02 (M+). Analysis for $C_{17}H_{12}ClF_3N_2O_3S$: Theory: C, 48.99; H, 2.90; N, 6.72. Found: C, 49.24; H, 3.18; N, 6.48.

Preparation 63
Preparation of 4-(ethenyl)-2-[(4-chlorophenoxy)methyl]benzimidazole

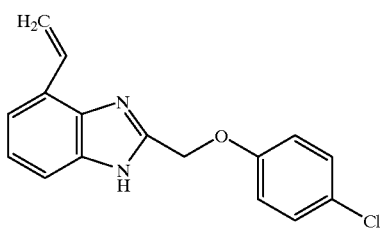

In a 100 ml round bottom flask, under a nitrogen atmosphere, were added 4-(ethenyl)-2-[(4-chlorophenoxy)methyl]-1-trifluoromethanesulfonylbenzimidazole (1.42 g, 3.29 mmol) and anhydrous methanol (20 ml). This solution was cooled to 0° C. and potassium carbonate (911 mg, 6.59 mmol) was added. The resulting mixture was stirred for two hours at 0° C., permitted to warm to room temperature, and stirred at this temperature for about three days. The progress of the reaction was monitored by thin layer chromatography. The desired title product was further purified by radial chromatography.

Yield: 0.74 g (75.1%); IR and FDMS were consistent with the proposed title structure. Analysis for $C_{16}H_{13}ClN_2O$: Theory: C, 67.49; H, 4.60; N, 9.84. Found: C, 67.47; H, 4.86; N, 9.73.

EXAMPLE 304
Preparation of 4-(ethenyl)-2-[(4-chlorophenoxy)methyl]-1-[3-[1-(t-butoxycarbonyl)piperidin-4-yl]propyl]

benzimidazole

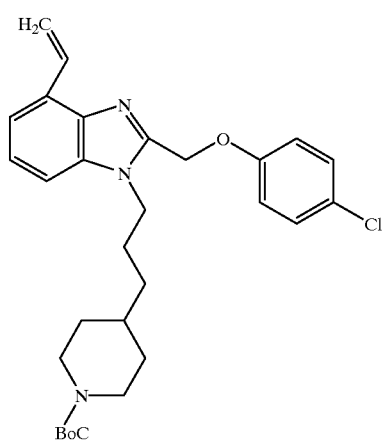

In a 100 ml round bottom flask, under a nitrogen atmosphere, were added 4-(ethenyl)-2-[(4-chlorophenoxy)methyl]benzimidazole (670 mg, 2.24 mmol) and anhydrous N,N-dimethylformamide (34 ml). To this solution was added sodium hydride (60% in mineral oil, 98.67 mg, 2.46 mmol). The resulting mixture was stirred at room temperature for 45 minutes, and then 3-[1-(t-butoxycarbonyl)piperidin-4-yl]propyl bromide (755 mg, 2.47 mmol) was added. The resulting mixture was heated to 100° C. and stirred at this temperature for about four hours. The progress of the reaction was monitored by thin layer chromatography. The reaction mixture was partitioned between ethyl acetate and brine. The aqueous fraction was extracted twice with brine. The organic fractions were combined and dried over sodium sulfate. The solvents were removed in vacuo. The desired title product was further purified by radial chromatography.

Yield: 800 mg (68.1%); IR and FDMS were consistent with the proposed title structure. Analysis for $C_{29}H_{36}ClN_3O_3$: Theory: C, 68.29; H, 7.11; N, 8.24. Found: C, 68.01; H, 7.07; N, 8.30.

Preparation 64
Preparation of 4-(prop-2-enyl)-2-[(4-chlorophenoxy)methyl]benzimidazole

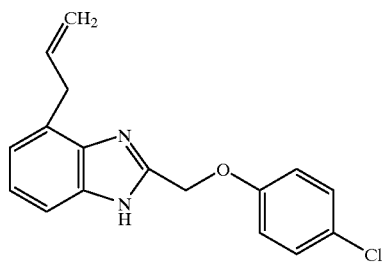

In a 100 ml round bottom flask, under a nitrogen atmosphere, were added 4-(prop-2-enyl)-2-[(4-chlorophenoxy)methyl]-1-trifluoromethanesulfonylbenzimidazole (1.00 g, 2.32 mmol) and anhydrous methanol (18 ml). This solution was cooled to 0° C. and potassium carbonate (641 mg, 4.64 mmol) was added. The resulting mixture was stirred for two hours at 0° C., permitted to warm to room temperature, and stirred at this temperature for about three days. The progress of the reaction was monitored by thin layer chromatography. The desired title product was further purified by radial chromatography.

Yield: 0.90 g (>99%); IR and FDMS were consistent with the proposed title structure. Analysis for $C_{17}H_{15}ClN_2O$: Theory: C, 68.34; H, 5.06; N, 9.38. Found: C, 68.46; H, 5.24; N, 9.35.

EXAMPLE 305

Preparation of 4-(prop-2-enyl)-2-[(4-chlorophenoxy)methyl]-1-[3-[1-(t-butoxycarbonyl)piperidin-4-yl]propyl]benzimidazole

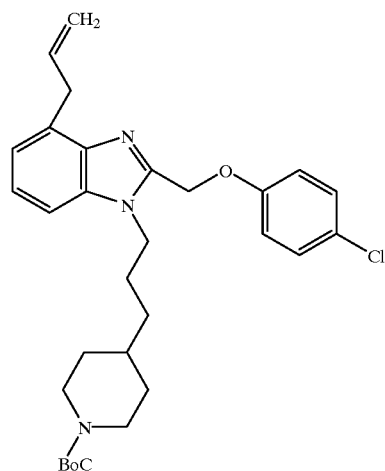

In a 100 ml round bottom flask, under a nitrogen atmosphere, were added 4-(prop-2-enyl)-2-[(4-chlorophenoxy)methyl]benzimidazole (550 mg, 1.84 mmol) and anhydrous N,N-dimethylformamide (59 ml). To this solution was added sodium hydride (60% in mineral oil, 81.04 mg, 2.03 mmol). The resulting mixture was stirred at room temperature for 60 minutes, and then 3-[1-(t-butoxycarbonyl)piperidin-4-yl]propyl bromide (620 mg, 2.03 mmol) was added. The resulting mixture was heated to 100° C. and stirred at this temperature for about three hours. The progress of the reaction was monitored by thin layer chromatography. The reaction mixture was partitioned between ethyl acetate and brine. The aqueous fraction was extracted twice with brine. The organic fractions were combined and dried over sodium sulfate. The solvents were removed in vacuo. The desired title product was further purified by radial chromatography.

Yield: 622 mg (64.4%); IR and FDMS were consistent with the proposed title structure. Analysis for $C_{30}H_{38}ClN_3O_3$: Theory: C, 68.75; H, 7.31; N, 8.02. Found: C, 68.47; H, 7.35; N, 8.22.

EXAMPLE 306

Preparation of 4-(prop-2-enyl)-2-[(4-chlorophenoxy)methyl]-1-[3-(piperidin-4-yl)propyl]benzimidazole trifluoroacetate

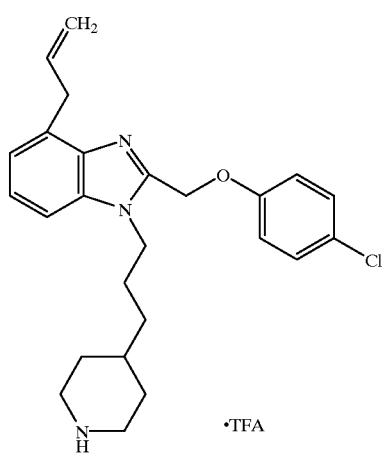

In a 100 ml single neck round bottom flask, under a nitrogen atmosphere, 4-(prop-2-enyl)-2-[(4-chlorophenoxy)methyl]-1-[3-[1-(t-butoxycarbonyl)piperidin-4-yl]propyl]benzimidazole (300 mg, 0.572 mmol) was added to anhydrous methylene chloride (20 ml). To this was added trifluoroacetic acid (0.44 ml, 652 mg, 5.72 mmol). The resulting mixture is stirred overnight at room temperature. The progress of the reaction was monitored by thin layer chromatography. The solvents were removed in vacuo.

Yield: 222 mg (72.3%); NMR was consistent with the proposed title structure.

EXAMPLE 307
Preparation of 4-(propyl)-2-[(4-chlorophenoxy)methyl]-1-[3-[1-(t-butoxycarbonyl)piperidin-4-yl]propyl]benzimidazole

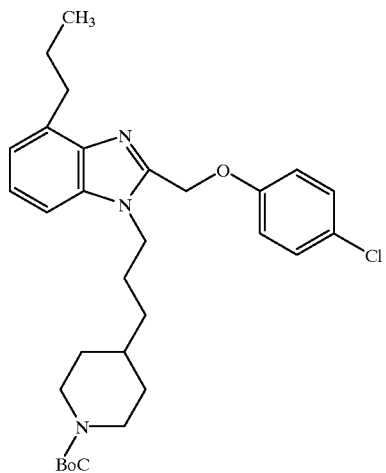

In a 50 ml sinfle neck round bottom flask, under a nitrogen atmosphere, 4-(prop-2-enyl)-2-[(4-chlorophenoxy)methyl]-1-[3-[1-(t-butoxycarbonyl)piperidin-4-yl]propyl]benzimidazole (100 mg, 0.19 mmol) was added to ethyl acetate (4 ml). To this solution was added 10% palladium on activated carbon (100 mg), followed by the addition of a hydrogen balloon. The reaction mixture was stirred for three hours at room temperature, then filtered through a bed of CELITE™. The desired title product was further purified by radial chromatography.

Yield: 86 mg (85.6%); IR and NMR were consistent with the proposed title structure. Analysis for $C_{30}H_{40}ClN_3O_3$: Theory: C, 68.49; H, 7.66; N, 7.99. Found: C, 68.76; H, 7.70; N, 8.03.

EXAMPLE 308
Preparation of 4-(prop-2-enyl)-2-[(4-chlorophenoxy)methyl]-1-[3-[1-[3-(piperidin-1-yl)propyl]piperidin-4-yl]propyl]benzimidazole

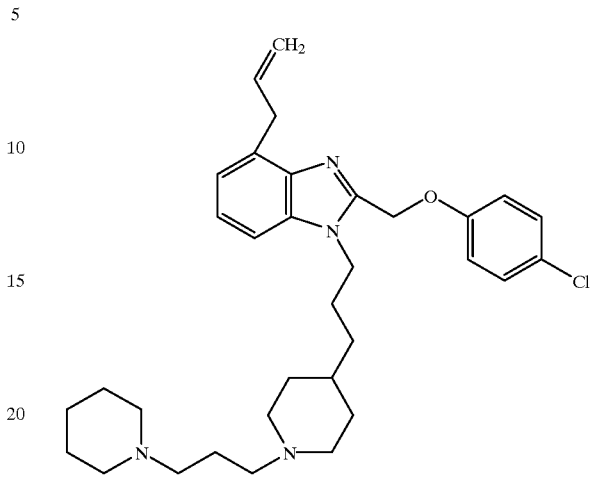

In a 25 ml round bottom flask, under a nitrogen atmosphere, were added 4-(prop-2-enyl)-2-[(4-chlorophenoxy)methyl]-1-[3-(piperidin-4-yl)propyl]benzimidazole (69.9 mg, 0.13 mmol), potassium carbonate (161.9 mg, 1.17 mmol), potassium iodide (21.6 mg, 0.13 mmol), 3-(piperidin-1-yl)propyl chloride (33.52 mg, 0.17 mmol) and N,N-dimethylformamide (3 ml). The resulting mixture was heated to 100° C. and maintained at this temperature. The progress of the reaction was monitored by thin layer chromatography. The reaction was quenched by the addition of water. The aqueous fraction was extracted wtih ethyl acetate. The organic fractions were combined, washed with water, and then dried over sodium sulfate. The solvents were removed in vacuo. The desired title product was further purified by radial chromatography.

Yield: 40 mg (55.9%); NMR was consistent with the proposed title structure. FDMS 548.22 (M+).

EXAMPLE 309
Preparation of 4-(prop-2-enyl)-2-[(4-chlorophenoxy)methyl]-1-[3-[1-[3-(phenyl)propyl]piperidin-4-yl]propyl]benzimidazole

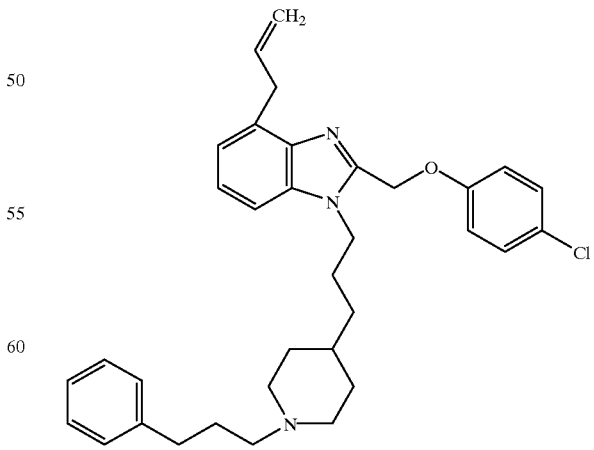

In a 50 ml round bottom flask, under a nitrogen atmosphere, were added 4-(prop-2-enyl)-2-[(4- chlorophenoxy)methyl]-1-[3-(piperidin-4-yl)propyl] benzimidazole (898 mg, 2.12 mmol), potassium carbonate (1.46 g, 10.58 mmol), 3-(phenyl)propyl chloride (0.2 ml, 506 mg, 2.54 mmol) and N,N-dimethylformamide (7 ml). The resulting mixture was heated to 60° C. and maintained at this temperature overnight. The progress of the reaction was monitored by thin layer chromatography. An additional 1 equivalent of potassium carbonate and 0.2 ml of 3-(phenyl)propyl chloride were added and the resulting contents were stirred at 60° C. for an additional two hours. The reaction was quenched by the addition of water. The aqueous fraction was extracted wtih ethyl acetate. The organic fractions were combined, washed with water, and then dried over sodium sulfate. The solvents were removed in vacuo. The desired title product was further purified by radial chromatography.

Yield: 920 mg (80.2%); NMR and IR was consistent with the proposed title structure. Analysis for $C_{34}H_{40}ClN_3O$: Theory: C, 75.32; H, 7.44; N, 7.75. Found: C, 72.84; H, 7.22; N, 7.64.

EXAMPLE 310
Preparation of 4-(ethenyl)2-[(4-chlorophenoxy)methyl]-1-[3-[1-[3-(phenyl)propyl]piperidin-4-yl]propyl] benzimidazole

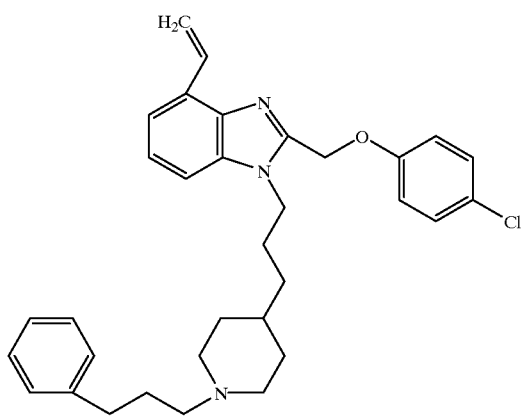

In a 50 ml round bottom flask, under a nitrogen atmosphere, were added 4-(prop-2-enyl)-2-[(4-chlorophenoxy)methyl]-1-[3-(piperidin-4-yl)propyl] benzimidazole (898 mg, 2.12 mmol), potassium carbonate (1.46 g, 10.58 mmol), 3-(phenyl)propyl chloride (0.2 ml, 506 mg, 2.54 mmol) and N,N-dimethylformamide (7 ml). The resulting mixture was heated to 60° C. and maintained at this temperature overnight. The progress of the reaction was monitored by thin layer chromatography. The reaction was quenched by the addition of water. The aqueous fraction was extracted wtih ethyl acetate. The organic fractions were combined, washed thrice with saturated sodium bicarbonate solution, and then dried over sodium sulfate. The solvents were removed in vacuo. The desired title product was further purified by radial chromatography.

Yield: 810 mg (77.2%); NMR and IR was consistent with the proposed title structure. Analysis for $C_{33}H_{38}ClN_3O$: Theory: C, 75.05; H, 7.25; N, 7.96. Found: C, 74.81; H, 7.05; N, 8.15.

EXAMPLE 311
Preparation of 4-methoxy-2-[(4-chlorophenoxy)methyl]-1-[3-[1-(t-butoxycarbonyl)piperidin-4-yl]propyl] benzimidazole

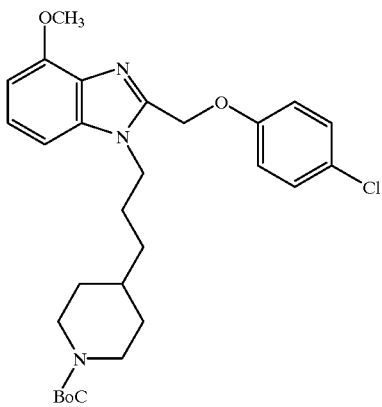

A solution of 4-hydroxy-2-[(4-chlorophenoxy)methyl]-1-[3-[1-(t-butoxycarbonyl)piperidin-4-yl]propyl] benzimidazole (300 mg, 0.6 mmol, 1 eq) in anhydrous N,N-dimethylformamide (3 m) was treated with sodium hydride (60% in mineral oil, 26 mg, 0.66 mmol, 1.1 eq). The resulting mixture was stirred for thirty minutes at room temperature. Methyl iodide (94 mg, 0.66 mmol, 1 eq) was added to the reaction and the resulting mixture was stirred for two hours at room temperature. The reaction was quenched with the addition of water (5 ml). The aqueous fraction was extracted with ethyl acetate (3×10 ml). The organic fractions were combined, washed with water (2×10 ml), then brine (1×10 ml), and then dried over sodium sulfate. The solvents were removed in vacuo. The residue was further purified by flash column chromatography to yield the title product as a crystalline product in 50% yield.

NMR and IR were consistent with the proposed title structure. Analysis for $C_{28}H_{36}ClN_3O_4$: Theory: C, 65.42; H, 7.06; N, 8.17. Found: C, 65.63; H, 7.14; N, 8.30.

EXAMPLE 312
Preparation of 4-methoxy-2-[(4-chlorophenoxy)methyl]-1-[3-(piperidin-4-yl)propyl]benzimidazole trifluoroacetate

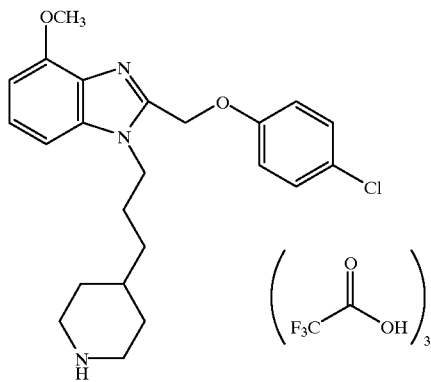

This product was prepared from 4-methoxy-2-[(4-chlorophenoxy)methyl]-1-[3-(piperidin-4-yl)propyl] benzimidazole trifluoroacetate using standard trifluoroacetic acid deprotection protocols.

IR and NMR were consistent with the proposed title structure. FDMS 413 (M+). Analysis for $C_{23}H_{28}ClN_3O_2 \cdot 3C_2HF_3O_2$: Theory: C, 46.07; H, 4.13; N, 5.56. Found: C, 46.55; H, 4.38; N, 5.74.

EXAMPLE 313
Preparation of 4-methoxy-2-[(4-chlorophenoxy)methyl]-1-[3-[1-(3-phenylpropyl)piperidin-4-yl]propyl]benzimidazole

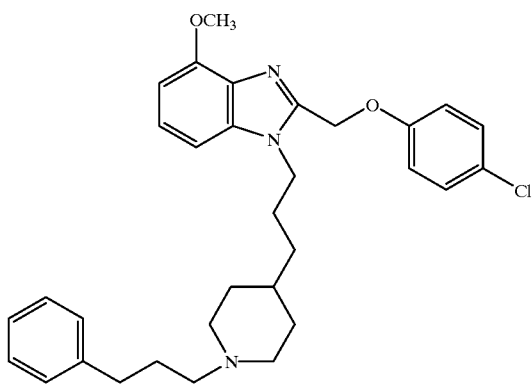

A solution of 4-methoxy-2-[(4-chlorophenoxy)methyl]-1-[3-(piperidin-4-yl)propyl]benzimidazole trifluoroacetate (177 mg, 0.29 mmol, 1 eq) in anhydrous N,N-dimethylformamide (2 ml) was treated with potassium carbonate (120 mg, 0.87 mmol, 3 eq) and 3-phenylpropyl bromide (87 mg, 0.43 mmol, 1.5 eq). The resulting mixture was stirred at 80° C. for six hours. The reaction was quenched by the addition of water (5 ml). The aqueous fraction was extracted with ethyl acetate (3×10 ml). The organic fractions were combined, washed with water (3×10 ml), and brine (1×10 ml), and then dried over sodium sulfate. The solvents were removed in vacuo. The residue was further purified by column chromatography to yield the title product as a white crystalline solid.

Yield: 72%; NMR and IR were consistent with the proposed title structure. FDMS 531.2, 532 (M+). Analysis for $C_{32}H_{38}ClN_3O_2$: Theory: C, 72.23; H, 7.20; N, 7.90. Found: C, 72.14; H, 7.35; N, 7.82.

EXAMPLE 314
Preparation of 4-cyclopentoxy-2-[(4-chlorophenoxy)methyl]-1-[3-[1-(t-butoxycarbonyl)piperidin-4-yl]propyl]benzimidazole trifluoroacetate

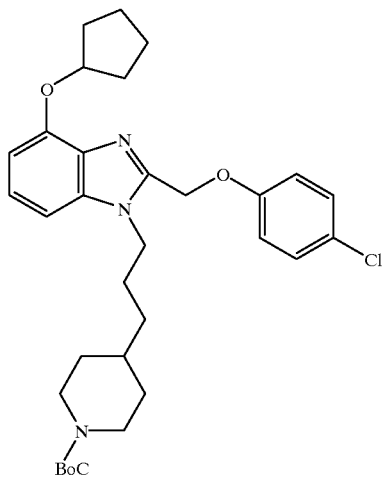

A solution of 4-hydroxy-2-[(4-chlorophenoxy)methyl]-1-[3-[1-(t-butoxycarbonyl)piperidin-4-yl]propyl]benzimidazole trifluoroacetate (300 mg, 0.6 mmol, 1 eq) in anhydrous N,N-dimethylformamide (3 m) was treated with sodium hydride (60% in mineral oil, 26 mg, 0.66 mmol, 1.1 eq). The resulting mixture was stirred for thirty minutes at room temperature. Cyclopropyl bromide (0.66 mmol, 1 eq) was added to the reaction and the resulting mixture was stirred for two hours at room temperature. The reaction was quenched with the addition of water (5 ml). The aqueous fraction was extracted with ethyl acetate (3×10 ml). The organic fractions were combined, washed with water (2×10 ml), then brine (1×10 ml), and then dried over sodium sulfate. The solvents were removed in vacuo. The residue was further purified by flash column chromatography to yield the title product as a crystalline product in 50% yield.

NMR and IR were consistent with the proposed title structure. FDMS 567 (M+). Analysis for $C_{32}H_{42}ClN_3O_4$: Theory: C, 67.65; H, 7.45; N, 7.40. Found: C, 68.82; H, 7.87; N, 7.55.

EXAMPLE 315
Preparation of 4-cyclopentoxy-2-[(4-chlorophenoxy)methyl]-1-[3-(piperidin-4-yl)propyl]benzimidazole trifluoroacetate

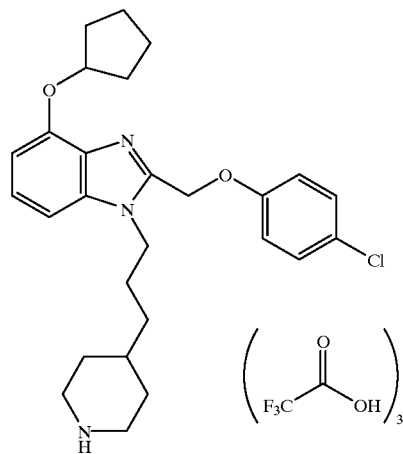

This product was prepared from 4-cyclopentoxy-2-[(4-chlorophenoxy)methyl]-1-[3-(piperidin-4-yl)propyl]benzimidazole trifluoroacetate using standard trifluoroacetic acid deprotection protocols.

IR and NMR were consistent with the proposed title structure. FDMS 468 (M+). Analysis for $C_{29}H_{38}ClN_3O_2 \cdot 3C_2HF_3O_2$: Theory: C, 48.93; H, 4.60; N, 5.19. Found: C, 47.33; H, 4.82; N, 5.37.

EXAMPLE 316
Preparation of 4-cyclopentoxy-2-[(4-chlorophenoxy)methyl]-1-[3-[1-(3-phenylpropyl)piperidin-4-yl]propyl]benzimidazole

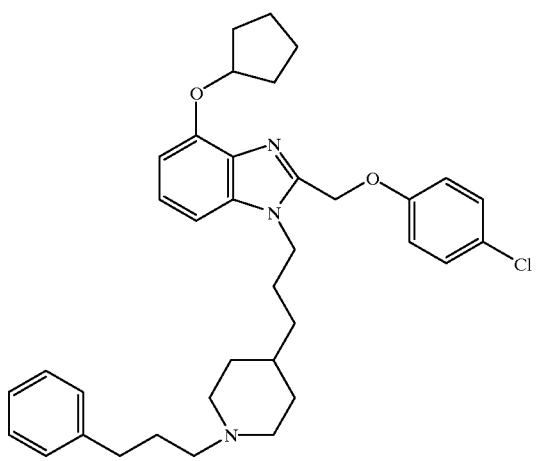

A solution of 4-cyclopentoxy-2-[(4-chlorophenoxy)methyl]-1-[3-(piperidin-4-yl)propyl]benzimidazole trifluoroacetate (0.29 mmol, 1 eq) in anhydrous N,N-dimethylformamide (2 ml) was treated with potassium carbonate (120 mg, 0.87 mmol, 3 eq) and 3-phenylpropyl bromide (87 mg, 0.43 mmol, 1.5 eq). The resulting mixture was stirred at 80° C. for six hours. The reaction was quenched by the addition of water (5 ml). The aqueous fraction was extracted with ethyl acetate (3×10 ml). The organic fractions were combined, washed with water (3×10 ml), and brine (1×10 ml), and then dried over sodium sulfate. The solvents were removed in vacuo. The residue was further purified by column chromatography to yield the title product as a white crystalline solid.

NMR and IR were consistent with the proposed title structure. FDMS 586 (M+). Analysis for $C_{36}H_{44}ClN_3O_2$: Theory: C, 73.76; H, 7.56; N, 7.17. Found: C, 75.08; H, 7.85; N, 7.30.

EXAMPLE 317

Preparation of 4-isopropoxy-2-[(4-chlorophenoxy)methyl]-1-[3-[1-(t-butoxycarbonyl)piperidin-4-yl]propyl]benzimidazole trifluoroacetate

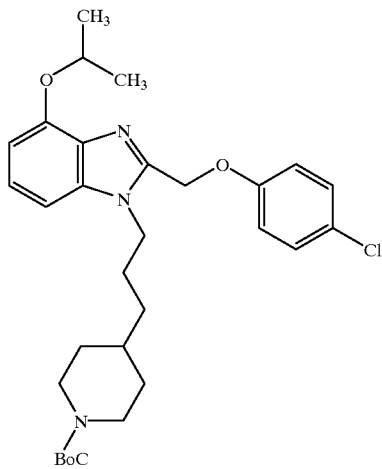

A solution of 4-hydroxy-2-[(4-chlorophenoxy)methyl]-1-[3-[1-(t-butoxycarbonyl)piperidin-4-yl]propyl]benzimidazole trifluoroacetate (300 mg, 0.6 mmol, 1 eq) in anhydrous N,N-dimethylformamide (3 m) was treated with sodium hydride (60% in mineral oil, 26 mg, 0.66 mmol, 1.1 eq). The resulting mixture was stirred for thirty minutes at room temperature. Isopropyl bromide (0.66 mmol, 1 eq) was added to the reaction and the resulting mixture was stirred for two hours at room temperature. The reaction was quenched with the addition of water (5 ml). The aqueous fraction was extracted with ethyl acetate (3×10 ml). The organic fractions were combined, washed with water (2×10 ml), then brine (1×10 ml), and then dried over sodium sulfate. The solvents were removed in vacuo. The residue was further purified by flash column chromatography to yield the title product as a crystalline product.

NMR and IR were consistent with the proposed title structure. FDMS 541,542 (M+). Analysis for $C_{28}H_{36}ClN_3O_4$: Theory: C, 66.47; H, 7.44; N, 7.75. Found: C, 66.31; H, 7.54; N, 7.75.

EXAMPLE 318

Preparation of 4-isopropoxy-2-[(4-chlorophenoxy)methyl]-1-[3-(piperidin-4-yl)propyl]benzimidazole trifluoroacetate

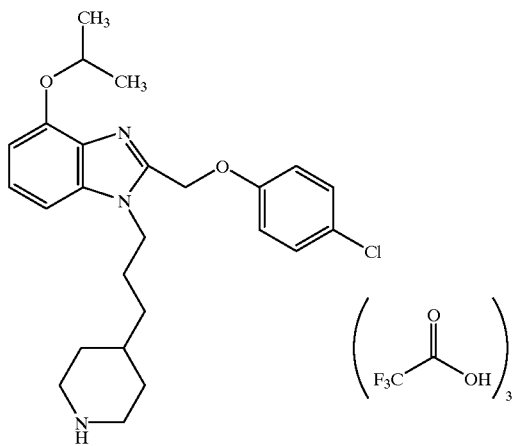

This product was prepared from 4-isopropoxy-2-[(4-chlorophenoxy)methyl]-1-[3-(piperidin-4-yl)propyl]benzimidazole trifluoroacetate using standard trifluoroacetic acid deprotection protocols.

IR and NMR were consistent with the proposed title structure. FDMS 413 (M+). Analysis for $C_{25}H_{32}ClN_3O_2 \cdot 3C_2HF_3O_2$: Theory: C, 47.49; H, 4.50; N, 5.36. Found: C, 48.46; H, 5.03; N, 5.86.

EXAMPLE 319

Preparation of 4-isopropoxy-2-[(4-chlorophenoxy)methyl]-1-[3-[1-(3-phenylpropyl)piperidin-4-yl]propyl]benzimidazole

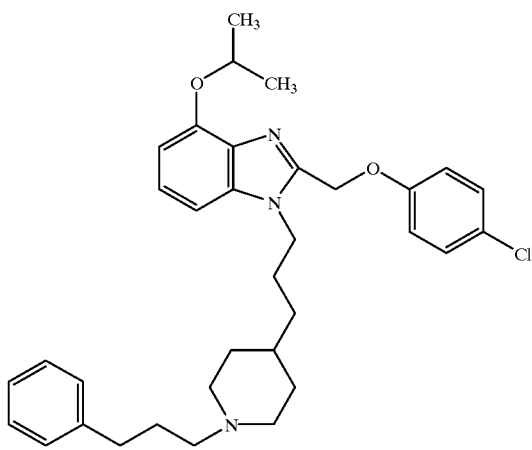

A solution of 4-isopropoxy-2-[(4-chlorophenoxy) methyl]-1-[3-(piperidin-4-yl)propyl]benzimidazole trifluoroacetate (0.29 mmol, 1 eq) in anhydrous N,N-dimethylformamide (2 ml) was treated with potassium carbonate (120 mg, 0.87 mmol, 3 eq) and 3-phenylpropyl bromide (87 mg, 0.43 mmol, 1.5 eq). The resulting mixture was stirred at 80° C. for six hours. The reaction was quenched by the addition of water (5 ml). The aqueous fraction was extracted with ethyl acetate (3×10 ml). The organic fractions were combined, washed with water (3×10 ml), and brine (1×10 ml), and then dried over sodium sulfate. The solvents were removed in vacuo. The residue was further purified by column chromatography to yield the title product as a white crystalline solid.

NMR and IR were consistent with the proposed title structure. FDMS 559.1,560 (M+). Analysis for $C_{34}H_{42}ClN_3O_2$: Theory: C, 72.09; H, 7.56; N, 7.50. Found: C, 73.09; H, 7.47; N, 7.52.

EXAMPLE 320
Preparation of 4-(cyclohexylmethoxy)-2-[(4-chlorophenoxy)methyl]-1-[3-[1-(t-butoxycarbonyl) piperidin-4-yl]propyl]benzimidazole trifluoroacetate

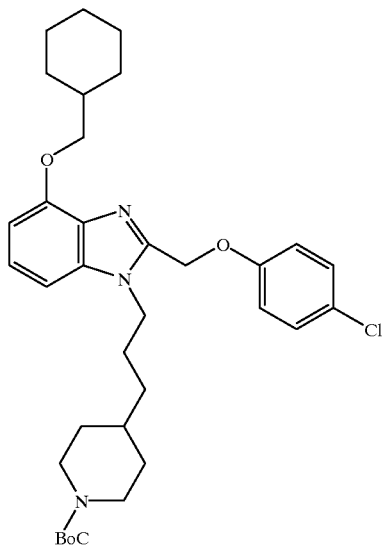

A solution of 4-hydroxy-2-[(4-chlorophenoxy)methyl]-1-[3-[1-(t-butoxycarbonyl)piperidin-4-yl]propyl] benzimidazole trifluoroacetate (300 mg, 0.6 mmol, 1 eq) in anhydrous N,N-dimethylformamide (3 m) was treated with sodium hydride (60% in mineral oil, 26 mg, 0.66 mmol, 1.1 eq). The resulting mixture was stirred for thirty minutes at room temperature. Cyclopropylmethyl bromide (0.66 mmol, 1 eq) was added to the reaction and the resulting mixture was stirred for two hours at room temperature. The reaction was quenched with the addition of water (5 ml). The aqueous fraction was extracted with ethyl acetate (3×10 ml). The organic fractions were combined, washed with water (2×10 ml), then brine (1×10 ml), and then dried over sodium sulfate. The solvents were removed in vacuo. The residue was further purified by flash column chromatography to yield the title product as a crystalline product.

NMR and IR were consistent with the proposed title structure. FDMS 595, 596 (M+). Analysis for $C_{34}H_{46}ClN_3O_4$: Theory: C, 68.50; H, 7.78; N, 7.05. Found: C, 68.62; H, 7.83; N, 7.03.

EXAMPLE 321

Preparation of 4-(cyclohexylmethoxy)-2-[(4-chlorophenoxy)methyl]-1-[3-(piperidin-4-yl)propyl] benzimidazole trifluoroacetate

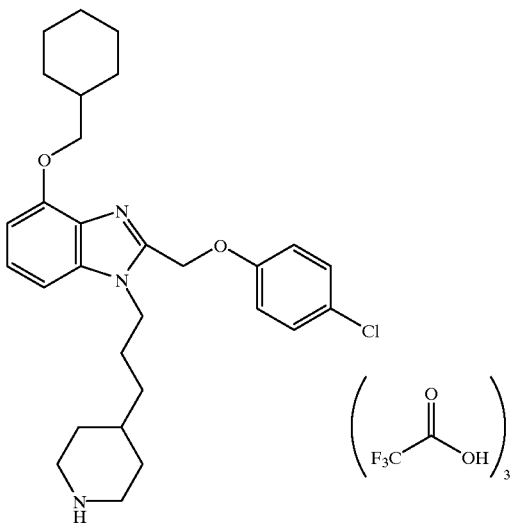

This product was prepared from 4-(cyclohexylmethoxy)-2-[(4-chlorophenoxy)methyl]-1-[3-(piperidin-4-yl)propyl] benzimidazole trifluoroacetate using standard trifluoroacetic acid deprotection protocols.

IR and NMR were consistent with the proposed title structure. FDMS 496 (M+). Analysis for $C_{31}H_{42}ClN_3O_2 \cdot 3C_2HF_3O_2$: Theory: C, 50.16; H, 4.93; N, 5.01. Found: C, 50.01; H, 5.04; N, 4.96.

EXAMPLE 322

Preparation of 4-(cyclohexylmethoxy)-2-[(4-chlorophenoxy)methyl]-1-[3-[1-(3-phenylpropyl)piperidin-4-yl]propyl]benzimidazole

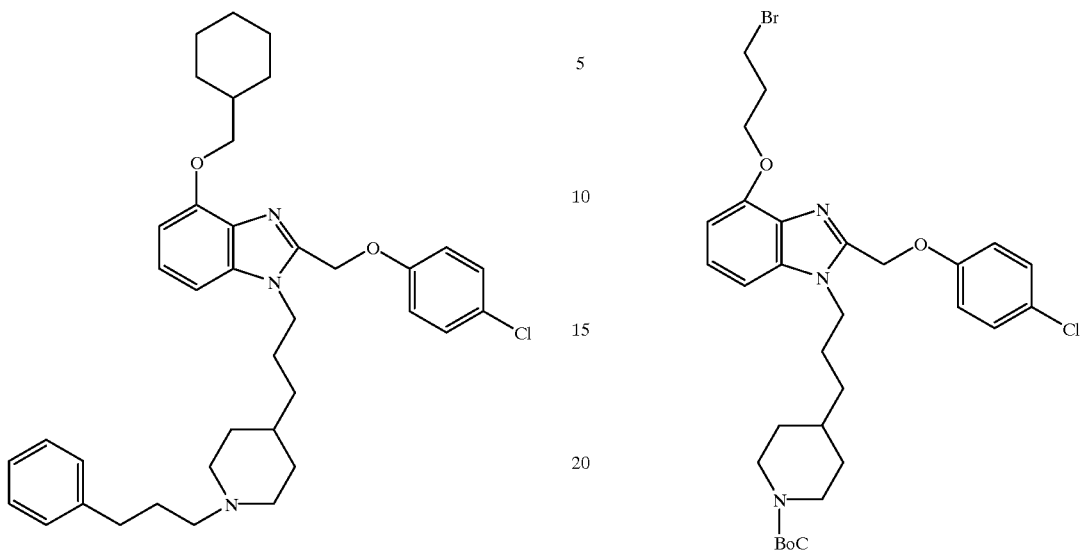

A solution of 4-(cyclohexylmethoxy)-2-[(4-chlorophenoxy)methyl]-1-[3-(piperidin-4-yl)propyl]benzimidazole trifluoroacetate (0.29 mmol, 1 eq) in anhydrous N,N-dimethylformamide (2 ml) was treated with potassium carbonate (120 mg, 0.87 mmol, 3 eq) and 3-phenylpropyl bromide (87 mg, 0.43 mmol, 1.5 eq). The resulting mixture was stirred at 80° C. for six hours. The reaction was quenched by the addition of water (5 ml). The aqueous fraction was extracted with ethyl acetate (3×10 ml). The organic fractions were combined, washed with water (3×10 ml), and brine (1×10 ml), and then dried over sodium sulfate. The solvents were removed in vacuo. The residue was further purified by column chromatography to yield the title product as a white crystalline solid.

NMR and IR were consistent with the proposed title structure. FDMS 614 (M+). Analysis for $C_{38}H_{48}ClN_3O_2$: Theory: C, 74.30; H, 7.88; N, 6.84. Found: C, 74.26; H, 7.93; N, 6.91.

EXAMPLE 323
Preparation of 4-(3-bromopropoxy)-2-[(4-chlorophenoxy)methyl]-1-[3-[1-(t-butoxycarbonyl)piperidin-4-yl]propyl]benzimidazole A solution of 1,3-dibromopropane (41.3 mg, 0.3 mmol, 1.5 eq) in anhydrous N,N-dimethylformamide (2 ml) was treated with a solution of 4-hydroxy-2-[(4-chlorophenoxy)methyl]-1-[3-[1-(t-butoxycarbonyl)piperidin-4-yl]propyl]benzimidazole (100 mg, 0.2 mmol, 1 eq) in anhydrous N,N-dimethylformamide (1 ml). The resulting mixture was stirred for twelve hours. The reaction was quenched by the addition of water (10 ml). The aqueous fraction was extracted with diethyl ether (3×10 ml). The organic fractions were combined, washed with water (3×10 ml), and brine (1×10 ml), and then dried over sodium sulfate. The solvents were removed in vacuo. The residue was subjected to column chromatography to yield the desired title product as a white crystalline product.

Yield: 80%; NMR and IR were consistent with the proposed title structure. FDMS 620, 621 (M+).

EXAMPLE 324
Preparation of 4-[3-[2-(pyrroldin-1-ylmethyl)pyrrolidin-1-yl]propoxy]-2-[(4-chlorophenoxy)methyl]-1-[3-[1-(t-butoxycarbonyl)piperidin-4-yl]propyl]benzimidazole

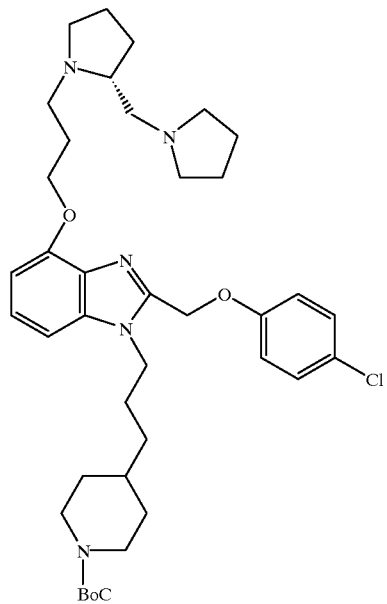

A solution of 4-[3-bromopropoxy]-2-[(4-chlorophenoxy)methyl]-1-[3-[1-(t-butoxycarbonyl)piperidin-4-yl]propyl]benzimidazole (77 mg, 0.124 mmol, 1 eq) in anhydrous N,N-dimethylformamide (2 ml) was treated with potassium carbonate (51.3 mg, 0.37 mmol, 2 eq) and (S)-(+)-2-(pyrroldin-1-ylmethyl)pyrrolidine (28.7 mg, 0.19 mmol, 1.5 eq). The resulting mixture was stirred at 80° C. for six hours. The reaction was quenched by the addition of water (10 ml). The aqueous fraction was extracted with ethyl acetate (3×10 ml). The organic fractions were combined, washed with water (3×10 ml), brine (1×10 ml), and then dried over sodium sulfate. The solvents were removed in vacuo to yield an oily crude product which was purified by flash chromatography to provide the title product.

Yield: 78%. NMR and IR were consistent with the proposed title structure. FDMS 694 (M+).

EXAMPLE 325

Preparation of (RS) 4-[3-[2-(pyrroldin-1-ylmethyl)pyrrolidin-1-yl]propoxy]-2-[(4-chlorophenoxy)methyl]-1-[3-(piperidin-4-yl)propyl]benzimidazole

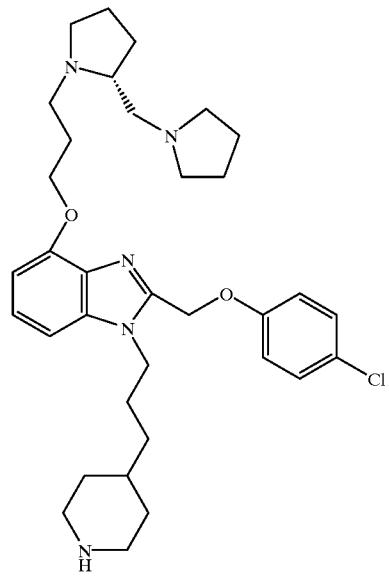

The title compound was prepared from (RS) 4-[3-[2-(pyrroldin-1-ylmethyl)pyrrolidin-1-yl]propoxy]-2-[(4-chlorophenoxy)methyl]-1-[3-[1-(t-butoxycarbonyl)piperidin-4-yl]propyl]benzimidazole using trifluoroacetic acid deprotection as described supra.

IR and NMR were consistent with the proposed title structure. FDMS 594 (M+). Analysis for $C_{34}H_{51}ClN_5O_2$: Theory: C, 68.72; H, 8.14; N, 11.79. Found: C, 68.91; H, 8.08; N, 11.70.

EXAMPLE 326

Preparation of (RS) 4-[3-[2-[2-(piperidin-1-yl)ethyl]piperidin-1-yl]propoxy]-2-[(4-chlorophenoxy)methyl]-1-[3-[1-(t-butoxycarbonyl)piperidin-4-yl]propyl]benzimidazole

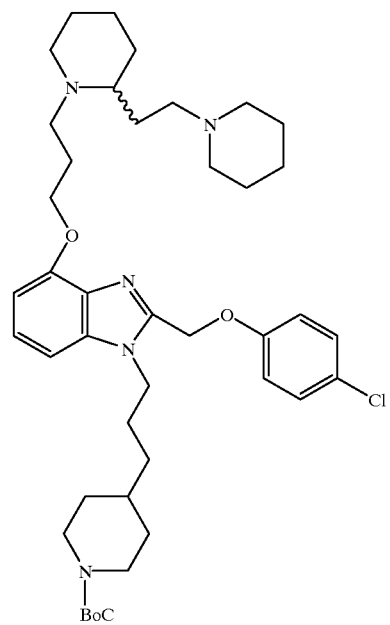

A solution of 4-[3-bromopropoxy]-2-[(4-chlorophenoxy) methyl]-1-[3-[1-(t-butoxycarbonyl)piperidin-4-yl]propyl] benzimidazole (77 mg, 0.124 mmol, 1 eq) in anhydrous N,N-dimethylformamide (2 ml) was treated with potassium carbonate (51.3 mg, 0.37 mmol, 2 eq) and 2-[2-(piperidin-1-yl)ethyl]piperidine (0.19 mmol, 1.5 eq). The resulting mixture was stirred at 80° C. for six hours. The reaction was quenched by the addition of water (10 ml). The aqueous fraction was extracted with ethyl acetate (3×10 ml). The organic fractions were combined, washed with water (3×10 ml), brine (1×10 ml), and then dried over sodium sulfate. The solvents were removed in vacuo to yield an oily crude product which was purified by flash chromatography to provide the title product.

NMR and IR were consistent with the proposed title structure. FDMS 736.4 (M+).

EXAMPLE 327

Preparation of (RS) 4-[3-[2-[2-(piperidin-1-yl)ethyl] piperidin-1-yl]propoxy]-2-[(4-chlorophenoxy)methyl]-1-[3-(piperidin-4-yl)propyl]benzimidazole

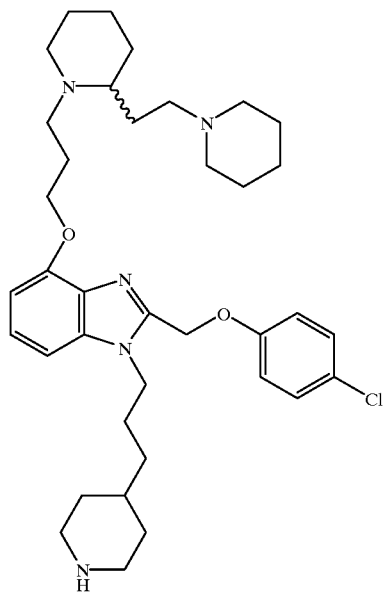

The title compound was prepared from (RS) 4-[3-[2-[2-(piperidin-1-yl)ethyl]piperidin-1-yl]propoxy]-2-[(4-chlorophenoxy)methyl]-1-[3-[1-(t-butoxycarbonyl) piperidin-4-yl]propyl]benzimidazole using trifluoroacetic acid deprotection as described supra.

NMR and IR were consistent with the proposed title structure. FDMS 636 (M+). Analysis for $C_{37}H_{54}ClN_5O_2$: Theory: C, 69.84; H, 8.55; N, 11.01. Found: C, 69.51; H, 8.76; N, 10.13.

EXAMPLE 328

Preparation of 4-[3-[4-(carboxamido)piperidin-1-yl] propoxy]-2-[(4-chlorophenoxy)methyl]-1-[3-[1-(t-butoxycarbonyl)piperidin-4-yl]propyl]benzimidazole

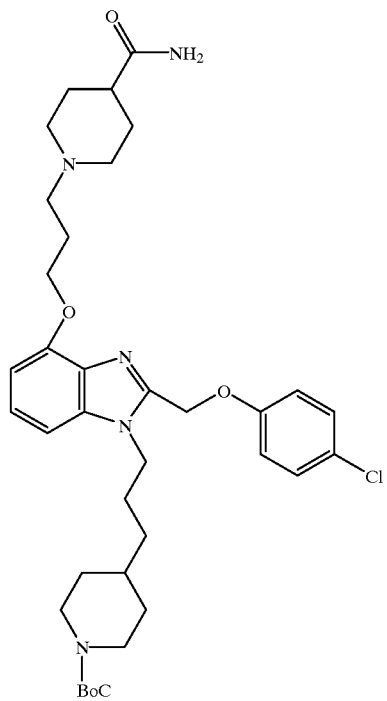

A solution of 4-[3-bromopropoxy]-2-[(4-chlorophenoxy) methyl]-1-[3-[1-(t-butoxycarbonyl)piperidin-4-yl]propyl] benzimidazole (77 mg, 0.124 mmol, 1 eq) in anhydrous N,N-dimethylformamide (2 ml) was treated with potassium carbonate (51.3 mg, 0.37 mmol, 2 eq) and 4-(carboxamido) piperidine (0.19 mmol, 1.5 eq). The resulting mixture was stirred at 80° C. for six hours. The reaction was quenched by the addition of water (10 ml). The aqueous fraction was extracted with ethyl acetate (3×10 ml). The organic fractions were combined, washed with water (3×10 ml), brine (1×10 ml), and then dried over sodium sulfate. The solvents were removed in vacuo to yield an oily crude product which was purified by flash chromatography to provide the title product.

NMR and IR were consistent with the proposed title structure. FDMS 668 (M+).

EXAMPLE 329

Preparation of 4-[3-[4-(carboxamido)piperidin-1-yl] propoxy]-2-[(4-chlorophenoxy)methyl]-1-[3-[1-(t-butoxycarbonyl)piperidin-4-yl]propyl]benzimidazole

207 / 208

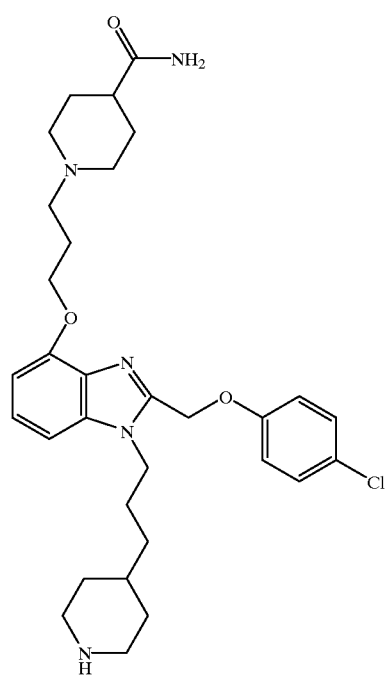

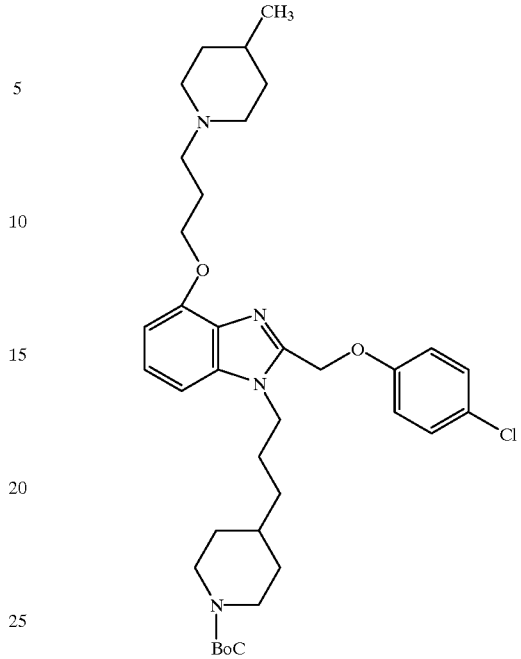

The title compound was prepared from 4-[3-[4-carboxamido)piperidin-1-yl]propoxy]-2-[(4-chlorophenoxy)methyl]-1-[3-[1-(t-butoxycarbonyl)piperidin-4-yl]propyl]benzimidazole using standard trifluoroacetic acid deprotection techniques, as described supra.

NMR and IR were consistent with the proposed title structure. FDMS 568 (M+). Analysis for $C_{31}H_{43}ClN_5O_3$: Theory: C, 65.53; H, 7.45; N, 12.33. Found: C, 65.26; H, 7.48; N, 12.11.

EXAMPLE 330

Preparation of 4-[3-[4-(methyl)piperidin-1-yl]propoxy]-2-[(4-chlorophenoxy)methyl]-1-[3-[1-(t-butoxycarbonyl)piperidin-4-yl]propyl]benzimidazole A solution of 4-[3-bromopropoxy]-2-[(4-chlorophenoxy)methyl]-1-[3-[1-(t-butoxycarbonyl)piperidin-4-yl]propyl]benzimidazole (77 mg, 0.124 mmol, 1 eq) in anhydrous N,N-dimethylformamide (2 ml) was treated with potassium carbonate (51.3 mg, 0.37 mmol, 2 eq) and 4-(methyl)piperidine (0.19 mmol, 1.5 eq). The resulting mixture was stirred at 80° C. for six hours. The reaction was quenched by the addition of water (10 ml). The aqueous fraction was extracted with ethyl acetate (3×10 ml). The organic fractions were combined, washed with water (3×10 ml), brine (1×10 ml), and then dried over sodium sulfate. The solvents were removed in vacuo to yield an oily crude product which was purified by flash chromatography to provide the title product.

NMR and IR were consistent with the proposed title structure. FDMS 639 (M+). Analysis for $C_{36}H_{51}ClN_4O_4$: Theory: C, 67.64; H, 8.04; N, 8.76. Found: C, 67.89; H, 8.05; N, 8.84.

EXAMPLE 331

Preparation of 4-[3-[4-(methyl)piperidin-1-yl]propoxy]-2-[(4-chlorophenoxy)methyl]-1-[3-(piperidin-4-yl)propyl]benzimidazole

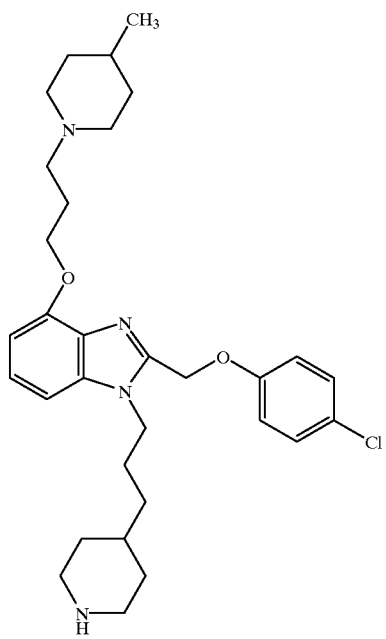

The title compound was prepared from 4-[3-[4-(methyl)piperidin-1-yl]propoxy]-2-[(4-chlorophenoxy)methyl]-1-[3-[1-(t-butoxycarbonyl)piperidin-4-yl]propyl]benzimidazole by standard trifluoroacetic acid deprotection as described supra.

NMR and IR were consistent with the proposed title structure. FDMS 539 (M+). Analysis for $C_{31}H_{43}ClN_4O_2$: Theory: C, 69.06; H, 8.04; N, 10.39. Found: C, 69.15; H, 8.02; N, 10.13.

EXAMPLE 332
Preparation of (RS) 4-[3-[3-(methyl)piperidin-1-yl]propoxy]-2-[(4-chlorophenoxy)methyl]-1-[3-[1-(t-butoxycarbonyl)piperidin-4-yl]propyl]benzimidazole

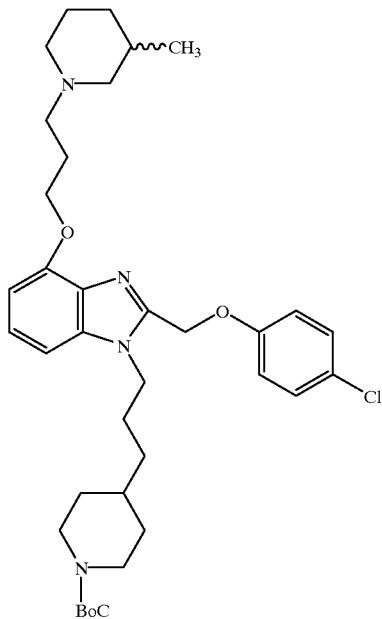

A solution of 4-[3-bromopropoxy]-2-[(4-chlorophenoxy)methyl]-1-[3-[1-(t-butoxycarbonyl)piperidin-4-yl]propyl]benzimidazole (77 mg, 0.124 mmol, 1 eq) in anhydrous N,N-dimethylformamide (2 ml) was treated with potassium carbonate (51.3 mg, 0.37 mmol, 2 eq) and (RS) 3-(methyl)piperidine (0.19 mmol, 1.5 eq). The resulting mixture was stirred at 80° C. for six hours. The reaction was quenched by the addition of water (10 ml). The aqueous fraction was extracted with ethyl acetate (3×10 ml). The organic fractions were combined, washed with water (3×10 ml), brine (1×10 ml), and then dried over sodium sulfate. The solvents were removed in vacuo to yield an oily crude product which was purified by flash chromatography to provide the title product.

NMR and IR were consistent with the proposed title structure. FDMS 639 (M+). Analysis for $C_{36}H_{51}ClN_4O_4$: Theory: C, 67.64; H, 8.04; N, 8.76. Found: C, 67.91; H, 7.95; N, 8.82.

EXAMPLE 333

Preparation of (RS) 4-[3-[3-(methyl)piperidin-1-yl]propoxy]-2-[(4-chlorophenoxy)methyl]-1-[3-(piperidin-4-yl)propyl]benzimidazole

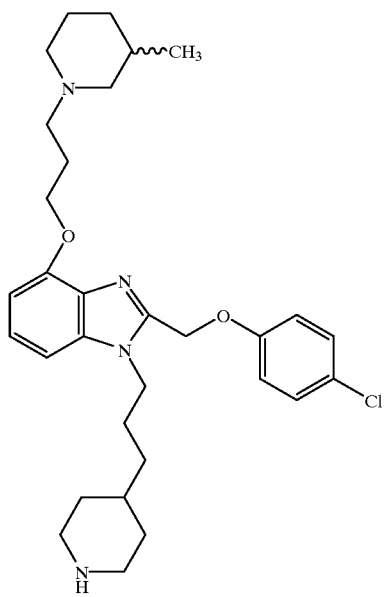

The title compound was prepared from (RS) 4-[3-[3-(methyl)piperidin-1-yl]propoxy]-2-[(4-chlorophenoxy)methyl]-1-[3-[1-(t-butoxycarbonyl)piperidin-4-yl]propyl]benzimidazole by standard trifluoroacetic acid deprotection as described supra.

NMR and IR were consistent with the proposed title structure. FDMS 539 (M+). Analysis for $C_{31}H_{43}ClN_4O_2$: Theory: C, 69.06; H, 8.04; N, 10.39. Found: C, 69.29; H, 8.19; N, 10.24.

EXAMPLE 334

Preparation of (RS) 4-[3-[2-(methyl)piperidin-1-yl]propoxy]-2-[(4-chlorophenoxy)methyl]-1-[3-[1-(t-butoxycarbonyl)piperidin-4-yl]propyl]benzimidazole

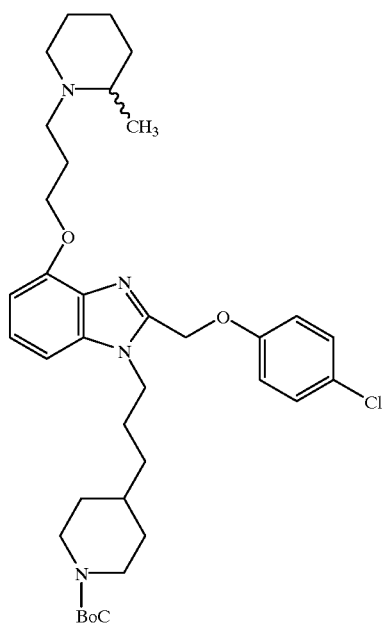

A solution of 4-[3-bromopropoxy]-2-[(4-chlorophenoxy) methyl]-1-[3-[1-(t-butoxycarbonyl)piperidin-4-yl]propyl] benzimidazole (77 mg, 0.124 mmol, 1 eq) in anhydrous N,N-dimethylformamide (2 ml) was treated with potassium carbonate (51.3 mg, 0.37 mmol, 2 eq) and (RS) 2-(methyl) piperidine (0.19 mmol, 1.5 eq). The resulting mixture was stirred at 80° C. for six hours. The reaction was quenched by the addition of water (10 ml). The aqueous fraction was extracted with ethyl acetate (3×10 ml). The organic fractions were combined, washed with water (3×10 ml), brine (1×10 ml), and then dried over sodium sulfate. The solvents were removed in vacuo to yield an oily crude product which was purified by flash chromatography to provide the title product.

NMR and IR were consistent with the proposed title structure. FDMS 639 (M+). Analysis for $C_{36}H_{51}ClN_4O_4$: Theory: C, 67.64; H, 8.04; N, 8.76. Found: C, 67.89; H, 8.05; N, 8.84.

EXAMPLE 335

Preparation of (RS) 4-[3-[2-(methyl)piperidin-1-yl] propoxy]-2-[(4-chlorophenoxy)methyl]-1-[3-(piperidin-4-yl)propyl]benzimidazole

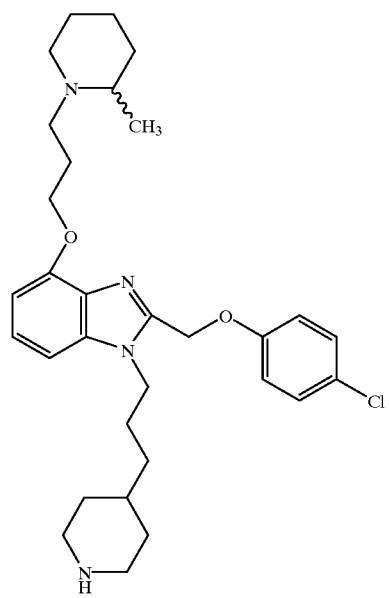

The title compound was prepared from (RS) 4-[3-[2-(methyl)piperidin-1-yl]propoxy]-2-[(4-chlorophenoxy) methyl]-1-[3-[1-(t-butoxycarbonyl)piperidin- 4-yl]propyl] benzimidazole by standard trifluoroacetic acid deprotection as described supra.

NMR and IR were consistent with the proposed title structure. FDMS 539 (M+). Analysis for $C_{31}H_{43}ClN_4O_2$: Theory: C, 69.06; H, 8.04; N, 10.39. Found: C, 70.89; H, 8.65; N, 9.05.

EXAMPLE 336

Preparation of 2-(4-chlorophenoxymethyl)-4-methyl-1-[3-[1-[3-(1,1-diphenyl)propyl]piperidin-4-yl]propyl] benzimidazole trihydrochloride

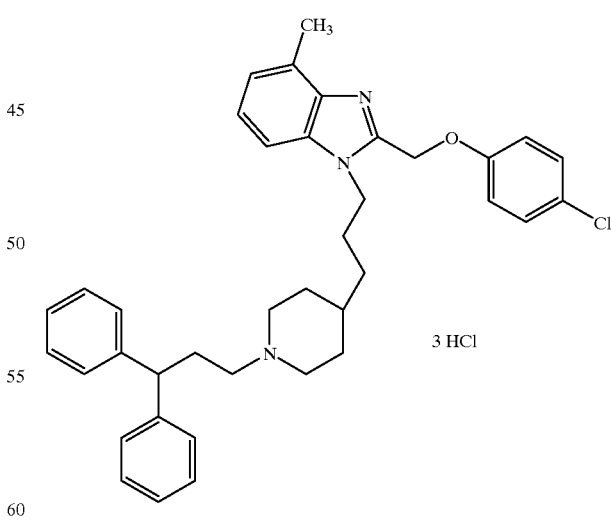

NMR was consistent with the desired title structure. FDMS 591 (M+). Analysis calculated for $C_{38}H_{42}ClN_3O \cdot 3HCl \cdot 0.25H_2O$. Theory: C, 64.64; H, 6.50; N, 5.95. Found: C, 64.61; H, 6.36; N, 5.99.

EXAMPLE 337
Prepartion of 2-(4-chlorophenoxymethyl)-4-methyl-1-[3-[1-(benzimidzol-2-ylmethyl)piperidin-4-yl]propyl]benzimidazole

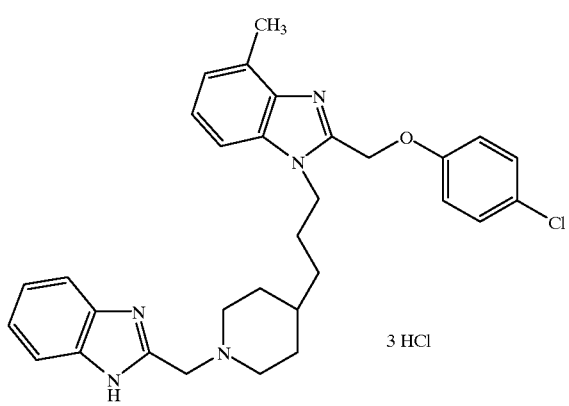

3 HCl mp 218–20°. NMR was consistent with the desired title structure. FDMS 528 (M+). FAB exact mass calculated for $C_{31}H_{35}ClN_5O$: Theory: 528.2530. Found: 528.2541.

EXAMPLE 338
Preparation of 2-(4-chlorophenoxymethyl)-4-methyl-1-[3-[1-[3-(2,4-dimethoxybenzoyl)propyl]piperidin-4-yl]propyl]benzimidazole

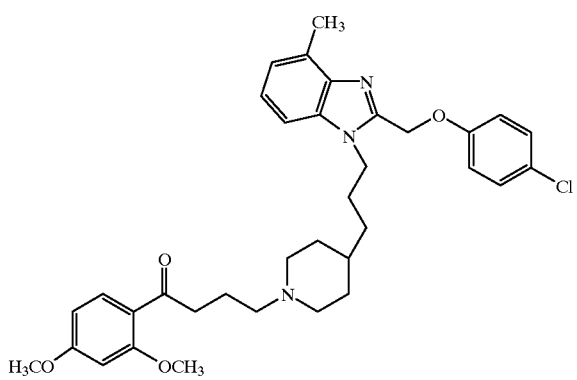

NMR was consistent with desired title structure. ESI MS 604 (M+1). Single compound of high purity as evidenced by chromatographic methods.

EXAMPLE 339
Preparation of 2-(4-chlorophenoxymethyl)-4-methyl-1-[3-[1-[3-(4-methoxybenzoyl)propyl]piperidin-4-yl]propyl]benzimidazole

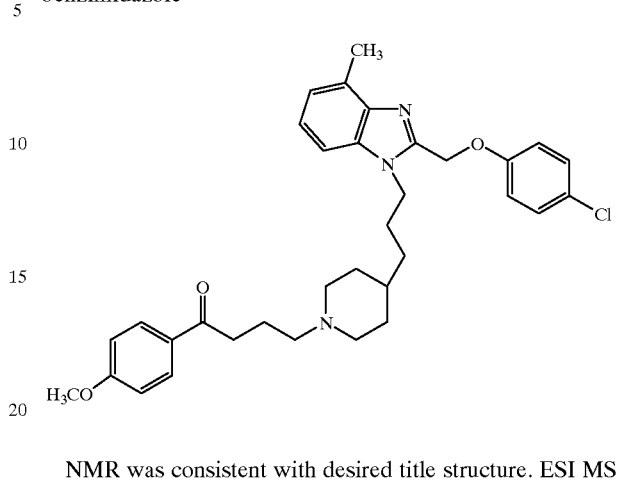

NMR was consistent with desired title structure. ESI MS 574 (M+1). Single compound of high purity as evidenced by chromatographic methods.

EXAMPLE 340
Preparation of 2-(4-chlorophenoxymethyl-4-methyl-1-[3-[1-[2-(quinazolin-4-yloxy)acetyl]piperidin-4-yl]propyl]benzimidazole

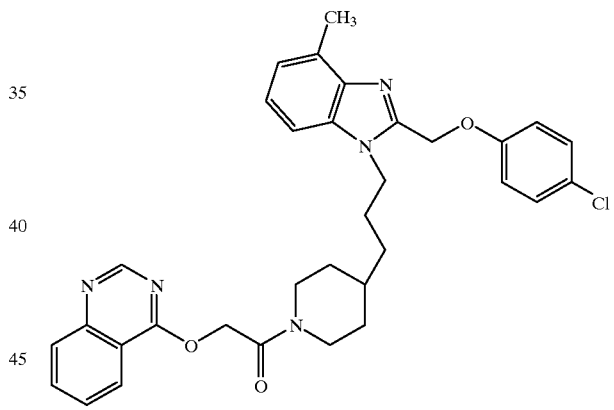

NMR was consistent with desired title structure. FAB exact mass calculated for $C_{33}H_{35}ClN_5O_3$: Theory: 584.2420. Found: 584.2428.

EXAMPLE 341
Preparation of 2-(4-chlorophenoxymethyl)-4-methyl-1-[3-[1-[2-(quinolin-2-yloxy)acetyl]piperidin-4-yl]propyl]benzimidazole

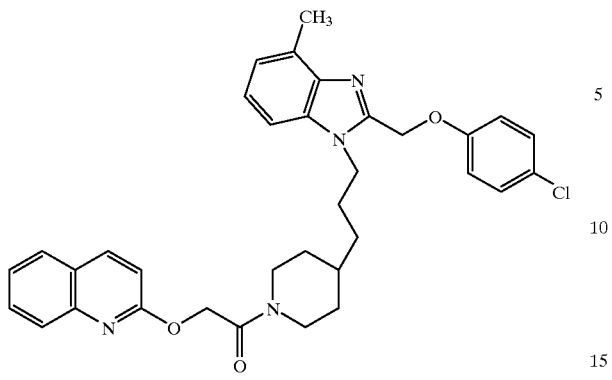

FAB exact mass calculated for $C_{34}H_{36}ClN_4O_3$: Theory: 583.2476. Found: 583.2484.

Single compound of high purity as evidenced by chromatographic methods.

EXAMPLE 342

Preparation of 2-(4-chlorophenoxymethyl)-4-methyl-1-[3-[1-[3-(indol-3-yl)propan-1-oyl]piperidin-4-yl]propyl]benzimidazole

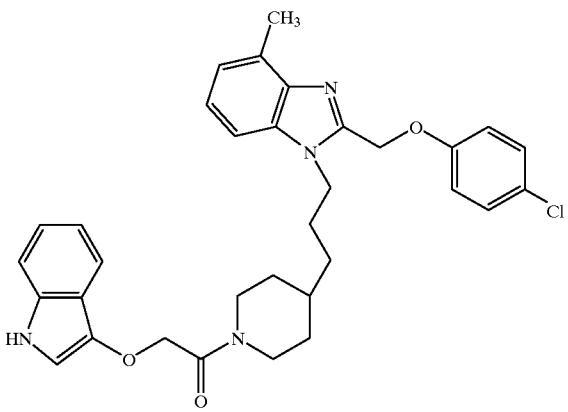

mp 153° C.; NMR, IR and UV were consistent with the desired title structure. FDMS 568 (M+). Analysis calculated for $C_{34}H_{37}ClN_4O_2$: Theory: C, 71.75; H, 6.55; N, 9.84. Found: C, 71.56; H, 6.41; N, 9.89.

EXAMPLE 343

Preparation of 2-(4-chlorophenoxymethyl)-4-methyl-1-[3-[1-[4-(indol-3-yl)butan-1-oyl]piperidin-4-yl]propyl]benzimidazole

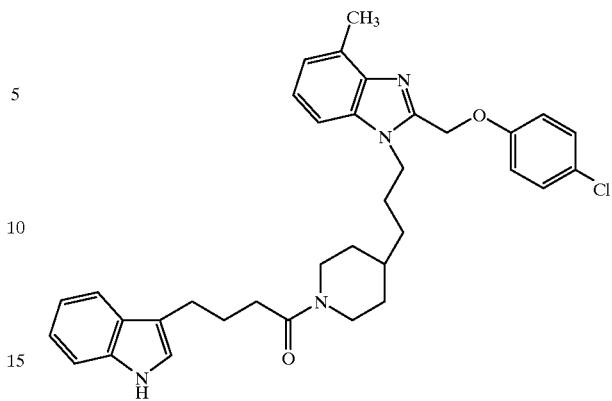

mp 151° C.; NMR, IR and UV were consistent with the desired title structure. FDMS 582 (M+). Analysis calculated for $C_{35}H_{39}ClN_4O_2$: Theory: C, 72.09; H, 6.74; N, 9.61. Found: C, 72.22; H, 6.69; N, 9.67.

EXAMPLE 344

Preparation of 2-(4-chlorophenoxymethyl)-4-methyl-1-[3-[1-[1-(2-phenylethylamino)butan-4-oyl]piperidin-4-yl]propyl]benzimidazole

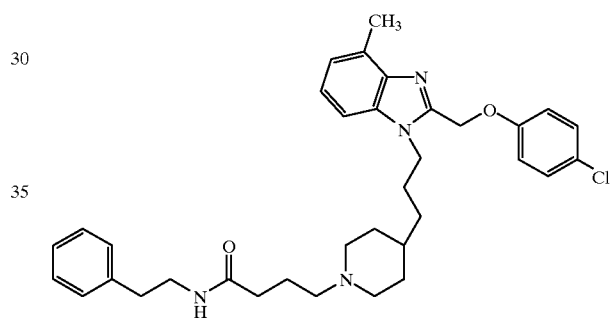

mp 112° C.; NMR, IR and UV were consistent with the desired title structure. FDMS 587 (M+).

Single compound of high purity as evidenced by chromatographic methods.

EXAMPLE 345

Preparation of 2-(4-chlorophenoxymethyl)-4-methyl-1-[3-[1-[1-(3-phenylpropylamino)butan-4-oyl]piperidin-4-yl]propyl]benzimidazole

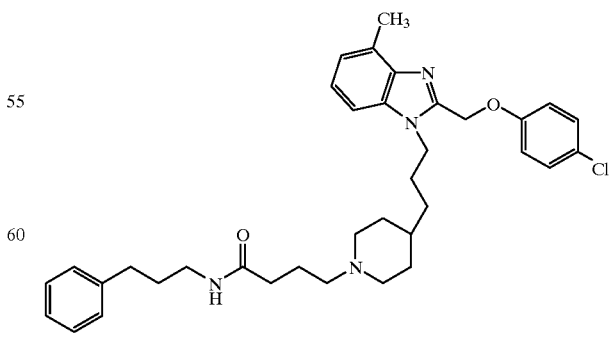

mp 113° C.; NMR, IR and UV were consistent with the desired title structure. FDMS 601 (M+). Analysis calculated

EXAMPLE 346
Preparation of 2-(4-chlorophenoxymethyl-4-methyl-1-[3-[1-[4-(1-indol-3-yl)butyl]piperidin-4-yl]propyl]benzimidazole

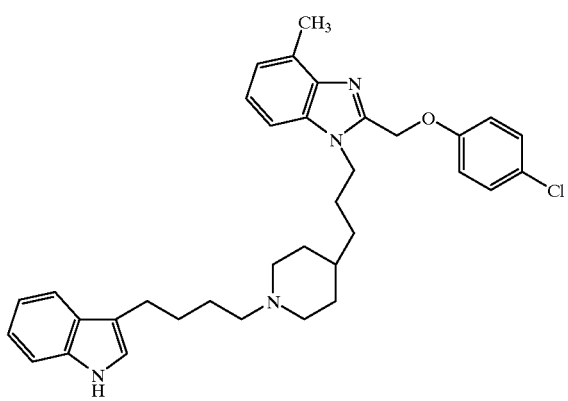

NMR was consistent with the desired title structure. ESI MS 569 (M+1).

Single compound of high purity as evidenced by chromatographic methods.

EXAMPLE 347
Preparation of 2-(4-chlorophenoxymethyl)-4-methyl-1-[3-[1-[3-(1-indol-3-yl)propyl]piperidin-4-yl]propyl]benzimidazole

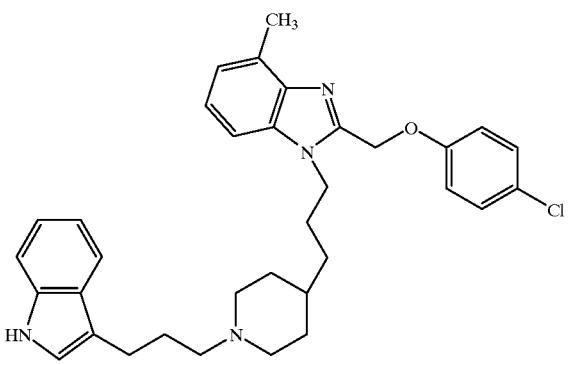

NMR was consistent with the desired title structure. ESI MS 555 (M+1).

Single compound of high purity as evidenced by chromatographic methods.

for $C_{36}H_{45}ClN_4O_2$: Theory: C, 71.92; H, 7.54, N, 9.32. Found: C, 71.72; H, 7.49; N, 9.24.

EXAMPLE 348
Preparation of 2-(4-chlorophenoxymethyl-4-methyl-1-[3-[1-[3-(4-iodophenyl)propyl]piperidin-4-yl]propyl]benzimidazole

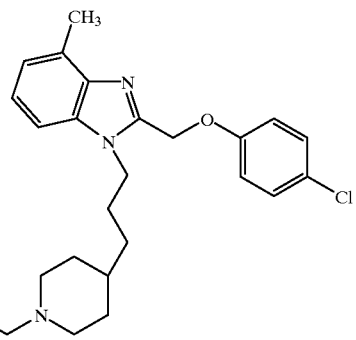

NMR was consistent with the desired title structure. ESI MS 642 (M+1).

Single compound of high purity as evidenced by chromatographic methods.

EXAMPLE 349
Preparation of 2-(4-chorophenoxymethyl)-4-methyl-1-[3-[1-[2-(4-iodophenyl)ethyl]piperidin-4-yl]propyl]benzimidazole

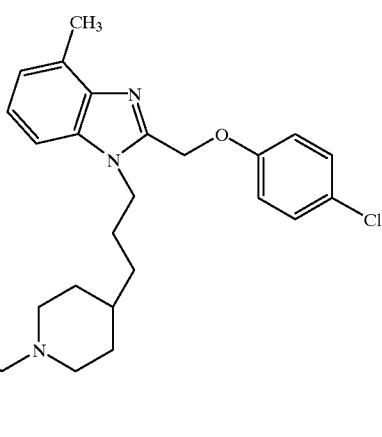

mp 121–122° C.; NMR and IR were consistent with the desired title structure. ESI MS 628 (M+1). Analysis calculated for $C_{31}H_{35}ClN_3O$: Theory: C, 59.29; H, 5.62; N, 6.69. Found: C, 59.22; H, 5.62; N, 6.70.

EXAMPLE 350
Preparation of 2-(4-chlorophenoxymethyl)-4-methyl-1-[3-[1-(3-acetylpropyl)piperidin-4-yl]propyl]benzimidazole

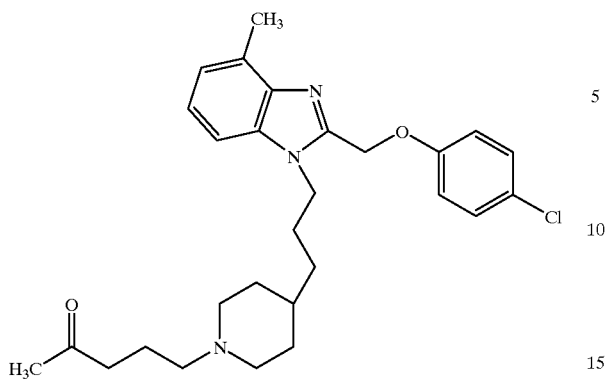

NMR was consistent with the desired title structure. ESI MS 482 (M+1).

Single compound of high purity as evidenced by chromatographic methods.

EXAMPLE 351

Preparation of 2-(4-chlorophenoxymethyl)-4-methyl-1-[3-[1,1-dimethylpiperidin-4-ium]propyl]benzimidazole iodide

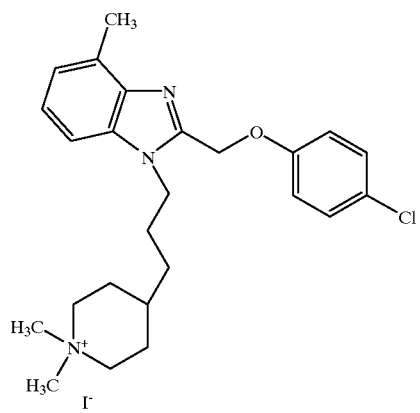

mp 198–199° C.;

NMR, IR and UV were consistent with the desired title structure. FDMS 426 (M+ for $C_{25}H_{33}N_3O$). Analysis for $C_{25}H_{33}N_3ClIN_3O \cdot 0.5H_2O$: Theory: C, 53.34; H, 6.09; N, 7.49. Found: C, 53.19; H, 6.07; N, 7.46.

EXAMPLE 352

Preparation of 2-(4-chlorophenoxymethyl)-4-methyl-1-[3-[1-methylpiperidin-4-yl]propyl]benzimidazole

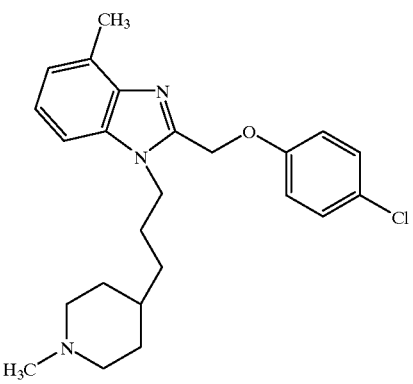

The NMR was consistent with the desired title structure. FAB exact mass calculated for $C_{24}H_{31}ClN_3O$: Theory: 412.2156. Found: 412.2146.

Single compound of high purity as evidenced by chromatographic methods.

EXAMPLE 353

Preparation of 2-(4-chlorophenoxymethyl)-4-meyhyl-1-[3-[1-[4-(phenyl)butyl]piperidin-4-yl]propyl]benzimidazole

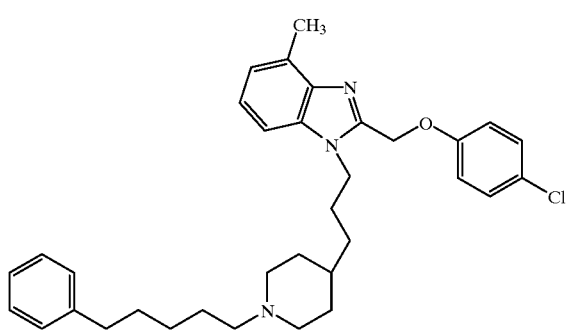

The NMR was consistent with the desired title structure. ESI MS 530 (M+1).

Single compound of high purity as evidenced by chromatographic methods.

EXAMPLE 354

Preparation of 2-(4-chlorophenoxymethyl)-4-methyl-1-[3-[1-[5-(phenyl)pentyl]piperidin-4-yl]propyl]benzimidazole The NMR was consistent with the desired title structure. FDMS 543 (M+). ESI MS 544 (M+1). Analysis calculated for $C_{34}H_{42}ClN_3O$: Theory: C, 75.04; H, 7.78; N, 7.72. Found: C, 74.84; H, 7.78; N, 7.89.

EXAMPLE 354A
Preparation of 2-(4-methylphenoxymethyl)-4-benzyloxybenzimidazole Yield: 53%; NMR was consistent with the proposed title structure. mp 156–158° C.; Analysis for $C_{22}H_{20}N_2O_2$: Theory: C, 76.72; H, 5.85; N, 8.13. Found: C, 77.00; H, 5.84; N, 8.11.

EXAMPLE 355
Preparation of 2-(4-chlorophenoxymethyl)-4-benzyloxy-1-[3-[1-(t-butoxycarbonyl)piperidin-4-yl]propyl]benzimidazole Yield: 9.0 grams; NMR was consistent with the proposed title structure. mp 116–118° C.; Analysis for $C_{34}H_{40}N_3O_4Cl$: Theory: C, 69.20; H, 6.83; N, 7.12. Found: C, 69.43; H, 6.69; N, 7.17.

EXAMPLE 356
Preparation of 2-(4-chlorophenoxymethyl)-7-benzyloxy-1-[3-[1-(t-butoxycarbonyl)piperidin-4-yl]propyl]benzimidazole Yield: 5.27 grams; NMR was consistent with the proposed title structure. Analysis for $C_{34}H_{40}N_3O_4Cl$: Theory: C, 69.20; H, 6.83; N, 7.12. Found: C, 69.75; H, 7.23; N, 7.26.

EXAMPLE 357
Preparation of 2-(4-methylphenoxymethyl)-4-benzyloxy-1-[3-[1-(t-butoxycarbonyl)piperidin-4-yl]propyl]benzimidazole Yield: 7.50 grams; NMR was consistent with the proposed title structure. mp 116–118° C.; Analysis for $C_{35}H_{43}N_3O_4$: Theory: C, 73.78; H, 7.61; N, 7.37. Found: C, 73.85; H, 7.72; N, 7.50.

EXAMPLE 358
Preparation of 2-(4-methylphenoxymethyl)-7-benzyloxy-1-[3-[1-(t-butoxycarbonyl)piperidin-4-yl]propyl]benzimidazole Yield: 4.50 grams; NMR was consistent with the proposed title structure. mp 153–154.5° C.; Analysis for $C_{35}H_{43}N_3O_4$: Theory: C, 73.78; H, 7.61; N, 7.37. Found: C, 73.62; H, 7.66; N, 7.34.

EXAMPLE 359
Preparation of 2-(4-chlorophenoxymethyl)-4-benzyloxy-1-[3-(piperidin-4-yl)propyl]benzimidazole Yield: 55%; NMR was consistent with the proposed title structure. mp 140–141° C.; Analysis for $C_{29}H_{32}N_3O_2Cl$: Theory: C, 71.08; H, 6.58; N, 8.58. Found: C, 71.20; H, 6.54; N, 8.61.

EXAMPLE 360
Preparation of 2-(4-chlorophenoxymethyl)-7-benzyloxy-1-[3-(piperidin-4-yl)propyl]benzimidazole Yield: 98%; NMR was consistent with the proposed title structure. Analysis for $C_{29}H_{32}N_3O_2Cl$: Theory: C, 71.08; H, 6.58; N, 8.58. Found: C, 71.00; H, 6.80; N, 8.67.

EXAMPLE 361
Preparation of 2-(4-chlorophenoxymethyl)-4-benzyloxy-1-[3-[1-(ethoxycarbonylpropyl)piperidin-4-yl]propyl]benzimidazole The title compound was prepared from the compound of Example 360 by reacting the compound with sodium bicarbonate and 3-(ethoxycarbonyl)propyl bromide in N,N-dimethylformamide, essentially as described supra.

Yield: 78%; NMR was consistent with the proposed title structure. mp 63–65° C.; Analysis for $C_{35}H_{42}N_3O_2Cl$: Theory: C, 69.58; H, 7.01; N, 6.95. Found: C, 69.77; H, 7.21; N, 6.70.

EXAMPLE 362
Preparation of 2-(4-chlorophenoxymethyl)-4-benzyloxy-1-[3-[1-[3-(piperidin-1-yl)propyl]piperidin-4-yl]propyl]benzimidazole The title compound was prepared from the compound of Example 360 by reacting the compound with sodium bicarbonate, sodium iodide, and 1-(3-chloropropyl)piperidine hydrochloride in N,N-dimethylformamide, essentially as described supra.

Yield: 64%; NMR was consistent with the proposed title structure. mp 58–60° C.; Analysis for $C_{37}H_{47}N_4O_2Cl$: Theory: C, 72.23; H, 7.70; N, 9.11. Found: C, 72.08; H, 7.53; N, 8.86.

EXAMPLE 363
Preparation of 2-(4-chlorophenoxymethyl)-4-benzyloxy-1-[3-[1-[3-(carboxy)propyl]piperidin-4-yl]propyl]benzimidazole Yield: 74%; NMR was consistent with the proposed title structure. mp 101–103° C.; Analysis for $C_{33}H_{38}N_3O_4Cl$: Theory: C, 68.80; H, 6.65; N, 7.29. Found: C, 68.60; H, 6.89; N, 7.52.

EXAMPLE 364
Preparation of 2-(4-chlorophenoxymethyl)-4-benzyloxy-1-[3-[1-[3-(piperidin-1-ylcarbonyl)propyl]piperidin-4-yl]propyl]benzimidazole Yield: 47%; NMR was consistent with the proposed title structure. mp 145.5–147° C.; Analysis for $C_{38}H_{47}N_4O_3Cl$: Theory: C, 70.95; H, 7.37; N, 8.71. Found: C, 70.86; H, 7.34; N, 8.68.

EXAMPLE 365
Preparation of 2-(4-chlorophenoxymethyl)-4-benzyloxy-1-[3-[1-[4-(piperidin-1-yl)butyl]piperidin-4-yl]propyl]benzimidazole hemihydrate Yield: 34%; NMR was consistent with the proposed title structure. mp 98–100° C.; Analysis for $C_{38}H_{49}N_4O_2Cl$: Theory: C, 71.49; H, 7.90; N, 8.78. Found: C, 71.15; H, 7.73; N, 8.71.

EXAMPLE 366
Preparation of 2-(4-chlorophenoxymethyl)-4-benzyloxy-1-[3-[1-[3-(piperidin-1-yl)propyl]piperidin-4-yl]propyl]benzimidazole hemihydrate Yield: 86%; NMR was consistent with the proposed title structure. mp 108–110° C.; Analysis for $C_{37}H_{47}N_4O_2Cl$: Theory: C, 72.23; H, 7.70; N, 9.11. Found: C, 72.48; H, 7.85; N, 9.05.

EXAMPLE 367
Preparation of 2-(4-chlorophenoxymethyl)-7-[3-[1-(t-butoxycarbonyl)piperidin-3-yl]propoxy]-1-[3-[1-[3-(piperidin-1-yl)propyl]piperidin-4-yl]propyl]benzimidazole hemihydrate Yield: 86%; NMR was consistent with the proposed title structure. mp 108–110° C.; Analysis for $C_{37}H_{47}N_4O_2Cl$: Theory: C, 72.23; H, 7.70; N, 9.11. Found: C, 72.48; H, 7.85; N, 9.05.

By substantially following the procedures described above one skilled in the art can prepare the other compounds of Formula I.

The compounds of the present invention bind to receptors specific for neuropeptide Y as well as the closely related neuropeptides. [For a review of neuropeptide Y receptors, see, D. Gehlert, *Life Sciences*, 55:551–562 (1994); P. A. Hipskind and D. R. Gehlert, *Annual Reports in Medicinal Chemistry*, 31:1 (1996)]. Receptors for neuropeptide Y and peptide YY have considerable overlap while pancreatic polypeptide appears to have its own distinct set of receptors. Many, but not all, of the effects of neuropeptide Y can be replicated using peptide YY.

Two subtypes of receptors for neuropeptide Y were initially proposed on the basis of the affinity of the 13–36 fragment of neuropeptide Y using a preparation of the sympathetic nervous system. While these are the best established receptors for neuropeptide Y, a substantial body of evidence exists that there are additional receptor subtypes. The best established is a Y-3 receptor that is responsive to neuropeptide Y, but not to peptide YY. Another recently delineated receptor has been described that binds peptide YY with high affinity and neuropeptide Y with lower affinity. While the pharmacology of the feeding response to neuropeptide Y appears to be Y-1 in nature, a separate "feeding receptor" has been proposed. Several of the receptors have been successfully cloned to date. The following paragraphs summarize the available information on the known neuropeptide Y receptor subtypes and their potential role in physiological finction.

Y-1 Receptor

The Y-1 receptor is the best characterized receptor for neuropeptide Y. This receptor is generally considered to be postsynaptic and mediates many of the known actions of neuropeptide Y in the periphery. Originally, this receptor was described as having poor affinity for C-terminal fragments of neuropeptide Y, such as the 13–36 fragment, but interacts with the full length neuropeptide Y and peptide YY with equal affinity. C. Wahlestedt, et al, *Regulatory Peptides*, 13:307–318 (1986); C. Wahlestedt, et al., NEURONAL MESSENGERS IN VASCULAR FUNCTION, 231–241 (Nobin, et al., eds. 1987). Substitution of the amino acid at position 34 with a proline (Pro$^{34}$) results in a protein which is specific for the Y-1 receptor. E. K. Potter, et al., *European Journal of Pharmacology*, 193:15–19 (1991). This tool has been used to establish a role for the Y-1 receptor in a variety of finctions. The receptor is thought to be coupled to adenylate cyclase in an inhibitory manner in cerebral cortex, vascular smooth muscle cells, and SK-N-MC cells. [For a review, see, B. J. McDermott, etal., *Cardiovascular Research*, 27:893–905 (1993)]. This action is prevented by application of pertussis toxin confirming the role of a G-protein coupled receptor. The Y-1 receptor mediates the mobilization of intracellular calcium in a porcine vascular smooth muscle cells and human erythroleukemia cells.

The cloned human Y-1 receptor can couple to either phosphotidylinositol hydrolysis or the inhibition of adenylate cyclase, depending on the type of cell in which the receptor is expressed. H. Herzog, et al., *Proceedings of the National Academy of Sciences (USA)*, 89:5794–5798 (1992). The Y-1 receptor has been reported to couple to either second messenger system when studied using tissue preparations or cell lines naturally expressing the receptor. D. Gehlert, supra, at 553. The Y-1 receptor cannot, therefore, be distinguished solely on the basis of coupling to a single second messenger.

Modulation of a Y-1 receptor (either a typical or an atypical Y-1 receptor) is believed to influence multiple physiological conditions, including, but not limited to, obesity or appetite disorder, adult onset diabetes, bulimia nervosa, pheochromocytoma-induced hypertension, subarachnoid hemorrhage, neurogenic vascular hypertrophy, hypertension, anxiety, and anorexia nervosa. PCT Patent Publication WO 96/16542, published Jun. 6, 1996, at page 135, and the references cited therein.

Y-2 Receptor

As with the Y-1 receptor, this receptor subtype was first delineated using vascular preparations. Pharmacologically, the Y-2 receptor is distinguished from Y-1 by exhibiting affinity for C-terminal fragments of neuropeptide Y. The receptor is most often differentiated by the use of neuropeptide Y(13–36), though the 3–36 fragment of neuropeptide Y and peptide YY provides improved affinity and selectivity. Y. Dumont, et al., *Society for Neuroscience Abstracts*, 19:726 (1993). Like Y-1 receptor, this receptor is coupled to the inhibition of adenylate cyclase, though in some preparations it may not be sensitive to pertussis toxin. The Y-2 receptor was found to reduce the intracellular levels of calcium in the synapse by selective inhibition of N-type calcium channels. Like the Y-1 receptor, the Y-2 receptor may exhibit differential coupling to second messengers. The Y2 receptor is believed to be involved in modulating hypertension, epileptic seizure, and neurogenic vascular hypertrophy. PCT Patent Publication WO 96/16542, published Jun. 6, 1996, at page 135, and the references cited therein.

The Y-2 receptors are found in a variety of brain regions, including the hippocampus, substantia nigra-lateralis, thalamus, hypothalamus, and brainstem. In the periphery, Y-2 is found in the peripheral nervous system, such as sympathetic, parasympathetic, and sensory neurons. In all these tissues, Y-2 receptors mediate a decrease in the release of neurotransmitters. The Y-2 receptor has been cloned using expression cloning techniques. P. M. Rose, et al., *Journal of Biological Chemistry*, 270:22661 (1995); C. Gerald, et al., *Journal of Biological Chemistry*, 270:26758 (1995); D. R. Gehlert, et al., *Molecular Pharmacology*, 49:224 (1996).

Y-3 Receptor

This receptor has high affinity for neuropeptide Y while having lower affinity for peptide YY. While neuropeptide Y is a fully efficacious agonist at this receptor population, peptide YY is weakly efficacious. This pharmacological property is used to define this receptor. A receptor that has similar pharmacology to the Y-3 receptor has been identified in the CA3 region of the hippocampus using electrophysiological techniques. This receptor may potentiate the excitatory response of these neurons to N-methyl-D-aspartate (NMDA). F. P. Monnet, et al., *European Journal of Pharmacology*, 182:207–208 (1990). This receptor is believed to modulate hypertension. PCT Patent Publication WO 96/16542, published Jun. 6, 1996, at page 135, and the references cited therein.

The presence of this receptor is best established in the rat brainstem, specifically in the nucleus tractus solitarius. Application of neuropeptide Y to this region produces a dose-dependent reduction in blood pressure and heart rate. This area of the brain also may have significant contributions from the Y-1 and Y-2 receptor. Neuropeptide Y also inhibits the acetylcholine-induced release of catecholamines from the adrenal medulla, presumably through a Y-3 receptor. C. Wahlestedt, et al., *Life Sciences*, 50:PL7–PL14 (1992).

Peptide YY Preferring Receptor

A fourth receptor has been described that exhibits a modest preference for peptide YY over neuropeptide Y. This receptor was first described in the rat small intestine as having a 5–10 fold higher affinity for peptide YY over neuropeptide Y. M. Laburthe, et al., *Endocrinology*, 118:1910–1917 (1986). Subsequently, this receptor was found in the adipocyte and a kidney proximal tubule cell line. This receptor is coupled in an inhibitory manner to adenylate cyclase and is sensitive to pertussis toxin.

In the intestine, this receptor produces a potent inhibition of fluid and electrolyte secretion. The receptor is localized to the crypt cells where intestinal chloride secretion is believed to take place. The peptide YY preferring receptor in adipocytes mediates a reduction in lipolysis by way of a cyclic adenosine monophosphate (cAMP)-dependent mechanism.
"Feeding Receptor"

One of the earliest discovered central effects of neuropeptide Y was a profound increase in food intake that was observed following the hypothalmic administration of the peptide to rats. The response was greatest when the peptide was infused into the perifornical region of the hypothalamus. B. G. Stanley, et al., *Brain Research*, 604:304–317 (1993). While the pharmacology of this response resembled the Y-1 receptor, the 2–36 fragment of neuropeptide Y was significantly more potent than neuropeptide Y. In addition, intracerebroventricular neuropeptide Y(2–36) fully stimulates feeding, but does not reduce body temperature as does full length neuropeptide Y. F. B. Jolicoeur, et al., *Brain Research Bulletin*, 26:309–311 (1991). Two recent patent publications describe the cloning and expression of the Y5 receptor, believed to be the "feeding receptor". Patent Cooperation Treaty Publication WO 96/16542, published Jun. 6, 1996; and Australian Patent Publication AU 956467 A0, published Nov. 30, 1995.

The biological activity of the compounds of the present invention was evaluated employing an initial screening assay which rapidly and accurately measured the binding of the tested compound to known neuropeptide Y receptor sites. Assays useful for evaluating neuropeptide Y receptor antagonists are well known in the art. See. e.g., U.S. Pat. No. 5,284,839, issued Feb. 8, 1994, which is herein incorporated by reference. See also, M. W. Walker, et al., *Journal of Neurosciences*, 8:2438–2446 (1988).

Neuropeptide Y Binding Assay

The ability of the compounds of the instant invention were assessed as to their ability to bind to neuropeptide Y using a protocol essentially as described in M. W. Walker, et al., supra. In this assay the cell line SK-N-MC was employed. This cell line was received from Sloane-Kettering Memorial Hospital, New York. These cells were cultured in T-150 flasks using Dulbecco's Minimal Essential Media (DMEM) supplemented with 5% fetal calf serum. The cells were manually removed from the flasks by scraping, pelleted, and stored at −70° C.

The pellets were resuspended using a glass homogenizer in 25 mM HEPES (pH 7.4) buffer containing 2.5 mM calcium chloride, 1 mM magnesium chloride, and 2 g/L bacitracin. Incubations were performed in a final volume of 200 μl containing 0.1 nM $^{125}$I-peptide YY (2200 Ci/mmol) and 0.2–0.4 mg protein for about two hours at room temperature.

Nonspecific binding was defined as the amount of radioactivity remaining bound to the tissue after incubating in the presence of 1 μM neuropeptide Y. In some experiments various concentrations of compounds were included in the incubation mixture.

Incubations were terminated by rapid filtration through glass fiber filters which had been presoaked in 0.3% polyethyleneimine using a 96-well harvester. The filters were washed with 5 ml of 50 mM Tris (pH 7.4) at 4° C. and rapidly dried at 60° C. The filters were then treated with melt-on scintillation sheets and the radioactivity retained on the filters were counted. The results were analyzed using various software packages. Protein concentrations were measured using standard coumassie protein assay reagents using bovine serum albumin as standards.

Many of the compounds prepared supra showed significant activity as neuropeptide Y receptor antagonists ($K_i$=10 μM to 0.1 nM). As the compounds of Formula I are effective neuropeptide Y receptor antagonists, these compounds are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, a compound of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid compositions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dipsersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compsoitions may be administered, preferably orally or nasally, from devices which deliver the formulation in an appropriate manner.

The following examples illustrate the pharmaceutical compositions of the present invention.

Formulation Preparation 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient | 250.0 mg |
| Isotonic saline | 1000 ml |

Formulation Preparation 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by refernce.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A compound of the formula

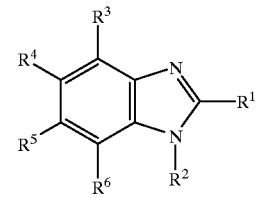

wherein:

$R^1$ is phenoxy($C_1$–$C_6$ alkylenyl)-,
of which phenoxy moieties may be substituted with one or more groups selected from the group consisting of halo, trifluoromethyl, $C_1$–$C_6$ alkyl, nitro, amino, t-butoxycarbonylamino, $C_2$–$C_7$ alkenyl, $C_2$–$C_7$ alkynyl, $C_1$–$C_6$ alkoxy, $C_1$–$C_6$ alkylthio, $C_1$–$C_6$ alkylamino, heterocyclic, unsaturated heterocyclic, $C_3$–$C_8$ cycloalkyl, $C_3$–$C_8$ cycloalkenyl, phenyl, phenoxy, phenyl($C_1$–$C_6$ alkylenyl)-, phenyl($C_1$–$C_6$ alkoxy)-, benzoyl, phenyl($C_2$–$C_7$ alkanoyl)-, and phenyl($C_2$–$C_7$ alkanoyloxy)-;

$R^2$ is $C_2$–$C_7$ alkenyl, $C_2$–$C_7$ alkynyl, $C_2$–$C_7$ alkanoyl, $C_1$–$C_6$ alkoxy, heterocyclic($C_2$–$C_6$ alkylenyl)-, $C_3$–$C_8$ cycloalkyl, $C_3$–$C_8$ cycloalkenyl, unsaturated heterocyclic($C_2$–$C_6$ alkylenyl)-, heterocyclic($C_1$–$C_6$ alkoxy)-, unsaturated heterocyclic($C_1$–$C_6$ alkoxy)-, phenyl, phenyl($C_1$–$C_6$ alkylenyl)-, naphthyl, naphthyl ($C_1$–$C_6$ alkylenyl)-, phenoxy($C_1$–$C_6$ alkylenyl)-, naphthyloxy($C_1$–$C_6$ alkylenyl)-, benzoyl($C_1$–$C_6$ alkylenyl)-, $C_2$–$C_7$ carbamoyl, $C_2$–$C_7$ amido, $C_1$–$C_6$ alkoxycarbonyl-, or $C_1$–$C_6$ haloalkyl, any one of which phenyl, naphthyl, phenoxy, naphthyloxy, benzoyl, $C_3$–$C_8$ cycloalkyl, $C_3$–$C_8$ cycloalkenyl, heterocyclic($C_1$–$C_6$ alkoxy)-, unsaturated heterocyclic($C_1$–$C_6$ alkoxy)-, heterocyclic, or unsaturated heterocyclic moieties may be substituted with one or more groups selected from the group consisting of $C_1$–$C_6$ alkyl, $C_1$–$C_6$ alkoxy, phenyl, naphthyl, phenyl($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, dimethylamino, $C_1$–$C_6$ alkylthio, $C_1$–$C_6$ haloalkyl, amino, nitro, and hydroxy, or $R^2$ may also be —$(CH_2)_n$—$NR^7R^8$, where, n is 2 to 10, and $R^7$ and $R^8$ are independently hydrogen, $C_1$–$C_6$ alkyl, $C_2$–$C_7$ alkanoyl, $C_1$–$C_6$ alkoxy, heterocyclic($C_1$–$C_6$ alkylenyl)-, unsaturated heterocyclic($C_1$–$C_6$ alkylenyl)-, phenyl, phenyl($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, benzoyl($C_1$–$C_6$ alkylenyl)-, heterocyclic($C_1$–$C_6$ alkoxy)-, unsaturated heterocyclic($C_1$–$C_6$ alkoxy)-, $C_1$–$C_6$ haloalkyl, $C_2$–$C_7$ alkenyl, $C_2$–$C_7$ alkynyl, $C_3$–$C_8$ cycloalkenyl, or $C_3$–$C_8$ cycloalkyl, any one of which phenyl, naphthyl, phenoxy, naphthyloxy, $C_3$–$C_8$ cycloalkyl, benzoyl, heterocyclic, unsaturated heterocyclic, heterocyclic($C_1$–$C_6$ alkoxy)-, or unsaturated heterocyclic($C_1$–$C_6$ alkoxy)- moieties may be substituted with one or more groups selected from the group consisting of $C_1$–$C_6$ alkyl, $C_1$–$C_6$ alkoxy, halo, trifluoromethyl, alkoxy, $C_3$–$C_8$ cycloalkyl, $C_3$–$C_8$ cycloalkenyl, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_2$–$C_7$ alkanoyl, $C_2$–$C_7$ alkanoyloxy, $C_1$–$C_6$ alkylamino, $C_1$–$C_6$ alkylthio, $C_2$–$C_7$ alkenyl, $C_2$–$C_7$ alkynyl, $C_1$–$C_6$ haloalkyl, amino, nitro, and hydroxy;

and $R^3$, $R^4$, $R^5$, and $R^6$ are independently hydrogen, halo, $C_1$–$C_6$ alkyl, $C_1$–$C_6$ alkoxy, $C_2$–$C_7$ alkenyl, $C_2$–$C_7$ alkynyl, $C_2$–$C_7$ alkanoyl, $C_2$–$C_7$ alkanoyloxy, $C_1$–$C_6$ alkylamino, $C_1$–$C_6$ alkylthio, benzoyl, phenoxy, phenyl($C_1$–$C_6$ alkylenyl)-, $C_3$–$C_8$ cycloalkyl, $C_3$–$C_8$ cycloalkenyl, phenyl($C_1$–$C_6$ alkoxy)-, phenyl($C_1$–$C_6$ alkyleneamino)-, phenyl($C_1$–$C_6$ alkyleneamino)-, phenyl($C_2$–$C_7$ alkanoyl)-, phenyl($C_2$–$C_7$ alkanoyloxy)-, heterocyclic, unsaturated heterocyclic, heterocyclic($C_1$–$C_6$ alkylenyl)-, heterocyclic($C_1$–$C_6$ alkoxy)-, unsaturated heterocyclic($C_1$–$C_6$ alkylenyl)-, unsaturated heterocyclic($C_1$–$C_6$ alkoxy)-, amino, nitro, hydroxy, trifluoromethyl, or —$(CH_2)_n$—$NR^7R^8$;

or a salt or solvate thereof.

2. A compound as in claim 1 wherein $R^1$ is phenoxymethyl, of which phenoxy moieties may be substituted with one or more groups selected from the group consisting of halo, trifluoromethyl, $C_1$–$C_6$ alkyl, nitro, amino, and t-butoxycarbonylamino.

3. A compound as in claim 2 wherein $R^1$ is 4-chlorophenoxymethyl.

4. A compound as in claim 2 wherein $R^1$ is 2,4-dichlorophenoxymethyl.

5. A compound as in claim 2 wherein $R^2$ is heterocyclic($C_2$–$C_6$ alkylenyl)-, of which heterocyclic moieties may be substituted with one or more groups selected from the group consisting of $C_1$–$C_6$ alkyl, $C_1$–$C_6$ alkoxy, phenyl, naphthyl, phenyl($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, dimethylamino, $C_1$–$C_6$ alkylthio, $C_1$–$C_6$ haloalkyl, amino, nitro, and hydroxy.

6. A compound as in claim 5 wherein the heterocyclic($C_2$–$C_6$ alkylenyl)- is piperidinyl($C_2$–$C_6$ alkylenyl)-, of which piperidinyl moieties may be substituted with one or more groups selected from the group consisting of $C_1$–$C_6$ alkyl, $C_1$–$C_6$ alkoxy, phenyl, naphthyl, phenyl($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, dimethylamino, $C_1$–$C_6$ alkylthio, $C_1$–$C_6$ haloalkyl, amino, nitro, and hydroxy.

7. A compound as in claim 6 wherein the piperidinyl($C_2$–$C_6$ alkylenyl)- is piperidinyl(propylenyl)-, of which piperidinyl moieties may be substituted with one or more groups selected from the group consisting of $C_1$–$C_6$ alkyl, $C_1$–$C_6$ alkoxy, phenyl, naphthyl, phenyl($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, dimethylamino, $C_1$–$C_6$ alkylthio, $C_1$–$C_6$ haloalkyl, amino, nitro, and hydroxy.

8. A compound as in claim 7 wherein the piperidinyl(propylenyl)- is 3-(piperidin-1-yl)propyl, of which piperidinyl moieties may be substituted with one or more groups selected from the group consisting of $C_1$–$C_6$ alkyl, $C_1$–$C_6$ alkoxy, phenyl, naphthyl, phenyl($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, dimethylamino, $C_1$–$C_6$ alkylthio, $C_1$–$C_6$ haloalkyl, amino, nitro, and hydroxy.

9. A compound as in claim 7 wherein the piperidinyl(propylenyl)- is 3-(piperidin-3-yl)propyl, of which piperidinyl moieties may be substituted with one or more groups selected from the group consisting of $C_1$–$C_6$ alkyl, $C_1$–$C_6$ alkoxy, phenyl, naphthyl, phenyl($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, heterocyclic, unsaturated heterocyclic, heterocyclic ($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, dimethylamino, $C_1$–$C_6$ alkylthio, $C_1$–$C_6$ haloalkyl, amino, nitro, and hydroxy.

10. A compound as in claim 7 wherein the piperidinyl (propylenyl)- is 3-(piperidin-4-yl)propyl, of which piperidinyl moieties may be substituted with one or more groups selected from the group consisting of $C_1$–$C_6$ alkyl, $C_1$–$C_6$ alkoxy, phenyl, naphthyl, phenyl ($C_1$–$C_6$ alkylenyl)-, naphthyl($C_1$–$C_6$ alkylenyl)-, halo, trifluoromethyl, $C_2$–$C_7$ alkenyl, $C_2$–$C_7$ alkynyl, heterocyclic, unsaturated heterocyclic, heterocyclic ($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, dimethylamino, $C_1$–$C_6$ alkylthio, $C_1$–$C_6$ haloalkyl, amino, nitro, and hydroxy.

* * * * *